US010981968B2

(12) United States Patent
Retallack et al.

(10) Patent No.: US 10,981,968 B2
(45) Date of Patent: *Apr. 20, 2021

(54) FUSION PARTNERS FOR PEPTIDE PRODUCTION

(71) Applicant: Pfenex Inc., San Diego, CA (US)

(72) Inventors: Diane M. Retallack, Poway, CA (US); Adam Chapman, San Diego, CA (US); Torben R. Bruck, Lakeside, CA (US); Hongfan Jin, San Diego, CA (US)

(73) Assignee: Pfenex Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/135,875

(22) Filed: Sep. 19, 2018

(65) Prior Publication Data
US 2019/0135889 A1 May 9, 2019

Related U.S. Application Data

(62) Division of application No. 14/954,766, filed on Nov. 30, 2015, now Pat. No. 10,118,956.

(60) Provisional application No. 62/086,119, filed on Dec. 1, 2014.

(51) Int. Cl.
| C07K 14/635 | (2006.01) |
| C07K 14/535 | (2006.01) |
| C07K 14/62  | (2006.01) |
| C12N 9/64   | (2006.01) |

(52) U.S. Cl.
CPC .......... *C07K 14/635* (2013.01); *C07K 14/535* (2013.01); *C07K 14/62* (2013.01); *C12N 9/6424* (2013.01); *C12Y 304/21009* (2013.01); *C07K 2319/35* (2013.01); *C07K 2319/50* (2013.01)

(58) Field of Classification Search
None
See application file for complete search history.

(56) References Cited

U.S. PATENT DOCUMENTS

| 4,551,433 A | 11/1985 | Deboer |
| 4,695,455 A | 9/1987 | Barnes et al. |
| 4,755,465 A | 7/1988 | Gray et al. |
| 4,769,326 A | 9/1988 | Rutter |
| 4,861,595 A | 8/1989 | Barnes et al. |
| 5,013,653 A | 5/1991 | Huston et al. |
| 5,055,294 A | 10/1991 | Gilroy |
| 5,128,130 A | 7/1992 | Gilroy et al. |
| 5,169,760 A | 12/1992 | Wilcox |
| 5,281,532 A | 1/1994 | Rammler et al. |
| 5,648,237 A | 7/1997 | Carter |
| 5,750,374 A | 5/1998 | Dobeli et al. |
| 5,891,671 A | 4/1999 | Suzuki et al. |
| 5,989,868 A | 11/1999 | Harrison et al. |
| 6,207,420 B1 | 3/2001 | Harrison et al. |
| 6,242,219 B1 | 6/2001 | Better et al. |
| 6,500,648 B1 | 12/2002 | Better et al. |
| 6,906,176 B2 | 6/2005 | Ley et al. |
| 6,916,623 B2 | 7/2005 | Seki et al. |
| 7,150,974 B1 | 12/2006 | Segre et al. |
| 7,208,585 B2 | 4/2007 | Fong et al. |
| 7,247,454 B2 | 7/2007 | Better et al. |
| 7,476,532 B2 | 1/2009 | Schneider et al. |
| 7,618,799 B2 | 11/2009 | Coleman et al. |
| 7,626,004 B2 | 12/2009 | Fong et al. |
| 7,749,731 B2 | 7/2010 | Better et al. |
| 7,794,972 B2 | 9/2010 | Retallack et al. |
| 7,833,752 B2 | 11/2010 | Coleman et al. |
| 7,985,564 B2 | 7/2011 | Retallack et al. |
| 8,017,355 B2 | 9/2011 | Schneider et al. |
| 8,106,158 B2 | 1/2012 | Kim et al. |
| 8,288,127 B2 | 10/2012 | Schneider et al. |
| 8,298,789 B2 | 10/2012 | Sankararaman et al. |
| 8,378,076 B2 | 2/2013 | Shen et al. |
| 8,455,218 B2 | 6/2013 | Jin et al. |
| 8,569,015 B2 | 10/2013 | Rasochova et al. |
| 8,603,824 B2 | 12/2013 | Ramseier et al. |
| 9,169,304 B2 | 10/2015 | Allen et al. |
| 9,394,571 B2 | 7/2016 | Ramseier et al. |
| 9,453,251 B2 | 9/2016 | Retallack et al. |
| 9,580,719 B2 | 2/2017 | Retallack et al. |
| 2007/0026501 A1 | 2/2007 | Izumoto et al. |
| 2007/0141662 A1 | 6/2007 | Stennicke et al. |
| 2007/0202573 A1 | 8/2007 | Nelson et al. |
| 2007/0292918 A1 | 12/2007 | Stelman et al. |
| 2008/0171852 A9 | 7/2008 | Kim et al. |
| 2008/0206811 A1 | 8/2008 | Shodai et al. |

(Continued)

FOREIGN PATENT DOCUMENTS

| AU | 2012251584 A1 | 11/2013 |
| CA | 2834456 A1 | 11/2012 |

(Continued)

OTHER PUBLICATIONS

Schroder & Harder, "Human beta-defensin-2", The International Journal of Biochemistry & Cell Biology, 1999, vol. 31, pp. 645-651.*
Ahn, et al., 2011, "Expression screening of fusion partners from an *E.coli* genome for soluble expression of recombinant proteins in a cell-free protein synthesis system," PLoS One, 6(11): e26875.
"Baneyx, F., 1999, Recombinant protein expression in *Escherichia coli*, Curr. Opin. Biotech. 10:411-421".
Bardwell et al., 1994, Pathways of disulfide bond formation in proteins in vivo.Chapter 45 in Phosphate Microorg, p. 270-275.
Chen, et al., 1994, "Determination of the optimal aligned spacing between the Shine-Dalgarno sequence and the translation initiation codon of *Escherichia coli* mRNAs," Nucleic Acids Research 22(23):4953-4957.

(Continued)

*Primary Examiner* — Suzanne M Noakes
(74) *Attorney, Agent, or Firm* — Wilson Sonsini Goodrich & Rosati

(57) ABSTRACT

The present invention relates to the field of medicine, in particular, to the production of large amounts of a soluble recombinant polypeptide as part of a fusion protein comprising an N-terminal fusion partner linked to the polypeptide of interest.

30 Claims, 9 Drawing Sheets
Specification includes a Sequence Listing.

(56) References Cited

U.S. PATENT DOCUMENTS

| | | | |
|---|---|---|---|
| 2009/0123972 A1 | 5/2009 | Su et al. | |
| 2014/0178393 A1 | 6/2014 | Andres et al. | |
| 2015/0010944 A1 | 1/2015 | Salunkhe et al. | |
| 2016/0159877 A1 | 6/2016 | Retallack et al. | |

FOREIGN PATENT DOCUMENTS

| | | |
|---|---|---|
| EP | 0207459 A2 | 1/1987 |
| EP | 0978565 B1 | 10/2007 |
| EP | 1873251 A1 | 1/2008 |
| EP | 2127679 A1 | 12/2009 |
| EP | 2705147 A1 | 3/2014 |
| EP | 3227455 A1 | 10/2017 |
| EP | 3257941 A1 | 12/2017 |
| JP | H1175879 A | 3/1999 |
| JP | 2004535195 A | 11/2004 |
| JP | 2005110591 A | 4/2005 |
| JP | 2010006745 A | 1/2010 |
| JP | 2014138600 A | 7/2014 |
| JP | 2014520073 A | 8/2014 |
| WO | WO-03000878 A2 | 1/2003 |
| WO | WO-03010204 A1 | 2/2003 |
| WO | WO-2005069913 A2 | 8/2005 |
| WO | WO-2005113768 A1 | 12/2005 |
| WO | WO-2006078273 A2 | 7/2006 |
| WO | WO-2010064748 A1 | 6/2010 |
| WO | WO-2012150320 A1 | 11/2012 |
| WO | WO-2016089782 A1 | 6/2016 |

OTHER PUBLICATIONS

Chunxiao et al., 2007, Study on preparation and activity of a novel recombinant human parathyroid hormone(1-34) analog with N-terminal Pro-Pro extension Regulatory Peptides, 141:35-43.

Davis, B. D., and Mingioli, E. S., 1950, Mutants of *Escherichia coli* requiring methionine or vitamin B12 J. Bact. 60(1):17-28.

*Bergey's Manual of Determinative Bacteriology*, R. E. Buchanan and N. E. Gibbons (eds.), Part 7, "Gram-Negative Aerobic Rods and Cocci," p. 217-289. Baltimore, MD: The Williams & Wilkins Co., 8th edition, 1974.

European Patent Application No. 15866061.3 Extended Search Report dated Jun. 1, 2018.

Forteo, Application No. 21-318, Chemistry Review(s), 13 pages, Oct. 15, 2002.

Forteo, Application No. 21-318, New Drug Application Filing and Review Form, Clinical Pharmacology and Biopharmaceutics Review(s), 57 pages, submitted Nov. 11, 2000.

Forted Label description, 22 pages.

Frishman et al., 1999, Starts of bacterial genes: estimating the reliability of computer predictions. Gene 234(2):257-65.

Fu et al., Extracellular production of human parathyroid hormone as a thioredoxin fusion form in *Escherichia coli* by chemical permeabilization combined with heat treatment. Biotechnol. Prog., 21:1429-1435, 2005.

Gangireddy et al., High yield expression of human recombinant PTH (1-34), Current Trends in Biotechnology and Pharmacy, 4(1):568-577, 2010.

Grimsley, G. R., and Pace, C. N., "Spectrophotometric Determination of Protein Concentration," Unit 3.1 in Current Protocols in Protein Science 3.1.1-3.1.9, Copyright © 2003, John Wiley & Sons, Inc.

Hamedifar et al., A novel approach for high level expression of soluble recombinant human parathyroid hormone (rhPTH 1-34) in *Escherichia coli*. Avicanna Journal of Medical Biotechnology, 5(3):193-201, 2013.

Ikehata et al., Primary structure of nitrile hydratase deduced from the nucleotide sequence of a *rhodococcus* species and its expression in *Escherichia coli*. Eur. J. Biochem., 181:563-570 (1989).

Jin, et al., 2000 "Crystal Structure of Human Parathyroid Hormone 1-34 at 0.9 Å Resolution," J. Biol. Chem. 275(35):27238-44.

Khairnar et al., FrnE, a Calmium-inducible protein in Deinococcus radiodurans, is characterized as a disulfide isomerase chaperone In Vitro and for its role in oxidative stress tolerance In Vivo. Journal of Bacteriology, 195(12):2880-2886, 2013.

Kyratsous et al., Chaperone-fusion expression plasmid vectors for improved solubility of recombinant proteins in *Escherichia coli* Gene, 440:9-15, 2009.

Lichty et al., 2005, Comparison of affinity tags for protein purification Protein Expression and Purification, 41:98-105.

Lombardo et al., 1997, *Escherichia coli* PapD, in*Guidebook to Molecular Chaperones and Protein-Folding Catalysts*, Mary-Jane Gething, editorOxford University Press Inc., New York, p. 463-465.

Ma, et al., 2002, "Correlations between Shine-Dalgarno Sequences and Gene Features Such as Predicted Expression Levels and Operon Structures," J. Bact. 184(20):5733-45.

Manoil, 2000, Chapter 3, "Tagging exported proteins using *Escherichia coli* alkaline phosphatase gene fusions." In*Methods in Enzymol.*,326:35-47.

Nissenson, et al., 1985, "Activation of the Parathyroid Hormone Receptor-Adenylate Cyclase System in Osteosarcoma Cells by a Human Renal Carcinoma Factor," Cancer Res. 45:5358-5363.

Obi et al., Varying dependency of periplasmic peptidylprolyl cis-trans isomerases in promoting Yersinia pseudotuberculosis stress tolerance and pathogenicity. Biochem.J., 439:321-332, 2011.

PCT/US2015/063027 International Preliminary Report on Patentability dated Jun. 15, 2017.

PCT/US2015/063027 International Search Report and Written Opinion dated May 6, 2016.

Peters et al., The Development of an Elisa assay for the determination of PTH (1-34) in human plasma (EDTA) and for the determination of anti-PTH (1-34) antibodies in human serum. White Paper. Global Clinical ResearchClinical Pharmacology Sciences, Global Bioanalytical Services, Drug Development Services, Celerion Applied Translational Medicine, 4 pages, not dated.

Rawlings et al., MEROPS: the database of proteolytic enzymes, their substrates and inhibitors. Nucleic Acids Research, 42:D503-D509, 2014.

"Retallack, et al., 2012, "Reliable protein production in a Pseudomonas fluorescens expression system," Prot. Exp. And Purif. 81:157-165".

Riesenberg, D et al., 1991, "High cell density cultivation of *Escherichia coli* at controlled specific growth rate," J. Biotechnol. 20 (1):17-27.

Sanchez-Romero & V. De Lorenzo, 1999, Manual of Industrial Microbiology and Biotechnology (A. Demain & J. Davies, eds.) pp. 460-474 (ASM Press, Washington, D.C.).

Schneider et al., 2005, "Auxotrophic markerspyrFandproCcan replace antibiotic markers on protein production plasmids in high-cell-densityPseudomonas fluorescensfermentation," Biotechnol. Progress 21(2): 343-8.

Schweizer, 2001, Vectors to express foreign genes and techniques to monitor gene expression in Pseudomonads. Current Opinion in Biotechnology, 12:439-445.

Shimizu, et al., 2001, "Parathyroid hormone (1-14) and (1-11) analogs conformationally constrained by α-aminoisobutyric acid mediate full agonist responses via the Juxtamembrane region of the PTH-1 receptor," J. Biol. Chem. 276: 49003-49012.

Slater & R. Williams, 2000, Molecular Biology and Biotechnology (J. Walker & R. Rapley, eds.) pp. 125-154 (The Royal Society of Chemistry, Cambridge, UK).

Suzek et al., 2001, A probabilistic method for identifying start codons in bacterial genomes Bioinformatics 17(12):1123-30.

Suzuki et al., 1998, High-level production of recombinant human parathyroid hormone 1-34 Applied and Environmental Microbiology, 64(2):526-529.

Tan et al., 2007, Purification and refolding optimization of recombinant bovine enterokinase light chain overexpressed in*Escherichia coli*Protein Expression and Purification, 56:40-47.

Terpe K., 2003, "Overview of Tag Protein Fusions: from molecular and biochemical fundamentals to commercial systems," Applied Microbiology and Biotechnology (60):523-533.

Uniprot 12BRJ0 (online) Oct. 1, 2014, 1 page Retrieved on Apr. 14, 2016: http://www.uniprot.org/uniprot/12BRJ0.txt?version=12>.

(56) References Cited

OTHER PUBLICATIONS

UniProtKB—P0A9L3 (FKBB_*Ecoli*). (FKBP-type 22 kDa peptidyl-prolyl cis-trans isomerase), integrated into UniProtKB/Swiss-Prot Jul. 19, 2005, UniProt Consortium, entered Jan. 31, 2018, 6 pages.
U.S. Appl. No. 14/954,766 Office Action dated May 15, 2018.
Vad et al., 2005, Engineering of a*Pichia pastoris*expression system for secretion of high amounts of intact human parathyroid hormone Journal of Biotechnology, 116:251-260.
Varshaysky, 1996, The N-end rule: Functions, mysteries, uses Proc. Nat. Acad. Sci. USA, 93:12142-12149.
Welch, et al., 2009, Design Parameters to Control Synthetic Gene Expression in *Escherichia coli*, PLoS One, 4(9): e7002.
Australian Patent Application No. 2015355242 Office Action dated Nov. 21, 2019.
GenBank Accession No. AFJ56873.1 Entry for hypothetical protein PflA506_1569 Pseudomonas fluorescens A506 (2014).
GenBank Accession No. WP_003188927.1 Entry for DSBA oxidoreductase Pseudomonas fluorescens (2013).
GenBank Accession No. WP_003190451 Entry for molecular chaperone EcpD Pseudomonas fluorescens (2013).
Japanese Patent Application No. 2017-530121 Office Action dated Nov. 5, 2019.
Singapore Patent Application No. 11201704362V Office Action dated Jan. 10, 2020.
Squires, et al., "Heterologous protein production in P. Fluorescens," Bioprocess International, 2004, vol. 2, No. 11, pp. 54-59.
Taiwanese Patent Application No. 10414019 Office Action and Search Report dated Jan. 2, 2020.

\* cited by examiner

FIGURE 2A

DnaJ-like Protein - PTH 1-34 Fusion (SEQ ID NO: 45)

mkvepglyqhykgpqyrvfsvarhseteeevvfyqalygeygfwvrplsmfletvevdgeqvprfalvtae
pslftgq*ggggsggggs*hhhhhhddddk*svseiqlmhnlgkhlnsmervewlrkklqdvhnf*

FIGURE 2B

FklB - PTH 1-34 Fusion (SEQ ID NO: 46)

msevnlstdetrvsygigrqlgdqlrdnpppgvsldailagltdafagkpsrvdqeqmaasfkvireimqae
aaakaeaaagaglaflaenakrdgittlasglqfevltagtgakptredqvrthyhgtlidgtvfdssyergqpa
efpvggviagwtealqlmnagskwrvyvpselaygaqgvsipphsvlvfdvelldvl*ggggsggggshh
hhhddddk*svseiqlmhnlgkhlnsmervewlrkklqdvhnf

FIGURE 2C

FrnE - PTH 1-34 Fusion (SEQ ID NO: 47)

mstplkidfvsdvscpwciiglrglteoldqlgsevqaeihfqpfelnpnmpaeggnivehitekygstaees
qanrarirdmgaalgfafrtdgqsriyntfdahrllhwagleglqynlkealfkayfsdgqdpsdhatlaiiaes
vgldlaraaeilasdeyaaevreqeqlwvsrgvssvptivfndqyavsggqpaeafvgairqiinesks*ggg
gsggggs*hhhhhhddddk*svseiqlmhnlgkhlnsmervewlrkklqdvhnf*

```
SEQUENCE LISTING

<160> NUMBER OF SEQ ID NOS: 242

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 2
<211> LENGTH: 78
<212> TYPE: PRT
<213> ORGANISM: Pseudomonas fluorescens

<400> SEQUENCE: 2

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
```

-continued

```
                35                  40                  45
Ser Met Phe Leu Glu Thr Val Glu Val Asp Gly Glu Gln Val Pro Arg
 50                  55                  60

Phe Ala Leu Val Thr Ala Glu Pro Ser Leu Phe Thr Gly Gln
 65                  70                  75

<210> SEQ ID NO 3
<211> LENGTH: 217
<212> TYPE: PRT
<213> ORGANISM: Pseudomonas fluorescens

<400> SEQUENCE: 3

Met Ser Thr Pro Leu Lys Ile Asp Phe Val Ser Asp Val Ser Cys Pro
  1               5                  10                  15

Trp Cys Ile Ile Gly Leu Arg Gly Leu Thr Glu Ala Leu Asp Gln Leu
                 20                  25                  30

Gly Ser Glu Val Gln Ala Glu Ile His Phe Gln Pro Phe Glu Leu Asn
             35                  40                  45

Pro Asn Met Pro Ala Glu Gly Gln Asn Ile Val Glu His Ile Thr Glu
 50                  55                  60

Lys Tyr Gly Ser Thr Ala Glu Glu Ser Gln Ala Asn Arg Ala Arg Ile
 65                  70                  75                  80

Arg Asp Met Gly Ala Ala Leu Gly Phe Ala Phe Arg Thr Asp Gly Gln
                 85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
            115                 120                 125

Tyr Phe Ser Asp Gly Gln Asp Pro Ser Asp His Ala Thr Leu Ala Ile
        130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser
        210                 215

<210> SEQ ID NO 4
<211> LENGTH: 205
<212> TYPE: PRT
<213> ORGANISM: Pseudomonas fluorescens

<400> SEQUENCE: 4

Met Ser Glu Val Asn Leu Ser Thr Asp Glu Thr Arg Val Ser Tyr Gly
  1               5                  10                  15

Ile Gly Arg Gln Leu Gly Asp Gln Leu Arg Asp Asn Pro Pro Pro Gly
                 20                  25                  30

Val Ser Leu Asp Ala Ile Leu Ala Gly Leu Thr Asp Ala Phe Ala Gly
             35                  40                  45

Lys Pro Ser Arg Val Asp Gln Glu Gln Met Ala Ala Ser Phe Lys Val
 50                  55                  60

Ile Arg Glu Ile Met Gln Ala Glu Ala Ala Ala Lys Ala Glu Ala Ala
```

```
              65                  70                  75                  80
Ala Gly Ala Gly Leu Ala Phe Leu Ala Glu Asn Ala Lys Arg Asp Gly
                    85                  90                  95

Ile Thr Thr Leu Ala Ser Gly Leu Gln Phe Glu Val Leu Thr Ala Gly
                100                 105                 110

Thr Gly Ala Lys Pro Thr Arg Glu Asp Gln Val Arg Thr His Tyr His
                115                 120                 125

Gly Thr Leu Ile Asp Gly Thr Val Phe Asp Ser Ser Tyr Glu Arg Gly
130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
                180                 185                 190

Ser Val Leu Val Phe Asp Val Glu Leu Leu Asp Val Leu
                195                 200                 205

<210> SEQ ID NO 5
<211> LENGTH: 225
<212> TYPE: PRT
<213> ORGANISM: Pseudomonas fluorescens

<400> SEQUENCE: 5

Met Ser Arg Tyr Leu Phe Leu Val Phe Gly Leu Ala Ile Cys Val Ala
1               5                   10                  15

Asp Ala Ser Glu Gln Pro Ser Ser Asn Ile Thr Asp Ala Thr Pro His
                20                  25                  30

Asp Leu Ala Tyr Ser Leu Gly Ala Ser Leu Gly Glu Arg Leu Arg Gln
            35                  40                  45

Glu Val Pro Asp Leu Gln Ile Gln Ala Leu Leu Asp Gly Leu Lys Gln
        50                  55                  60

Ala Tyr Gln Gly Lys Pro Leu Ala Leu Asp Lys Ala Arg Ile Glu Gln
65                  70                  75                  80

Ile Leu Ser Gln His Glu Ala Gln Asn Thr Ala Asp Ala Gln Leu Pro
                85                  90                  95

Gln Ser Glu Lys Ala Leu Ala Ala Glu Gln Gln Phe Leu Thr Arg Glu
                100                 105                 110

Lys Ala Ala Ala Gly Val Arg Gln Leu Ala Asp Gly Ile Leu Leu Thr
            115                 120                 125

Glu Leu Ala Pro Gly Thr Gly Asn Lys Pro Leu Ala Ser Asp Glu Val
        130                 135                 140

Gln Val Lys Tyr Val Gly Arg Leu Pro Asp Gly Thr Val Phe Asp Lys
145                 150                 155                 160

Ser Thr Gln Pro Gln Trp Phe Arg Val Asn Ser Val Ile Ser Gly Trp
                165                 170                 175

Ser Ser Ala Leu Gln Gln Met Pro Val Gly Ala Lys Trp Arg Leu Val
                180                 185                 190

Ile Pro Ser Ala Gln Ala Tyr Gly Ala Asp Gly Ala Gly Glu Leu Ile
            195                 200                 205

Pro Pro Tyr Thr Pro Leu Val Phe Glu Ile Glu Leu Leu Gly Thr Arg
        210                 215                 220

His
225
```

```
<210> SEQ ID NO 6
<211> LENGTH: 159
<212> TYPE: PRT
<213> ORGANISM: Pseudomonas fluorescens

<400> SEQUENCE: 6

Met Thr Asp Gln Gln Asn Thr Glu Ala Ala Gln Asp Gln Gly Pro Gln
1               5                   10                  15

Phe Ser Leu Gln Arg Ile Tyr Val Arg Asp Leu Ser Phe Glu Ala Pro
            20                  25                  30

Lys Ser Pro Ala Ile Phe Arg Gln Glu Trp Thr Pro Ser Val Ala Leu
        35                  40                  45

Asp Leu Asn Thr Arg Gln Lys Ser Leu Glu Gly Asp Phe His Glu Val
    50                  55                  60

Val Leu Thr Leu Ser Val Thr Val Lys Asn Gly Glu Glu Val Ala Phe
65                  70                  75                  80

Ile Ala Glu Val Gln Gln Ala Gly Ile Phe Leu Ile Gln Gly Leu Asp
                85                  90                  95

Glu Ala Ser Met Ser His Thr Leu Gly Ala Phe Cys Pro Asn Ile Leu
            100                 105                 110

Phe Pro Tyr Ala Arg Glu Thr Leu Asp Ser Leu Val Thr Arg Gly Ser
        115                 120                 125

Phe Pro Ala Leu Met Leu Ala Pro Val Asn Phe Asp Ala Leu Tyr Ala
    130                 135                 140

Gln Glu Leu Gln Arg Met Gln Gln Gly Ala Pro Thr Val Gln
145                 150                 155

<210> SEQ ID NO 7
<211> LENGTH: 241
<212> TYPE: PRT
<213> ORGANISM: Pseudomonas fluorescens

<400> SEQUENCE: 7

Met Gly Cys Val Pro Leu Pro Asp His Gly Ile Thr Val Phe Met Phe
1               5                   10                  15

Leu Leu Arg Met Val Leu Leu Ala Cys Gly Leu Val Leu Ala Pro
            20                  25                  30

Pro Pro Ala Asp Ala Ala Leu Lys Ile Glu Gly Thr Arg Leu Ile Tyr
        35                  40                  45

Phe Gly Gln Asp Lys Ala Ala Gly Ile Ser Val Val Asn Gln Ala Ser
    50                  55                  60

Arg Glu Val Val Val Gln Thr Trp Ile Thr Gly Glu Asp Glu Ser Ala
65                  70                  75                  80

Asp Arg Thr Val Pro Phe Ala Thr Glu Pro Leu Val Gln Leu Gly
                85                  90                  95

Ala Gly Glu His His Lys Leu Arg Ile Leu Tyr Ala Gly Gly Leu
            100                 105                 110

Pro Ser Asp Arg Glu Ser Leu Phe Trp Leu Asn Ile Met Glu Ile Pro
        115                 120                 125

Leu Lys Pro Glu Asp Pro Asn Ser Val Gln Phe Ala Ile Arg Gln Arg
    130                 135                 140

Leu Lys Leu Phe Tyr Arg Pro Pro Ala Leu Gln Gly Gly Ser Ala Glu
145                 150                 155                 160

Ala Val Gln Gln Leu Val Trp Ser Ser Asp Gly Arg Thr Val Thr Val
                165                 170                 175
```

```
Asn Asn Pro Ser Ala Phe His Leu Ser Leu Val Asn Leu Arg Ile Asp
            180                 185                 190

Ser Gln Thr Leu Ser Asp Tyr Leu Leu Lys Pro His Glu Arg Lys
        195                 200                 205

Thr Leu Thr Ala Leu Asp Ala Val Pro Lys Gly Ala Thr Leu His Phe
    210                 215                 220

Thr Glu Ile Thr Asp Ile Gly Leu Gln Ala Arg His Ser Thr Ala Leu
225                 230                 235                 240

Asn

<210> SEQ ID NO 8
<211> LENGTH: 141
<212> TYPE: PRT
<213> ORGANISM: Escherichia coli

<400> SEQUENCE: 8

Ala Asp Lys Ile Ala Ile Val Asn Met Gly Ser Leu Phe Gln Gln Val
1               5                   10                  15

Ala Gln Lys Thr Gly Val Ser Asn Thr Leu Glu Asn Glu Phe Lys Gly
            20                  25                  30

Arg Ala Ser Glu Leu Gln Arg Met Glu Thr Asp Leu Gln Ala Lys Met
        35                  40                  45

Lys Lys Leu Gln Ser Met Lys Ala Gly Ser Asp Arg Thr Lys Leu Glu
    50                  55                  60

Lys Asp Val Met Ala Gln Arg Gln Thr Phe Ala Gln Lys Ala Gln Ala
65                  70                  75                  80

Phe Glu Gln Asp Arg Ala Arg Arg Ser Asn Glu Glu Arg Gly Lys Leu
                85                  90                  95

Val Thr Arg Ile Gln Thr Ala Val Lys Ser Val Ala Asn Ser Gln Asp
            100                 105                 110

Ile Asp Leu Val Val Asp Ala Asn Ala Val Ala Tyr Asn Ser Ser Asp
        115                 120                 125

Val Lys Asp Ile Thr Ala Asp Val Leu Lys Gln Val Lys
    130                 135                 140

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser Gly Gly Gly His His His His His His Asp
1               5                   10                  15

Asp Asp Asp Lys
            20

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Ser Gly Gly Gly His His His His His His Arg
1               5                   10                  15
```

Lys Arg

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly His His His His His His Arg
1               5                   10                  15

Arg Arg

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Gly His His His His His His Leu
1               5                   10                  15

Val Pro Arg

<210> SEQ ID NO 13
<211> LENGTH: 5
<212> TYPE: PRT
<213> ORGANISM: Unknown
<220> FEATURE:
<223> OTHER INFORMATION: Description of Unknown:
      Enterokinase cleavage site sequence

<400> SEQUENCE: 13

Asp Asp Asp Asp Lys
1               5

<210> SEQ ID NO 14
<211> LENGTH: 798
<212> TYPE: PRT
<213> ORGANISM: Pseudomonas fluorescens

<400> SEQUENCE: 14

Met Lys Thr Thr Ile Glu Leu Pro Leu Leu Pro Leu Arg Asp Val Val
1               5                   10                  15

Val Tyr Pro His Met Val Ile Pro Leu Phe Val Gly Arg Glu Lys Ser
                20                  25                  30

Ile Glu Ala Leu Glu Ala Ala Met Thr Gly Asp Lys Gln Ile Leu Leu
        35                  40                  45

Leu Ala Gln Lys Asn Pro Ala Asp Asp Pro Gly Glu Asp Ala Leu
    50                  55                  60

Tyr Arg Val Gly Thr Ile Ala Thr Val Leu Gln Leu Leu Lys Leu Pro
65                  70                  75                  80

Asp Gly Thr Val Lys Val Leu Val Glu Gly Gln Arg Gly Ala Val
                85                  90                  95

Glu Arg Phe Met Glu Val Asp Gly His Leu Arg Ala Glu Val Ala Leu
                100                 105                 110

Ile Glu Glu Val Glu Ala Pro Glu Arg Glu Ser Glu Val Phe Val Arg

```
            115                 120                 125
Ser Leu Leu Ser Gln Phe Glu Gln Tyr Val Gln Leu Gly Lys Lys Val
        130                 135                 140
Pro Ala Glu Val Leu Ser Ser Leu Asn Ser Ile Asp Glu Pro Ser Arg
145                 150                 155                 160
Leu Val Asp Thr Met Ala Ala His Met Ala Leu Lys Ile Glu Gln Lys
                165                 170                 175
Gln Asp Ile Leu Glu Ile Ile Asp Leu Ser Ala Arg Val Glu His Val
            180                 185                 190
Leu Ala Met Leu Asp Gly Glu Ile Asp Leu Leu Gln Val Glu Lys Arg
        195                 200                 205
Ile Arg Gly Arg Val Lys Lys Gln Met Glu Arg Ser Gln Arg Glu Tyr
    210                 215                 220
Tyr Leu Asn Glu Gln Met Lys Ala Ile Gln Lys Glu Leu Gly Asp Gly
225                 230                 235                 240
Glu Glu Gly His Asn Glu Ile Glu Glu Leu Lys Lys Arg Ile Asp Ala
                245                 250                 255
Ala Gly Leu Pro Lys Asp Ala Leu Thr Lys Ala Thr Ala Glu Leu Asn
            260                 265                 270
Lys Leu Lys Gln Met Ser Pro Met Ser Ala Glu Ala Thr Val Val Arg
        275                 280                 285
Ser Tyr Ile Asp Trp Leu Val Gln Val Pro Trp Lys Ala Gln Thr Lys
    290                 295                 300
Val Arg Leu Asp Leu Ala Arg Ala Glu Glu Ile Leu Asp Ala Asp His
305                 310                 315                 320
Tyr Gly Leu Glu Glu Val Lys Glu Arg Ile Leu Glu Tyr Leu Ala Val
                325                 330                 335
Gln Lys Arg Val Lys Lys Ile Arg Gly Pro Val Leu Cys Leu Val Gly
            340                 345                 350
Pro Pro Gly Val Gly Lys Thr Ser Leu Ala Glu Ser Ile Ala Ser Ala
        355                 360                 365
Thr Asn Arg Lys Phe Val Arg Met Ala Leu Gly Gly Val Arg Asp Glu
    370                 375                 380
Ala Glu Ile Arg Gly His Arg Arg Thr Tyr Ile Gly Ser Met Pro Gly
385                 390                 395                 400
Arg Leu Ile Gln Lys Met Thr Lys Val Gly Val Arg Asn Pro Leu Phe
                405                 410                 415
Leu Leu Asp Glu Ile Asp Lys Met Gly Ser Asp Met Arg Gly Asp Pro
            420                 425                 430
Ala Ser Ala Leu Leu Glu Val Leu Asp Pro Glu Gln Asn His Asn Phe
        435                 440                 445
Asn Asp His Tyr Leu Glu Val Asp Tyr Asp Leu Ser Asp Val Met Phe
    450                 455                 460
Leu Cys Thr Ser Asn Ser Met Asn Ile Pro Pro Ala Leu Leu Asp Arg
465                 470                 475                 480
Met Glu Val Ile Arg Leu Pro Gly Tyr Thr Glu Asp Glu Lys Ile Asn
                485                 490                 495
Ile Ala Val Lys Tyr Leu Ala Pro Lys Gln Ile Ser Ala Asn Gly Leu
            500                 505                 510
Lys Lys Gly Glu Ile Glu Phe Glu Val Glu Ala Ile Arg Asp Ile Val
        515                 520                 525
Arg Tyr Tyr Thr Arg Glu Ala Gly Val Arg Gly Leu Glu Arg Gln Ile
    530                 535                 540
```

-continued

```
Ala Lys Ile Cys Arg Lys Ala Val Lys Glu His Ala Leu Glu Lys Arg
545                 550                 555                 560

Phe Ser Val Lys Val Val Ala Asp Ser Leu Glu His Phe Leu Gly Val
                565                 570                 575

Lys Lys Phe Arg Tyr Gly Leu Ala Glu Gln Gln Asp Gln Val Gly Gln
            580                 585                 590

Val Thr Gly Leu Ala Trp Thr Gln Val Gly Gly Glu Leu Leu Thr Ile
        595                 600                 605

Glu Ala Ala Val Ile Pro Gly Lys Gly Gln Leu Ile Lys Thr Gly Ser
610                 615                 620

Leu Gly Asp Val Met Val Glu Ser Ile Thr Ala Ala Gln Thr Val Val
625                 630                 635                 640

Arg Ser Arg Ala Arg Ser Leu Gly Ile Pro Leu Asp Phe His Glu Lys
                645                 650                 655

His Asp Thr His Ile His Met Pro Glu Gly Ala Thr Pro Lys Asp Gly
            660                 665                 670

Pro Ser Ala Gly Val Gly Met Cys Thr Ala Leu Val Ser Ala Leu Thr
        675                 680                 685

Gly Ile Pro Val Arg Ala Asp Val Ala Met Thr Gly Glu Ile Thr Leu
690                 695                 700

Arg Gly Gln Val Leu Ala Ile Gly Gly Leu Lys Glu Lys Leu Leu Ala
705                 710                 715                 720

Ala His Arg Gly Gly Ile Lys Thr Val Ile Ile Pro Glu Glu Asn Val
                725                 730                 735

Arg Asp Leu Lys Glu Ile Pro Asp Asn Ile Lys Gln Asp Leu Gln Ile
            740                 745                 750

Lys Pro Val Lys Trp Ile Asp Glu Val Leu Gln Ile Ala Leu Gln Tyr
        755                 760                 765

Ala Pro Glu Pro Leu Pro Asp Val Ala Pro Glu Ile Val Ala Lys Asp
770                 775                 780

Glu Lys Arg Glu Ser Asp Ser Lys Glu Arg Ile Ser Thr His
785                 790                 795

<210> SEQ ID NO 15
<211> LENGTH: 806
<212> TYPE: PRT
<213> ORGANISM: Pseudomonas fluorescens

<400> SEQUENCE: 15

Met Ser Asp Gln Gln Glu Phe Pro Asp Tyr Asp Leu Asn Asp Tyr Ala
1               5                   10                  15

Asp Pro Glu Asn Ala Glu Ala Pro Ser Ser Asn Thr Gly Leu Ala Leu
            20                  25                  30

Pro Gly Gln Asn Leu Pro Asp Lys Val Tyr Ile Ile Pro Ile His Asn
        35                  40                  45

Arg Pro Phe Phe Pro Ala Gln Val Leu Pro Val Ile Val Asn Glu Glu
    50                  55                  60

Pro Trp Ala Glu Thr Leu Glu Leu Val Ser Lys Ser Asp His His Ser
65                  70                  75                  80

Leu Ala Leu Phe Phe Met Asp Thr Pro Pro Asp Pro Arg His Phe
                85                  90                  95

Asp Thr Ser Ala Leu Pro Leu Tyr Gly Thr Leu Val Lys Val His His
            100                 105                 110

Ala Ser Arg Glu Asn Gly Lys Leu Gln Phe Val Ala Gln Gly Leu Thr
```

```
            115                 120                 125
Arg Val Arg Ile Lys Thr Trp Leu Lys His His Arg Pro Pro Tyr Leu
            130                 135                 140

Val Glu Val Glu Tyr Pro His Gln Pro Ser Glu Pro Thr Asp Glu Val
145                 150                 155                 160

Lys Ala Tyr Gly Met Ala Leu Ile Asn Ala Ile Lys Glu Leu Leu Pro
                165                 170                 175

Leu Asn Pro Leu Tyr Ser Glu Glu Leu Lys Asn Tyr Leu Asn Arg Phe
            180                 185                 190

Ser Pro Asn Asp Pro Ser Pro Leu Thr Asp Phe Ala Ala Ala Leu Thr
            195                 200                 205

Ser Ala Thr Gly Asn Glu Leu Gln Glu Val Leu Asp Cys Val Pro Met
210                 215                 220

Leu Lys Arg Met Glu Lys Val Leu Pro Met Leu Arg Lys Glu Val Glu
225                 230                 235                 240

Val Ala Arg Leu Gln Lys Glu Leu Ser Ala Glu Val Asn Arg Lys Ile
                245                 250                 255

Gly Glu His Gln Arg Glu Phe Phe Leu Lys Glu Gln Leu Lys Val Ile
                260                 265                 270

Gln Gln Glu Leu Gly Leu Thr Lys Asp Asp Arg Ser Ala Asp Val Glu
            275                 280                 285

Gln Phe Glu Gln Arg Leu Gln Gly Lys Val Leu Pro Ala Gln Ala Gln
290                 295                 300

Lys Arg Ile Asp Glu Glu Leu Asn Lys Leu Ser Ile Leu Glu Thr Gly
305                 310                 315                 320

Ser Pro Glu Tyr Ala Val Thr Arg Asn Tyr Leu Asp Trp Ala Thr Ser
                325                 330                 335

Val Pro Trp Gly Val Tyr Gly Ala Asp Lys Leu Asp Leu Lys His Ala
                340                 345                 350

Arg Lys Val Leu Asp Lys His His Ala Gly Leu Asp Asp Ile Lys Ser
            355                 360                 365

Arg Ile Leu Glu Phe Leu Ala Val Gly Ala Tyr Lys Gly Glu Val Ala
            370                 375                 380

Gly Ser Ile Val Leu Leu Val Gly Pro Pro Gly Val Gly Lys Thr Ser
385                 390                 395                 400

Val Gly Lys Ser Ile Ala Glu Ser Leu Gly Arg Pro Phe Tyr Arg Phe
                405                 410                 415

Ser Val Gly Gly Met Arg Asp Glu Ala Glu Ile Lys Gly His Arg Arg
            420                 425                 430

Thr Tyr Ile Gly Ala Leu Pro Gly Lys Leu Val Gln Ala Leu Lys Asp
            435                 440                 445

Val Glu Val Met Asn Pro Val Ile Met Leu Asp Glu Ile Asp Lys Met
            450                 455                 460

Gly Gln Ser Phe Gln Gly Asp Pro Ala Ser Ala Leu Leu Glu Thr Leu
465                 470                 475                 480

Asp Pro Glu Gln Asn Val Glu Phe Leu Asp His Tyr Leu Asp Leu Arg
                485                 490                 495

Leu Asp Leu Ser Lys Val Leu Phe Val Cys Thr Ala Asn Thr Leu Asp
            500                 505                 510

Ser Ile Pro Gly Pro Leu Leu Asp Arg Met Glu Val Ile Arg Leu Ser
            515                 520                 525

Gly Tyr Ile Thr Glu Glu Lys Val Ala Ile Ala Lys Arg His Leu Trp
530                 535                 540
```

-continued

Pro Lys Gln Leu Glu Lys Ala Gly Val Ala Lys Asn Ser Leu Thr Ile
545                 550                 555                 560

Ser Asp Gly Ala Leu Arg Ala Leu Ile Asp Gly Tyr Ala Arg Glu Ala
                565                 570                 575

Gly Val Arg Gln Leu Glu Lys Gln Leu Gly Lys Leu Val Arg Lys Ala
            580                 585                 590

Val Val Lys Leu Leu Asp Glu Pro Asp Ser Val Ile Lys Ile Gly Asn
        595                 600                 605

Lys Asp Leu Glu Ser Ser Leu Gly Met Pro Val Phe Arg Asn Glu Gln
610                 615                 620

Val Leu Ser Gly Thr Gly Val Ile Thr Gly Leu Ala Trp Thr Ser Met
625                 630                 635                 640

Gly Gly Ala Thr Leu Pro Ile Glu Ala Thr Arg Ile His Thr Leu Asn
                645                 650                 655

Arg Gly Phe Lys Leu Thr Gly Gln Leu Gly Glu Val Met Lys Glu Ser
            660                 665                 670

Ala Glu Ile Ala Tyr Ser Tyr Ile Ser Ser Asn Leu Lys Ser Phe Gly
        675                 680                 685

Gly Asp Ala Lys Phe Phe Asp Glu Ala Phe Val His Leu His Val Pro
690                 695                 700

Glu Gly Ala Thr Pro Lys Asp Gly Pro Ser Ala Gly Val Thr Met Ala
705                 710                 715                 720

Ser Ala Leu Leu Ser Leu Ala Arg Asn Gln Pro Pro Lys Lys Gly Val
                725                 730                 735

Ala Met Thr Gly Glu Leu Thr Leu Thr Gly His Val Leu Pro Ile Gly
            740                 745                 750

Gly Val Arg Glu Lys Val Ile Ala Ala Arg Arg Gln Lys Ile His Glu
        755                 760                 765

Leu Ile Leu Pro Glu Pro Asn Arg Gly Ser Phe Glu Glu Leu Pro Asp
770                 775                 780

Tyr Leu Lys Glu Gly Met Thr Val His Phe Ala Lys Arg Phe Ala Asp
785                 790                 795                 800

Val Ala Lys Val Leu Phe
                805

<210> SEQ ID NO 16
<211> LENGTH: 477
<212> TYPE: PRT
<213> ORGANISM: Pseudomonas fluorescens

<400> SEQUENCE: 16

Met Ser Lys Val Lys Asp Lys Ala Ile Val Ser Ala Ala Gln Ala Ser
1               5                   10                  15

Thr Ala Tyr Ser Gln Ile Asp Ser Phe Ser His Leu Tyr Asp Arg Gly
                20                  25                  30

Gly Asn Leu Thr Val Asn Gly Lys Pro Ser Tyr Thr Val Asp Gln Ala
            35                  40                  45

Ala Thr Gln Leu Leu Arg Asp Gly Ala Ala Tyr Arg Asp Phe Asp Gly
        50                  55                  60

Asn Gly Lys Ile Asp Leu Thr Tyr Thr Phe Leu Thr Ser Ala Thr Gln
65                  70                  75                  80

Ser Thr Met Asn Lys His Gly Ile Ser Gly Phe Ser Gln Phe Asn Thr
                85                  90                  95

Gln Gln Lys Ala Gln Ala Ala Leu Ala Met Gln Ser Trp Ala Asp Val

```
            100                 105                 110
Ala Asn Val Thr Phe Thr Glu Lys Ala Ser Gly Gly Asp Gly His Met
            115                 120                 125

Thr Phe Gly Asn Tyr Ser Ser Gly Gln Asp Gly Ala Ala Phe Ala
    130                 135                 140

Tyr Leu Pro Gly Thr Gly Ala Gly Tyr Asp Gly Thr Ser Trp Tyr Leu
145                 150                 155                 160

Thr Asn Asn Ser Tyr Thr Pro Asn Lys Thr Pro Asp Leu Asn Asn Tyr
                165                 170                 175

Gly Arg Gln Thr Leu Thr His Glu Ile Gly His Thr Leu Gly Leu Ala
            180                 185                 190

His Pro Gly Asp Tyr Asn Ala Gly Asn Gly Asn Pro Thr Tyr Asn Asp
        195                 200                 205

Ala Thr Tyr Gly Gln Asp Thr Arg Gly Tyr Ser Leu Met Ser Tyr Trp
    210                 215                 220

Ser Glu Ser Asn Thr Asn Gln Asn Phe Ser Lys Gly Gly Val Glu Ala
225                 230                 235                 240

Tyr Ala Ser Gly Pro Leu Ile Asp Asp Ile Ala Ala Ile Gln Lys Leu
                245                 250                 255

Tyr Gly Ala Asn Leu Ser Thr Arg Ala Thr Asp Thr Thr Tyr Gly Phe
            260                 265                 270

Asn Ser Asn Thr Gly Arg Asp Phe Leu Ser Ala Thr Ser Asn Ala Asp
        275                 280                 285

Lys Leu Val Phe Ser Val Trp Asp Gly Gly Gly Asn Asp Thr Leu Asp
    290                 295                 300

Phe Ser Gly Phe Thr Gln Asn Gln Lys Ile Asn Leu Thr Ala Thr Ser
305                 310                 315                 320

Phe Ser Asp Val Gly Gly Leu Val Gly Asn Val Ser Ile Ala Lys Gly
                325                 330                 335

Val Thr Ile Glu Asn Ala Phe Gly Gly Ala Gly Asn Asp Leu Ile Ile
            340                 345                 350

Gly Asn Gln Val Ala Asn Thr Ile Lys Gly Gly Ala Gly Asn Asp Leu
        355                 360                 365

Ile Tyr Gly Gly Gly Gly Ala Asp Gln Leu Trp Gly Gly Ala Gly Ser
    370                 375                 380

Asp Thr Phe Val Tyr Gly Ala Ser Ser Asp Ser Lys Pro Gly Ala Ala
385                 390                 395                 400

Asp Lys Ile Phe Asp Phe Thr Ser Gly Ser Asp Lys Ile Asp Leu Ser
                405                 410                 415

Gly Ile Thr Lys Gly Ala Gly Val Thr Phe Val Asn Ala Phe Thr Gly
            420                 425                 430

His Ala Gly Asp Ala Val Leu Ser Tyr Ala Ser Gly Thr Asn Leu Gly
        435                 440                 445

Thr Leu Ala Val Asp Phe Ser Gly His Gly Val Ala Asp Phe Leu Val
    450                 455                 460

Thr Thr Val Gly Gln Ala Ala Ser Asp Ile Val Ala
465                 470                 475

<210> SEQ ID NO 17
<211> LENGTH: 295
<212> TYPE: PRT
<213> ORGANISM: Pseudomonas fluorescens

<400> SEQUENCE: 17
```

Met Met Arg Ile Leu Leu Phe Leu Ala Thr Asn Leu Ala Val Val Leu
1               5                   10                  15

Ile Ala Ser Val Thr Leu Ser Leu Phe Gly Phe Asn Gly Phe Met Ala
            20                  25                  30

Ala Asn Gly Val Asp Leu Asn Leu Asn Gln Leu Leu Ile Phe Cys Ala
            35                  40                  45

Val Phe Gly Phe Ala Gly Ser Leu Phe Ser Leu Phe Ile Ser Lys Trp
50                  55                  60

Met Ala Lys Met Ser Thr Ser Thr Gln Ile Ile Thr Gln Pro Arg Thr
65                  70                  75                  80

Arg His Glu Gln Trp Leu Met Gln Thr Val Glu Gln Leu Ser Gln Glu
                85                  90                  95

Ala Gly Ile Lys Met Pro Glu Val Gly Ile Phe Pro Ala Tyr Glu Ala
            100                 105                 110

Asn Ala Phe Ala Thr Gly Trp Asn Lys Asn Asp Ala Leu Val Ala Val
            115                 120                 125

Ser Gln Gly Leu Leu Glu Arg Phe Ser Pro Asp Glu Val Lys Ala Val
            130                 135                 140

Leu Ala His Glu Ile Gly His Val Ala Asn Gly Asp Met Val Thr Leu
145                 150                 155                 160

Ala Leu Val Gln Gly Val Val Asn Thr Phe Val Met Phe Phe Ala Arg
                165                 170                 175

Ile Ile Gly Asn Phe Val Asp Lys Val Ile Phe Lys Asn Glu Glu Gly
            180                 185                 190

Arg Gly Ile Ala Tyr Phe Val Ala Thr Ile Phe Ala Glu Leu Val Leu
            195                 200                 205

Gly Phe Leu Ala Ser Ala Ile Val Met Trp Phe Ser Arg Lys Arg Glu
210                 215                 220

Phe Arg Ala Asp Glu Ala Gly Ala Arg Leu Ala Gly Thr Ser Ala Met
225                 230                 235                 240

Ile Gly Ala Leu Gln Arg Leu Arg Ser Glu Gly Leu Pro Val His
                245                 250                 255

Met Pro Asp Ser Leu Thr Ala Phe Gly Ile Asn Gly Gly Ile Lys Gln
            260                 265                 270

Gly Leu Ala Arg Leu Phe Met Ser His Pro Pro Leu Glu Glu Arg Ile
            275                 280                 285

Asp Ala Leu Arg Arg Arg Gly
290                 295

<210> SEQ ID NO 18
<211> LENGTH: 386
<212> TYPE: PRT
<213> ORGANISM: Pseudomonas fluorescens

<400> SEQUENCE: 18

Met Leu Lys Ala Leu Arg Phe Phe Gly Trp Pro Leu Leu Ala Gly Val
1               5                   10                  15

Leu Ile Ala Met Leu Ile Ile Gln Arg Tyr Pro Gln Trp Val Gly Leu
            20                  25                  30

Pro Thr Leu Asp Val Asn Leu Gln Gln Ala Pro Gln Thr Asn Thr Val
            35                  40                  45

Val Gln Gly Pro Val Thr Tyr Ala Asp Ala Val Ile Ala Ala Pro
50                  55                  60

Ala Val Val Asn Leu Tyr Thr Thr Lys Val Ile Asn Lys Pro Ala His
65                  70                  75                  80

```
Pro Leu Phe Glu Asp Pro Gln Phe Arg Arg Tyr Phe Gly Asp Asn Gly
                85                  90                  95

Pro Lys Gln Arg Arg Met Glu Ser Ser Leu Gly Ser Gly Val Ile Met
            100                 105                 110

Ser Pro Glu Gly Tyr Ile Leu Thr Asn Asn His Val Thr Thr Gly Ala
        115                 120                 125

Asp Gln Ile Val Val Ala Leu Arg Asp Gly Arg Glu Thr Leu Ala Arg
    130                 135                 140

Val Val Gly Ser Asp Pro Glu Thr Asp Leu Ala Val Leu Lys Ile Asp
145                 150                 155                 160

Leu Lys Asn Leu Pro Ala Ile Thr Leu Gly Arg Ser Asp Gly Leu Arg
                165                 170                 175

Val Gly Asp Val Ala Leu Ala Ile Gly Asn Pro Phe Gly Val Gly Gln
            180                 185                 190

Thr Val Thr Met Gly Ile Ile Ser Ala Thr Gly Arg Asn Gln Leu Gly
        195                 200                 205

Leu Asn Ser Tyr Glu Asp Phe Ile Gln Thr Asp Ala Ala Ile Asn Pro
    210                 215                 220

Gly Asn Ser Gly Gly Ala Leu Val Asp Ala Asn Gly Asn Leu Thr Gly
225                 230                 235                 240

Ile Asn Thr Ala Ile Phe Ser Lys Ser Gly Ser Gln Gly Ile Gly
                245                 250                 255

Phe Ala Ile Pro Val Lys Leu Ala Met Glu Val Met Lys Ser Ile Ile
            260                 265                 270

Glu His Gly Gln Val Ile Arg Gly Trp Leu Gly Ile Glu Val Gln Pro
        275                 280                 285

Leu Thr Lys Glu Leu Ala Glu Ser Phe Gly Leu Thr Gly Arg Pro Gly
    290                 295                 300

Ile Val Val Ala Gly Ile Phe Arg Asp Gly Pro Ala Gln Lys Ala Gly
305                 310                 315                 320

Leu Gln Leu Gly Asp Val Ile Leu Ser Ile Asp Gly Ala Pro Ala Gly
                325                 330                 335

Asp Gly Arg Lys Ser Met Asn Gln Val Ala Arg Ile Lys Pro Thr Asp
            340                 345                 350

Lys Val Ala Ile Leu Val Met Arg Asn Gly Lys Glu Ile Lys Leu Ser
        355                 360                 365

Ala Glu Ile Gly Leu Arg Pro Pro Ala Thr Ala Pro Val Lys Glu
    370                 375                 380

Glu Gln
385

<210> SEQ ID NO 19
<211> LENGTH: 478
<212> TYPE: PRT
<213> ORGANISM: Pseudomonas fluorescens

<400> SEQUENCE: 19

Met Ser Ile Pro Arg Leu Lys Ser Tyr Leu Ser Ile Val Ala Thr Val
1               5                   10                  15

Leu Val Leu Gly Gln Ala Leu Pro Ala Gln Ala Val Glu Leu Pro Asp
            20                  25                  30

Phe Thr Gln Leu Val Glu Gln Ala Ser Pro Ala Val Val Asn Ile Ser
        35                  40                  45

Thr Thr Gln Lys Leu Pro Asp Arg Lys Val Ser Asn Gln Gln Met Pro
```

```
            50                  55                  60
Asp Leu Glu Gly Leu Pro Pro Met Leu Arg Glu Phe Phe Glu Arg Gly
65                  70                  75                  80

Met Pro Gln Pro Arg Ser Pro Arg Gly Gly Gly Gln Arg Glu Ala
                85                  90                  95

Gln Ser Leu Gly Ser Gly Phe Ile Ile Ser Pro Asp Gly Tyr Ile Leu
                100                 105                 110

Thr Asn Asn His Val Ile Ala Asp Ala Asp Glu Ile Leu Val Arg Leu
                115                 120                 125

Ala Asp Arg Ser Glu Leu Lys Ala Lys Leu Ile Gly Thr Asp Pro Arg
130                 135                 140

Ser Asp Val Ala Leu Leu Lys Ile Glu Gly Lys Asp Leu Pro Val Leu
145                 150                 155                 160

Lys Leu Gly Lys Ser Gln Asp Leu Lys Ala Gly Gln Trp Val Val Ala
                165                 170                 175

Ile Gly Ser Pro Phe Gly Phe Asp His Thr Val Thr Gln Gly Ile Val
                180                 185                 190

Ser Ala Ile Gly Arg Ser Leu Pro Asn Glu Asn Tyr Val Pro Phe Ile
                195                 200                 205

Gln Thr Asp Val Pro Ile Asn Pro Gly Asn Ser Gly Gly Pro Leu Phe
210                 215                 220

Asn Leu Ala Gly Glu Val Val Gly Ile Asn Ser Gln Ile Tyr Thr Arg
225                 230                 235                 240

Ser Gly Gly Phe Met Gly Val Ser Phe Ala Ile Pro Ile Asp Val Ala
                245                 250                 255

Met Asp Val Ser Asn Gln Leu Lys Ser Gly Gly Lys Val Ser Arg Gly
                260                 265                 270

Trp Leu Gly Val Val Ile Gln Glu Val Asn Lys Asp Leu Ala Glu Ser
                275                 280                 285

Phe Gly Leu Asp Lys Pro Ala Gly Ala Leu Val Ala Gln Ile Gln Asp
                290                 295                 300

Asn Gly Pro Ala Ala Lys Gly Gly Leu Lys Val Gly Asp Val Ile Leu
305                 310                 315                 320

Ser Met Asn Gly Gln Pro Ile Ile Met Ser Ala Asp Leu Pro His Leu
                325                 330                 335

Val Gly Ala Leu Lys Ala Gly Lys Ala Lys Leu Glu Val Ile Arg
                340                 345                 350

Asp Gly Lys Arg Gln Asn Val Glu Leu Thr Val Gly Ala Ile Pro Glu
                355                 360                 365

Glu Gly Ala Thr Leu Asp Ala Leu Gly Asn Ala Lys Pro Gly Ala Glu
                370                 375                 380

Arg Ser Ser Asn Arg Leu Gly Ile Ala Val Val Glu Leu Thr Ala Glu
385                 390                 395                 400

Gln Lys Lys Thr Phe Asp Leu Gln Ser Gly Val Val Ile Lys Glu Val
                405                 410                 415

Gln Asp Gly Pro Ala Ala Leu Ile Gly Leu Gln Pro Gly Asp Val Ile
                420                 425                 430

Thr His Leu Asn Asn Gln Ala Ile Asp Thr Thr Lys Glu Phe Ala Asp
                435                 440                 445

Ile Ala Lys Ala Leu Pro Lys Asn Arg Ser Val Ser Met Arg Val Leu
                450                 455                 460

Arg Gln Gly Arg Ala Ser Phe Ile Thr Phe Lys Leu Ala Glu
465                 470                 475
```

```
<210> SEQ ID NO 20
<211> LENGTH: 353
<212> TYPE: PRT
<213> ORGANISM: Pseudomonas fluorescens

<400> SEQUENCE: 20

Met Cys Val Arg Gln Pro Arg Asn Pro Ile Phe Cys Leu Ile Pro Pro
1               5                   10                  15

Tyr Met Leu Asp Gln Ile Ala Arg His Gly Asp Lys Ala Gln Arg Glu
            20                  25                  30

Val Ala Leu Arg Thr Arg Ala Lys Asp Ser Thr Phe Arg Ser Leu Arg
        35                  40                  45

Met Val Ala Val Pro Ala Lys Gly Pro Ala Arg Met Ala Leu Ala Val
    50                  55                  60

Gly Ala Glu Lys Gln Arg Ser Ile Tyr Ser Ala Glu Asn Thr Asp Ser
65                  70                  75                  80

Leu Pro Gly Lys Leu Ile Arg Gly Glu Gly Gln Pro Ala Ser Gly Asp
                85                  90                  95

Ala Ala Val Asp Glu Ala Tyr Asp Gly Leu Gly Ala Thr Phe Asp Phe
            100                 105                 110

Phe Asp Gln Val Phe Asp Arg Asn Ser Ile Asp Asp Ala Gly Met Ala
        115                 120                 125

Leu Asp Ala Thr Val His Phe Gly Gln Asp Tyr Asn Asn Ala Phe Trp
130                 135                 140

Asn Ser Thr Gln Met Val Phe Gly Asp Gly Asp Gln Gln Leu Phe Asn
145                 150                 155                 160

Arg Phe Thr Val Ala Leu Asp Val Ile Gly His Glu Leu Ala His Gly
                165                 170                 175

Val Thr Glu Asp Glu Ala Lys Leu Met Tyr Phe Asn Gln Ser Gly Ala
            180                 185                 190

Leu Asn Glu Ser Leu Ser Asp Val Phe Gly Ser Leu Ile Lys Gln Tyr
        195                 200                 205

Ala Leu Lys Gln Thr Ala Glu Asp Ala Asp Trp Leu Ile Gly Lys Gly
    210                 215                 220

Leu Phe Thr Lys Lys Ile Lys Gly Thr Ala Leu Arg Ser Met Lys Ala
225                 230                 235                 240

Pro Gly Thr Ala Phe Asp Asp Lys Leu Leu Gly Lys Asp Pro Gln Pro
                245                 250                 255

Gly His Met Asp Asp Phe Val Gln Thr Tyr Glu Asp Asn Gly Gly Val
            260                 265                 270

His Ile Asn Ser Gly Ile Pro Asn His Ala Phe Tyr Gln Val Ala Ile
        275                 280                 285

Asn Ile Gly Gly Phe Ala Trp Glu Arg Ala Gly Arg Ile Trp Tyr Asp
    290                 295                 300

Ala Leu Arg Asp Ser Arg Leu Arg Pro Asn Ser Gly Phe Leu Arg Phe
305                 310                 315                 320

Ala Arg Ile Thr His Asp Ile Ala Gly Gln Leu Tyr Gly Val Asn Lys
                325                 330                 335

Ala Glu Gln Lys Ala Val Lys Glu Gly Trp Lys Ala Val Gly Ile Asn
            340                 345                 350

Val

<210> SEQ ID NO 21
```

```
<211> LENGTH: 704
<212> TYPE: PRT
<213> ORGANISM: Pseudomonas fluorescens

<400> SEQUENCE: 21

Met Arg Tyr Gln Leu Pro Pro Arg Arg Ile Ser Met Lys His Leu Phe
1               5                   10                  15

Pro Ser Thr Ala Leu Ala Phe Phe Ile Gly Leu Gly Phe Ala Ser Met
            20                  25                  30

Ser Thr Asn Thr Phe Ala Ala Asn Ser Trp Asp Asn Leu Gln Pro Asp
        35                  40                  45

Arg Asp Glu Val Ile Ala Ser Leu Asn Val Val Glu Leu Leu Lys Arg
    50                  55                  60

His His Tyr Ser Lys Pro Pro Leu Asp Asp Ala Arg Ser Val Ile Ile
65                  70                  75                  80

Tyr Asp Ser Tyr Leu Lys Leu Leu Asp Pro Ser Arg Ser Tyr Phe Leu
                85                  90                  95

Ala Ser Asp Ile Ala Glu Phe Asp Lys Trp Lys Thr Gln Phe Asp Asp
            100                 105                 110

Phe Leu Lys Ser Gly Asp Leu Gln Pro Gly Phe Thr Ile Tyr Lys Arg
        115                 120                 125

Tyr Leu Asp Arg Val Lys Ala Arg Leu Asp Phe Ala Leu Gly Glu Leu
    130                 135                 140

Asn Lys Gly Val Asp Lys Leu Asp Phe Thr Gln Lys Glu Thr Leu Leu
145                 150                 155                 160

Val Asp Arg Lys Asp Ala Pro Trp Leu Thr Ser Thr Ala Ala Leu Asp
                165                 170                 175

Asp Leu Trp Arg Lys Arg Val Lys Asp Glu Val Leu Arg Leu Lys Ile
            180                 185                 190

Ala Gly Lys Glu Pro Lys Ala Ile Gln Glu Leu Leu Thr Lys Arg Tyr
        195                 200                 205

Lys Asn Gln Leu Ala Arg Leu Asp Gln Thr Arg Ala Glu Asp Ile Phe
    210                 215                 220

Gln Ala Tyr Ile Asn Thr Phe Ala Met Ser Tyr Asp Pro His Thr Asn
225                 230                 235                 240

Tyr Leu Ser Pro Asp Asn Ala Glu Asn Phe Asp Ile Asn Met Ser Leu
                245                 250                 255

Ser Leu Glu Gly Ile Gly Ala Val Leu Gln Ser Asp Asn Asp Gln Val
            260                 265                 270

Lys Ile Val Arg Leu Val Pro Ala Gly Pro Ala Asp Lys Thr Lys Gln
        275                 280                 285

Val Ala Pro Ala Asp Lys Ile Ile Gly Val Ala Gln Ala Asp Lys Glu
    290                 295                 300

Met Val Asp Val Val Gly Trp Arg Leu Asp Glu Val Val Lys Leu Ile
305                 310                 315                 320

Arg Gly Pro Lys Gly Ser Val Val Arg Leu Glu Val Ile Pro His Thr
                325                 330                 335

Asn Ala Pro Asn Asp Gln Thr Ser Lys Ile Val Ser Ile Thr Arg Glu
            340                 345                 350

Ala Val Lys Leu Glu Asp Gln Ala Val Gln Lys Val Leu Asn Leu
        355                 360                 365

Lys Gln Asp Gly Lys Asp Tyr Lys Leu Gly Val Ile Glu Ile Pro Ala
    370                 375                 380

Phe Tyr Leu Asp Phe Lys Ala Phe Arg Ala Gly Asp Pro Asp Tyr Lys
```

Ser Thr Thr Arg Asp Val Lys Lys Ile Leu Thr Glu Leu Gln Lys Glu
385                 390                 395                 400

Lys Val Asp Gly Val Val Ile Asp Leu Arg Asn Asn Gly Gly Gly Ser
            405                 410                 415

Leu Gln Glu Ala Thr Glu Leu Thr Ser Leu Phe Ile Asp Lys Gly Pro
        420                 425                 430

Thr Val Leu Val Arg Asn Ala Asp Gly Arg Val Asp Val Leu Glu Asp
    435                 440                 445

Glu Asn Pro Gly Ala Phe Tyr Lys Gly Pro Met Ala Leu Leu Val Asn
450                 455                 460

Arg Leu Ser Ala Ser Ala Ser Glu Ile Phe Ala Gly Ala Met Gln Asp
465                 470                 475                 480

Tyr His Arg Ala Leu Ile Ile Gly Gly Gln Thr Phe Gly Lys Gly Thr
            485                 490                 495

Val Gln Thr Ile Gln Pro Leu Asn His Gly Glu Leu Lys Leu Thr Leu
        500                 505                 510

Ala Lys Phe Tyr Arg Val Ser Gly Gln Ser Thr Gln His Gln Gly Val
    515                 520                 525

Leu Pro Asp Ile Asp Phe Pro Ser Ile Ile Asp Thr Lys Glu Ile Gly
530                 535                 540

Glu Ser Ala Leu Pro Glu Ala Met Pro Trp Asp Thr Ile Arg Pro Ala
545                 550                 555                 560

Ile Lys Pro Ala Ser Asp Pro Phe Lys Pro Phe Leu Ala Gln Leu Lys
            565                 570                 575

Ala Asp His Asp Thr Arg Ser Ala Lys Asp Ala Glu Phe Val Phe Ile
        580                 585                 590

Arg Asp Lys Leu Ala Leu Ala Lys Lys Leu Met Glu Glu Lys Thr Val
    595                 600                 605

Ser Leu Asn Glu Ala Asp Arg Arg Ala Gln His Ser Ser Ile Glu Asn
610                 615                 620

Gln Gln Leu Val Leu Glu Asn Thr Arg Arg Lys Ala Lys Gly Glu Asp
625                 630                 635                 640

Pro Leu Lys Glu Leu Lys Lys Glu Asp Glu Asp Ala Leu Pro Thr Glu
            645                 650                 655

Ala Asp Lys Thr Lys Pro Glu Asp Asp Ala Tyr Leu Ala Glu Thr Gly
        660                 665                 670

Arg Ile Leu Leu Asp Tyr Leu Lys Ile Thr Lys Gln Val Ala Lys Gln
    675                 680                 685
                                                        690

<210> SEQ ID NO 22
<211> LENGTH: 437
<212> TYPE: PRT
<213> ORGANISM: Pseudomonas fluorescens
<400> SEQUENCE: 22

Met Leu His Leu Ser Arg Leu Thr Ser Leu Ala Leu Thr Ile Ala Leu
1               5                   10                  15

Val Ile Gly Ala Pro Leu Ala Phe Ala Asp Gln Ala Ala Pro Ala Ala
            20                  25                  30

Pro Ala Thr Ala Ala Thr Thr Lys Ala Pro Leu Pro Leu Asp Glu Leu
        35                  40                  45

Arg Thr Phe Ala Glu Val Met Asp Arg Ile Lys Ala Ala Tyr Val Glu
    50                  55                  60

Pro Val Asp Asp Lys Ala Leu Leu Glu Asn Ala Ile Lys Gly Met Leu
65                  70                  75                  80

Ser Asn Leu Asp Pro His Ser Ala Tyr Leu Gly Pro Glu Asp Phe Ala
                85                  90                  95

Glu Leu Gln Glu Ser Thr Ser Gly Phe Gly Gly Leu Gly Ile Glu
            100                 105                 110

Val Gly Ser Glu Asp Gly Gln Ile Lys Val Val Ser Pro Ile Asp Asp
            115                 120                 125

Thr Pro Ala Ser Lys Ala Gly Ile Gln Ala Gly Asp Leu Ile Val Lys
130                 135                 140

Ile Asn Gly Gln Pro Thr Arg Gly Gln Thr Met Thr Glu Ala Val Asp
145                 150                 155                 160

Lys Met Arg Gly Lys Leu Gly Gln Lys Ile Thr Leu Thr Leu Val Arg
                165                 170                 175

Asp Gly Gly Asn Pro Phe Asp Val Thr Leu Ala Arg Ala Thr Ile Thr
                180                 185                 190

Val Lys Ser Val Lys Ser Gln Leu Leu Glu Ser Gly Tyr Gly Tyr Ile
            195                 200                 205

Arg Ile Thr Gln Phe Gln Val Lys Thr Gly Asp Glu Val Ala Lys Ala
210                 215                 220

Leu Ala Lys Leu Arg Lys Asp Asn Gly Lys Lys Leu Asn Gly Ile Val
225                 230                 235                 240

Leu Asp Leu Arg Asn Asn Pro Gly Gly Val Leu Gln Ser Ala Val Glu
                245                 250                 255

Val Val Asp His Phe Val Thr Lys Gly Leu Ile Val Tyr Thr Lys Gly
                260                 265                 270

Arg Ile Ala Asn Ser Glu Leu Arg Phe Ser Ala Thr Gly Asn Asp Leu
            275                 280                 285

Ser Glu Asn Val Pro Leu Ala Val Leu Ile Asn Gly Gly Ser Ala Ser
290                 295                 300

Ala Ser Glu Ile Val Ala Gly Ala Leu Gln Asp Leu Lys Arg Gly Val
305                 310                 315                 320

Leu Met Gly Thr Thr Ser Phe Gly Lys Gly Ser Val Gln Thr Val Leu
                325                 330                 335

Pro Leu Asn Asn Glu Arg Ala Leu Lys Ile Thr Thr Ala Leu Tyr Tyr
                340                 345                 350

Thr Pro Asn Gly Arg Ser Ile Gln Ala Gln Gly Ile Val Pro Asp Ile
            355                 360                 365

Glu Val Arg Arg Ala Lys Ile Thr Asn Glu Ile Asp Gly Glu Tyr Tyr
370                 375                 380

Lys Glu Ala Asp Leu Gln Gly His Leu Gly Asn Gly Asn Gly Ala
385                 390                 395                 400

Asp Gln Pro Thr Gly Ser Arg Ala Lys Ala Lys Pro Met Pro Gln Asp
                405                 410                 415

Asp Asp Tyr Gln Leu Ala Gln Ala Leu Ser Leu Leu Lys Gly Leu Ser
            420                 425                 430

Ile Thr Arg Ser Arg
        435

<210> SEQ ID NO 23
<211> LENGTH: 1242
<212> TYPE: PRT
<213> ORGANISM: Pseudomonas fluorescens

<400> SEQUENCE: 23

```
Met Asp Val Ala Gly Asn Gly Phe Thr Val Ser Gln Arg Asn Arg Thr
1               5                   10                  15

Pro Arg Phe Lys Thr Thr Pro Leu Thr Pro Ile Ala Leu Gly Leu Ala
                20                  25                  30

Leu Trp Leu Gly His Gly Ser Val Ala Arg Ala Asp Asp Asn Pro Tyr
            35                  40                  45

Thr Pro Gln Val Leu Glu Ser Ala Phe Arg Thr Ala Val Ala Ser Phe
        50                  55                  60

Gly Pro Glu Thr Ala Val Tyr Lys Asn Leu Arg Phe Ala Tyr Ala Asp
65                  70                  75                  80

Ile Val Asp Leu Ala Ala Lys Asp Phe Ala Ala Gln Ser Gly Lys Phe
                85                  90                  95

Asp Ser Ala Leu Lys Gln Asn Tyr Glu Leu Gln Pro Glu Asn Leu Thr
                100                 105                 110

Ile Gly Ala Met Leu Gly Asp Thr Arg Arg Pro Leu Asp Tyr Ala Ser
            115                 120                 125

Arg Leu Asp Tyr Tyr Arg Ser Arg Leu Phe Ser Asn Ser Gly Arg Tyr
    130                 135                 140

Thr Thr Asn Ile Leu Asp Phe Ser Lys Ala Ile Ile Ala Asn Leu Pro
145                 150                 155                 160

Ala Ala Lys Pro Tyr Thr Tyr Val Glu Pro Gly Val Ser Ser Asn Leu
                165                 170                 175

Asn Gly Gln Leu Asn Ala Gly Gln Ser Trp Ala Gly Ala Thr Arg Asp
            180                 185                 190

Trp Ser Ala Asn Ala Gln Thr Trp Lys Thr Pro Glu Ala Gln Val Asn
        195                 200                 205

Ser Gly Leu Asp Arg Thr Asn Ala Tyr Tyr Ala Tyr Ala Leu Gly Ile
        210                 215                 220

Thr Gly Lys Gly Val Asn Val Gly Val Leu Asp Ser Gly Ile Phe Thr
225                 230                 235                 240

Glu His Ser Glu Phe Gln Gly Lys Asn Ala Gln Gly Gln Asp Arg Val
                245                 250                 255

Gln Ala Val Thr Ser Thr Gly Glu Tyr Tyr Ala Thr His Pro Arg Tyr
                260                 265                 270

Arg Leu Glu Val Pro Ser Gly Glu Phe Lys Gln Gly Glu His Phe Ser
    275                 280                 285

Ile Pro Gly Glu Tyr Asp Pro Ala Phe Asn Asp Gly His Gly Thr Glu
    290                 295                 300

Met Ser Gly Val Leu Ala Ala Asn Arg Asn Gly Thr Gly Met His Gly
305                 310                 315                 320

Ile Ala Phe Asp Ala Asn Leu Phe Val Ala Asn Thr Gly Gly Ser Asp
                325                 330                 335

Asn Asp Arg Tyr Gln Gly Ser Asn Asp Leu Asp Tyr Asn Ala Phe Met
            340                 345                 350

Ala Ser Tyr Asn Ala Leu Ala Ala Lys Asn Val Ala Ile Val Asn Gln
        355                 360                 365

Ser Trp Gly Gln Ser Ser Arg Asp Asp Val Glu Asn His Phe Gly Asn
        370                 375                 380

Val Gly Asp Ser Ala Ala Gln Asn Leu Arg Asp Met Thr Ala Ala Tyr
385                 390                 395                 400

Arg Pro Phe Trp Asp Lys Ala His Ala Gly His Lys Thr Trp Met Asp
                405                 410                 415
```

```
Ala Met Ala Asp Ala Ala Arg Gln Asn Thr Phe Ile Gln Ile Ile Ser
            420                 425                 430

Ala Gly Asn Asp Ser His Gly Ala Asn Pro Asp Thr Asn Ser Asn Leu
            435                 440                 445

Pro Phe Phe Lys Pro Asp Ile Glu Ala Lys Phe Leu Ser Ile Thr Gly
            450                 455                 460

Tyr Asp Glu Thr Ser Ala Gln Val Tyr Asn Arg Cys Gly Thr Ser Lys
465                 470                 475                 480

Trp Trp Cys Val Met Gly Ile Ser Gly Ile Pro Ser Ala Gly Pro Glu
                485                 490                 495

Gly Glu Ile Ile Pro Asn Ala Asn Gly Thr Ser Ala Ala Pro Ser
            500                 505                 510

Val Ser Gly Ala Leu Ala Leu Val Met Gln Arg Phe Pro Tyr Met Thr
            515                 520                 525

Ala Ser Gln Ala Arg Asp Val Leu Leu Thr Thr Ser Ser Leu Gln Ala
            530                 535                 540

Pro Asp Gly Pro Asp Thr Pro Val Gly Thr Leu Thr Gly Gly Arg Thr
545                 550                 555                 560

Tyr Asp Asn Leu Gln Pro Val His Asp Ala Ala Pro Gly Leu Pro Gln
                565                 570                 575

Val Pro Gly Val Val Ser Gly Trp Gly Leu Pro Asn Leu Gln Lys Ala
            580                 585                 590

Met Gln Gly Pro Gly Gln Phe Leu Gly Ala Val Ala Val Ala Leu Pro
            595                 600                 605

Ser Gly Thr Arg Asp Ile Trp Ala Asn Pro Ile Ser Asp Glu Ala Ile
            610                 615                 620

Arg Ala Arg Arg Val Glu Asp Ala Ala Glu Gln Ala Thr Trp Ala Ala
625                 630                 635                 640

Thr Lys Gln Gln Lys Gly Trp Leu Ser Gly Leu Pro Ala Asn Ala Ser
                645                 650                 655

Ala Asp Asp Gln Phe Glu Tyr Asp Ile Gly His Ala Arg Glu Gln Ala
            660                 665                 670

Thr Leu Thr Arg Gly Gln Asp Val Leu Thr Gly Ser Thr Tyr Val Gly
            675                 680                 685

Ser Leu Val Lys Ser Gly Asp Gly Glu Leu Val Leu Glu Gly Gln Asn
            690                 695                 700

Thr Tyr Ser Gly Ser Thr Trp Val Arg Gly Gly Lys Leu Ser Val Asp
705                 710                 715                 720

Gly Ala Leu Thr Ser Ala Val Thr Val Asp Ser Ser Ala Val Gly Thr
                725                 730                 735

Arg Asn Ala Asp Asn Gly Val Met Thr Thr Leu Gly Gly Thr Leu Ala
            740                 745                 750

Gly Asn Gly Thr Val Gly Ala Leu Thr Val Asn Asn Gly Gly Arg Val
            755                 760                 765

Ala Pro Gly His Ser Ile Gly Thr Leu Arg Thr Gly Asp Val Thr Phe
            770                 775                 780

Asn Pro Gly Ser Val Tyr Ala Val Glu Val Gly Ala Asp Gly Arg Ser
785                 790                 795                 800

Asp Gln Leu Gln Ser Ser Gly Val Ala Thr Leu Asn Gly Gly Val Val
                805                 810                 815

Ser Val Ser Leu Glu Asn Ser Pro Asn Leu Leu Thr Ala Thr Glu Ala
            820                 825                 830

Arg Ser Leu Leu Gly Gln Gln Phe Asn Ile Leu Ser Ala Ser Gln Gly
```

-continued

```
            835                 840                 845
Ile Gln Gly Gln Phe Ala Ala Phe Ala Pro Asn Tyr Leu Phe Ile Gly
        850                 855                 860

Thr Ala Leu Asn Tyr Gln Pro Asn Gln Leu Thr Leu Ala Ile Ala Arg
865                 870                 875                 880

Asn Gln Thr Thr Phe Ala Ser Val Ala Gln Thr Arg Asn Glu Arg Ser
                885                 890                 895

Val Ala Thr Val Ala Glu Thr Leu Gly Ala Gly Ser Pro Val Tyr Glu
                900                 905                 910

Ser Leu Leu Ala Ser Asp Ser Ala Ala Gln Ala Arg Glu Gly Phe Lys
                915                 920                 925

Gln Leu Ser Gly Gln Leu His Ser Asp Val Ala Ala Gln Met Ala
930                 935                 940

Asp Ser Arg Tyr Leu Arg Glu Ala Val Asn Ala Arg Leu Gln Gln Ala
945                 950                 955                 960

Gln Ala Leu Asp Ser Ser Ala Gln Ile Asp Ser Arg Asp Asn Gly Gly
                965                 970                 975

Trp Val Gln Leu Leu Gly Gly Arg Asn Asn Val Ser Gly Asp Asn Asn
                980                 985                 990

Ala Ser Gly Tyr Ser Ser Ser Thr  Ser Gly Val Leu Leu  Gly Leu Asp
                995                 1000                1005

Thr Glu  Val Asn Asp Gly Trp  Arg Val Gly Ala Ala  Thr Gly Tyr
    1010                1015                1020

Thr Gln  Ser His Leu Asn Gly  Gln Ser Ala Ser Ala  Asp Ser Asp
    1025                1030                1035

Asn Tyr  His Leu Ser Val Tyr  Gly Gly Lys Arg Phe  Glu Ala Ile
    1040                1045                1050

Ala Leu  Arg Leu Gly Gly Ala  Ser Thr Trp His Arg  Leu Asp Thr
    1055                1060                1065

Ser Arg  Arg Val Ala Tyr Ala  Asn Gln Ser Asp His  Ala Lys Ala
    1070                1075                1080

Asp Tyr  Asn Ala Arg Thr Asp  Gln Val Phe Ala Glu  Ile Gly Tyr
    1085                1090                1095

Thr Gln  Trp Thr Val Phe Glu  Pro Phe Ala Asn Leu  Thr Tyr Leu
    1100                1105                1110

Asn Tyr  Gln Ser Asp Ser Phe  Lys Glu Lys Gly Gly  Ala Ala Ala
    1115                1120                1125

Leu His  Ala Ser Gln Gln Ser  Gln Asp Ala Thr Leu  Ser Thr Leu
    1130                1135                1140

Gly Val  Arg Gly His Thr Gln  Leu Pro Leu Thr Ser  Thr Ser Ala
    1145                1150                1155

Val Thr  Leu Arg Gly Glu Leu  Gly Trp Glu His Gln  Phe Gly Asp
    1160                1165                1170

Thr Asp  Arg Glu Ala Ser Leu  Lys Phe Ala Gly Ser  Asp Thr Ala
    1175                1180                1185

Phe Ala  Val Asn Ser Val Pro  Val Ala Arg Asp Gly  Ala Val Ile
    1190                1195                1200

Lys Ala  Ser Ala Glu Met Ala  Leu Thr Lys Asp Thr  Leu Val Ser
    1205                1210                1215

Leu Asn  Tyr Ser Gly Leu Leu  Ser Asn Arg Gly Asn  Asn Asn Gly
    1220                1225                1230

Ile Asn  Ala Gly Phe Thr Phe  Leu Phe
    1235                1240
```

```
<210> SEQ ID NO 24
<211> LENGTH: 450
<212> TYPE: PRT
<213> ORGANISM: Pseudomonas fluorescens

<400> SEQUENCE: 24

Met Ser Ala Leu Tyr Met Ile Val Gly Thr Leu Val Ala Leu Gly Val
1               5                   10                  15

Leu Val Thr Phe His Glu Phe Gly Phe Trp Val Ala Arg Arg Cys
                20                  25                  30

Gly Val Lys Val Leu Arg Phe Ser Val Gly Phe Gly Met Pro Leu Leu
            35                  40                  45

Arg Trp His Asp Arg Arg Gly Thr Glu Phe Val Ile Ala Ala Ile Pro
    50                  55                  60

Leu Gly Gly Tyr Val Lys Met Leu Asp Glu Arg Gly Glu Val Pro
65                  70                  75                  80

Ala Asp Gln Leu Asp Gln Ser Phe Asn Arg Lys Thr Val Arg Gln Arg
                85                  90                  95

Ile Ala Ile Val Ala Ala Gly Pro Ile Ala Asn Phe Leu Leu Ala Met
            100                 105                 110

Val Phe Phe Trp Val Leu Ala Met Leu Gly Ser Gln Gln Val Arg Pro
        115                 120                 125

Val Ile Gly Ala Val Glu Ala Asp Ser Ile Ala Ala Lys Ala Gly Leu
    130                 135                 140

Thr Ala Gly Gln Glu Ile Val Ser Ile Asp Gly Glu Pro Thr Thr Gly
145                 150                 155                 160

Trp Gly Ala Val Asn Leu Gln Leu Val Arg Arg Leu Gly Glu Ser Gly
                165                 170                 175

Thr Val Asn Val Val Arg Asp Gln Asp Ser Ser Ala Glu Thr Pro
            180                 185                 190

Arg Ala Leu Ala Leu Asp His Trp Leu Lys Gly Ala Asp Glu Pro Asp
    195                 200                 205

Pro Ile Lys Ser Leu Gly Ile Arg Pro Trp Arg Pro Ala Leu Pro Pro
    210                 215                 220

Val Leu Ala Glu Leu Asp Pro Lys Gly Pro Ala Gln Ala Ala Gly Leu
225                 230                 235                 240

Lys Thr Gly Asp Arg Leu Leu Ala Leu Asp Gly Gln Ala Leu Gly Asp
                245                 250                 255

Trp Gln Gln Val Val Asp Leu Val Arg Val Arg Pro Asp Thr Lys Ile
            260                 265                 270

Val Leu Lys Val Glu Arg Glu Gly Ala Gln Ile Asp Val Pro Val Thr
        275                 280                 285

Leu Ser Val Arg Gly Glu Ala Lys Ala Gly Gly Tyr Leu Gly Ala
    290                 295                 300

Gly Val Lys Gly Val Glu Trp Pro Pro Ser Met Val Arg Glu Val Ser
305                 310                 315                 320

Tyr Gly Pro Leu Ala Ala Ile Gly Glu Gly Ala Lys Arg Thr Trp Thr
                325                 330                 335

Met Ser Val Leu Thr Leu Glu Ser Leu Lys Lys Met Leu Phe Gly Glu
            340                 345                 350

Leu Ser Val Lys Asn Leu Ser Gly Pro Ile Thr Ile Ala Lys Val Ala
        355                 360                 365

Gly Ala Ser Ala Gln Ser Gly Val Ala Asp Phe Leu Asn Phe Leu Ala
```

```
                    370                 375                 380
Tyr Leu Ser Ile Ser Leu Gly Val Leu Asn Leu Pro Ile Pro Val
385                 390                 395                 400

Leu Asp Gly Gly His Leu Leu Phe Tyr Leu Val Glu Trp Val Arg Gly
                405                 410                 415

Arg Pro Leu Ser Asp Arg Val Gln Gly Trp Gly Ile Gln Ile Gly Ile
                420                 425                 430

Ser Leu Val Val Gly Val Met Leu Leu Ala Leu Val Asn Asp Leu Gly
                435                 440                 445

Arg Leu
    450

<210> SEQ ID NO 25
<211> LENGTH: 246
<212> TYPE: PRT
<213> ORGANISM: Pseudomonas fluorescens

<400> SEQUENCE: 25

Met Lys Gln His Arg Leu Ala Ala Val Ala Leu Val Ser Leu Val
1               5                   10                  15

Leu Ala Gly Cys Asp Ser Gln Thr Ser Val Glu Leu Lys Thr Pro Ala
                20                  25                  30

Gln Lys Ala Ser Tyr Gly Ile Gly Leu Asn Met Gly Lys Ser Leu Ala
                35                  40                  45

Gln Glu Gly Met Asp Asp Leu Asp Ser Lys Ala Val Ala Gln Gly Ile
            50                  55                  60

Glu Asp Ala Val Gly Lys Glu Gln Lys Leu Lys Asp Glu Leu
65                  70                  75                  80

Val Glu Ala Phe Ala Ala Leu Gln Lys Arg Ala Glu Glu Arg Met Thr
                85                  90                  95

Lys Met Ser Glu Glu Ser Ala Ala Gly Lys Lys Phe Leu Glu Asp
                100                 105                 110

Asn Ala Lys Lys Asp Gly Val Val Thr Thr Ala Ser Gly Leu Gln Tyr
                115                 120                 125

Lys Ile Val Lys Lys Ala Asp Gly Ala Gln Pro Lys Pro Thr Asp Val
                130                 135                 140

Val Thr Val His Tyr Thr Gly Lys Leu Thr Asn Gly Thr Thr Phe Asp
145                 150                 155                 160

Ser Ser Val Asp Arg Gly Ser Pro Ile Asp Leu Pro Val Ser Gly Val
                165                 170                 175

Ile Pro Gly Trp Val Glu Gly Leu Gln Leu Met His Val Gly Glu Lys
                180                 185                 190

Val Glu Leu Tyr Ile Pro Ser Asp Leu Ala Tyr Gly Ala Gln Ser Pro
                195                 200                 205

Ser Pro Ala Ile Pro Ala Asn Ser Val Leu Val Phe Asp Leu Glu Leu
                210                 215                 220

Leu Gly Ile Lys Asp Pro Ala Lys Ala Glu Ala Ala Asp Ala Pro Ala
225                 230                 235                 240

Ala Pro Ala Ala Lys Lys
                245

<210> SEQ ID NO 26
<211> LENGTH: 427
<212> TYPE: PRT
<213> ORGANISM: Pseudomonas fluorescens
```

```
<400> SEQUENCE: 26

Met Thr Asp Thr Arg Asn Gly Glu Asp Asn Gly Lys Leu Leu Tyr Cys
1               5                   10                  15

Ser Phe Cys Gly Lys Ser Gln His Glu Val Arg Lys Leu Ile Ala Gly
            20                  25                  30

Pro Ser Val Phe Ile Cys Asp Glu Cys Val Asp Leu Cys Asn Asp Ile
        35                  40                  45

Ile Arg Glu Glu Val Gln Glu Ala Gln Ala Glu Ser Ser Ala His Lys
    50                  55                  60

Leu Pro Ser Pro Lys Glu Ile Ser Gly Ile Leu Asp Gln Tyr Val Ile
65                  70                  75                  80

Gly Gln Glu Arg Ala Lys Lys Val Leu Ala Val Ala Val Tyr Asn His
                85                  90                  95

Tyr Lys Arg Leu Asn Gln Arg Asp Lys Lys Gly Asp Glu Val Glu Leu
            100                 105                 110

Gly Lys Ser Asn Ile Leu Leu Ile Gly Pro Thr Gly Ser Gly Lys Thr
        115                 120                 125

Leu Leu Ala Glu Thr Leu Ala Arg Leu Leu Asn Val Pro Phe Thr Ile
    130                 135                 140

Ala Asp Ala Thr Thr Leu Thr Glu Ala Gly Tyr Val Gly Glu Asp Val
145                 150                 155                 160

Glu Asn Ile Ile Gln Lys Leu Leu Gln Lys Cys Asp Tyr Asp Val Glu
                165                 170                 175

Lys Ala Gln Met Gly Ile Val Tyr Ile Asp Glu Ile Asp Lys Ile Ser
            180                 185                 190

Arg Lys Ser Asp Asn Pro Ser Ile Thr Arg Asp Val Ser Gly Glu Gly
        195                 200                 205

Val Gln Gln Ala Leu Leu Lys Leu Ile Glu Gly Thr Val Ala Ser Val
    210                 215                 220

Pro Pro Gln Gly Gly Arg Lys His Pro Gln Gln Glu Phe Leu Gln Val
225                 230                 235                 240

Asp Thr Arg Asn Ile Leu Phe Ile Cys Gly Gly Ala Phe Ser Gly Leu
                245                 250                 255

Glu Lys Val Ile Gln Gln Arg Ser Thr Arg Gly Gly Ile Gly Phe Ser
            260                 265                 270

Ala Glu Val Arg Ser Lys Glu Glu Gly Lys Lys Val Gly Glu Ser Leu
        275                 280                 285

Arg Glu Val Glu Pro Asp Asp Leu Val Lys Phe Gly Leu Ile Pro Glu
    290                 295                 300

Phe Val Gly Arg Leu Pro Val Leu Ala Thr Leu Asp Glu Leu Asp Glu
305                 310                 315                 320

Ala Ala Leu Ile Gln Ile Leu Thr Glu Pro Lys Asn Ala Leu Thr Lys
                325                 330                 335

Gln Tyr Gly Lys Leu Phe Glu Met Glu Gly Val Asp Leu Glu Phe Arg
            340                 345                 350

Thr Asp Ala Leu Lys Ser Val Ala Lys Arg Ala Leu Glu Arg Lys Thr
        355                 360                 365

Gly Ala Arg Gly Leu Arg Ser Ile Leu Glu Gly Val Leu Leu Asp Thr
    370                 375                 380

Met Tyr Glu Ile Pro Ser Gln Ser Glu Val Ser Lys Val Val Ile Asp
385                 390                 395                 400

Glu Ser Val Ile Glu Gly Lys Ser Lys Pro Leu Tyr Ile Tyr Glu Asn
                405                 410                 415
```

```
Ser Glu Pro Ala Ala Lys Ala Ala Pro Asp Ala
            420                 425
```

<210> SEQ ID NO 27
<211> LENGTH: 756
<212> TYPE: PRT
<213> ORGANISM: Pseudomonas fluorescens
<400> SEQUENCE: 27

```
Met Leu Asn Arg Glu Leu Glu Val Thr Leu Asn Leu Ala Phe Lys Glu
1               5                   10                  15

Ala Arg Ser Lys Arg His Glu Phe Met Thr Val Glu His Leu Leu Leu
            20                  25                  30

Ala Leu Leu Asp Asn Glu Ala Ala Thr Val Leu Arg Ala Cys Gly
        35                  40                  45

Ala Asn Leu Asp Lys Leu Lys His Asp Leu Gln Glu Phe Ile Asp Ser
        50                  55                  60

Thr Thr Pro Leu Ile Pro Val His Asp Glu Arg Glu Thr Gln Pro
65                  70                  75                  80

Thr Leu Gly Phe Gln Arg Val Leu Gln Arg Ala Val Phe His Val Gln
                85                  90                  95

Ser Ser Gly Lys Arg Glu Val Thr Gly Ala Asn Val Leu Val Ala Ile
            100                 105                 110

Phe Ser Glu Gln Glu Ser Gln Ala Val Phe Leu Leu Lys Gln Gln Ser
        115                 120                 125

Val Ala Arg Ile Asp Val Val Asn Tyr Ile Ala His Gly Ile Ser Lys
    130                 135                 140

Val Pro Gly His Gly Asp His Ser Glu Gly Glu Gln Asp Met Gln Asp
145                 150                 155                 160

Glu Glu Gly Gly Glu Ser Ser Ser Ser Asn Pro Leu Asp Ala Tyr
                165                 170                 175

Ala Ser Asn Leu Asn Glu Met Ala Arg Gln Gly Arg Ile Asp Pro Leu
            180                 185                 190

Val Gly Arg Glu His Glu Val Glu Arg Val Ala Gln Ile Leu Ala Arg
        195                 200                 205

Arg Arg Lys Asn Asn Pro Leu Leu Val Gly Glu Ala Gly Val Gly Lys
    210                 215                 220

Thr Ala Ile Ala Glu Gly Leu Ala Lys Arg Ile Val Asp Asn Gln Val
225                 230                 235                 240

Pro Asp Leu Leu Ala Ser Ser Val Val Tyr Ser Leu Asp Leu Gly Ala
                245                 250                 255

Leu Leu Ala Gly Thr Lys Tyr Arg Gly Asp Phe Glu Lys Arg Phe Lys
            260                 265                 270

Ala Leu Leu Gly Glu Leu Lys Lys Arg Pro Gln Ala Ile Leu Phe Ile
        275                 280                 285

Asp Glu Ile His Thr Ile Gly Ala Gly Ala Ala Ser Gly Gly Val
    290                 295                 300

Met Asp Ala Ser Asn Leu Leu Lys Pro Leu Leu Ser Ser Gly Asp Ile
305                 310                 315                 320

Arg Cys Ile Gly Ser Thr Thr Phe Gln Glu Phe Arg Gly Ile Phe Glu
                325                 330                 335

Lys Asp Arg Ala Leu Ala Arg Arg Phe Gln Lys Val Asp Val Ser Glu
            340                 345                 350

Pro Ser Val Glu Asp Thr Ile Gly Ile Leu Arg Gly Leu Lys Gly Arg
```

```
            355                 360                 365
Phe Glu Ala His His Gly Ile Glu Tyr Thr Asp Glu Ala Leu Arg Ala
    370                 375                 380

Ala Ala Glu Leu Ala Ser Arg Tyr Ile Asn Asp Arg His Met Pro Asp
385                 390                 395                 400

Lys Ala Ile Asp Val Ile Asp Glu Ala Gly Ala Tyr Gln Arg Leu Gln
                405                 410                 415

Pro Val Glu Lys Arg Val Lys Arg Ile Asp Val Pro Gln Val Glu Asp
            420                 425                 430

Ile Val Ala Lys Ile Ala Arg Ile Pro Pro Lys His Val Thr Ser Ser
        435                 440                 445

Asp Lys Glu Leu Leu Arg Asn Leu Glu Arg Asp Leu Lys Leu Thr Val
    450                 455                 460

Phe Gly Gln Asp Ala Ala Ile Asp Ser Leu Ser Thr Ala Ile Lys Leu
465                 470                 475                 480

Ser Arg Ala Gly Leu Lys Ser Pro Asp Lys Pro Val Gly Ser Phe Leu
                485                 490                 495

Phe Ala Gly Pro Thr Gly Val Gly Lys Thr Glu Ala Ala Arg Gln Leu
            500                 505                 510

Ala Lys Ala Met Gly Ile Glu Leu Val Arg Phe Asp Met Ser Glu Tyr
        515                 520                 525

Met Glu Arg His Thr Val Ser Arg Leu Ile Gly Ala Pro Pro Gly Tyr
    530                 535                 540

Val Gly Phe Asp Gln Gly Gly Leu Leu Thr Glu Ala Ile Thr Lys Gln
545                 550                 555                 560

Pro His Cys Val Leu Leu Leu Asp Glu Ile Glu Lys Ala His Pro Glu
                565                 570                 575

Val Phe Asn Leu Leu Leu Gln Val Met Asp His Gly Thr Leu Thr Asp
            580                 585                 590

Asn Asn Gly Arg Lys Ala Asp Phe Arg Asn Val Ile Val Ile Met Thr
        595                 600                 605

Thr Asn Ala Gly Ala Glu Thr Ala Ala Arg Ala Ser Ile Gly Phe Thr
    610                 615                 620

His Gln Asp His Ser Ser Asp Ala Met Glu Val Ile Lys Lys Ser Phe
625                 630                 635                 640

Thr Pro Glu Phe Arg Asn Arg Leu Asp Thr Ile Ile Gln Phe Gly Arg
                645                 650                 655

Leu Ser His Glu Val Ile Lys Ser Val Val Asp Lys Phe Leu Thr Glu
            660                 665                 670

Leu Gln Ala Gln Leu Glu Asp Lys Arg Val Gln Leu Asp Val Thr Glu
        675                 680                 685

Ala Ala Arg Ser Trp Ile Glu Gly Gly Tyr Asp Ala Ala Met Gly
    690                 695                 700

Ala Arg Pro Met Ala Arg Leu Ile Gln Asp Lys Ile Lys Arg Pro Leu
705                 710                 715                 720

Ala Glu Glu Ile Leu Phe Gly Glu Leu Ser Asp His Gly Gly Val Val
                725                 730                 735

His Ile Asp Leu Lys Asp Gly Glu Leu Thr Phe Glu Phe Glu Thr Thr
            740                 745                 750

Ala Glu Met Ala
        755

<210> SEQ ID NO 28
```

```
<211> LENGTH: 243
<212> TYPE: PRT
<213> ORGANISM: Pseudomonas fluorescens

<400> SEQUENCE: 28
```

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Ser Tyr Glu Arg Gly
    130                 135                 140

Gln Pro Ala Glu Phe Pro Val Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Tyr Ser Thr Ser Ser Cys Ser Thr Phe Cys Lys Thr Cys
        195                 200                 205

Trp Leu Pro Val Gly Thr Asn Ala Phe Ala Pro Thr Gly Val Cys Gln
    210                 215                 220

Phe Leu His Gly Trp Asn Leu Pro Leu Ser Ser Val Ala Gly Arg Asn
225                 230                 235                 240

Ala Arg Ala

```
<210> SEQ ID NO 29
<211> LENGTH: 187
<212> TYPE: PRT
<213> ORGANISM: Pseudomonas fluorescens

<400> SEQUENCE: 29
```

Met Leu Lys Lys Ile Ala Leu Phe Ala Gly Ser Ala Leu Phe Ala Ala
1               5                   10                  15

Asn Leu Met Ala Ala Glu Pro Ala Lys Ala Pro His Val Leu Leu Asp
            20                  25                  30

Thr Thr Asn Gly Gln Ile Glu Ile Glu Leu Asp Pro Val Lys Ala Pro
        35                  40                  45

Ile Ser Thr Lys Asn Phe Leu Glu Tyr Val Asp Ser Gly Phe Tyr Thr
    50                  55                  60

Asn Thr Ile Phe His Arg Val Ile Pro Gly Phe Met Val Gln Gly Gly
65                  70                  75                  80

Gly Phe Thr Gln Gln Met Gln Gln Lys Asp Thr Lys Ala Pro Ile Lys
                85                  90                  95

Asn Glu Ala Ser Asn Gly Leu His Asn Val Arg Gly Thr Leu Ser Met
                100                 105                 110

Ala Arg Thr Ser Asn Pro Asn Ser Ala Thr Ser Gln Phe Phe Ile Asn
            115                 120                 125

Val Ala Asp Asn Ala Phe Leu Asp Pro Gly Arg Asp Ala Gly Tyr Ala
        130                 135                 140

Val Phe Ala Lys Val Val Lys Gly Met Asp Val Val Asp Ile Ile Val
145                 150                 155                 160

Asn Ser Gln Thr Thr Thr Lys Gln Gly Met Gln Asn Val Pro Ile Asp
                165                 170                 175

Pro Val Leu Ile Lys Ser Ala Lys Arg Ile Asp
                180                 185

<210> SEQ ID NO 30
<211> LENGTH: 674
<212> TYPE: PRT
<213> ORGANISM: Pseudomonas fluorescens

<400> SEQUENCE: 30

Met Pro Glu Ser Asn Pro Leu Leu Pro Tyr Asp Leu Pro Pro Phe
1               5                   10                  15

Ser Ala Ile Arg Ala Glu His Leu Val Pro Ala Ile Glu Gln Ile Ile
            20                  25                  30

Thr Glu Ser Arg Asn Thr Thr Ala Thr Ile Ile Ala Ser Gln Thr Pro
        35                  40                  45

Phe Pro Thr Trp Asp Asp Leu Val Gln Ala Val Glu Ala Leu Glu Ala
    50                  55                  60

Arg Leu Asp Gly Val Leu Lys Ile Ile Glu Leu Leu Asp Ser His Pro
65                  70                  75                  80

Gln Gly Pro Ala Trp Thr Leu Ala Ser His Arg Ser Tyr Glu Leu Ala
                85                  90                  95

Met Gln Tyr Arg Val Glu Leu Ala Gly Asn Asn Asp Leu Tyr Gln Leu
            100                 105                 110

His Arg Gln Leu Ala Asp Ser Pro Ile Ala Thr Leu Phe Asn Glu Gln
        115                 120                 125

Arg His Ser Ala Leu Arg Lys Ile Leu Arg Lys Tyr His Leu Ala Gly
    130                 135                 140

Leu Asp Leu Ser Pro Glu Lys Gln Arg Leu Lys Ala Leu Asn Leu
145                 150                 155                 160

Gln Ile Asp Glu Phe Ser His Glu Phe Leu Arg Arg Val Ser Asp Ser
                165                 170                 175

Ser Asp Ala Trp Arg Lys His Ile Gln Asp Lys Ala Leu Leu Ser Gly
            180                 185                 190

Leu Pro Asp Ala Ala Leu Ala Arg Leu Glu Phe Ala Ala Arg Asp Ala
        195                 200                 205

Gly Leu Gly Gly Trp Leu Leu Thr Leu Ser Lys Gln Ser Phe Gln Glu
    210                 215                 220

Val Met Ser Tyr Ala Asp His Arg Ala Leu Arg Gln Glu Met Met Leu
225                 230                 235                 240

Ala Tyr Tyr Ser Arg Ala Val Gly Thr Gly Pro Asp Ala Ile Ala Thr
                245                 250                 255

Asp Asn Glu Ala Val Leu Thr Val Leu Leu Asp Ser Arg His Gln Lys
            260                 265                 270

Ala Gln Leu Leu Gly Tyr Ala Asn Phe Ala Glu Leu Ala Leu Val Glu
        275                 280                 285

```
Gln Met Ala Glu Thr Thr Asp Glu Val Thr Ala Cys Val His Gln Gln
    290                 295                 300

Ile Asp Gln Ala Arg Thr Thr Phe Ala His Asp Ala Gln Gln Leu Gln
305                 310                 315                 320

Arg Tyr Ala Ala Gln Arg Gly Val Asp Ala Leu Glu Pro Trp Asp Tyr
                325                 330                 335

Asp Phe Phe Ala Glu Lys Ile Arg Gln Asp Val Ala Gly Val Ser Gln
            340                 345                 350

Asp Ala Val Arg Leu Tyr Phe Pro Leu Glu Thr Val Leu Gln Arg Leu
        355                 360                 365

Cys Thr Phe Thr Gln Thr Leu Phe Gly Val Glu Leu Ile Glu Gln Ala
    370                 375                 380

Thr Val Asp Thr Trp His Pro Asp Val Arg Val Phe Glu Leu Arg Glu
385                 390                 395                 400

Tyr Ala Gln Pro Ile Gly His Leu Phe Ile Asp Pro Tyr Arg Arg Val
                405                 410                 415

Ala Gly Gly Glu Ile Gly Ala Ala Met Gly Leu Arg Asn His Arg Met
            420                 425                 430

Thr Ala Glu Gly Arg Pro Gln Arg Pro Ile Ala Val Leu Arg Ser Gln
        435                 440                 445

Leu Pro Arg Pro Thr Ala Ala Gln Pro Cys Leu Leu Asp His Leu Gln
    450                 455                 460

Leu Arg Val Leu Leu His Glu Phe Gly His Cys Leu Gln His Leu Leu
465                 470                 475                 480

Ser Ala Ala Pro Tyr Arg Ala Ile Ser Gly Met Gly Gln Leu Ser His
                485                 490                 495

Asp Thr Thr Glu Phe Phe Gly Leu Val Leu Glu Gln Phe Cys Leu Thr
            500                 505                 510

Pro Ser Phe Leu Ile Tyr Leu Ser Gly His Val Gln Thr Gly Asp Pro
        515                 520                 525

Leu Pro Asp Lys Met Ala Thr Gln Met Ser Arg Phe Ala His Thr Gln
    530                 535                 540

Thr Ser Gln Glu Thr Ala Ser Ile Leu Leu Thr Gly Leu Val Asp Phe
545                 550                 555                 560

Glu Leu His Arg Thr Tyr Gly Asp Gly Arg Thr Pro His Glu Val Phe
                565                 570                 575

Thr Asp Ala Asn Val Glu Val Gly His Leu Gln Trp Pro Asp Gly Ala
            580                 585                 590

Arg Pro Ile Asn Ser Phe Glu Gln Pro Met Gly Ser Tyr Gly Ala Lys
        595                 600                 605

Leu Tyr Ser Tyr Thr Trp Ser Gly Val Leu Ala Arg Gln Ala Phe Glu
    610                 615                 620

Arg Phe Glu Arg Asp Gly Leu Phe Asn Pro Gln Thr Gly Lys Ala Phe
625                 630                 635                 640

Arg Asp Ala Phe Ile Thr Glu Gly Asp Thr Gly Thr Leu Leu Ser Ala
                645                 650                 655

Leu Ala Leu Phe Arg Gly Asp Gly Ala Gly Cys Val Gly His Ser Thr
            660                 665                 670

Gly Val

<210> SEQ ID NO 31
<211> LENGTH: 235
<212> TYPE: PRT
```

```
<213> ORGANISM: Bos taurus

<400> SEQUENCE: 31

Ile Val Gly Gly Ser Asp Ser Arg Glu Gly Ala Trp Pro Trp Val Val
1               5                   10                  15

Ala Leu Tyr Phe Asp Asp Gln Gln Val Cys Gly Ala Ser Leu Val Ser
            20                  25                  30

Arg Asp Trp Leu Val Ser Ala Ala His Cys Val Tyr Gly Arg Asn Met
        35                  40                  45

Glu Pro Ser Lys Trp Lys Ala Val Leu Gly Leu His Met Ala Ser Asn
    50                  55                  60

Leu Thr Ser Pro Gln Ile Glu Thr Arg Leu Ile Asp Gln Ile Val Ile
65                  70                  75                  80

Asn Arg His Tyr Asn Lys Arg Lys Asn Asn Asp Ile Ala Met Met
                85                  90                  95

His Leu Glu Met Lys Val Asn Tyr Thr Asp Tyr Ile Gln Pro Ile Cys
            100                 105                 110

Leu Pro Glu Glu Asn Gln Val Phe Pro Pro Gly Arg Ile Cys Ser Ile
        115                 120                 125

Ala Gly Trp Gly Ala Leu Ile Tyr Gln Gly Ser Thr Ala Asp Val Leu
    130                 135                 140

Gln Glu Ala Asp Val Pro Leu Leu Ser Asn Glu Lys Cys Gln Gln Gln
145                 150                 155                 160

Met Pro Glu Tyr Asn Ile Thr Glu Asn Met Val Cys Ala Gly Tyr Asp
                165                 170                 175

Ala Gly Gly Val Asp Ser Cys Gln Gly Asp Ser Gly Gly Pro Leu Met
            180                 185                 190

Cys Gln Glu Asn Asn Arg Trp Leu Leu Ala Gly Val Thr Ser Phe Gly
        195                 200                 205

Tyr Gln Cys Ala Leu Pro Asn Arg Pro Gly Val Tyr Ala Arg Val Pro
    210                 215                 220

Arg Phe Thr Glu Trp Ile Gln Ser Phe Leu His
225                 230                 235

<210> SEQ ID NO 32
<211> LENGTH: 86
<212> TYPE: PRT
<213> ORGANISM: Homo sapiens

<400> SEQUENCE: 32

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 33
<211> LENGTH: 84
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 33

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr Glu Ala
                20                  25                  30

Glu Asp Leu Gln Val Gly Gln Val Glu Leu Gly Gly Pro Gly Ala
            35                  40                  45

Gly Ser Leu Gln Pro Leu Ala Leu Glu Gly Ser Leu Gln Lys Arg Gly
        50                  55                  60

Ile Val Glu Gln Cys Cys Thr Ser Ile Cys Ser Leu Tyr Gln Leu Glu
65                  70                  75                  80

Asn Tyr Cys Asn

<210> SEQ ID NO 34
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr Arg Arg
                20                  25                  30

Glu Ala Glu Asp Leu Gln Val Gly Gln Val Glu Leu Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 35
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala
65                  70
```

```
<210> SEQ ID NO 36
<211> LENGTH: 31
<212> TYPE: PRT
<213> ORGANISM: Unknown
<220> FEATURE:
<223> OTHER INFORMATION: Description of Unknown:
      GLP-1 sequence

<400> SEQUENCE: 36

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 38
<211> LENGTH: 33
<212> TYPE: PRT
<213> ORGANISM: Unknown
<220> FEATURE:
<223> OTHER INFORMATION: Description of Unknown:
      GLP-2 sequence

<400> SEQUENCE: 38

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 39
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 40
<211> LENGTH: 37
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 40

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 41
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Lys Leu Thr Cys Val Val Ile Val Ala Val Leu Leu Leu Thr Ala
1               5                   10                  15

Cys Gln Leu Ile Thr Ala Asp Asp Ser Arg Gly Thr Gln Lys His Arg
            20                  25                  30

Ala Leu Arg Ser Thr Thr Lys Leu Ser Thr Ser Thr Arg Cys Lys Gly
        35                  40                  45

Lys Gly Ala Lys Cys Ser Arg Leu Met Tyr Asp Cys Cys Thr Gly Ser
50                  55                  60

Cys Arg Ser Gly Lys Cys Gly
65                  70

<210> SEQ ID NO 42
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr
            100                 105

<210> SEQ ID NO 43
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 43

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 45
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
            35                  40                  45

Ser Met Phe Leu Glu Thr Val Glu Val Asp Gly Glu Gln Val Pro Arg
        50                  55                  60

Phe Ala Leu Val Thr Ala Glu Pro Ser Leu Phe Thr Gly Gln Gly Gly
65                  70                  75                  80

Gly Gly Ser Gly Gly Gly Ser His His His His His Asp Asp
            85                  90                  95

Asp Asp Lys Ser Val Ser Glu Ile Gln Leu Met His Asn Leu Gly Lys
            100                 105                 110

His Leu Asn Ser Met Glu Arg Val Glu Trp Leu Arg Lys Lys Leu Gln
            115                 120                 125

Asp Val His Asn Phe
        130

<210> SEQ ID NO 46
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 46

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
            115                 120                 125

Gly Thr Leu Ile Asp Gly Thr Val Phe Asp Ser Ser Tyr Glu Arg Gly
        130                 135                 140

Gln Pro Ala Glu Phe Pro Val Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
        195                 200                 205

Gly Ser Gly Gly Gly Ser His His His His His Asp Asp Asp
    210                 215                 220

Asp Lys Ser Val Ser Glu Ile Gln Leu Met His Asn Leu Gly Lys His
225                 230                 235                 240

Leu Asn Ser Met Glu Arg Val Glu Trp Leu Arg Lys Lys Leu Gln Asp
                245                 250                 255

Val His Asn Phe
            260
```

<210> SEQ ID NO 47
<211> LENGTH: 272
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80
```

```
Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
        115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser Gly Gly Gly Ser Gly Gly Gly
    210                 215                 220

Gly Gly Ser His His His His His His Asp Asp Asp Asp Lys Ser Val
225                 230                 235                 240

Ser Glu Ile Gln Leu Met His Asn Leu Gly Lys His Leu Asn Ser Met
                245                 250                 255

Glu Arg Val Glu Trp Leu Arg Lys Lys Leu Gln Asp Val His Asn Phe
            260                 265                 270

<210> SEQ ID NO 48
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
        35                  40                  45

Ser Met Phe Leu Glu Thr Val Glu Val Asp Gly Glu Gln Val Pro Arg
    50                  55                  60

Phe Ala Leu Val Thr Ala Glu Pro Ser Leu Phe Thr Gly Gln Gly Gly
65                  70                  75                  80

Gly Gly Ser Gly Gly Gly Ser Asp Asp Asp Lys Ile Val Gly
                85                  90                  95

Gly Ser Asp Ser Arg Glu Gly Ala Trp Pro Trp Val Ala Leu Tyr
            100                 105                 110

Phe Asp Asp Gln Gln Val Cys Gly Ala Ser Leu Val Ser Arg Asp Trp
        115                 120                 125

Leu Val Ser Ala Ala His Cys Val Tyr Gly Arg Asn Met Glu Pro Ser
    130                 135                 140

Lys Trp Lys Ala Val Leu Gly Leu His Met Ala Ser Asn Leu Thr Ser
145                 150                 155                 160

Pro Gln Ile Glu Thr Arg Leu Ile Asp Gln Ile Val Ile Asn Arg His
                165                 170                 175
```

```
Tyr Asn Lys Arg Arg Lys Asn Asn Asp Ile Ala Met Met His Leu Glu
            180                 185                 190

Met Lys Val Asn Tyr Thr Asp Tyr Ile Gln Pro Ile Cys Leu Pro Glu
        195                 200                 205

Glu Asn Gln Val Phe Pro Pro Gly Arg Ile Cys Ser Ile Ala Gly Trp
    210                 215                 220

Gly Ala Leu Ile Tyr Gln Gly Ser Thr Ala Asp Val Leu Gln Glu Ala
225                 230                 235                 240

Asp Val Pro Leu Leu Ser Asn Glu Lys Cys Gln Gln Met Pro Glu
                245                 250                 255

Tyr Asn Ile Thr Glu Asn Met Val Cys Ala Gly Tyr Asp Ala Gly Gly
                260                 265                 270

Val Asp Ser Cys Gln Gly Asp Ser Gly Gly Pro Leu Met Cys Gln Glu
        275                 280                 285

Asn Asn Arg Trp Leu Leu Ala Gly Val Thr Ser Phe Gly Tyr Gln Cys
        290                 295                 300

Ala Leu Pro Asn Arg Pro Gly Val Tyr Ala Arg Val Pro Arg Phe Thr
305                 310                 315                 320

Glu Trp Ile Gln Ser Phe Leu His His His His His His
                325                 330

<210> SEQ ID NO 49
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Tyr Glu Arg Gly
    130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
```

```
                195                 200                 205
Gly Ser Gly Gly Gly Ser Asp Asp Asp Lys Ile Val Gly
    210                 215                 220
Ser Asp Ser Arg Glu Gly Ala Trp Pro Trp Val Ala Leu Tyr Phe
225                 230                 235                 240
Asp Asp Gln Gln Val Cys Gly Ala Ser Leu Val Ser Arg Asp Trp Leu
                245                 250                 255
Val Ser Ala Ala His Cys Val Tyr Gly Arg Asn Met Glu Pro Ser Lys
            260                 265                 270
Trp Lys Ala Val Leu Gly Leu His Met Ala Ser Asn Leu Thr Ser Pro
        275                 280                 285
Gln Ile Glu Thr Arg Leu Ile Asp Gln Ile Val Ile Asn Arg His Tyr
    290                 295                 300
Asn Lys Arg Lys Asn Asn Asp Ile Ala Met Met His Leu Glu Met
305                 310                 315                 320
Lys Val Asn Tyr Thr Asp Tyr Ile Gln Pro Ile Cys Leu Pro Glu Glu
                325                 330                 335
Asn Gln Val Phe Pro Pro Gly Arg Ile Cys Ser Ile Ala Gly Trp Gly
            340                 345                 350
Ala Leu Ile Tyr Gln Gly Ser Thr Ala Asp Val Leu Gln Glu Ala Asp
        355                 360                 365
Val Pro Leu Leu Ser Asn Glu Lys Cys Gln Gln Met Pro Glu Tyr
    370                 375                 380
Asn Ile Thr Glu Asn Met Val Cys Ala Gly Tyr Asp Ala Gly Val
385                 390                 395                 400
Asp Ser Cys Gln Gly Asp Ser Gly Pro Leu Met Cys Gln Glu Asn
                405                 410                 415
Asn Arg Trp Leu Leu Ala Gly Val Thr Ser Phe Gly Tyr Gln Cys Ala
            420                 425                 430
Leu Pro Asn Arg Pro Gly Val Tyr Ala Arg Val Pro Arg Phe Thr Glu
        435                 440                 445
Trp Ile Gln Ser Phe Leu His His His His His His
    450                 455                 460

<210> SEQ ID NO 50
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Ser Cys Thr Arg Ala Phe Lys Pro Leu Leu Leu Ile Gly Leu Ala
1               5                   10                  15
Thr Leu Met Cys Ser His Ala Phe Ala Ala Val Val Ile Thr Gly Thr
                20                  25                  30
Arg Leu Val Tyr Pro Ala Asp Gln Lys Glu Ile Thr Val Lys Leu Asn
            35                  40                  45
Asn Asn Gly Thr Leu Pro Ala Leu Val Gln Ser Trp Ile Asp Thr Gly
        50                  55                  60
Ser Val Glu Ser Thr Pro Thr Ser Ser Lys Ala Pro Phe Leu Leu Ser
65                  70                  75                  80
Pro Pro Val Ala Arg Ile Asp Pro Thr Lys Gly Gln Ser Leu Arg Val
                85                  90                  95
```

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro Gly Gly Gly Ser Asp Asp Asp
                245                 250                 255

Asp Lys Ile Val Gly Ser Asp Ser Arg Glu Gly Ala Trp Pro Trp
            260                 265                 270

Val Val Ala Leu Tyr Phe Asp Asp Gln Gln Val Cys Gly Ala Ser Leu
        275                 280                 285

Val Ser Arg Asp Trp Leu Val Ser Ala Ala His Cys Val Tyr Gly Arg
    290                 295                 300

Asn Met Glu Pro Ser Lys Trp Lys Ala Val Leu Gly Leu His Met Ala
305                 310                 315                 320

Ser Asn Leu Thr Ser Pro Gln Ile Glu Thr Arg Leu Ile Asp Gln Ile
                325                 330                 335

Val Ile Asn Arg His Tyr Asn Lys Arg Lys Asn Asn Asp Ile Ala
            340                 345                 350

Met Met His Leu Glu Met Lys Val Asn Tyr Thr Asp Tyr Ile Gln Pro
        355                 360                 365

Ile Cys Leu Pro Glu Glu Asn Gln Val Phe Pro Pro Gly Arg Ile Cys
    370                 375                 380

Ser Ile Ala Gly Trp Gly Ala Leu Ile Tyr Gln Gly Ser Thr Ala Asp
385                 390                 395                 400

Val Leu Gln Glu Ala Asp Val Pro Leu Leu Ser Asn Glu Lys Cys Gln
                405                 410                 415

Gln Gln Met Pro Glu Tyr Asn Ile Thr Glu Asn Met Val Cys Ala Gly
            420                 425                 430

Tyr Asp Ala Gly Gly Val Asp Ser Cys Gln Gly Asp Ser Gly Gly Pro
        435                 440                 445

Leu Met Cys Gln Glu Asn Asn Arg Trp Leu Leu Ala Gly Val Thr Ser
    450                 455                 460

Phe Gly Tyr Gln Cys Ala Leu Pro Asn Arg Pro Gly Val Tyr Ala Arg
465                 470                 475                 480

Val Pro Arg Phe Thr Glu Trp Ile Gln Ser Phe Leu His His His
                485                 490                 495

His His His

<210> SEQ ID NO 51

```
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ile Val Gly Gly Ser Asp Ser Arg Glu Gly Ala Trp Pro Trp Val Val
1               5                   10                  15

Ala Leu Tyr Phe Asp Asp Gln Gln Val Cys Gly Ala Ser Leu Val Ser
            20                  25                  30

Arg Asp Trp Leu Val Ser Ala Ala His Cys Val Tyr Gly Arg Asn Met
        35                  40                  45

Glu Pro Ser Lys Trp Lys Ala Val Leu Gly Leu His Met Ala Ser Asn
    50                  55                  60

Leu Thr Ser Pro Gln Ile Glu Thr Arg Leu Ile Asp Gln Ile Val Ile
65                  70                  75                  80

Asn Arg His Tyr Asn Lys Arg Lys Asn Asn Asp Ile Ala Met Met
                85                  90                  95

His Leu Glu Met Lys Val Asn Tyr Thr Asp Tyr Ile Gln Pro Ile Cys
            100                 105                 110

Leu Pro Glu Glu Asn Gln Val Phe Pro Pro Gly Arg Ile Cys Ser Ile
        115                 120                 125

Ala Gly Trp Gly Ala Leu Ile Tyr Gln Gly Ser Thr Ala Asp Val Leu
    130                 135                 140

Gln Glu Ala Asp Val Pro Leu Leu Ser Asn Glu Lys Cys Gln Gln
145                 150                 155                 160

Met Pro Glu Tyr Asn Ile Thr Glu Asn Met Val Cys Ala Gly Tyr Asp
                165                 170                 175

Ala Gly Gly Val Asp Ser Cys Gln Gly Asp Ser Gly Gly Pro Leu Met
            180                 185                 190

Cys Gln Glu Asn Asn Arg Trp Leu Leu Ala Gly Val Thr Ser Phe Gly
        195                 200                 205

Tyr Gln Cys Ala Leu Pro Asn Arg Pro Gly Val Tyr Ala Arg Val Pro
    210                 215                 220

Arg Phe Thr Glu Trp Ile Gln Ser Phe Leu His His His His His
225                 230                 235                 240

His

<210> SEQ ID NO 52
<211> LENGTH: 431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
actagtagga ggtctagaat gaaagtcgaa ccgggtctgt accagcatta caagggtccc      60
caatatcgcg tgttttcggt agcgcggcac agcgaaaccg aagaagaagt ggtgttctac     120
caagcgctct acggcgagta cggcttctgg gtgcgtccgc tgtcgatgtt cctggagact     180
gtcgaggtag acgtgagca agtcccgcgc ttcgccctgg tgacggccga gcccagcctg     240
ttcaccggcc agggcggggg cggcagcggc gtggggctc gcatcaccac caccatcacg     300
acgacgacga taagagcgtg tccgagatcc agctcatgca taatctgggc aagcacttga     360
```

```
acagcatgga gcgcgtggag tggctccgga agaaactgca agatgtccac aacttttaat    420
gatagctcga g                                                          431
```

<210> SEQ ID NO 53
<211> LENGTH: 431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
actagtagga ggtctagaat gaaagtcgaa ccagggctct accagcatta aaggggccg     60 cagtaccgtg ttttcagcgt ggcgcgccac tctgaaaccg aagaagaagt ggtgttttac    120
caagcgctgt atggcgaata cggcttttgg gtgcgccctt tgagcatgtt cctggagacc    180
gtcgaagttg acggcgagca ggtcccgcgc tttgctttgg tcacggccga acccagtctt    240
tttacagggc aaggtggcgg tggttcgggc gtggcggcag ccatcatcac caccaccacg    300
acgacgatga taagagcgtg tccgagatcc aactgatgca taatctgggc aagcacctga    360
actcgatgga gcgggtagag tggctccgga aaaagctcca agacgtgcac aacttctaat    420
gatagctcga g                                                          431
```

<210> SEQ ID NO 54
<211> LENGTH: 815
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
actagtagga ggtctagaat gagcgaagtc aacttgagca ctgatgaaac ccgggtaagc    60
tatggtattg gcggcagct gggggaccaa ctgcgggaca acccgcctcc cggcgtgagc    120
ctcgacgcga tcctcgcggg tctgaccgac gccttcgccg gcaagccgag ccgcgtggac    180
caagaacaga tggccgcctc gttcaaggtc atccgcgaaa tcatgcaggc cgaagcggca    240
gcgaaggccg aggccgcagc gggtgccggc ctggcgttcc tggccgagaa cgccaagcgt    300
gacggcatca cgaccctggc gtcgggcctc caattcgaag tcctgacggc cggtactggc    360
gcgaagccca ctcgcgagga tcaggtgcgc acccacctac catggcacgc tgatcgatgg    420
caccgtattc gacagcagct acgagcgtgg ccaaccggcg gagtttccgg tgggcggtgt    480
gatcgccggc tggaccgagg ccctgcaact catgaacgcg gggctcgaag tggcgcgtgt    540
acgtccccag cgagctggcg tacggtgcgc aaggcgtggg ctcgattccg ccccacagcg    600
tactcgtctt tgacgtggaa ctgctggatg tgctgggcgg tggcgggagt gggggtggcg    660
gctcccacca ccatcaccac catgatgacg atgacaagtc cgtgtcggag atccagctga    720
tgcataatct cggcaagcac ctgaactcga tggagcgcgt cgagtggctc cgcaaaaagc    780
tccaagacgt gcacaacttc taatgatagc tcgag                                815
```

<210> SEQ ID NO 55
<211> LENGTH: 815
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
actagtagga ggtctagaat gtccgaagtt aatctgtcca ccgacgaaac ccgcgtcagc    60
tacggtatcg gccgtcagtt gggcgaccaa ctgcgtgaca acccgccacc gggcgtcagc   120
ctggacgcga tcctggccgg cctgaccgac gcgttcgcag gcaagccaag ccgtgttgac   180
caagagcaaa tggcggccag cttcaaagtg atccgcgaaa tcatgcaagc cgaagccgct   240
gccaaggctg aagctgcagc aggcgctggc ctggctttcc tggcggaaaa cgccaagcgt   300
gatggcatca ccaccctggc ttccggcctg caatttgaag tgctgacggc tggtaccggc   360
gccaagccga cccgtgaaga ccaagtgcgt actcacctac cacggcaccc tgatcgacgg   420
cactgtgttc gacagctcct acgagcgcgg ccagcctgca gaattcccgg ttggcggcgt   480
gatcgccggc tggaccgaag ccctgcaact gatgaatgcc gggcagcaaa tggcgcgtgt   540
acgtgccgag cgaactggct tacggcgctc aaggcgttgg cagcatcccg ccgcacagcg   600
ttctggtatt cgacgtcgag ctgctcgacg ttctgggtgg gggtgggtcg ggtggtggtg   660
ggtcgcatca tcatcaccac cacgatgatg atgataagag tgtctcggag attcagctca   720
tgcacaacct cggtaagcat ctcaactcga tggagcgggt agagtggctc cggaagaaac   780
tccaagatgt gcacaacttt taatgatagc tcgag                              815
```

<210> SEQ ID NO 56
<211> LENGTH: 847
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
actagtagga ggtctagaat gtccaccccc ctgaagattg attttgtctc cgacgtatcg    60
tgcccgtggt gtatcatcgg cctgcgtggc ctgactgaag ccctcgacca actgggcagc   120
gaagtccagg ccgagatcca cttccaaccg tttgagctga accccaacat gcctgccgag   180
ggccaaaaca tcgtggagca tatcacggag aagtacggca gcaccgccga ggaatcgcag   240
gcgaaccgtg cgcggatccg ggatatgggt ccgcactcgg gttcgcgttc cgcacggacg   300
gccagtcgcg catctacaat actttcgatg cccaccggct cctgcattgg gccggtctgg   360
aaggcctgca atacaacctg aaagaagcgc tgttcaaggc ctacttctcg gacggccaag   420
acccgtcgga ccacgcgacc ctcgcgatca tcgccgagag tgtagggctg gacttggccc   480
gcgcggccga aattctcgcg agcgacgagt atgccgcgga agtccgggag caagagcagc   540
tctgggtgag ccgcggtgtg agcagcgtcc ccaccatcgt gttcaacgat cagtacgccg   600
tgagcggtgg ccaacccgcg gaagccttcg tgggcgcgat ccgccagaca tcaacgagtc   660
aaagtcgggc ggtggcggca gcggcggtgg tggcagccat caccatcatc accacgacga   720
cgatgataag tccgtgtcgg agatccaact gatgcacaat ctcgggaagc acctgaacag   780
catggagcgc gtcgaatggc tgcgcaagaa actgcaagac gtgcacaact tttaatgata   840
gctcgag                                                              847
```

<210> SEQ ID NO 57
<211> LENGTH: 848
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
actagtagga ggtctagaat gagtactccc ctgaaaatcg atttcgtcag cgacgtatcc    60
tgcccctggt gcatcatcgg cctgcgcggc ttgaccgaag ccctcgacca gctcggcagc   120
gaggtgcagg ccgagattca ttttcaaccg ttcgaactga acccgaacat gcccgccgaa   180
ggtcagaaca tcgtcgagca cattaccgaa aagtacggct ccacggctga agagtcccag   240
gctaatcgtg cgcgtatccg tgacatgggc ccgcgttggg ctttgctttt cgcaccgatg   300
gccagagccg tatctacaac accttcgacg cgcaccgtct gttgcactgg gccgggttgg   360
aaggcttgca gtacaacctc aaggaagcgc tgttcaaggc gtacttcagc gatggccagg   420
accttccga ccacgcgacc ttggcgatca tcgccgaaag cgtcgggctg gaccttgcgc    480
gcgccgccga gattcttgcc agcgatgaat acgccgccga ggtccgcgag caggagcagc   540
tgtgggtttc ccgtggggtg agttcggtgc cgaccattgt cttcaatgac caatatgcgg   600
tgagcggtgg gcaaccggct gaagccttcg tgggtgcgat tcgccagatc atcaacgaat   660
ccaaatccgg tggtggcggc tcgggcggtg gtggctcgca tcatcatcac caccacgatg   720
acgatgacaa gagcgtatcg gagatccaac tcatgcacaa cctgggcaag cacctcaact   780
cgatggagcg ggtggagtgg ctgcggaaga aactgcaaga cgtgcataac ttctaatgat   840
agctcgag                                                            848
```

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58

```
actagtagga ggtctaga                                                  18
```

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Gly Gly Gly Gly Ser Gly Gly Gly Gly Ser
1               5                   10

<210> SEQ ID NO 60
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60

```
aggagg                                                               6
```

<210> SEQ ID NO 61
<211> LENGTH: 100
<212> TYPE: PRT
<213> ORGANISM: Pseudomonas fluorescens

<400> SEQUENCE: 61

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu
            100
```

<210> SEQ ID NO 62
<211> LENGTH: 50
<212> TYPE: PRT
<213> ORGANISM: Pseudomonas fluorescens

<400> SEQUENCE: 62

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro
    50
```

<210> SEQ ID NO 63
<211> LENGTH: 100
<212> TYPE: PRT
<213> ORGANISM: Pseudomonas fluorescens

<400> SEQUENCE: 63

```
Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr
            100
```

<210> SEQ ID NO 64
<211> LENGTH: 50
<212> TYPE: PRT
<213> ORGANISM: Pseudomonas fluorescens

<400> SEQUENCE: 64

```
Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
            35                  40                  45

Pro Asn
    50

<210> SEQ ID NO 65
<211> LENGTH: 248
<212> TYPE: PRT
<213> ORGANISM: Pseudomonas fluorescens

<400> SEQUENCE: 65

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
            35                  40                  45

Asn Asn Gly Thr Leu Pro Ala Leu Val Gln Ser Trp Ile Asp Thr Gly
        50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro
                245

<210> SEQ ID NO 66
<211> LENGTH: 99
<212> TYPE: PRT
<213> ORGANISM: Pseudomonas fluorescens

<400> SEQUENCE: 66

Met Ser Cys Thr Arg Ala Phe Lys Pro Leu Leu Leu Ile Gly Leu Ala
1               5                   10                  15
```

-continued

```
Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr
```

<210> SEQ ID NO 67
<211> LENGTH: 50
<212> TYPE: PRT
<213> ORGANISM: Pseudomonas fluorescens

<400> SEQUENCE: 67

```
Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn
    50
```

<210> SEQ ID NO 68
<211> LENGTH: 564
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
atatgctctt caaagatgac tcctctgggt cctgcaagta gtctgccgca aagttttctc      60
ctgaagtgcc tggaacaggt gcgcaaaatt cagggcgacg gcgcagcact gcaggaaaaa     120
ctgtgcgcga cctataagtt gtgccacccc gaagaactgg tgctgctggg ccatagcctg     180
gggattccat gggcgccgct gtcgtcctgt cctagtcaag ccttgcaatt ggccggttgc     240
ctctcgcaac tgcatagcgg cctgttcctg taccaaggcc tgctgcaggc cttggaaggc     300
atctccccgg aactgggccc gacgctggat accctgcaac tggacgtagc agatttcgcc     360
acgaccatct ggcagcagat ggaagaactg ggcatggccc cggccctcca gcccacgcaa     420
ggcgcgatgc ctgcattcgc ctcggcgttt caacgccgtg cgggtggcgt gctggtagcc     480
agccatttgc agagctttct ggaggtgagc tatcgcgtcc tccgtcatct cgcccaaccg     540
tgataatagt tcagaagagc atat                                             564
```

<210> SEQ ID NO 69
<211> LENGTH: 175
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 70
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
        35                  40                  45

Ser Met Phe Leu Glu Thr Val Glu Val Asp Gly Glu Gln Val Pro Arg
50                  55                  60

Phe Ala Leu Val Thr Ala Glu Pro Ser Leu Phe Thr Gly Gln Gly Gly
65                  70                  75                  80

Gly Gly Ser Gly Gly Gly Gly Ser His His His His His Asp Asp
                85                  90                  95

Asp Asp Lys Met Thr Pro Leu Gly Pro Ala Ser Ser Leu Pro Gln Ser
            100                 105                 110

Phe Leu Leu Lys Cys Leu Glu Gln Val Arg Lys Ile Gln Gly Asp Gly
        115                 120                 125

Ala Ala Leu Gln Glu Lys Leu Cys Ala Thr Tyr Lys Leu Cys His Pro
        130                 135                 140

Glu Glu Leu Val Leu Leu Gly His Ser Leu Gly Ile Pro Trp Ala Pro
145                 150                 155                 160

Leu Ser Ser Cys Pro Ser Gln Ala Leu Gln Leu Ala Gly Cys Leu Ser
                165                 170                 175

Gln Leu His Ser Gly Leu Phe Leu Tyr Gln Gly Leu Leu Gln Ala Leu
```

```
                180             185              190
Glu Gly Ile Ser Pro Glu Leu Gly Pro Thr Leu Asp Thr Leu Gln Leu
            195                 200             205

Asp Val Ala Asp Phe Ala Thr Thr Ile Trp Gln Gln Met Glu Glu Leu
        210                 215             220

Gly Met Ala Pro Ala Leu Gln Pro Thr Gln Gly Ala Met Pro Ala Phe
225                 230             235                 240

Ala Ser Ala Phe Gln Arg Arg Ala Gly Gly Val Leu Val Ala Ser His
            245                 250             255

Leu Gln Ser Phe Leu Glu Val Ser Tyr Arg Val Leu Arg His Leu Ala
            260                 265             270

Gln Pro

<210> SEQ ID NO 71
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro Gly Gly Gly Ser Gly Gly Gly
                245                 250                 255

Gly Ser His His His His His His Asp Asp Asp Asp Lys Met Thr Pro
```

```
                260                 265                 270
Leu Gly Pro Ala Ser Ser Leu Pro Gln Ser Phe Leu Leu Lys Cys Leu
            275                 280                 285

Glu Gln Val Arg Lys Ile Gln Gly Asp Gly Ala Ala Leu Gln Glu Lys
        290                 295                 300

Leu Cys Ala Thr Tyr Lys Leu Cys His Pro Glu Glu Leu Val Leu Leu
305                 310                 315                 320

Gly His Ser Leu Gly Ile Pro Trp Ala Pro Leu Ser Ser Cys Pro Ser
                325                 330                 335

Gln Ala Leu Gln Leu Ala Gly Cys Leu Ser Gln Leu His Ser Gly Leu
            340                 345                 350

Phe Leu Tyr Gln Gly Leu Leu Gln Ala Leu Glu Gly Ile Ser Pro Glu
        355                 360                 365

Leu Gly Pro Thr Leu Asp Thr Leu Gln Leu Asp Val Ala Asp Phe Ala
370                 375                 380

Thr Thr Ile Trp Gln Gln Met Glu Glu Leu Gly Met Ala Pro Ala Leu
385                 390                 395                 400

Gln Pro Thr Gln Gly Ala Met Pro Ala Phe Ala Ser Ala Phe Gln Arg
                405                 410                 415

Arg Ala Gly Gly Val Leu Val Ala Ser His Leu Gln Ser Phe Leu Glu
            420                 425                 430

Val Ser Tyr Arg Val Leu Arg His Leu Ala Gln Pro
        435                 440

<210> SEQ ID NO 72
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
            35                  40                  45

Asn Asn Gly Thr Leu Pro Ala Leu Val Gln Ser Trp Ile Asp Thr Gly
        50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Ser His His
            100                 105                 110

His His His His Asp Asp Asp Lys Met Thr Pro Leu Gly Pro Ala
        115                 120                 125

Ser Ser Leu Pro Gln Ser Phe Leu Leu Lys Cys Leu Glu Gln Val Arg
130                 135                 140

Lys Ile Gln Gly Asp Gly Ala Ala Leu Gln Glu Lys Leu Cys Ala Thr
145                 150                 155                 160

Tyr Lys Leu Cys His Pro Glu Glu Leu Val Leu Leu Gly His Ser Leu
                165                 170                 175
```

```
Gly Ile Pro Trp Ala Pro Leu Ser Ser Cys Pro Ser Gln Ala Leu Gln
            180                 185                 190

Leu Ala Gly Cys Leu Ser Gln Leu His Ser Gly Leu Phe Leu Tyr Gln
        195                 200                 205

Gly Leu Leu Gln Ala Leu Glu Gly Ile Ser Pro Glu Leu Gly Pro Thr
    210                 215                 220

Leu Asp Thr Leu Gln Leu Asp Val Ala Asp Phe Ala Thr Thr Ile Trp
225                 230                 235                 240

Gln Gln Met Glu Glu Leu Gly Met Ala Pro Ala Leu Gln Pro Thr Gln
                245                 250                 255

Gly Ala Met Pro Ala Phe Ala Ser Ala Phe Gln Arg Arg Ala Gly Gly
            260                 265                 270

Val Leu Val Ala Ser His Leu Gln Ser Phe Leu Glu Val Ser Tyr Arg
        275                 280                 285

Val Leu Arg His Leu Ala Gln Pro
    290                 295

<210> SEQ ID NO 73
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Gly Gly Gly Ser Gly Gly Gly Gly Ser His His His His
    50                  55                  60

His His Asp Asp Asp Asp Lys Met Thr Pro Leu Gly Pro Ala Ser Ser
65                  70                  75                  80

Leu Pro Gln Ser Phe Leu Leu Lys Cys Leu Glu Gln Val Arg Lys Ile
                85                  90                  95

Gln Gly Asp Gly Ala Ala Leu Gln Glu Lys Leu Cys Ala Thr Tyr Lys
            100                 105                 110

Leu Cys His Pro Glu Glu Leu Val Leu Leu Gly His Ser Leu Gly Ile
        115                 120                 125

Pro Trp Ala Pro Leu Ser Ser Cys Pro Ser Gln Ala Leu Gln Leu Ala
    130                 135                 140

Gly Cys Leu Ser Gln Leu His Ser Gly Leu Phe Leu Tyr Gln Gly Leu
145                 150                 155                 160

Leu Gln Ala Leu Glu Gly Ile Ser Pro Glu Leu Gly Pro Thr Leu Asp
                165                 170                 175

Thr Leu Gln Leu Asp Val Ala Asp Phe Ala Thr Thr Ile Trp Gln Gln
            180                 185                 190

Met Glu Glu Leu Gly Met Ala Pro Ala Leu Gln Pro Thr Gln Gly Ala
        195                 200                 205

Met Pro Ala Phe Ala Ser Ala Phe Gln Arg Arg Ala Gly Gly Val Leu
    210                 215                 220

Val Ala Ser His Leu Gln Ser Phe Leu Glu Val Ser Tyr Arg Val Leu
225                 230                 235                 240
```

Arg His Leu Ala Gln Pro
            245

<210> SEQ ID NO 74
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Ser Tyr Glu Arg Gly
    130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
        195                 200                 205

Gly Ser Gly Gly Gly Ser His His His His His Asp Asp Asp
    210                 215                 220

Asp Lys Met Thr Pro Leu Gly Pro Ala Ser Ser Leu Pro Gln Ser Phe
225                 230                 235                 240

Leu Leu Lys Cys Leu Glu Gln Val Arg Lys Ile Gln Gly Asp Gly Ala
                245                 250                 255

Ala Leu Gln Glu Lys Leu Cys Ala Thr Tyr Lys Leu Cys His Pro Glu
            260                 265                 270

Glu Leu Val Leu Leu Gly His Ser Leu Gly Ile Pro Trp Ala Pro Leu
        275                 280                 285

Ser Ser Cys Pro Ser Gln Ala Leu Gln Leu Ala Gly Cys Leu Ser Gln
    290                 295                 300

Leu His Ser Gly Leu Phe Leu Tyr Gln Gly Leu Leu Gln Ala Leu Glu
305                 310                 315                 320

Gly Ile Ser Pro Glu Leu Gly Pro Thr Leu Asp Thr Leu Gln Leu Asp
                325                 330                 335

Val Ala Asp Phe Ala Thr Thr Ile Trp Gln Gln Met Glu Glu Leu Gly

```
              340                 345                 350
Met Ala Pro Ala Leu Gln Pro Thr Gln Gly Ala Met Pro Ala Phe Ala
            355                 360                 365

Ser Ala Phe Gln Arg Arg Ala Gly Gly Val Leu Val Ala Ser His Leu
        370                 375                 380

Gln Ser Phe Leu Glu Val Ser Tyr Arg Val Leu Arg His Leu Ala Gln
385                 390                 395                 400

Pro

<210> SEQ ID NO 75
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
            100                 105                 110

His His His His Asp Asp Asp Lys Met Thr Pro Leu Gly Pro Ala
        115                 120                 125

Ser Ser Leu Pro Gln Ser Phe Leu Leu Lys Cys Leu Glu Gln Val Arg
130                 135                 140

Lys Ile Gln Gly Asp Gly Ala Ala Leu Gln Glu Lys Leu Cys Ala Thr
145                 150                 155                 160

Tyr Lys Leu Cys His Pro Glu Glu Leu Val Leu Leu Gly His Ser Leu
                165                 170                 175

Gly Ile Pro Trp Ala Pro Leu Ser Ser Cys Pro Ser Gln Ala Leu Gln
            180                 185                 190

Leu Ala Gly Cys Leu Ser Gln Leu His Ser Gly Leu Phe Leu Tyr Gln
        195                 200                 205

Gly Leu Leu Gln Ala Leu Glu Gly Ile Ser Pro Glu Leu Gly Pro Thr
    210                 215                 220

Leu Asp Thr Leu Gln Leu Asp Val Ala Asp Phe Ala Thr Thr Ile Trp
225                 230                 235                 240

Gln Gln Met Glu Glu Leu Gly Met Ala Pro Ala Leu Gln Pro Thr Gln
                245                 250                 255

Gly Ala Met Pro Ala Phe Ala Ser Ala Phe Gln Arg Arg Ala Gly Gly
            260                 265                 270

Val Leu Val Ala Ser His Leu Gln Ser Phe Leu Glu Val Ser Tyr Arg
        275                 280                 285

Val Leu Arg His Leu Ala Gln Pro
```

```
                 290                 295

<210> SEQ ID NO 76
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Gly Gly Gly Gly Ser Gly Gly Gly Gly Ser His His His His
    50                  55                  60

His His Asp Asp Asp Lys Met Thr Pro Leu Gly Pro Ala Ser Ser
65                  70                  75                  80

Leu Pro Gln Ser Phe Leu Leu Lys Cys Leu Glu Gln Val Arg Lys Ile
                85                  90                  95

Gln Gly Asp Gly Ala Ala Leu Gln Glu Lys Leu Cys Ala Thr Tyr Lys
            100                 105                 110

Leu Cys His Pro Glu Glu Leu Val Leu Leu Gly His Ser Leu Gly Ile
        115                 120                 125

Pro Trp Ala Pro Leu Ser Ser Cys Pro Ser Gln Ala Leu Gln Leu Ala
    130                 135                 140

Gly Cys Leu Ser Gln Leu His Ser Gly Leu Phe Leu Tyr Gln Gly Leu
145                 150                 155                 160

Leu Gln Ala Leu Glu Gly Ile Ser Pro Glu Leu Gly Pro Thr Leu Asp
                165                 170                 175

Thr Leu Gln Leu Asp Val Ala Asp Phe Ala Thr Thr Ile Trp Gln Gln
            180                 185                 190

Met Glu Glu Leu Gly Met Ala Pro Ala Leu Gln Pro Thr Gln Gly Ala
        195                 200                 205

Met Pro Ala Phe Ala Ser Ala Phe Gln Arg Arg Ala Gly Gly Val Leu
    210                 215                 220

Val Ala Ser His Leu Gln Ser Phe Leu Glu Val Ser Tyr Arg Val Leu
225                 230                 235                 240

Arg His Leu Ala Gln Pro
                245

<210> SEQ ID NO 77
<211> LENGTH: 413
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
```

```
              35                  40                  45
Pro Asn Met Pro Ala Glu Gly Gln Asn Ile Val Glu His Ile Thr Glu
 50                  55                  60

Lys Tyr Gly Ser Thr Ala Glu Glu Ser Gln Ala Asn Arg Ala Arg Ile
 65                  70                  75                  80

Arg Asp Met Gly Ala Ala Leu Gly Phe Ala Phe Arg Thr Asp Gly Gln
                     85                  90                  95

Ser Arg Ile Tyr Asn Thr Phe Asp Ala His Arg Leu Leu His Trp Ala
                    100                 105                 110

Gly Leu Glu Gly Leu Gln Tyr Asn Leu Lys Glu Ala Leu Phe Lys Ala
                    115                 120                 125

Tyr Phe Ser Asp Gly Gln Asp Pro Ser Asp His Ala Thr Leu Ala Ile
                    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                    165                 170                 175

Val Ser Arg Gly Val Ser Ser Val Pro Thr Ile Val Phe Asn Asp Gln
                    180                 185                 190

Tyr Ala Val Ser Gly Gly Gln Pro Ala Glu Ala Phe Val Gly Ala Ile
                    195                 200                 205

Arg Gln Ile Ile Asn Glu Ser Lys Ser Gly Gly Gly Ser Gly Gly
                    210                 215                 220

Gly Gly Ser His His His His His His Asp Asp Asp Lys Met Thr
225                 230                 235                 240

Pro Leu Gly Pro Ala Ser Ser Leu Pro Gln Ser Phe Leu Leu Lys Cys
                    245                 250                 255

Leu Glu Gln Val Arg Lys Ile Gln Gly Asp Gly Ala Ala Leu Gln Glu
                    260                 265                 270

Lys Leu Cys Ala Thr Tyr Lys Leu Cys His Pro Glu Glu Leu Val Leu
                    275                 280                 285

Leu Gly His Ser Leu Gly Ile Pro Trp Ala Pro Leu Ser Ser Cys Pro
                    290                 295                 300

Ser Gln Ala Leu Gln Leu Ala Gly Cys Leu Ser Gln Leu His Ser Gly
305                 310                 315                 320

Leu Phe Leu Tyr Gln Gly Leu Leu Gln Ala Leu Glu Gly Ile Ser Pro
                    325                 330                 335

Glu Leu Gly Pro Thr Leu Asp Thr Leu Gln Leu Asp Val Ala Asp Phe
                    340                 345                 350

Ala Thr Thr Ile Trp Gln Gln Met Glu Glu Leu Gly Met Ala Pro Ala
                    355                 360                 365

Leu Gln Pro Thr Gln Gly Ala Met Pro Ala Phe Ala Ser Ala Phe Gln
                    370                 375                 380

Arg Arg Ala Gly Gly Val Leu Val Ala Ser His Leu Gln Ser Phe Leu
385                 390                 395                 400

Glu Val Ser Tyr Arg Val Leu Arg His Leu Ala Gln Pro
                    405                 410

<210> SEQ ID NO 78
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 78

```
Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Gly Gly Gly Ser Gly Gly Gly Ser His His
            100                 105                 110

His His His His Asp Asp Asp Lys Met Thr Pro Leu Gly Pro Ala
        115                 120                 125

Ser Ser Leu Pro Gln Ser Phe Leu Leu Lys Cys Leu Glu Gln Val Arg
130                 135                 140

Lys Ile Gln Gly Asp Gly Ala Ala Leu Gln Glu Lys Leu Cys Ala Thr
145                 150                 155                 160

Tyr Lys Leu Cys His Pro Glu Glu Leu Val Leu Leu Gly His Ser Leu
                165                 170                 175

Gly Ile Pro Trp Ala Pro Leu Ser Ser Cys Pro Ser Gln Ala Leu Gln
            180                 185                 190

Leu Ala Gly Cys Leu Ser Gln Leu His Ser Gly Leu Phe Leu Tyr Gln
        195                 200                 205

Gly Leu Leu Gln Ala Leu Glu Gly Ile Ser Pro Glu Leu Gly Pro Thr
    210                 215                 220

Leu Asp Thr Leu Gln Leu Asp Val Ala Asp Phe Ala Thr Thr Ile Trp
225                 230                 235                 240

Gln Gln Met Glu Glu Leu Gly Met Ala Pro Ala Leu Gln Pro Thr Gln
                245                 250                 255

Gly Ala Met Pro Ala Phe Ala Ser Ala Phe Gln Arg Arg Ala Gly Gly
            260                 265                 270

Val Leu Val Ala Ser His Leu Gln Ser Phe Leu Glu Val Ser Tyr Arg
        275                 280                 285

Val Leu Arg His Leu Ala Gln Pro
    290                 295
```

<210> SEQ ID NO 79
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45
```

Pro Asn Gly Gly Gly Ser Gly Gly Gly Ser His His His
    50                  55                  60

His His Asp Asp Asp Lys Met Thr Pro Leu Gly Pro Ala Ser Ser
65          70                  75                  80

Leu Pro Gln Ser Phe Leu Leu Lys Cys Leu Glu Gln Val Arg Lys Ile
                85                  90                  95

Gln Gly Asp Gly Ala Ala Leu Gln Glu Lys Leu Cys Ala Thr Tyr Lys
            100                 105                 110

Leu Cys His Pro Glu Glu Leu Val Leu Leu Gly His Ser Leu Gly Ile
        115                 120                 125

Pro Trp Ala Pro Leu Ser Ser Cys Pro Ser Gln Ala Leu Gln Leu Ala
    130                 135                 140

Gly Cys Leu Ser Gln Leu His Ser Gly Leu Phe Leu Tyr Gln Gly Leu
145                 150                 155                 160

Leu Gln Ala Leu Glu Gly Ile Ser Pro Glu Leu Gly Pro Thr Leu Asp
                165                 170                 175

Thr Leu Gln Leu Asp Val Ala Asp Phe Ala Thr Thr Ile Trp Gln Gln
            180                 185                 190

Met Glu Glu Leu Gly Met Ala Pro Ala Leu Gln Pro Thr Gln Gly Ala
        195                 200                 205

Met Pro Ala Phe Ala Ser Ala Phe Gln Arg Arg Ala Gly Gly Val Leu
    210                 215                 220

Val Ala Ser His Leu Gln Ser Phe Leu Glu Val Ser Tyr Arg Val Leu
225                 230                 235                 240

Arg His Leu Ala Gln Pro
            245

<210> SEQ ID NO 80
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
atatgctctt caaagtttgt aaaccaacac ctgtgtggct cccatctcgt cgaagccctg    60
tacctcgtct gcggtgagcg cggcttcttc tacactccca agacccggcg tgaagccgag   120
gacttgcaag tgggccaagt ggagctcggc ggtggtcccg gtgcgggcag cctgcaaccg   180
ctcgcgctgg aagggtcgct gcagaagcgc ggcatcgtgg agcagtgctg cacgagcatc   240
tgctcgctgt accagctgga gaactactgc ggctgataat agttcagaag agcatat     297

<210> SEQ ID NO 81
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
atatgctctt caaagttcgt aaaccaacat ctgtgtggct cccacctcgt cgaagccctg    60
tacctcgtct gcggtgagcg cggcttcttt tacacgccca agacccggcg tgacgtgccg   120
caagtggagc tggggggtgg ccccggcgcg ggtagcctgc agccgctggc cctggaaggc   180
tcgctccaaa agcgcggcat cgtggagcag tgctgcacta gcatctgctc gctgtaccag   240

```
ttggagaact actgcggctg ataatagttc agaagagcat at              282
```

<210> SEQ ID NO 82
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
atatgctctt caaagttcgt caaccaacac ctgtgcggct cccatctcgt cgaagccctg    60
tacctcgtat gcggtgagcg cgggttttc tacacgccca agactcgccg ggacgtgccg    120
caagtggagc tgggcggtgg cccgggcgcg ggctcgctgc agccctggc gctgaaggc     180 agcttgcaag cccgtggcat cgtggagcag tgctgtacct cgatctgcag cctctaccag    240
ctggagaact actgcggttg ataatagttc agaagagcat at                     282
```

<210> SEQ ID NO 83
<211> LENGTH: 231
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
atatgctctt caaagttcgt caaccaacac ctgtgtggct cccatctcgt cgaagcgctg    60
tacctcgtat gcggtgagcg gggtttcttt tacacgccca agacccgtcg cgaggccgag    120
gaccagggct cgctgcagaa gcgcgggatc gtggaacaat gctgcactag catctgcagc    180
ctgtaccaac tggagaacta ctgcggctga taatagttca gaagagcata t            231
```

<210> SEQ ID NO 84
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
atatgctctt cacgattcgt caaccaacac ctctgcggca gccatctcgt cgaagccctc    60
tacctcgtat gtggcgaacg gggcttcttt tacaccccca agacgcgccg tgaggccgag    120
gacttgcaag tgggccaagt ggagctgggc ggtggtcccg gtgcgggctc gctgcaaccg    180
ctggcgctgg aagggtcgct gcagaagcgc ggcatcgtgg agcagtgctg cactagcatc    240
tgctccctgt accagctgga gaactactgc ggctgataat agttcagaag agcatat      297
```

<210> SEQ ID NO 85
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atatgctctt cacgattcgt aaaccaacac ctctgcggct cccatttggt cgaagccctc    60
tacctcgtct gcggtgagcg ggggttttc tacactccca agacccgtcg cgacgtgccg    120
```

```
caagtggagc tgggcggtgg ccccggcgcc ggctcgctgc aaccgctggc gctggaaggt    180
tcgctgcaga agcgcggcat cgtggagcag tgctgcacga gcatctgcag cctgtaccag    240
ctggagaact actgtggctg ataatagttc agaagagcat at                      282
```

<210> SEQ ID NO 86
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
atatgctctt cacgattcgt caaccaacat ctctgcggct cccacctggt cgaagccctc     60
tacctcgtat gcggcgaacg cggcttttc tacaccccca agactcggcg cgacgtgccg    120
caagtggagc tgggcggtgg tcccggtgcg ggctcgctgc agccgttggc cctggaaggg    180
agcctgcagg cgcgtggcat cgtggagcaa tgctgcacgt cgatctgtag cctgtaccag    240
ctggagaact actgcggctg ataatagttc agaagagcat at                      282
```

<210> SEQ ID NO 87
<211> LENGTH: 231
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
atatgctctt cacgattcgt caaccaacac ctgtgcggct cccatctggt cgaagccctc     60
tacctcgtat gcggcgagcg cggcttcttt tacaccccca agacgcgtcg ggaagcggaa    120
gatcagggta gcctgcaaaa gcgcggtatc gtggagcagt gctgcacttc gatctgtagc    180
ctgtaccaac tggagaacta ctgcggggtga taatagttca gaagagcata t            231
```

<210> SEQ ID NO 88
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Gly
                85
```

<210> SEQ ID NO 89
<211> LENGTH: 81
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 89

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Asp Val Pro Gln Val Glu Leu Gly Gly Pro Gly Ala Gly Ser Leu
        35                  40                  45

Gln Pro Leu Ala Leu Glu Gly Ser Leu Gln Lys Arg Gly Ile Val Glu
    50                  55                  60

Gln Cys Cys Thr Ser Ile Cys Ser Leu Tyr Gln Leu Glu Asn Tyr Cys
65                  70                  75                  80

Gly
```

<210> SEQ ID NO 90
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Asp Val Pro Gln Val Glu Leu Gly Gly Pro Gly Ala Gly Ser Leu
        35                  40                  45

Gln Pro Leu Ala Leu Glu Gly Ser Leu Gln Ala Arg Gly Ile Val Glu
    50                  55                  60

Gln Cys Cys Thr Ser Ile Cys Ser Leu Tyr Gln Leu Glu Asn Tyr Cys
65                  70                  75                  80

Gly
```

<210> SEQ ID NO 91
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Gln Gly Ser Leu Gln Lys Arg Gly Ile Val Glu Gln
            35                  40                  45

Cys Cys Thr Ser Ile Cys Ser Leu Tyr Gln Leu Glu Asn Tyr Cys Gly
        50                  55                  60
```

<210> SEQ ID NO 92
<211> LENGTH: 21
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 92

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 94
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr Glu Ala
            20                  25                  30

Glu Asp Leu Gln Val Gly Gln Val Glu Leu Gly Gly Gly Pro Gly Ala
        35                  40                  45

Gly Ser Leu Gln Pro Leu Ala Leu Glu Gly Ser Leu Gln Lys Arg Gly
    50                  55                  60

Ile Val Glu Gln Cys Cys Thr Ser Ile Cys Ser Leu Tyr Gln Leu Glu
65                  70                  75                  80

Asn Tyr Cys Asn

<210> SEQ ID NO 95
<211> LENGTH: 21
<212> TYPE: PRT
<213> ORGANISM: Homo sapiens

<400> SEQUENCE: 95

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 96
<211> LENGTH: 30
<212> TYPE: PRT
<213> ORGANISM: Homo sapiens

<400> SEQUENCE: 96

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 97
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln Lys
            20                  25                  30

Arg

<210> SEQ ID NO 98
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asp Val Pro Gln Val Glu Leu Gly Gly Gly Pro Gly Ala Gly Ser Leu
1               5                   10                  15

Gln Pro Leu Ala Leu Glu Gly Ser Leu Gln Lys Arg
            20                  25

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Val Pro Gln Val Glu Leu Gly Gly Gly Pro Gly Ala Gly Ser Leu
1               5                   10                  15

Gln Pro Leu Ala Leu Glu Gly Ser Leu Gln Ala Arg
            20                  25

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Ala Glu Asp Gln Gly Ser Leu Gln Lys Arg
1               5                   10

<210> SEQ ID NO 101
<211> LENGTH: 95
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 101

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
            35                  40                  45

Ser Met Phe Leu Glu Thr Val Glu Val Asp Gly Glu Gln Val Pro Arg
50                  55                  60

Phe Ala Leu Val Thr Ala Glu Pro Ser Leu Phe Thr Gly Gln Gly Gly
65                  70                  75                  80

Gly Gly Ser Gly Gly Gly Gly Ser His His His His His Arg
                85                  90                  95

<210> SEQ ID NO 102
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
            35                  40                  45

Asn Asn Gly Thr Leu Pro Ala Leu Val Gln Ser Trp Ile Asp Thr Gly
50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
            85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
            115                 120                 125

Asn Thr Leu Gln Met Ala Phe Arg Ser Arg Ile Lys Leu Phe Tyr Arg
130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
            165                 170                 175

Tyr Pro Ser Ala Phe His Val Ser Leu Ile Glu Leu Asp Leu Val Ala
            180                 185                 190

Gly Asn Gln Arg Tyr Arg Ser Glu Asp Gly Met Val Gly Pro Gly Glu
            195                 200                 205

Thr Arg Gln Phe Ala Leu Pro Thr Leu Lys Ala Arg Pro Ser Ser Gln
            210                 215                 220

Ala Gln Val Glu Phe Ser Ala Ile Asn Asp Tyr Gly Ala Leu Val Pro
225                 230                 235                 240
```

```
Thr Arg Asn Thr Leu Gln Pro Gly Gly Gly Ser Gly Gly Gly
            245                 250                 255

Ser His His His His His Arg
            260

<210> SEQ ID NO 103
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro Gly Gly Gly Ser Gly Gly Gly Gly
                245                 250                 255

Gly Ser His His His His His His Arg
            260                 265

<210> SEQ ID NO 104
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104
```

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Gly Ser His His
                100                 105                 110

His His His His Arg
        115

<210> SEQ ID NO 105
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Gly Gly Gly Ser Gly Gly Gly Gly Ser His His His His
    50                  55                  60

His His Arg
65

<210> SEQ ID NO 106
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Ser Tyr Glu Arg Gly
    130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
        195                 200                 205

Gly Ser Gly Gly Gly Gly Ser His His His His His His Arg
    210                 215                 220

<210> SEQ ID NO 107
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Gly Ser Gly Gly Gly Ser His His
            100                 105                 110

His His His Arg
        115

<210> SEQ ID NO 108
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Gly Gly Gly Ser Gly Gly Gly Ser His His His His
        50                  55                  60

His His Arg
 65

<210> SEQ ID NO 109
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Ser Thr Pro Leu Lys Ile Asp Phe Val Ser Asp Val Ser Cys Pro
  1               5                  10                  15

Trp Cys Ile Ile Gly Leu Arg Gly Leu Thr Glu Ala Leu Asp Gln Leu
                 20                  25                  30

Gly Ser Glu Val Gln Ala Glu Ile His Phe Gln Pro Phe Glu Leu Asn
             35                  40                  45

Pro Asn Met Pro Ala Glu Gly Gln Asn Ile Val Glu His Ile Thr Glu
         50                  55                  60

Lys Tyr Gly Ser Thr Ala Glu Glu Ser Gln Ala Asn Arg Ala Arg Ile
 65                  70                  75                  80

Arg Asp Met Gly Ala Ala Leu Gly Phe Ala Phe Arg Thr Asp Gly Gln
                 85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
        115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser Gly Gly Gly Ser Gly Gly
    210                 215                 220

Gly Gly Ser His His His His His His Arg
225                 230

<210> SEQ ID NO 110
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Ser Thr Pro Leu Lys Ile Asp Phe Val Ser Asp Val Ser Cys Pro
  1               5                  10                  15

Trp Cys Ile Ile Gly Leu Arg Gly Leu Thr Glu Ala Leu Asp Gln Leu
                 20                  25                  30

```
Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
 50                  55                  60

Lys Tyr Gly Ser Thr Ala Glu Glu Ser Gln Ala Asn Arg Ala Arg Ile
 65                  70                  75                  80

Arg Asp Met Gly Ala Ala Leu Gly Phe Ala Phe Arg Thr Asp Gly Gln
                 85                  90                  95

Ser Arg Ile Tyr Gly Gly Gly Ser Gly Gly Gly Ser His His
                100                 105                 110

His His His His Arg
            115

<210> SEQ ID NO 111
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Ser Thr Pro Leu Lys Ile Asp Phe Val Ser Asp Val Ser Cys Pro
 1               5                  10                  15

Trp Cys Ile Ile Gly Leu Arg Gly Leu Thr Glu Ala Leu Asp Gln Leu
                20                  25                  30

Gly Ser Glu Val Gln Ala Glu Ile His Phe Gln Pro Phe Glu Leu Asn
        35                  40                  45

Pro Asn Gly Gly Gly Gly Ser Gly Gly Gly Gly Ser His His His His
 50                  55                  60

His His Arg
 65

<210> SEQ ID NO 112
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Lys Val Glu Pro Gly Leu Tyr Gln His Tyr Lys Gly Pro Gln Tyr
 1               5                  10                  15

Arg Val Phe Ser Val Ala Arg His Ser Glu Thr Glu Glu Val Val
                20                  25                  30

Phe Tyr Gln Ala Leu Tyr Gly Tyr Gly Phe Trp Val Arg Pro Leu
        35                  40                  45

Ser Met Phe Leu Glu Thr Val Glu Val Asp Gly Glu Gln Val Pro Arg
 50                  55                  60

Phe Ala Leu Val Thr Ala Glu Pro Ser Leu Phe Thr Gly Gln Gly Gly
 65                  70                  75                  80

Gly Gly Ser Gly Gly Gly Gly Ser His His His His His Asp Asp
                85                  90                  95

Asp Asp Lys

<210> SEQ ID NO 113
<211> LENGTH: 269
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro Gly Gly Gly Ser Gly Gly Gly
                245                 250                 255

Gly Ser His His His His His His Asp Asp Asp Lys
            260                 265

<210> SEQ ID NO 114
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45
```

```
Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
 65                  70                  75                  80

Pro Pro Val Ala Arg Ile Asp Pro Thr Lys Gly Gln Ser Leu Arg Val
                 85                  90                  95

Leu Phe Thr Gly Gly Gly Gly Ser Gly Gly Gly Ser His His
            100                 105                 110

His His His His Asp Asp Asp Lys
            115                 120
```

<210> SEQ ID NO 115
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Met Ser Cys Thr Arg Ala Phe Lys Pro Leu Leu Ile Gly Leu Ala
 1               5                  10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
            35                  40                  45

Asn Asn Gly Gly Gly Gly Ser Gly Gly Gly Ser His His His His
        50                  55                  60

His His Asp Asp Asp Asp Lys
 65                  70
```

<210> SEQ ID NO 116
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Met Ser Glu Val Asn Leu Ser Thr Asp Glu Thr Arg Val Ser Tyr Gly
 1               5                  10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Ser Arg Val Asp Gln Glu Gln Met Ala Ala Ser Phe Lys Val
 50                  55                  60

Ile Arg Glu Ile Met Gln Ala Glu Ala Ala Lys Ala Glu Ala Ala
 65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Ser Tyr Glu Arg Gly
        130                 135                 140
```

```
Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
            165                 170                 175

Ser Glu Leu Ala Tyr Gly Ala Gln Gly Val Gly Ser Ile Pro Pro His
        180                 185                 190

Ser Val Leu Val Phe Asp Val Glu Leu Leu Asp Val Leu Gly Gly Gly
        195                 200                 205

Gly Ser Gly Gly Gly Ser His His His His His Asp Asp Asp
    210                 215                 220

Asp Lys
225

<210> SEQ ID NO 117
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
                100                 105                 110

His His His His Asp Asp Asp Lys
            115                 120

<210> SEQ ID NO 118
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Gly Gly Gly Gly Ser Gly Gly Gly Ser His His His His
    50                  55                  60

His His Asp Asp Asp Asp Lys
65                  70
```

```
<210> SEQ ID NO 119
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
        115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser Gly Gly Gly Ser Gly Gly
    210                 215                 220

Gly Gly Ser His His His His His Asp Asp Asp Lys
225                 230                 235

<210> SEQ ID NO 120
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60
```

```
Lys Tyr Gly Ser Thr Ala Glu Glu Ser Gln Ala Asn Arg Ala Arg Ile
 65                  70                  75                  80

Arg Asp Met Gly Ala Ala Leu Gly Phe Ala Phe Arg Thr Asp Gly Gln
                 85                  90                  95

Ser Arg Ile Tyr Gly Gly Gly Ser Gly Gly Gly Ser His His
            100                 105                 110

His His His His Asp Asp Asp Lys
            115                 120

<210> SEQ ID NO 121
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Ser Thr Pro Leu Lys Ile Asp Phe Val Ser Asp Val Ser Cys Pro
  1               5                  10                  15

Trp Cys Ile Ile Gly Leu Arg Gly Leu Thr Glu Ala Leu Asp Gln Leu
                 20                  25                  30

Gly Ser Glu Val Gln Ala Glu Ile His Phe Gln Pro Phe Glu Leu Asn
             35                  40                  45

Pro Asn Gly Gly Gly Gly Ser Gly Gly Gly Gly Ser His His His His
 50                  55                  60

His His Asp Asp Asp Asp Lys
 65                  70

<210> SEQ ID NO 122
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Lys Val Glu Pro Gly Leu Tyr Gln His Tyr Lys Gly Pro Gln Tyr
  1               5                  10                  15

Arg Val Phe Ser Val Ala Arg His Ser Glu Thr Glu Glu Val Val
                 20                  25                  30

Phe Tyr Gln Ala Leu Tyr Gly Glu Tyr Gly Phe Trp Val Arg Pro Leu
             35                  40                  45

Ser Met Phe Leu Glu Thr Val Glu Val Asp Gly Glu Gln Val Pro Arg
 50                  55                  60

Phe Ala Leu Val Thr Ala Glu Pro Ser Leu Phe Thr Gly Gln Gly Gly
 65                  70                  75                  80

Gly Gly Ser Gly Gly Gly Gly Ser His His His His His Asp Asp
                 85                  90                  95

Asp Asp Lys Phe Val Asn Gln His Leu Cys Gly Ser His Leu Val Glu
            100                 105                 110

Ala Leu Tyr Leu Val Cys Gly Glu Arg Gly Phe Phe Tyr Thr Pro Lys
            115                 120                 125

Thr Arg Arg Glu Ala Glu Asp Leu Gln Val Gly Gln Val Glu Leu Gly
            130                 135                 140

Gly Gly Pro Gly Ala Gly Ser Leu Gln Pro Leu Ala Leu Glu Gly Ser
145                 150                 155                 160
```

```
Leu Gln Lys Arg Gly Ile Val Glu Gln Cys Cys Thr Ser Ile Cys Ser
                165                 170                 175

Leu Tyr Gln Leu Glu Asn Tyr Cys Gly
            180                 185

<210> SEQ ID NO 123
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
            35                  40                  45

Ser Met Phe Leu Glu Thr Val Glu Val Asp Gly Glu Gln Val Pro Arg
    50                  55                  60

Phe Ala Leu Val Thr Ala Glu Pro Ser Leu Phe Thr Gly Gln Gly Gly
65                  70                  75                  80

Gly Gly Ser Gly Gly Gly Ser His His His His His Asp Asp
                85                  90                  95

Asp Asp Lys Phe Val Asn Gln His Leu Cys Gly Ser His Leu Val Glu
                100                 105                 110

Ala Leu Tyr Leu Val Cys Gly Glu Arg Gly Phe Phe Tyr Thr Pro Lys
            115                 120                 125

Thr Arg Arg Asp Val Pro Gln Val Glu Leu Gly Gly Pro Gly Ala
            130                 135                 140

Gly Ser Leu Gln Pro Leu Ala Leu Glu Gly Ser Leu Gln Lys Arg Gly
145                 150                 155                 160

Ile Val Glu Gln Cys Cys Thr Ser Ile Cys Ser Leu Tyr Gln Leu Glu
                165                 170                 175

Asn Tyr Cys Gly
            180

<210> SEQ ID NO 124
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
            35                  40                  45

Ser Met Phe Leu Glu Thr Val Glu Val Asp Gly Glu Gln Val Pro Arg
    50                  55                  60

Phe Ala Leu Val Thr Ala Glu Pro Ser Leu Phe Thr Gly Gln Gly Gly
65                  70                  75                  80
```

Gly Gly Ser Gly Gly Gly Gly Ser His His His His His Asp Asp
                85                  90                  95

Asp Asp Lys Phe Val Asn Gln His Leu Cys Gly Ser His Leu Val Glu
            100                 105                 110

Ala Leu Tyr Leu Val Cys Gly Glu Arg Gly Phe Phe Tyr Thr Pro Lys
            115                 120                 125

Thr Arg Arg Asp Val Pro Gln Val Glu Leu Gly Gly Gly Pro Gly Ala
            130                 135                 140

Gly Ser Leu Gln Pro Leu Ala Leu Glu Gly Ser Leu Gln Ala Arg Gly
145                 150                 155                 160

Ile Val Glu Gln Cys Cys Thr Ser Ile Cys Ser Leu Tyr Gln Leu Glu
            165                 170                 175

Asn Tyr Cys Gly
            180

<210> SEQ ID NO 125
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
            35                  40                  45

Ser Met Phe Leu Glu Thr Val Glu Val Asp Gly Glu Gln Val Pro Arg
50                  55                  60

Phe Ala Leu Val Thr Ala Glu Pro Ser Leu Phe Thr Gly Gln Gly Gly
65                  70                  75                  80

Gly Gly Ser Gly Gly Gly Gly Ser His His His His His Arg Phe
            85                  90                  95

Val Asn Gln His Leu Cys Gly Ser His Leu Val Glu Ala Leu Tyr Leu
            100                 105                 110

Val Cys Gly Glu Arg Gly Phe Phe Tyr Thr Pro Lys Thr Arg Arg Glu
            115                 120                 125

Ala Glu Asp Leu Gln Val Gly Gln Val Glu Leu Gly Gly Gly Pro Gly
            130                 135                 140

Ala Gly Ser Leu Gln Pro Leu Ala Leu Glu Gly Ser Leu Gln Lys Arg
145                 150                 155                 160

Gly Ile Val Glu Gln Cys Cys Thr Ser Ile Cys Ser Leu Tyr Gln Leu
            165                 170                 175

Glu Asn Tyr Cys Gly
            180

<210> SEQ ID NO 126
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Glu Val Val
            20                  25                  30

Phe Tyr Gln Ala Leu Tyr Gly Glu Tyr Gly Phe Trp Val Arg Pro Leu
        35                  40                  45

Ser Met Phe Leu Glu Thr Val Glu Val Asp Gly Glu Gln Val Pro Arg
    50                  55                  60

Phe Ala Leu Val Thr Ala Glu Pro Ser Leu Phe Thr Gly Gln Gly Gly
65                  70                  75                  80

Gly Gly Ser Gly Gly Gly Gly Ser His His His His His His Arg Phe
            85                  90                  95

Val Asn Gln His Leu Cys Gly Ser His Leu Val Glu Ala Leu Tyr Leu
            100                 105                 110

Val Cys Gly Glu Arg Gly Phe Phe Tyr Thr Pro Lys Thr Arg Arg Asp
            115                 120                 125

Val Pro Gln Val Glu Leu Gly Gly Gly Pro Gly Ala Gly Ser Leu Gln
            130                 135                 140

Pro Leu Ala Leu Glu Gly Ser Leu Gln Lys Arg Gly Ile Val Glu Gln
145                 150                 155                 160

Cys Cys Thr Ser Ile Cys Ser Leu Tyr Gln Leu Glu Asn Tyr Cys Gly
                165                 170                 175

<210> SEQ ID NO 127
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Glu Val Val
            20                  25                  30

Phe Tyr Gln Ala Leu Tyr Gly Glu Tyr Gly Phe Trp Val Arg Pro Leu
        35                  40                  45

Ser Met Phe Leu Glu Thr Val Glu Val Asp Gly Glu Gln Val Pro Arg
    50                  55                  60

Phe Ala Leu Val Thr Ala Glu Pro Ser Leu Phe Thr Gly Gln Gly Gly
65                  70                  75                  80

Gly Gly Ser Gly Gly Gly Gly Ser His His His His His His Arg Phe
            85                  90                  95

Val Asn Gln His Leu Cys Gly Ser His Leu Val Glu Ala Leu Tyr Leu
            100                 105                 110

Val Cys Gly Glu Arg Gly Phe Phe Tyr Thr Pro Lys Thr Arg Arg Asp
            115                 120                 125

Val Pro Gln Val Glu Leu Gly Gly Gly Pro Gly Ala Gly Ser Leu Gln
            130                 135                 140

Pro Leu Ala Leu Glu Gly Ser Leu Gln Ala Arg Gly Ile Val Glu Gln
145                 150                 155                 160

Cys Cys Thr Ser Ile Cys Ser Leu Tyr Gln Leu Glu Asn Tyr Cys Gly
                165                 170                 175

<210> SEQ ID NO 128
```

```
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
        35                  40                  45

Ser Met Phe Leu Glu Thr Val Glu Val Asp Gly Glu Gln Val Pro Arg
    50                  55                  60

Phe Ala Leu Val Thr Ala Glu Pro Ser Leu Phe Thr Gly Gln Gly Gly
65                  70                  75                  80

Gly Gly Ser Gly Gly Gly Ser His His His His His Asp Asp
                85                  90                  95

Asp Asp Lys Phe Val Asn Gln His Leu Cys Gly Ser His Leu Val Glu
            100                 105                 110

Ala Leu Tyr Leu Val Cys Gly Glu Arg Gly Phe Phe Tyr Thr Pro Lys
        115                 120                 125

Thr Arg Arg Glu Ala Glu Asp Gln Gly Ser Leu Gln Lys Arg Gly Ile
    130                 135                 140

Val Glu Gln Cys Cys Thr Ser Ile Cys Ser Leu Tyr Gln Leu Glu Asn
145                 150                 155                 160

Tyr Cys Gly

<210> SEQ ID NO 129
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Lys Val Glu Pro Gly Leu Tyr Gln His Tyr Lys Gly Pro Gln Tyr
1               5                   10                  15

Arg Val Phe Ser Val Ala Arg His Ser Glu Thr Glu Glu Val Val
            20                  25                  30

Phe Tyr Gln Ala Leu Tyr Gly Glu Tyr Gly Phe Trp Val Arg Pro Leu
        35                  40                  45

Ser Met Phe Leu Glu Thr Val Glu Val Asp Gly Glu Gln Val Pro Arg
    50                  55                  60

Phe Ala Leu Val Thr Ala Glu Pro Ser Leu Phe Thr Gly Gln Gly Gly
65                  70                  75                  80

Gly Gly Ser Gly Gly Gly Ser His His His His His Arg Phe
                85                  90                  95

Val Asn Gln His Leu Cys Gly Ser His Leu Val Glu Ala Leu Tyr Leu
            100                 105                 110

Val Cys Gly Glu Arg Gly Phe Phe Tyr Thr Pro Lys Thr Arg Arg Glu
        115                 120                 125

Ala Glu Asp Gln Gly Ser Leu Gln Lys Arg Gly Ile Val Glu Gln Cys
    130                 135                 140
```

```
Cys Thr Ser Ile Cys Ser Leu Tyr Gln Leu Glu Asn Tyr Cys Gly
145                 150                 155
```

<210> SEQ ID NO 130
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Ser Arg Val Asp Gln Glu Gln Met Ala Ala Ser Phe Lys Val
50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Ser Tyr Glu Arg Gly
130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
        195                 200                 205

Gly Ser Gly Gly Gly Ser His His His His His Asp Asp Asp
210                 215                 220

Asp Lys Phe Val Asn Gln His Leu Cys Gly Ser His Leu Val Glu Ala
225                 230                 235                 240

Leu Tyr Leu Val Cys Gly Glu Arg Gly Phe Phe Tyr Thr Pro Lys Thr
                245                 250                 255

Arg Arg Glu Ala Glu Asp Leu Gln Val Gly Gln Val Glu Leu Gly Gly
            260                 265                 270

Gly Pro Gly Ala Gly Ser Leu Gln Pro Leu Ala Leu Glu Gly Ser Leu
        275                 280                 285

Gln Lys Arg Gly Ile Val Glu Gln Cys Cys Thr Ser Ile Cys Ser Leu
290                 295                 300

Tyr Gln Leu Glu Asn Tyr Cys Gly
305                 310
```

<210> SEQ ID NO 131
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
                35                  40                  45

Lys Pro Ser Arg Val Asp Gln Glu Gln Met Ala Ala Ser Phe Lys Val
        50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                    85                  90                  95

Ile Thr Thr Leu Ala Ser Gly Leu Gln Phe Glu Val Leu Thr Ala Gly
                100                 105                 110

Thr Gly Ala Lys Pro Thr Arg Glu Asp Gln Val Arg Thr His Tyr His
                115                 120                 125

Gly Thr Leu Ile Asp Gly Thr Val Phe Asp Ser Ser Tyr Glu Arg Gly
    130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
                180                 185                 190

Ser Val Leu Val Phe Asp Val Glu Leu Leu Asp Val Leu Gly Gly Gly
                195                 200                 205

Gly Ser Gly Gly Gly Gly Ser His His His His His Asp Asp Asp
    210                 215                 220

Asp Lys Phe Val Asn Gln His Leu Cys Gly Ser His Leu Val Glu Ala
225                 230                 235                 240

Leu Tyr Leu Val Cys Gly Glu Arg Gly Phe Phe Tyr Thr Pro Lys Thr
                245                 250                 255

Arg Arg Asp Val Pro Gln Val Glu Leu Gly Gly Pro Gly Ala Gly
                260                 265                 270

Ser Leu Gln Pro Leu Ala Leu Glu Gly Ser Leu Gln Lys Arg Gly Ile
            275                 280                 285

Val Glu Gln Cys Cys Thr Ser Ile Cys Ser Leu Tyr Gln Leu Glu Asn
            290                 295                 300

Tyr Cys Gly
305
```

<210> SEQ ID NO 132
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Met Ser Glu Val Asn Leu Ser Thr Asp Glu Thr Arg Val Ser Tyr Gly
1               5                   10                  15
```

```
Ile Gly Arg Gln Leu Gly Asp Gln Leu Arg Asp Asn Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
 50                  55                  60

Ile Arg Glu Ile Met Gln Ala Glu Ala Ala Lys Ala Glu Ala Ala
 65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
            115                 120                 125

Gly Thr Leu Ile Asp Gly Thr Val Phe Asp Ser Ser Tyr Glu Arg Gly
    130                 135                 140

Gln Pro Ala Glu Phe Pro Val Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
            195                 200                 205

Gly Ser Gly Gly Gly Ser His His His His His Asp Asp Asp
    210                 215                 220

Asp Lys Phe Val Asn Gln His Leu Cys Gly Ser His Leu Val Glu Ala
225                 230                 235                 240

Leu Tyr Leu Val Cys Gly Glu Arg Gly Phe Phe Tyr Thr Pro Lys Thr
                245                 250                 255

Arg Arg Asp Val Pro Gln Val Glu Leu Gly Gly Pro Gly Ala Gly
            260                 265                 270

Ser Leu Gln Pro Leu Ala Leu Glu Gly Ser Leu Gln Ala Arg Gly Ile
            275                 280                 285

Val Glu Gln Cys Cys Thr Ser Ile Cys Ser Leu Tyr Gln Leu Glu Asn
            290                 295                 300

Tyr Cys Gly
305

<210> SEQ ID NO 133
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Ser Glu Val Asn Leu Ser Thr Asp Glu Thr Arg Val Ser Tyr Gly
  1               5                  10                  15

Ile Gly Arg Gln Leu Gly Asp Gln Leu Arg Asp Asn Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
```

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
            115                 120                 125

Gly Thr Leu Ile Asp Gly Thr Val Phe Asp Ser Ser Tyr Glu Arg Gly
130                 135                 140

Gln Pro Ala Glu Phe Pro Val Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
            195                 200                 205

Gly Ser Gly Gly Gly Ser His His His His His Arg Phe Val
210                 215                 220

Asn Gln His Leu Cys Gly Ser His Leu Val Glu Ala Leu Tyr Leu Val
225                 230                 235                 240

Cys Gly Glu Arg Gly Phe Phe Tyr Thr Pro Lys Thr Arg Arg Glu Ala
                245                 250                 255

Glu Asp Leu Gln Val Gly Gln Val Glu Leu Gly Gly Gly Pro Gly Ala
            260                 265                 270

Gly Ser Leu Gln Pro Leu Ala Leu Glu Gly Ser Leu Gln Lys Arg Gly
            275                 280                 285

Ile Val Glu Gln Cys Cys Thr Ser Ile Cys Ser Leu Tyr Gln Leu Glu
            290                 295                 300

Asn Tyr Cys Gly
305

<210> SEQ ID NO 134
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Gly
            20                  25                  30

Val Ser Leu Asp Ala Ile Leu Ala Gly Leu Thr Asp Ala Phe Ala Gly
            35                  40                  45

Lys Pro Ser Arg Val Asp Gln Glu Gln Met Ala Ala Ser Phe Lys Val
50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

```
Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Ser Tyr Glu Arg Gly
    130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
        195                 200                 205

Gly Ser Gly Gly Gly Gly Ser His His His His His His Arg Phe Val
    210                 215                 220

Asn Gln His Leu Cys Gly Ser His Leu Val Glu Ala Leu Tyr Leu Val
225                 230                 235                 240

Cys Gly Glu Arg Gly Phe Phe Tyr Thr Pro Lys Thr Arg Arg Asp Val
                245                 250                 255

Pro Gln Val Glu Leu Gly Gly Gly Pro Gly Ala Gly Ser Leu Gln Pro
            260                 265                 270

Leu Ala Leu Glu Gly Ser Leu Gln Lys Arg Gly Ile Val Glu Gln Cys
        275                 280                 285

Cys Thr Ser Ile Cys Ser Leu Tyr Gln Leu Glu Asn Tyr Cys Gly
    290                 295                 300

<210> SEQ ID NO 135
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Ser Tyr Glu Arg Gly
    130                 135                 140

Gln Pro Ala Glu Phe Pro Val Gly Gly Val Ile Ala Gly Trp Thr Glu
145                 150                 155                 160
```

```
Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
        195                 200                 205

Gly Ser Gly Gly Gly Ser His His His His His Arg Phe Val
    210                 215                 220

Asn Gln His Leu Cys Gly Ser His Leu Val Glu Ala Leu Tyr Leu Val
225                 230                 235                 240

Cys Gly Glu Arg Gly Phe Phe Tyr Thr Pro Lys Thr Arg Arg Asp Val
                245                 250                 255

Pro Gln Val Glu Leu Gly Gly Gly Pro Gly Ala Gly Ser Leu Gln Pro
            260                 265                 270

Leu Ala Leu Glu Gly Ser Leu Gln Ala Arg Gly Ile Val Glu Gln Cys
        275                 280                 285

Cys Thr Ser Ile Cys Ser Leu Tyr Gln Leu Glu Asn Tyr Cys Gly
    290                 295                 300

<210> SEQ ID NO 136
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Ser Arg Val Asp Gln Glu Gln Met Ala Ala Ser Phe Lys Val
        50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
                100                 105                 110

Thr Gly Ala Lys Pro Thr Arg Glu Asp Gln Val Arg Thr His Tyr His
            115                 120                 125

Gly Thr Leu Ile Asp Gly Thr Val Phe Asp Ser Ser Tyr Glu Arg Gly
        130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
        195                 200                 205

Gly Ser Gly Gly Gly Gly Ser His His His His His Asp Asp Asp
```

Asp Lys Phe Val Asn Gln His Leu Cys Gly Ser His Leu Val Glu Ala
225                 230                 235                 240

Leu Tyr Leu Val Cys Gly Glu Arg Gly Phe Phe Tyr Thr Pro Lys Thr
            245                 250                 255

Arg Arg Glu Ala Glu Asp Gln Gly Ser Leu Gln Lys Arg Gly Ile Val
                260                 265                 270

Glu Gln Cys Cys Thr Ser Ile Cys Ser Leu Tyr Gln Leu Glu Asn Tyr
        275                 280                 285

Cys Gly
    290

<210> SEQ ID NO 137
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Ala Ser Gly Leu Gln Phe Glu Val Leu Thr Ala Gly
            100                 105                 110

Thr Gly Ala Lys Pro Thr Arg Glu Asp Gln Val Arg Thr His Tyr His
        115                 120                 125

Gly Thr Leu Ile Asp Gly Thr Val Phe Asp Ser Ser Tyr Glu Arg Gly
    130                 135                 140

Gln Pro Ala Glu Phe Pro Val Gly Gly Val Ile Ala Gly Trp Thr Glu
145                 150                 155                 160

Ala Leu Gln Leu Met Asn Ala Gly Ser Lys Trp Arg Val Tyr Val Pro
                165                 170                 175

Ser Glu Leu Ala Tyr Gly Ala Gln Gly Val Gly Ser Ile Pro Pro His
            180                 185                 190

Ser Val Leu Val Phe Asp Val Glu Leu Leu Asp Val Leu Gly Gly Gly
        195                 200                 205

Gly Ser Gly Gly Gly Ser His His His His His Arg Phe Val
    210                 215                 220

Asn Gln His Leu Cys Gly Ser His Leu Val Glu Ala Leu Tyr Leu Val
225                 230                 235                 240

Cys Gly Glu Arg Gly Phe Phe Tyr Thr Pro Lys Thr Arg Arg Glu Ala
                245                 250                 255

Glu Asp Gln Gly Ser Leu Gln Lys Arg Gly Ile Val Glu Gln Cys Cys
            260                 265                 270

```
Thr Ser Ile Cys Ser Leu Tyr Gln Leu Glu Asn Tyr Cys Gly
        275                 280                 285
```

<210> SEQ ID NO 138
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
            100                 105                 110

His His His His Asp Asp Asp Lys Phe Val Asn Gln His Leu Cys
        115                 120                 125

Gly Ser His Leu Val Glu Ala Leu Tyr Leu Val Cys Gly Glu Arg Gly
    130                 135                 140

Phe Phe Tyr Thr Pro Lys Thr Arg Arg Glu Ala Glu Asp Leu Gln Val
145                 150                 155                 160

Gly Gln Val Glu Leu Gly Gly Pro Gly Ala Gly Ser Leu Gln Pro
                165                 170                 175

Leu Ala Leu Glu Gly Ser Leu Gln Lys Arg Gly Ile Val Glu Gln Cys
            180                 185                 190

Cys Thr Ser Ile Cys Ser Leu Tyr Gln Leu Glu Asn Tyr Cys Gly
        195                 200                 205
```

<210> SEQ ID NO 139
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80
```

```
Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
        100                 105                 110

His His His His Asp Asp Asp Lys Phe Val Asn Gln His Leu Cys
            115                 120                 125

Gly Ser His Leu Val Glu Ala Leu Tyr Leu Val Cys Gly Glu Arg Gly
        130                 135                 140

Phe Phe Tyr Thr Pro Lys Thr Arg Arg Asp Val Pro Gln Val Glu Leu
145                 150                 155                 160

Gly Gly Gly Pro Gly Ala Gly Ser Leu Gln Pro Leu Ala Leu Glu Gly
                165                 170                 175

Ser Leu Gln Lys Arg Gly Ile Val Glu Gln Cys Cys Thr Ser Ile Cys
        180                 185                 190

Ser Leu Tyr Gln Leu Glu Asn Tyr Cys Gly
        195                 200

<210> SEQ ID NO 140
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
 50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
        100                 105                 110

His His His His Asp Asp Asp Lys Phe Val Asn Gln His Leu Cys
            115                 120                 125

Gly Ser His Leu Val Glu Ala Leu Tyr Leu Val Cys Gly Glu Arg Gly
        130                 135                 140

Phe Phe Tyr Thr Pro Lys Thr Arg Arg Asp Val Pro Gln Val Glu Leu
145                 150                 155                 160

Gly Gly Gly Pro Gly Ala Gly Ser Leu Gln Pro Leu Ala Leu Glu Gly
                165                 170                 175

Ser Leu Gln Ala Arg Gly Ile Val Glu Gln Cys Cys Thr Ser Ile Cys
        180                 185                 190

Ser Leu Tyr Gln Leu Glu Asn Tyr Cys Gly
        195                 200

<210> SEQ ID NO 141
<211> LENGTH: 203
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 141

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Ser Arg Val Asp Gln Glu Gln Met Ala Ala Ser Phe Lys Val
        50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
            100                 105                 110

His His His His Arg Phe Val Asn Gln His Leu Cys Gly Ser His Leu
                115                 120                 125

Val Glu Ala Leu Tyr Leu Val Cys Gly Glu Arg Gly Phe Phe Tyr Thr
130                 135                 140

Pro Lys Thr Arg Arg Glu Ala Glu Asp Leu Gln Val Gly Gln Val Glu
145                 150                 155                 160

Leu Gly Gly Gly Pro Gly Ala Gly Ser Leu Gln Pro Leu Ala Leu Glu
                165                 170                 175

Gly Ser Leu Gln Lys Arg Gly Ile Val Glu Gln Cys Cys Thr Ser Ile
            180                 185                 190

Cys Ser Leu Tyr Gln Leu Glu Asn Tyr Cys Gly
            195                 200

<210> SEQ ID NO 142
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Ser Arg Val Asp Gln Glu Gln Met Ala Ala Ser Phe Lys Val
        50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
            100                 105                 110

His His His His Arg Phe Val Asn Gln His Leu Cys Gly Ser His Leu
                115                 120                 125
```

Val Glu Ala Leu Tyr Leu Val Cys Gly Glu Arg Gly Phe Phe Tyr Thr
            130                 135                 140

Pro Lys Thr Arg Arg Asp Val Pro Gln Val Glu Leu Gly Gly Gly Pro
145                 150                 155                 160

Gly Ala Gly Ser Leu Gln Pro Leu Ala Leu Glu Gly Ser Leu Gln Lys
                165                 170                 175

Arg Gly Ile Val Glu Gln Cys Cys Thr Ser Ile Cys Ser Leu Tyr Gln
            180                 185                 190

Leu Glu Asn Tyr Cys Gly
        195

<210> SEQ ID NO 143
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
            35                  40                  45

Lys Pro Ser Arg Val Asp Gln Glu Gln Met Ala Ala Ser Phe Lys Val
50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Gly Ser Gly Gly Gly Gly Ser His His
            100                 105                 110

His His His His Arg Phe Val Asn Gln His Leu Cys Gly Ser His Leu
            115                 120                 125

Val Glu Ala Leu Tyr Leu Val Cys Gly Glu Arg Gly Phe Phe Tyr Thr
            130                 135                 140

Pro Lys Thr Arg Arg Asp Val Pro Gln Val Glu Leu Gly Gly Gly Pro
145                 150                 155                 160

Gly Ala Gly Ser Leu Gln Pro Leu Ala Leu Glu Gly Ser Leu Gln Ala
                165                 170                 175

Arg Gly Ile Val Glu Gln Cys Cys Thr Ser Ile Cys Ser Leu Tyr Gln
            180                 185                 190

Leu Glu Asn Tyr Cys Gly
        195

<210> SEQ ID NO 144
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Ser Glu Val Asn Leu Ser Thr Asp Glu Thr Arg Val Ser Tyr Gly
1               5                   10                  15

```
Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
            100                 105                 110

His His His His Asp Asp Asp Lys Phe Val Asn Gln His Leu Cys
            115                 120                 125

Gly Ser His Leu Val Glu Ala Leu Tyr Leu Val Cys Gly Glu Arg Gly
130                 135                 140

Phe Phe Tyr Thr Pro Lys Thr Arg Arg Glu Ala Glu Asp Gln Gly Ser
145                 150                 155                 160

Leu Gln Lys Arg Gly Ile Val Glu Gln Cys Cys Thr Ser Ile Cys Ser
            165                 170                 175

Leu Tyr Gln Leu Glu Asn Tyr Cys Gly
            180                 185

<210> SEQ ID NO 145
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Ser Arg Val Asp Gln Glu Gln Met Ala Ala Ser Phe Lys Val
    50                  55                  60

Ile Arg Glu Ile Met Gln Ala Glu Ala Ala Lys Ala Glu Ala Ala
65                  70                  75                  80

Ala Gly Ala Gly Leu Ala Phe Leu Ala Glu Asn Ala Lys Arg Asp Gly
                85                  90                  95

Ile Thr Thr Leu Gly Gly Gly Ser Gly Gly Gly Ser His His
            100                 105                 110

His His His His Arg Phe Val Asn Gln His Leu Cys Gly Ser His Leu
            115                 120                 125

Val Glu Ala Leu Tyr Leu Val Cys Gly Glu Arg Gly Phe Phe Tyr Thr
130                 135                 140

Pro Lys Thr Arg Arg Glu Ala Glu Asp Gln Gly Ser Leu Gln Lys Arg
145                 150                 155                 160

Gly Ile Val Glu Gln Cys Cys Thr Ser Ile Cys Ser Leu Tyr Gln Leu
            165                 170                 175

Glu Asn Tyr Cys Gly
```

<210> SEQ ID NO 146
<211> LENGTH: 157
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Gly Gly Gly Gly Ser Gly Gly Gly Gly Ser His His His His
        50                  55                  60

His His Asp Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Glu Ala Glu Asp Leu Gln Val Gly Gln
                100                 105                 110

Val Glu Leu Gly Gly Gly Pro Gly Ala Gly Ser Leu Gln Pro Leu Ala
            115                 120                 125

Leu Glu Gly Ser Leu Gln Lys Arg Gly Ile Val Glu Gln Cys Cys Thr
        130                 135                 140

Ser Ile Cys Ser Leu Tyr Gln Leu Glu Asn Tyr Cys Gly
145                 150                 155
```

<210> SEQ ID NO 147
<211> LENGTH: 152
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

```
Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Gly Gly Gly Gly Ser Gly Gly Gly Gly Ser His His His His
        50                  55                  60

His His Asp Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Asp Val Pro Gln Val Glu Leu Gly Gly
                100                 105                 110

Gly Pro Gly Ala Gly Ser Leu Gln Pro Leu Ala Leu Glu Gly Ser Leu
            115                 120                 125

Gln Lys Arg Gly Ile Val Glu Gln Cys Cys Thr Ser Ile Cys Ser Leu
```

Tyr Gln Leu Glu Asn Tyr Cys Gly
145                 150

<210> SEQ ID NO 148
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Gly Gly Gly Gly Ser Gly Gly Gly Ser His His His His
    50                  55                  60

His His Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Asp Val Pro Gln Val Glu Leu Gly Gly
            100                 105                 110

Gly Pro Gly Ala Gly Ser Leu Gln Pro Leu Ala Leu Glu Gly Ser Leu
        115                 120                 125

Gln Ala Arg Gly Ile Val Glu Gln Cys Cys Thr Ser Ile Cys Ser Leu
    130                 135                 140

Tyr Gln Leu Glu Asn Tyr Cys Gly
145                 150

<210> SEQ ID NO 149
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Gly Gly Gly Gly Ser Gly Gly Gly Ser His His His His
    50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
                85                  90                  95

Thr Arg Arg Glu Ala Glu Asp Leu Gln Val Gly Gln Val Glu Leu Gly
            100                 105                 110

Gly Gly Pro Gly Ala Gly Ser Leu Gln Pro Leu Ala Leu Glu Gly Ser

```
                115                 120                 125
Leu Gln Lys Arg Gly Ile Val Glu Gln Cys Cys Thr Ser Ile Cys Ser
    130                 135                 140

Leu Tyr Gln Leu Glu Asn Tyr Cys Gly
145                 150

<210> SEQ ID NO 150
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Gly Gly Gly Gly Ser Gly Gly Gly Ser His His His His
    50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
                85                  90                  95

Thr Arg Arg Asp Val Pro Gln Val Glu Leu Gly Gly Gly Pro Gly Ala
            100                 105                 110

Gly Ser Leu Gln Pro Leu Ala Leu Glu Gly Ser Leu Gln Lys Arg Gly
        115                 120                 125

Ile Val Glu Gln Cys Cys Thr Ser Ile Cys Ser Leu Tyr Gln Leu Glu
    130                 135                 140

Asn Tyr Cys Gly
145

<210> SEQ ID NO 151
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
                20                  25                  30

Val Ser Leu Asp Ala Ile Leu Ala Gly Leu Thr Asp Ala Phe Ala Gly
            35                  40                  45

Lys Pro Gly Gly Gly Gly Ser Gly Gly Gly Ser His His His His
    50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
                85                  90                  95

Thr Arg Arg Asp Val Pro Gln Val Glu Leu Gly Gly Gly Pro Gly Ala
```

```
                100                 105                 110
Gly Ser Leu Gln Pro Leu Ala Leu Glu Gly Ser Leu Gln Ala Arg Gly
        115                 120                 125

Ile Val Glu Gln Cys Cys Thr Ser Ile Cys Ser Leu Tyr Gln Leu Glu
    130                 135                 140

Asn Tyr Cys Gly
145

<210> SEQ ID NO 152
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Gly Gly Gly Gly Ser Gly Gly Gly Ser His His His His
    50                  55                  60

His His Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Glu Ala Glu Asp Gln Gly Ser Leu Gln
            100                 105                 110

Lys Arg Gly Ile Val Glu Gln Cys Cys Thr Ser Ile Cys Ser Leu Tyr
        115                 120                 125

Gln Leu Glu Asn Tyr Cys Gly
    130                 135

<210> SEQ ID NO 153
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Ser Glu Val Asn Leu Ser Thr Asp Glu Thr Arg Val Ser Tyr Gly
1               5                   10                  15

Ile Gly Arg Gln Leu Gly Asp Gln Leu Arg Asp Asn Pro Pro Pro Gly
            20                  25                  30

Val Ser Leu Asp Ala Ile Leu Ala Gly Leu Thr Asp Ala Phe Ala Gly
        35                  40                  45

Lys Pro Gly Gly Gly Gly Ser Gly Gly Gly Ser His His His His
    50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
                85                  90                  95

Thr Arg Arg Glu Ala Glu Asp Gln Gly Ser Leu Gln Lys Arg Gly Ile
```

```
            100                 105                 110
Val Glu Gln Cys Cys Thr Ser Ile Cys Ser Leu Tyr Gln Leu Glu Asn
        115                 120                 125

Tyr Cys Gly
        130

<210> SEQ ID NO 154
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
        115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser Gly Gly Gly Ser Gly Gly
    210                 215                 220

Gly Gly Ser His His His His His Asp Asp Asp Lys Phe Val
225                 230                 235                 240

Asn Gln His Leu Cys Gly Ser His Leu Val Glu Ala Leu Tyr Leu Val
                245                 250                 255

Cys Gly Glu Arg Gly Phe Phe Tyr Thr Pro Lys Thr Arg Arg Glu Ala
            260                 265                 270

Glu Asp Leu Gln Val Gly Gln Val Glu Leu Gly Gly Gly Pro Gly Ala
        275                 280                 285

Gly Ser Leu Gln Pro Leu Ala Leu Glu Gly Ser Leu Gln Lys Arg Gly
    290                 295                 300

Ile Val Glu Gln Cys Cys Thr Ser Ile Cys Ser Leu Tyr Gln Leu Glu
305                 310                 315                 320
```

Asn Tyr Cys Gly

<210> SEQ ID NO 155
<211> LENGTH: 319
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
        115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser Gly Gly Gly Ser Gly Gly
    210                 215                 220

Gly Gly Ser His His His His His His Asp Asp Asp Lys Phe Val
225                 230                 235                 240

Asn Gln His Leu Cys Gly Ser His Leu Val Glu Ala Leu Tyr Leu Val
                245                 250                 255

Cys Gly Glu Arg Gly Phe Phe Tyr Thr Pro Lys Thr Arg Arg Asp Val
            260                 265                 270

Pro Gln Val Glu Leu Gly Gly Gly Pro Gly Ala Gly Ser Leu Gln Pro
        275                 280                 285

Leu Ala Leu Glu Gly Ser Leu Gln Lys Arg Gly Ile Val Glu Gln Cys
    290                 295                 300

Cys Thr Ser Ile Cys Ser Leu Tyr Gln Leu Glu Asn Tyr Cys Gly
305                 310                 315

<210> SEQ ID NO 156
<211> LENGTH: 319
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 156

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
        115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser Gly Gly Gly Ser Gly Gly
    210                 215                 220

Gly Gly Ser His His His His His Asp Asp Asp Lys Phe Val
225                 230                 235                 240

Asn Gln His Leu Cys Gly Ser His Leu Val Glu Ala Leu Tyr Leu Val
                245                 250                 255

Cys Gly Glu Arg Gly Phe Phe Tyr Thr Pro Lys Thr Arg Arg Asp Val
            260                 265                 270

Pro Gln Val Glu Leu Gly Gly Gly Pro Gly Ala Gly Ser Leu Gln Pro
        275                 280                 285

Leu Ala Leu Glu Gly Ser Leu Gln Ala Arg Gly Ile Val Glu Gln Cys
    290                 295                 300

Cys Thr Ser Ile Cys Ser Leu Tyr Gln Leu Glu Asn Tyr Cys Gly
305                 310                 315

<210> SEQ ID NO 157
<211> LENGTH: 320
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

Met Ser Thr Pro Leu Lys Ile Asp Phe Val Ser Asp Val Ser Cys Pro
1               5                   10                  15

-continued

Trp Cys Ile Ile Gly Leu Arg Gly Leu Thr Glu Ala Leu Asp Gln Leu
             20                  25                  30

Gly Ser Glu Val Gln Ala Glu Ile His Phe Gln Pro Phe Glu Leu Asn
         35                  40                  45

Pro Asn Met Pro Ala Glu Gly Gln Asn Ile Val Glu His Ile Thr Glu
     50                  55                  60

Lys Tyr Gly Ser Thr Ala Glu Glu Ser Gln Ala Asn Arg Ala Arg Ile
 65                  70                  75                  80

Arg Asp Met Gly Ala Ala Leu Gly Phe Ala Phe Arg Thr Asp Gly Gln
                 85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
        115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser Gly Gly Gly Ser Gly Gly
    210                 215                 220

Gly Gly Ser His His His His His His Arg Phe Val Asn Gln His Leu
225                 230                 235                 240

Cys Gly Ser His Leu Val Glu Ala Leu Tyr Leu Val Cys Gly Glu Arg
                245                 250                 255

Gly Phe Phe Tyr Thr Pro Lys Thr Arg Arg Glu Ala Glu Asp Leu Gln
            260                 265                 270

Val Gly Gln Val Glu Leu Gly Gly Pro Gly Ala Gly Ser Leu Gln
        275                 280                 285

Pro Leu Ala Leu Glu Gly Ser Leu Gln Lys Arg Gly Ile Val Glu Gln
    290                 295                 300

Cys Cys Thr Ser Ile Cys Ser Leu Tyr Gln Leu Glu Asn Tyr Cys Gly
305                 310                 315                 320

<210> SEQ ID NO 158
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Ser Thr Pro Leu Lys Ile Asp Phe Val Ser Asp Val Ser Cys Pro
 1               5                  10                  15

Trp Cys Ile Ile Gly Leu Arg Gly Leu Thr Glu Ala Leu Asp Gln Leu
             20                  25                  30

Gly Ser Glu Val Gln Ala Glu Ile His Phe Gln Pro Phe Glu Leu Asn
         35                  40                  45

Pro Asn Met Pro Ala Glu Gly Gln Asn Ile Val Glu His Ile Thr Glu
     50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala
            100                 105                 110

Gly Leu Glu Gly Leu Gln Tyr Asn Leu Lys Glu Ala Leu Phe Lys Ala
        115                 120                 125

Tyr Phe Ser Asp Gly Gln Asp Pro Ser Asp His Ala Thr Leu Ala Ile
    130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
        195                 200                 205

Arg Gln Ile Ile Asn Glu Ser Lys Ser Gly Gly Gly Ser Gly Gly
210                 215                 220

Gly Gly Ser His His His His His His Arg Phe Val Asn Gln His Leu
225                 230                 235                 240

Cys Gly Ser His Leu Val Glu Ala Leu Tyr Leu Val Cys Gly Glu Arg
                245                 250                 255

Gly Phe Phe Tyr Thr Pro Lys Thr Arg Arg Asp Val Pro Gln Val Glu
            260                 265                 270

Leu Gly Gly Gly Pro Gly Ala Gly Ser Leu Gln Pro Leu Ala Leu Glu
        275                 280                 285

Gly Ser Leu Gln Lys Arg Gly Ile Val Glu Gln Cys Cys Thr Ser Ile
    290                 295                 300

Cys Ser Leu Tyr Gln Leu Glu Asn Tyr Cys Gly
305                 310                 315

<210> SEQ ID NO 159
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala

```
            100                 105                 110
Gly Leu Glu Gly Leu Gln Tyr Asn Leu Lys Glu Ala Leu Phe Lys Ala
        115                 120                 125
Tyr Phe Ser Asp Gly Gln Asp Pro Ser Asp His Ala Thr Leu Ala Ile
    130                 135                 140
Ile Ala Glu Ser Val Gly Leu Asp Leu Ala Arg Ala Ala Glu Ile Leu
145                 150                 155                 160
Ala Ser Asp Glu Tyr Ala Ala Glu Val Arg Glu Gln Glu Gln Leu Trp
                165                 170                 175
Val Ser Arg Gly Val Ser Ser Val Pro Thr Ile Val Phe Asn Asp Gln
            180                 185                 190
Tyr Ala Val Ser Gly Gly Gln Pro Ala Glu Ala Phe Val Gly Ala Ile
        195                 200                 205
Arg Gln Ile Ile Asn Glu Ser Lys Ser Gly Gly Gly Ser Gly Gly
    210                 215                 220
Gly Gly Ser His His His His His His Arg Phe Val Asn Gln His Leu
225                 230                 235                 240
Cys Gly Ser His Leu Val Glu Ala Leu Tyr Leu Val Cys Gly Glu Arg
                245                 250                 255
Gly Phe Phe Tyr Thr Pro Lys Thr Arg Arg Asp Val Pro Gln Val Glu
            260                 265                 270
Leu Gly Gly Gly Pro Gly Ala Gly Ser Leu Gln Pro Leu Ala Leu Glu
        275                 280                 285
Gly Ser Leu Gln Ala Arg Gly Ile Val Glu Gln Cys Cys Thr Ser Ile
    290                 295                 300
Cys Ser Leu Tyr Gln Leu Glu Asn Tyr Cys Gly
305                 310                 315

<210> SEQ ID NO 160
<211> LENGTH: 302
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Ser Thr Pro Leu Lys Ile Asp Phe Val Ser Asp Val Ser Cys Pro
1               5                   10                  15
Trp Cys Ile Ile Gly Leu Arg Gly Leu Thr Glu Ala Leu Asp Gln Leu
            20                  25                  30
Gly Ser Glu Val Gln Ala Glu Ile His Phe Gln Pro Phe Glu Leu Asn
        35                  40                  45
Pro Asn Met Pro Ala Glu Gly Gln Asn Ile Val Glu His Ile Thr Glu
    50                  55                  60
Lys Tyr Gly Ser Thr Ala Glu Glu Ser Gln Ala Asn Arg Ala Arg Ile
65                  70                  75                  80
Arg Asp Met Gly Ala Ala Leu Gly Phe Ala Phe Arg Thr Asp Gly Gln
                85                  90                  95
Ser Arg Ile Tyr Asn Thr Phe Asp Ala His Arg Leu Leu His Trp Ala
            100                 105                 110
Gly Leu Glu Gly Leu Gln Tyr Asn Leu Lys Glu Ala Leu Phe Lys Ala
        115                 120                 125
Tyr Phe Ser Asp Gly Gln Asp Pro Ser Asp His Ala Thr Leu Ala Ile
    130                 135                 140
```

```
Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
            195                 200                 205

Arg Gln Ile Ile Asn Glu Ser Lys Ser Gly Gly Gly Ser Gly Gly
210                 215                 220

Gly Gly Ser His His His His His Asp Asp Asp Lys Phe Val
225                 230                 235                 240

Asn Gln His Leu Cys Gly Ser His Leu Val Glu Ala Leu Tyr Leu Val
                245                 250                 255

Cys Gly Glu Arg Gly Phe Phe Tyr Thr Pro Lys Thr Arg Arg Glu Ala
                260                 265                 270

Glu Asp Gln Gly Ser Leu Gln Lys Arg Gly Ile Val Glu Gln Cys Cys
                275                 280                 285

Thr Ser Ile Cys Ser Leu Tyr Gln Leu Glu Asn Tyr Cys Gly
290                 295                 300

<210> SEQ ID NO 161
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
                20                  25                  30

Gly Ser Glu Val Gln Ala Glu Ile His Phe Gln Pro Phe Glu Leu Asn
            35                  40                  45

Pro Asn Met Pro Ala Glu Gly Gln Asn Ile Val Glu His Ile Thr Glu
50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Asn Thr Phe Asp Ala His Arg Leu Leu His Trp Ala
                100                 105                 110

Gly Leu Glu Gly Leu Gln Tyr Asn Leu Lys Glu Ala Leu Phe Lys Ala
            115                 120                 125

Tyr Phe Ser Asp Gly Gln Asp Pro Ser Asp His Ala Thr Leu Ala Ile
130                 135                 140

Ile Ala Glu Ser Val Gly Leu Asp Leu Ala Arg Ala Ala Glu Ile Leu
145                 150                 155                 160

Ala Ser Asp Glu Tyr Ala Ala Glu Val Arg Glu Gln Glu Gln Leu Trp
                165                 170                 175

Val Ser Arg Gly Val Ser Ser Val Pro Thr Ile Val Phe Asn Asp Gln
            180                 185                 190

Tyr Ala Val Ser Gly Gly Gln Pro Ala Glu Ala Phe Val Gly Ala Ile
            195                 200                 205
```

```
Arg Gln Ile Ile Asn Glu Ser Lys Ser Gly Gly Gly Ser Gly Gly
    210                 215                 220

Gly Gly Ser His His His His His His Arg Phe Val Asn Gln His Leu
225                 230                 235                 240

Cys Gly Ser His Leu Val Glu Ala Leu Tyr Leu Val Cys Gly Glu Arg
                245                 250                 255

Gly Phe Phe Tyr Thr Pro Lys Thr Arg Arg Glu Ala Glu Asp Gln Gly
                260                 265                 270

Ser Leu Gln Lys Arg Gly Ile Val Glu Gln Cys Cys Thr Ser Ile Cys
        275                 280                 285

Ser Leu Tyr Gln Leu Glu Asn Tyr Cys Gly
        290                 295

<210> SEQ ID NO 162
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
                20                  25                  30

Gly Ser Glu Val Gln Ala Glu Ile His Phe Gln Pro Phe Glu Leu Asn
            35                  40                  45

Pro Asn Met Pro Ala Glu Gly Gln Asn Ile Val Glu His Ile Thr Glu
50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Gly Gly Gly Gly Ser Gly Gly Gly Gly Ser His His
                100                 105                 110

His His His His Asp Asp Asp Lys Phe Val Asn Gln His Leu Cys
            115                 120                 125

Gly Ser His Leu Val Glu Ala Leu Tyr Leu Val Cys Gly Glu Arg Gly
        130                 135                 140

Phe Phe Tyr Thr Pro Lys Thr Arg Arg Glu Ala Glu Asp Leu Gln Val
145                 150                 155                 160

Gly Gln Val Glu Leu Gly Gly Gly Pro Gly Ala Gly Ser Leu Gln Pro
                165                 170                 175

Leu Ala Leu Glu Gly Ser Leu Gln Lys Arg Gly Ile Val Glu Gln Cys
            180                 185                 190

Cys Thr Ser Ile Cys Ser Leu Tyr Gln Leu Glu Asn Tyr Cys Gly
        195                 200                 205

<210> SEQ ID NO 163
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163
```

```
Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Gly Gly Gly Gly Ser Gly Gly Gly Gly Ser His His
            100                 105                 110

His His His His Asp Asp Asp Asp Lys Phe Val Asn Gln His Leu Cys
        115                 120                 125

Gly Ser His Leu Val Glu Ala Leu Tyr Leu Val Cys Gly Glu Arg Gly
    130                 135                 140

Phe Phe Tyr Thr Pro Lys Thr Arg Arg Asp Val Pro Gln Val Glu Leu
145                 150                 155                 160

Gly Gly Gly Pro Gly Ala Gly Ser Leu Gln Pro Leu Ala Leu Glu Gly
                165                 170                 175

Ser Leu Gln Lys Arg Gly Ile Val Glu Gln Cys Cys Thr Ser Ile Cys
            180                 185                 190

Ser Leu Tyr Gln Leu Glu Asn Tyr Cys Gly
            195                 200

<210> SEQ ID NO 164
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Gly Gly Gly Gly Ser Gly Gly Gly Gly Ser His His
            100                 105                 110

His His His His Asp Asp Asp Asp Lys Phe Val Asn Gln His Leu Cys
        115                 120                 125

Gly Ser His Leu Val Glu Ala Leu Tyr Leu Val Cys Gly Glu Arg Gly
    130                 135                 140

Phe Phe Tyr Thr Pro Lys Thr Arg Arg Asp Val Pro Gln Val Glu Leu
```

```
145                 150                 155                 160

Gly Gly Gly Pro Gly Ala Gly Ser Leu Gln Pro Leu Ala Leu Glu Gly
                165                 170                 175

Ser Leu Gln Ala Arg Gly Ile Val Glu Gln Cys Cys Thr Ser Ile Cys
            180                 185                 190

Ser Leu Tyr Gln Leu Glu Asn Tyr Cys Gly
        195                 200

<210> SEQ ID NO 165
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Ile Tyr Gly Gly Gly Ser Gly Gly Gly Ser His His His
            100                 105                 110

His His His Arg Phe Val Asn Gln His Leu Cys Gly Ser His Leu Val
        115                 120                 125

Glu Ala Leu Tyr Leu Val Cys Gly Glu Arg Gly Phe Phe Tyr Thr Pro
    130                 135                 140

Lys Thr Arg Arg Glu Ala Glu Asp Leu Gln Val Gly Gln Val Glu Leu
145                 150                 155                 160

Gly Gly Gly Pro Gly Ala Gly Ser Leu Gln Pro Leu Ala Leu Glu Gly
                165                 170                 175

Ser Leu Gln Lys Arg Gly Ile Val Glu Gln Cys Cys Thr Ser Ile Cys
            180                 185                 190

Ser Leu Tyr Gln Leu Glu Asn Tyr Cys Gly
        195                 200

<210> SEQ ID NO 166
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
```

```
                    35                  40                  45

Pro Asn Met Pro Ala Glu Gly Gln Asn Ile Val Glu His Ile Thr Glu
            50                  55                  60

Lys Tyr Gly Ser Thr Ala Glu Glu Ser Gln Ala Asn Arg Ala Arg Ile
 65                  70                  75                  80

Arg Asp Met Gly Ala Ala Leu Gly Phe Ala Phe Arg Thr Asp Gly Gln
                 85                  90                  95

Ser Arg Ile Tyr Gly Gly Gly Ser Gly Gly Gly Gly Ser His His
            100                 105                 110

His His His His Arg Phe Val Asn Gln His Leu Cys Gly Ser His Leu
        115                 120                 125

Val Glu Ala Leu Tyr Leu Val Cys Gly Glu Arg Gly Phe Phe Tyr Thr
    130                 135                 140

Pro Lys Thr Arg Arg Asp Val Pro Gln Val Leu Gly Gly Gly Pro
145                 150                 155                 160

Gly Ala Gly Ser Leu Gln Pro Leu Ala Leu Glu Gly Ser Leu Gln Lys
                165                 170                 175

Arg Gly Ile Val Glu Gln Cys Cys Thr Ser Ile Cys Ser Leu Tyr Gln
            180                 185                 190

Leu Glu Asn Tyr Cys Gly
        195

<210> SEQ ID NO 167
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Ser Thr Pro Leu Lys Ile Asp Phe Val Ser Asp Val Ser Cys Pro
 1               5                  10                  15

Trp Cys Ile Ile Gly Leu Arg Gly Leu Thr Glu Ala Leu Asp Gln Leu
                20                  25                  30

Gly Ser Glu Val Gln Ala Glu Ile His Phe Gln Pro Phe Glu Leu Asn
            35                  40                  45

Pro Asn Met Pro Ala Glu Gly Gln Asn Ile Val Glu His Ile Thr Glu
        50                  55                  60

Lys Tyr Gly Ser Thr Ala Glu Glu Ser Gln Ala Asn Arg Ala Arg Ile
 65                  70                  75                  80

Arg Asp Met Gly Ala Ala Leu Gly Phe Ala Phe Arg Thr Asp Gly Gln
                 85                  90                  95

Ser Arg Ile Tyr Gly Gly Gly Ser Gly Gly Gly Gly Ser His His
            100                 105                 110

His His His His Arg Phe Val Asn Gln His Leu Cys Gly Ser His Leu
        115                 120                 125

Val Glu Ala Leu Tyr Leu Val Cys Gly Glu Arg Gly Phe Phe Tyr Thr
    130                 135                 140

Pro Lys Thr Arg Arg Asp Val Pro Gln Val Glu Leu Gly Gly Gly Pro
145                 150                 155                 160

Gly Ala Gly Ser Leu Gln Pro Leu Ala Leu Glu Gly Ser Leu Gln Ala
                165                 170                 175

Arg Gly Ile Val Glu Gln Cys Cys Thr Ser Ile Cys Ser Leu Tyr Gln
            180                 185                 190
```

Leu Glu Asn Tyr Cys Gly
        195

<210> SEQ ID NO 168
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

Ser Arg Ile Tyr Gly Gly Gly Gly Ser Gly Gly Gly Ser His His
            100                 105                 110

His His His His Asp Asp Asp Asp Lys Phe Val Asn Gln His Leu Cys
        115                 120                 125

Gly Ser His Leu Val Glu Ala Leu Tyr Leu Val Cys Gly Glu Arg Gly
    130                 135                 140

Phe Phe Tyr Thr Pro Lys Thr Arg Arg Glu Ala Glu Asp Gln Gly Ser
145                 150                 155                 160

Leu Gln Lys Arg Gly Ile Val Glu Gln Cys Cys Thr Ser Ile Cys Ser
                165                 170                 175

Leu Tyr Gln Leu Glu Asn Tyr Cys Gly
            180                 185

<210> SEQ ID NO 169
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Met Pro Ala Glu Gly Gln Asn Ile Val Glu His Ile Thr Glu
    50                  55                  60

Lys Tyr Gly Ser Thr Ala Glu Glu Ser Gln Ala Asn Arg Ala Arg Ile
65                  70                  75                  80

Arg Asp Met Gly Ala Ala Leu Gly Phe Ala Phe Arg Thr Asp Gly Gln
                85                  90                  95

```
Ser Arg Ile Tyr Gly Gly Gly Ser Gly Gly Gly Ser His His
            100                 105                 110

His His His His Arg Phe Val Asn Gln His Leu Cys Gly Ser His Leu
            115                 120                 125

Val Glu Ala Leu Tyr Leu Val Cys Gly Glu Arg Gly Phe Phe Tyr Thr
130                 135                 140

Pro Lys Thr Arg Arg Glu Ala Glu Asp Gln Gly Ser Leu Gln Lys Arg
145                 150                 155                 160

Gly Ile Val Glu Gln Cys Cys Thr Ser Ile Cys Ser Leu Tyr Gln Leu
                165                 170                 175

Glu Asn Tyr Cys Gly
            180

<210> SEQ ID NO 170
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Gly Gly Gly Ser Gly Gly Gly Ser His His His His
    50                  55                  60

His His Asp Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Glu Ala Glu Asp Leu Gln Val Gly Gln
            100                 105                 110

Val Glu Leu Gly Gly Gly Pro Gly Ala Gly Ser Leu Gln Pro Leu Ala
        115                 120                 125

Leu Glu Gly Ser Leu Gln Lys Arg Gly Ile Val Glu Gln Cys Cys Thr
    130                 135                 140

Ser Ile Cys Ser Leu Tyr Gln Leu Glu Asn Tyr Cys Gly
145                 150                 155

<210> SEQ ID NO 171
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45
```

Pro Asn Gly Gly Gly Gly Ser Gly Gly Gly Ser His His His His
    50                  55                  60

His His Asp Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Asp Val Pro Gln Val Glu Leu Gly Gly
            100                 105                 110

Gly Pro Gly Ala Gly Ser Leu Gln Pro Leu Ala Leu Glu Gly Ser Leu
        115                 120                 125

Gln Lys Arg Gly Ile Val Glu Gln Cys Cys Thr Ser Ile Cys Ser Leu
    130                 135                 140

Tyr Gln Leu Glu Asn Tyr Cys Gly
145                 150

<210> SEQ ID NO 172
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Gly Gly Gly Gly Ser Gly Gly Gly Ser His His His His
    50                  55                  60

His His Asp Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Asp Val Pro Gln Val Glu Leu Gly Gly
            100                 105                 110

Gly Pro Gly Ala Gly Ser Leu Gln Pro Leu Ala Leu Glu Gly Ser Leu
        115                 120                 125

Gln Ala Arg Gly Ile Val Glu Gln Cys Cys Thr Ser Ile Cys Ser Leu
    130                 135                 140

Tyr Gln Leu Glu Asn Tyr Cys Gly
145                 150

<210> SEQ ID NO 173
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

```
Gly Ser Glu Val Gln Ala Glu Ile His Phe Gln Pro Phe Glu Leu Asn
            35                  40                  45

Pro Asn Gly Gly Gly Gly Ser Gly Gly Gly Ser His His His His
 50                  55                  60

His His Arg Phe Val Asn Gln His Leu Cys Gly Ser His Leu Val Glu
 65                  70                  75                  80

Ala Leu Tyr Leu Val Cys Gly Glu Arg Gly Phe Phe Tyr Thr Pro Lys
                85                  90                  95

Thr Arg Arg Glu Ala Glu Asp Leu Gln Val Gly Gln Val Glu Leu Gly
                100                 105                 110

Gly Gly Pro Gly Ala Gly Ser Leu Gln Pro Leu Ala Leu Glu Gly Ser
                115                 120                 125

Leu Gln Lys Arg Gly Ile Val Glu Gln Cys Cys Thr Ser Ile Cys Ser
            130                 135                 140

Leu Tyr Gln Leu Glu Asn Tyr Cys Gly
145                 150

<210> SEQ ID NO 174
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
                20                  25                  30

Gly Ser Glu Val Gln Ala Glu Ile His Phe Gln Pro Phe Glu Leu Asn
            35                  40                  45

Pro Asn Gly Gly Gly Gly Ser Gly Gly Gly Ser His His His His
 50                  55                  60

His His Arg Phe Val Asn Gln His Leu Cys Gly Ser His Leu Val Glu
 65                  70                  75                  80

Ala Leu Tyr Leu Val Cys Gly Glu Arg Gly Phe Phe Tyr Thr Pro Lys
                85                  90                  95

Thr Arg Arg Asp Val Pro Gln Val Glu Leu Gly Gly Gly Pro Gly Ala
                100                 105                 110

Gly Ser Leu Gln Pro Leu Ala Leu Glu Gly Ser Leu Gln Lys Arg Gly
                115                 120                 125

Ile Val Glu Gln Cys Cys Thr Ser Ile Cys Ser Leu Tyr Gln Leu Glu
            130                 135                 140

Asn Tyr Cys Gly
145

<210> SEQ ID NO 175
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Met Ser Thr Pro Leu Lys Ile Asp Phe Val Ser Asp Val Ser Cys Pro
1               5                   10                  15
```

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Gly Gly Gly Gly Ser Gly Gly Gly Gly Ser His His His His
50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
            85                  90                  95

Thr Arg Arg Asp Val Pro Gln Val Glu Leu Gly Gly Gly Pro Gly Ala
            100                 105                 110

Gly Ser Leu Gln Pro Leu Ala Leu Glu Gly Ser Leu Gln Ala Arg Gly
        115                 120                 125

Ile Val Glu Gln Cys Cys Thr Ser Ile Cys Ser Leu Tyr Gln Leu Glu
130                 135                 140

Asn Tyr Cys Gly
145

<210> SEQ ID NO 176
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Ser Thr Pro Leu Lys Ile Asp Phe Val Ser Asp Val Ser Cys Pro
1               5                   10                  15

Trp Cys Ile Ile Gly Leu Arg Gly Leu Thr Glu Ala Leu Asp Gln Leu
            20                  25                  30

Gly Ser Glu Val Gln Ala Glu Ile His Phe Gln Pro Phe Glu Leu Asn
        35                  40                  45

Pro Asn Gly Gly Gly Gly Ser Gly Gly Gly Gly Ser His His His His
50                  55                  60

His His Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
            85                  90                  95

Tyr Thr Pro Lys Thr Arg Arg Glu Ala Glu Asp Gln Gly Ser Leu Gln
            100                 105                 110

Lys Arg Gly Ile Val Glu Gln Cys Cys Thr Ser Ile Cys Ser Leu Tyr
        115                 120                 125

Gln Leu Glu Asn Tyr Cys Gly
    130                 135

<210> SEQ ID NO 177
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Met Ser Thr Pro Leu Lys Ile Asp Phe Val Ser Asp Val Ser Cys Pro
1               5                   10                  15

```
Trp Cys Ile Ile Gly Leu Arg Gly Leu Thr Glu Ala Leu Asp Gln Leu
             20                  25                  30

Gly Ser Glu Val Gln Ala Glu Ile His Phe Gln Pro Phe Glu Leu Asn
         35                  40                  45

Pro Asn Gly Gly Gly Gly Ser Gly Gly Gly Gly Ser His His His His
     50                  55                  60

His His Arg Phe Val Asn Gln His Leu Cys Gly Ser His Leu Val Glu
 65                  70                  75                  80

Ala Leu Tyr Leu Val Cys Gly Glu Arg Gly Phe Phe Tyr Thr Pro Lys
                 85                  90                  95

Thr Arg Arg Glu Ala Glu Asp Gln Gly Ser Leu Gln Lys Arg Gly Ile
            100                 105                 110

Val Glu Gln Cys Cys Thr Ser Ile Cys Ser Leu Tyr Gln Leu Glu Asn
        115                 120                 125

Tyr Cys Gly
    130

<210> SEQ ID NO 178
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Met Ser Cys Thr Arg Ala Phe Lys Pro Leu Leu Leu Ile Gly Leu Ala
 1               5                  10                  15

Thr Leu Met Cys Ser His Ala Phe Ala Ala Val Val Ile Thr Gly Thr
             20                  25                  30

Arg Leu Val Tyr Pro Ala Asp Gln Lys Glu Ile Thr Val Lys Leu Asn
         35                  40                  45

Asn Asn Gly Thr Leu Pro Ala Leu Val Gln Ser Trp Ile Asp Thr Gly
     50                  55                  60

Ser Val Glu Ser Thr Pro Thr Ser Ser Lys Ala Pro Phe Leu Leu Ser
 65                  70                  75                  80

Pro Pro Val Ala Arg Ile Asp Pro Thr Lys Gly Gln Ser Leu Arg Val
                 85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240
```

```
Pro Thr Arg Asn Thr Leu Gln Pro Gly Gly Gly Gly Ser Gly Gly Gly
            245                 250                 255

Gly Ser His His His His His His Asp Asp Asp Lys Phe Val Asn
            260                 265                 270

Gln His Leu Cys Gly Ser His Leu Val Glu Ala Leu Tyr Leu Val Cys
            275                 280                 285

Gly Glu Arg Gly Phe Phe Tyr Thr Pro Lys Thr Arg Arg Glu Ala Glu
            290                 295                 300

Asp Leu Gln Val Gly Gln Val Glu Leu Gly Gly Pro Gly Ala Gly
305                 310                 315                 320

Ser Leu Gln Pro Leu Ala Leu Glu Gly Ser Leu Gln Lys Arg Gly Ile
            325                 330                 335

Val Glu Gln Cys Cys Thr Ser Ile Cys Ser Leu Tyr Gln Leu Glu Asn
            340                 345                 350

Tyr Cys Gly
        355
```

<210> SEQ ID NO 179
<211> LENGTH: 350
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

```
Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
            35                  40                  45

Asn Asn Gly Thr Leu Pro Ala Leu Val Gln Ser Trp Ile Asp Thr Gly
        50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
            85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
            115                 120                 125

Asn Thr Leu Gln Met Ala Phe Arg Ser Arg Ile Lys Leu Phe Tyr Arg
        130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Leu Ala Leu Lys Ala
            165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
            195                 200                 205

Glu Thr Arg Gln Phe Ala Leu Pro Thr Leu Lys Ala Arg Pro Ser Ser
            210                 215                 220

Gln Ala Gln Val Glu Phe Ser Ala Ile Asn Asp Tyr Gly Ala Leu Val
```

```
                225                 230                 235                 240
Pro Thr Arg Asn Thr Leu Gln Pro Gly Gly Gly Ser Gly Gly Gly
                245                 250                 255

Gly Ser His His His His His Asp Asp Asp Lys Phe Val Asn
                260                 265                 270

Gln His Leu Cys Gly Ser His Leu Val Glu Ala Leu Tyr Leu Val Cys
                275                 280                 285

Gly Glu Arg Gly Phe Phe Tyr Thr Pro Lys Thr Arg Arg Asp Val Pro
                290                 295                 300

Gln Val Glu Leu Gly Gly Pro Gly Ala Gly Ser Leu Gln Pro Leu
305                 310                 315                 320

Ala Leu Glu Gly Ser Leu Gln Lys Arg Gly Ile Val Glu Gln Cys Cys
                325                 330                 335

Thr Ser Ile Cys Ser Leu Tyr Gln Leu Glu Asn Tyr Cys Gly
                340                 345                 350

<210> SEQ ID NO 180
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
                35                  40                  45

Asn Asn Gly Thr Leu Pro Ala Leu Val Gln Ser Trp Ile Asp Thr Gly
                50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
                100                 105                 110

Leu Asn Val Leu Glu Ile Pro Pro Lys Pro Glu Ala Gly Ala Asp Leu
                115                 120                 125

Asn Thr Leu Gln Met Ala Phe Arg Ser Arg Ile Lys Leu Phe Tyr Arg
                130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
                180                 185                 190

Ala Gly Asn Gln Arg Tyr Arg Ser Glu Asp Gly Met Val Gly Pro Gly
                195                 200                 205

Glu Thr Arg Gln Phe Ala Leu Pro Thr Leu Lys Ala Arg Pro Ser Ser
                210                 215                 220

Gln Ala Gln Val Glu Phe Ser Ala Ile Asn Asp Tyr Gly Ala Leu Val
225                 230                 235                 240
```

```
Pro Thr Arg Asn Thr Leu Gln Pro Gly Gly Gly Ser Gly Gly Gly
                245                 250                 255

Gly Ser His His His His His His Asp Asp Asp Lys Phe Val Asn
            260                 265                 270

Gln His Leu Cys Gly Ser His Leu Val Glu Ala Leu Tyr Leu Val Cys
            275                 280                 285

Gly Glu Arg Gly Phe Phe Tyr Thr Pro Lys Thr Arg Arg Asp Val Pro
            290                 295                 300

Gln Val Glu Leu Gly Gly Pro Gly Ala Gly Ser Leu Gln Pro Leu
305                 310                 315                 320

Ala Leu Glu Gly Ser Leu Gln Ala Arg Gly Ile Val Glu Gln Cys Cys
                325                 330                 335

Thr Ser Ile Cys Ser Leu Tyr Gln Leu Glu Asn Tyr Cys Gly
                340                 345                 350
```

<210> SEQ ID NO 181
<211> LENGTH: 333
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

```
Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
                35                  40                  45

Asn Asn Gly Thr Leu Pro Ala Leu Val Gln Ser Trp Ile Asp Thr Gly
            50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
                100                 105                 110

Leu Asn Val Leu Glu Ile Pro Pro Lys Pro Glu Ala Gly Ala Asp Leu
            115                 120                 125

Asn Thr Leu Gln Met Ala Phe Arg Ser Arg Ile Lys Leu Phe Tyr Arg
130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
                180                 185                 190

Ala Gly Asn Gln Arg Tyr Arg Ser Glu Asp Gly Met Val Gly Pro Gly
            195                 200                 205

Glu Thr Arg Gln Phe Ala Leu Pro Thr Leu Lys Ala Arg Pro Ser Ser
            210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro Gly Gly Gly Ser Gly Gly Gly
                245                 250                 255
```

Gly Ser His His His His His Asp Asp Asp Lys Phe Val Asn
        260                 265                 270

Gln His Leu Cys Gly Ser His Leu Val Glu Ala Leu Tyr Leu Val Cys
            275                 280                 285

Gly Glu Arg Gly Phe Phe Tyr Thr Pro Lys Thr Arg Arg Glu Ala Glu
        290                 295                 300

Asp Gln Gly Ser Leu Gln Lys Arg Gly Ile Val Glu Gln Cys Cys Thr
305                 310                 315                 320

Ser Ile Cys Ser Leu Tyr Gln Leu Glu Asn Tyr Cys Gly
                325                 330

<210> SEQ ID NO 182
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro Gly Gly Gly Ser Gly Gly Gly
                245                 250                 255

Gly Ser His His His His His His Arg Phe Val Asn Gln His Leu Cys
            260                 265                 270

Gly Ser His Leu Val Glu Ala Leu Tyr Leu Val Cys Gly Glu Arg Gly

```
            275                 280                 285
Phe Phe Tyr Thr Pro Lys Thr Arg Arg Glu Ala Glu Asp Leu Gln Val
        290                 295                 300
Gly Gln Val Glu Leu Gly Gly Pro Gly Ala Gly Ser Leu Gln Pro
305                 310                 315                 320
Leu Ala Leu Glu Gly Ser Leu Gln Lys Arg Gly Ile Val Glu Gln Cys
                325                 330                 335
Cys Thr Ser Ile Cys Ser Leu Tyr Gln Leu Glu Asn Tyr Cys Gly
            340                 345                 350
```

<210> SEQ ID NO 183
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Met Ser Cys Thr Arg Ala Phe Lys Pro Leu Leu Ile Gly Leu Ala
1               5                   10                  15
Thr Leu Met Cys Ser His Ala Phe Ala Ala Val Val Ile Thr Gly Thr
                20                  25                  30
Arg Leu Val Tyr Pro Ala Asp Gln Lys Glu Ile Thr Val Lys Leu Asn
            35                  40                  45
Asn Asn Gly Thr Leu Pro Ala Leu Val Gln Ser Trp Ile Asp Thr Gly
        50                  55                  60
Ser Val Glu Ser Thr Pro Thr Ser Ser Lys Ala Pro Phe Leu Leu Ser
65                  70                  75                  80
Pro Pro Val Ala Arg Ile Asp Pro Thr Lys Gly Gln Ser Leu Arg Val
                85                  90                  95
Leu Phe Thr Gly Ala Pro Leu Ala Gln Asp Lys Glu Ser Val Phe Trp
            100                 105                 110
Leu Asn Val Leu Glu Ile Pro Pro Lys Pro Glu Ala Gly Ala Asp Leu
        115                 120                 125
Asn Thr Leu Gln Met Ala Phe Arg Ser Arg Ile Lys Leu Phe Tyr Arg
    130                 135                 140
Pro Val Gly Leu Pro Gly Asn Pro Asn Glu Ala Val Glu Gln Val Gln
145                 150                 155                 160
Trp Gln Leu Val Thr Ala Arg Asp Gly Gln Gly Leu Ala Leu Lys Ala
                165                 170                 175
Tyr Asn Pro Ser Ala Phe His Val Ser Leu Ile Glu Leu Asp Leu Val
            180                 185                 190
Ala Gly Asn Gln Arg Tyr Arg Ser Glu Asp Gly Met Val Gly Pro Gly
        195                 200                 205
Glu Thr Arg Gln Phe Ala Leu Pro Thr Leu Lys Ala Arg Pro Ser Ser
    210                 215                 220
Gln Ala Gln Val Glu Phe Ser Ala Ile Asn Asp Tyr Gly Ala Leu Val
225                 230                 235                 240
Pro Thr Arg Asn Thr Leu Gln Pro Gly Gly Gly Ser Gly Gly Gly
                245                 250                 255
Gly Ser His His His His His His Arg Phe Val Asn Gln His Leu Cys
            260                 265                 270
Gly Ser His Leu Val Glu Ala Leu Tyr Leu Val Cys Gly Glu Arg Gly
        275                 280                 285
```

```
Phe Phe Tyr Thr Pro Lys Thr Arg Arg Asp Val Pro Gln Val Glu Leu
            290                 295                 300

Gly Gly Gly Pro Gly Ala Gly Ser Leu Gln Pro Leu Ala Leu Glu Gly
305                 310                 315                 320

Ser Leu Gln Lys Arg Gly Ile Val Glu Gln Cys Cys Thr Ser Ile Cys
                325                 330                 335

Ser Leu Tyr Gln Leu Glu Asn Tyr Cys Gly
            340                 345

<210> SEQ ID NO 184
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro Gly Gly Gly Ser Gly Gly Gly
                245                 250                 255

Gly Ser His His His His His His Arg Phe Val Asn Gln His Leu Cys
            260                 265                 270

Gly Ser His Leu Val Glu Ala Leu Tyr Leu Val Cys Gly Glu Arg Gly
        275                 280                 285

Phe Phe Tyr Thr Pro Lys Thr Arg Arg Asp Val Pro Gln Val Glu Leu
    290                 295                 300
```

Gly Gly Gly Pro Gly Ala Gly Ser Leu Gln Pro Leu Ala Leu Glu Gly
305                 310                 315                 320

Ser Leu Gln Ala Arg Gly Ile Val Glu Gln Cys Cys Thr Ser Ile Cys
                325                 330                 335

Ser Leu Tyr Gln Leu Glu Asn Tyr Cys Gly
            340                 345

<210> SEQ ID NO 185
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
            35                  40                  45

Asn Asn Gly Thr Leu Pro Ala Leu Val Gln Ser Trp Ile Asp Thr Gly
        50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Ala Pro Leu Ala Gln Asp Lys Glu Ser Val Phe Trp
            100                 105                 110

Leu Asn Val Leu Glu Ile Pro Pro Lys Pro Glu Ala Gly Ala Asp Leu
        115                 120                 125

Asn Thr Leu Gln Met Ala Phe Arg Ser Arg Ile Lys Leu Phe Tyr Arg
    130                 135                 140

Pro Val Gly Leu Pro Gly Asn Pro Asn Glu Ala Val Glu Gln Val Gln
145                 150                 155                 160

Trp Gln Leu Val Thr Ala Arg Asp Gly Gln Gly Leu Ala Leu Lys Ala
                165                 170                 175

Tyr Asn Pro Ser Ala Phe His Val Ser Leu Ile Glu Leu Asp Leu Val
            180                 185                 190

Ala Gly Asn Gln Arg Tyr Arg Ser Glu Asp Gly Met Val Gly Pro Gly
        195                 200                 205

Glu Thr Arg Gln Phe Ala Leu Pro Thr Leu Lys Ala Arg Pro Ser Ser
    210                 215                 220

Gln Ala Gln Val Glu Phe Ser Ala Ile Asn Asp Tyr Gly Ala Leu Val
225                 230                 235                 240

Pro Thr Arg Asn Thr Leu Gln Pro Gly Gly Gly Ser Gly Gly Gly
                245                 250                 255

Gly Ser His His His His His His Arg Phe Val Asn Gln His Leu Cys
            260                 265                 270

Gly Ser His Leu Val Glu Ala Leu Tyr Leu Val Cys Gly Glu Arg Gly
        275                 280                 285

Phe Phe Tyr Thr Pro Lys Thr Arg Arg Glu Ala Glu Asp Gln Gly Ser
    290                 295                 300

Leu Gln Lys Arg Gly Ile Val Glu Gln Cys Cys Thr Ser Ile Cys Ser

```
                305                 310                 315                 320
Leu Tyr Gln Leu Glu Asn Tyr Cys Gly
                325

<210> SEQ ID NO 186
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
                35                  40                  45

Asn Asn Gly Thr Leu Pro Ala Leu Val Gln Ser Trp Ile Asp Thr Gly
            50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Ser His His
                100                 105                 110

His His His His Asp Asp Asp Lys Phe Val Asn Gln His Leu Cys
                115                 120                 125

Gly Ser His Leu Val Glu Ala Leu Tyr Leu Val Cys Gly Glu Arg Gly
            130                 135                 140

Phe Phe Tyr Thr Pro Lys Thr Arg Arg Glu Ala Glu Asp Leu Gln Val
145                 150                 155                 160

Gly Gln Val Glu Leu Gly Gly Pro Gly Ala Gly Ser Leu Gln Pro
                165                 170                 175

Leu Ala Leu Glu Gly Ser Leu Gln Lys Arg Gly Ile Val Glu Gln Cys
                180                 185                 190

Cys Thr Ser Ile Cys Ser Leu Tyr Gln Leu Glu Asn Tyr Cys Gly
            195                 200                 205

<210> SEQ ID NO 187
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
                35                  40                  45

Asn Asn Gly Thr Leu Pro Ala Leu Val Gln Ser Trp Ile Asp Thr Gly
            50                  55                  60

Ser Val Glu Ser Thr Pro Thr Ser Ser Lys Ala Pro Phe Leu Leu Ser
```

-continued

```
                 65                  70                  75                  80
Pro Pro Val Ala Arg Ile Asp Pro Thr Lys Gly Gln Ser Leu Arg Val
                 85                  90                  95

Leu Phe Thr Gly Gly Gly Gly Ser Gly Gly Gly Ser His His
                100                 105                 110

His His His Asp Asp Asp Lys Phe Val Asn Gln His Leu Cys
                115                 120                 125

Gly Ser His Leu Val Glu Ala Leu Tyr Leu Val Cys Gly Glu Arg Gly
            130                 135                 140

Phe Phe Tyr Thr Pro Lys Thr Arg Arg Asp Val Pro Gln Val Glu Leu
145                 150                 155                 160

Gly Gly Gly Pro Gly Ala Gly Ser Leu Gln Pro Leu Ala Leu Glu Gly
                165                 170                 175

Ser Leu Gln Lys Arg Gly Ile Val Glu Gln Cys Cys Thr Ser Ile Cys
            180                 185                 190

Ser Leu Tyr Gln Leu Glu Asn Tyr Cys Gly
            195                 200

<210> SEQ ID NO 188
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
            35                  40                  45

Asn Asn Gly Thr Leu Pro Ala Leu Val Gln Ser Trp Ile Asp Thr Gly
        50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Ser His His
                100                 105                 110

His His His Asp Asp Asp Lys Phe Val Asn Gln His Leu Cys
                115                 120                 125

Gly Ser His Leu Val Glu Ala Leu Tyr Leu Val Cys Gly Glu Arg Gly
            130                 135                 140

Phe Phe Tyr Thr Pro Lys Thr Arg Arg Asp Val Pro Gln Val Glu Leu
145                 150                 155                 160

Gly Gly Gly Pro Gly Ala Gly Ser Leu Gln Pro Leu Ala Leu Glu Gly
                165                 170                 175

Ser Leu Gln Ala Arg Gly Ile Val Glu Gln Cys Cys Thr Ser Ile Cys
            180                 185                 190

Ser Leu Tyr Gln Leu Glu Asn Tyr Cys Gly
            195                 200

<210> SEQ ID NO 189
<211> LENGTH: 203
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
            35                  40                  45

Asn Asn Gly Thr Leu Pro Ala Leu Val Gln Ser Trp Ile Asp Thr Gly
        50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Ser His His
                100                 105                 110

His His His His Arg Phe Val Asn Gln His Leu Cys Gly Ser His Leu
            115                 120                 125

Val Glu Ala Leu Tyr Leu Val Cys Gly Glu Arg Gly Phe Phe Tyr Thr
    130                 135                 140

Pro Lys Thr Arg Arg Glu Ala Glu Asp Leu Gln Val Gly Gln Val Glu
145                 150                 155                 160

Leu Gly Gly Gly Pro Gly Ala Gly Ser Leu Gln Pro Leu Ala Leu Glu
                165                 170                 175

Gly Ser Leu Gln Lys Arg Gly Ile Val Glu Gln Cys Cys Thr Ser Ile
            180                 185                 190

Cys Ser Leu Tyr Gln Leu Glu Asn Tyr Cys Gly
            195                 200

<210> SEQ ID NO 190
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
            35                  40                  45

Asn Asn Gly Thr Leu Pro Ala Leu Val Gln Ser Trp Ile Asp Thr Gly
        50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Ser His His
                100                 105                 110

His His His His Arg Phe Val Asn Gln His Leu Cys Gly Ser His Leu
            115                 120                 125

Val Glu Ala Leu Tyr Leu Val Cys Gly Glu Arg Gly Phe Phe Tyr Thr
        130                 135                 140

Pro Lys Thr Arg Arg Asp Val Pro Gln Val Glu Leu Gly Gly Gly Pro
145                 150                 155                 160

Gly Ala Gly Ser Leu Gln Pro Leu Ala Leu Glu Gly Ser Leu Gln Lys
                165                 170                 175

Arg Gly Ile Val Glu Gln Cys Cys Thr Ser Ile Cys Ser Leu Tyr Gln
            180                 185                 190

Leu Glu Asn Tyr Cys Gly
        195

<210> SEQ ID NO 191
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Ser His His
                100                 105                 110

His His His His Arg Phe Val Asn Gln His Leu Cys Gly Ser His Leu
            115                 120                 125

Val Glu Ala Leu Tyr Leu Val Cys Gly Glu Arg Gly Phe Phe Tyr Thr
        130                 135                 140

Pro Lys Thr Arg Arg Asp Val Pro Gln Val Glu Leu Gly Gly Gly Pro
145                 150                 155                 160

Gly Ala Gly Ser Leu Gln Pro Leu Ala Leu Glu Gly Ser Leu Gln Ala
                165                 170                 175

Arg Gly Ile Val Glu Gln Cys Cys Thr Ser Ile Cys Ser Leu Tyr Gln
            180                 185                 190

Leu Glu Asn Tyr Cys Gly
        195

<210> SEQ ID NO 192
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Ser His His
                100                 105                 110

His His His His Asp Asp Asp Lys Phe Val Asn Gln His Leu Cys
            115                 120                 125

Gly Ser His Leu Val Glu Ala Leu Tyr Leu Val Cys Gly Glu Arg Gly
        130                 135                 140

Phe Phe Tyr Thr Pro Lys Thr Arg Arg Glu Ala Glu Asp Gln Gly Ser
145                 150                 155                 160

Leu Gln Lys Arg Gly Ile Val Glu Gln Cys Cys Thr Ser Ile Cys Ser
                165                 170                 175

Leu Tyr Gln Leu Glu Asn Tyr Cys Gly
            180                 185

<210> SEQ ID NO 193
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Thr Leu Pro Ala Leu Val Gln Ser Trp Ile Asp Thr Gly
    50                  55                  60

Ser Val Glu Ser Thr Pro Thr Ser Ser Lys Ala Pro Phe Leu Leu Ser
65                  70                  75                  80

Pro Pro Val Ala Arg Ile Asp Pro Thr Lys Gly Gln Ser Leu Arg Val
                85                  90                  95

Leu Phe Thr Gly Gly Gly Gly Ser Gly Gly Gly Ser His His
                100                 105                 110

His His His His Arg Phe Val Asn Gln His Leu Cys Gly Ser His Leu
            115                 120                 125

Val Glu Ala Leu Tyr Leu Val Cys Gly Glu Arg Gly Phe Phe Tyr Thr
        130                 135                 140

Pro Lys Thr Arg Arg Glu Ala Glu Asp Gln Gly Ser Leu Gln Lys Arg
145                 150                 155                 160

Gly Ile Val Glu Gln Cys Cys Thr Ser Ile Cys Ser Leu Tyr Gln Leu
                165                 170                 175

Glu Asn Tyr Cys Gly
            180

<210> SEQ ID NO 194
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Gly Gly Gly Ser Gly Gly Gly Ser His His His His
    50                  55                  60

His His Asp Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Glu Ala Glu Asp Leu Gln Val Gly Gln
            100                 105                 110

Val Glu Leu Gly Gly Gly Pro Gly Ala Gly Ser Leu Gln Pro Leu Ala
        115                 120                 125

Leu Glu Gly Ser Leu Gln Lys Arg Gly Ile Val Glu Gln Cys Cys Thr
130                 135                 140

Ser Ile Cys Ser Leu Tyr Gln Leu Glu Asn Tyr Cys Gly
145                 150                 155

<210> SEQ ID NO 195
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Gly Gly Gly Ser Gly Gly Gly Ser His His His His
    50                  55                  60

His His Asp Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Asp Val Pro Gln Val Glu Leu Gly Gly
            100                 105                 110

Gly Pro Gly Ala Gly Ser Leu Gln Pro Leu Ala Leu Glu Gly Ser Leu
        115                 120                 125

```
Gln Lys Arg Gly Ile Val Glu Gln Cys Cys Thr Ser Ile Cys Ser Leu
    130                 135                 140

Tyr Gln Leu Glu Asn Tyr Cys Gly
145                 150

<210> SEQ ID NO 196
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
            35                  40                  45

Asn Asn Gly Gly Gly Gly Ser Gly Gly Gly Gly Ser His His His His
        50                  55                  60

His His Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Asp Val Pro Gln Val Glu Leu Gly Gly
            100                 105                 110

Gly Pro Gly Ala Gly Ser Leu Gln Pro Leu Ala Leu Glu Gly Ser Leu
        115                 120                 125

Gln Ala Arg Gly Ile Val Glu Gln Cys Cys Thr Ser Ile Cys Ser Leu
    130                 135                 140

Tyr Gln Leu Glu Asn Tyr Cys Gly
145                 150

<210> SEQ ID NO 197
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
                20                  25                  30

Arg Leu Val Tyr Pro Ala Asp Gln Lys Glu Ile Thr Val Lys Leu Asn
            35                  40                  45

Asn Asn Gly Gly Gly Gly Ser Gly Gly Gly Gly Ser His His His His
        50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
                85                  90                  95

Thr Arg Arg Glu Ala Glu Asp Leu Gln Val Gly Gln Val Glu Leu Gly
            100                 105                 110
```

Gly Gly Pro Gly Ala Gly Ser Leu Gln Pro Leu Ala Leu Glu Gly Ser
        115                 120                 125

Leu Gln Lys Arg Gly Ile Val Glu Gln Cys Cys Thr Ser Ile Cys Ser
    130                 135                 140

Leu Tyr Gln Leu Glu Asn Tyr Cys Gly
145                 150

<210> SEQ ID NO 198
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Gly Gly Gly Ser Gly Gly Gly Gly Ser His His His His
    50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
                85                  90                  95

Thr Arg Arg Asp Val Pro Gln Val Glu Leu Gly Gly Gly Pro Gly Ala
            100                 105                 110

Gly Ser Leu Gln Pro Leu Ala Leu Glu Gly Ser Leu Gln Lys Arg Gly
        115                 120                 125

Ile Val Glu Gln Cys Cys Thr Ser Ile Cys Ser Leu Tyr Gln Leu Glu
    130                 135                 140

Asn Tyr Cys Gly
145

<210> SEQ ID NO 199
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Ser Cys Thr Arg Ala Phe Lys Pro Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Gly Gly Gly Ser Gly Gly Gly Gly Ser His His His His
    50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
                85                  90                  95

```
Thr Arg Arg Asp Val Pro Gln Val Glu Leu Gly Gly Pro Gly Ala
            100                 105                 110

Gly Ser Leu Gln Pro Leu Ala Leu Glu Gly Ser Leu Gln Ala Arg Gly
        115                 120                 125

Ile Val Glu Gln Cys Cys Thr Ser Ile Cys Ser Leu Tyr Gln Leu Glu
130                 135                 140

Asn Tyr Cys Gly
145

<210> SEQ ID NO 200
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Gly Gly Gly Ser Gly Gly Gly Gly Ser His His His His
    50                  55                  60

His His Asp Asp Asp Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Pro Lys Thr Arg Arg Glu Ala Glu Asp Gln Gly Ser Leu Gln
            100                 105                 110

Lys Arg Gly Ile Val Glu Gln Cys Cys Thr Ser Ile Cys Ser Leu Tyr
        115                 120                 125

Gln Leu Glu Asn Tyr Cys Gly
    130                 135

<210> SEQ ID NO 201
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Ser Cys Thr Arg Ala Phe Lys Pro Leu Leu Leu Ile Gly Leu Ala
1               5                   10                  15

Thr Leu Met Cys Ser His Ala Phe Ala Ala Val Val Ile Thr Gly Thr
            20                  25                  30

Arg Leu Val Tyr Pro Ala Asp Gln Lys Glu Ile Thr Val Lys Leu Asn
        35                  40                  45

Asn Asn Gly Gly Gly Gly Ser Gly Gly Gly Gly Ser His His His His
    50                  55                  60

His His Arg Phe Val Asn Gln His Leu Cys Gly Ser His Leu Val Glu
65                  70                  75                  80

Ala Leu Tyr Leu Val Cys Gly Glu Arg Gly Phe Phe Tyr Thr Pro Lys
                85                  90                  95
```

```
Thr Arg Arg Glu Ala Glu Asp Gln Gly Ser Leu Gln Lys Arg Gly Ile
            100                 105                 110

Val Glu Gln Cys Cys Thr Ser Ile Cys Ser Leu Tyr Gln Leu Glu Asn
        115                 120                 125

Tyr Cys Gly
    130

<210> SEQ ID NO 202
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
atgaaagtcg aaccagggct ctaccagcat acaaggggc cgcagtaccg tgttttcagc     60
gtggcgcgcc actctgaaac cgaagaagaa gtggtgtttt accaagcgct gtatggcgaa   120 tacggcttt gggtgcgccc tttgagcatg ttcctggaga ccgtcgaagt tgacggcgag   180
caggtcccgc gctttgcttt ggtcacggcc gaacccagtc ttttttacagg gcaaggtggg   240 ggtgggtcgg gtggtggtgg gtcgcatcat catcaccacc accga                   285

<210> SEQ ID NO 203
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
atgtcgtgca cacgtgcatt caaaccactg ctgctgatcg gcctggccac actgatgtgt     60
tcccatgcat tcgctgcagt ggtgattacc ggtacgcgcc tggtctatcc ggcggaccag   120
aaagaaatca ccgtaaaact gaacaataac ggcacgttgc ccgcactggt ccaatcatgg   180
atcgacaccg gcagcgtcga atcgacaccc accagctcca aggcgccgtt cctattgtcg   240
cccccggtgg cgcgcattga cccgaccaag ggccaaagct tgcgagtgct ctttaccggc   300 gcgccttttgg cgcaggacaa agagtcggtg ttctggctca acgttctcga aatcccgccc   360
aaacccgagg cgggtgcaga cctcaacacg ctgcaaatgg cttttccgttc gcgcatcaag   420 ctgttctatc gcccggtcgg cttgcctgga aatcccaatg aggcggttga gcaggtgcag   480
tggcaattgg ttacggcacg cgatggccaa ggcctggcgc tgaaggcgta cccgtcggcg   540
ttccacgtct cgctgatcga gttggacctg gtggcgggta accaacgcta tcgcagtgag   600
gacggcatgg tcggccctgg ggaaacccgg cagttcgcgc tgcccacgct caaggccagg   660
ccgtcgagcc aggcacaagt ggagttcagc gccatcaacg attacggcgc gttggtcccg   720
acccgcaaca cgctgcagcc cggtggggt gggtcgggtg tggtgggtc gcatcatcat   780 caccaccacc ga                                                       792

<210> SEQ ID NO 204
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 204

```
atgtcgtgca cacgtgcatt caaaccactg ctgctgatcg gcctggccac actgatgtgt    60
tcccatgcat tcgctgcagt ggtgattacc ggtacgcgcc tggtctatcc ggcggaccag   120
aaagaaatca ccgtaaaact gaacaataac ggcacgttgc ccgcactggt ccaatcatgg   180
atcgacaccg gcagcgtcga atcgacaccc accagctcca aggcgccgtt cctattgtcg   240
cccccggtgg cgcgcattga cccgaccaag ggccaaagct tgcgagtgct ctttaccggc   300 ggtggggtg ggtcgggtgg tggtgggtcg catcatcatc accaccaccg a            351
```

<210> SEQ ID NO 205
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205

```
atgtcgtgca cacgtgcatt caaaccactg ctgctgatcg gcctggccac actgatgtgt    60
tcccatgcat tcgctgcagt ggtgattacc ggtacgcgcc tggtctatcc ggcggaccag   120
aaagaaatca ccgtaaaact gaacaataac ggtggggtg ggtcgggtgg tggtgggtcg   180
catcatcatc accaccaccg a                                              201
```

<210> SEQ ID NO 206
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206

```
atgtccgaag ttaatctgtc caccgacgaa acccgcgtca gctacggtat cggccgtcag    60
ttgggcgacc aactgcgtga caacccgcca ccgggcgtca gcctggacgc gatcctggcc   120
ggcctgaccg acgcgttcgc aggcaagcca agccgtgttg accaagagca atggcggcc   180 agcttcaaag tgatccgcga atcatgcaa gccgaagccg ctgccaaggc tgaagctgca   240
gcaggcgctg gcctggcttt cctggcggaa aacgccaagc gtgatggcat caccaccctg   300
gcttccggcc tgcaatttga agtgctgacg gctggtaccg gcgccaagcc gacccgtgaa   360
gaccaagtgc gtactcacta ccacggcacc ctgatcgacg gcactgtgtt cgacagctcc   420
tacgagcgcg gccagcctgc agaattcccg gttggcggcg tgatcgccgg ctggaccgaa   480
gccctgcaac tgatgaatgc cggcagcaaa tggcgcgtgt acgtgccgag cgaactggct   540
tacggcgctc aaggcgttgg cagcatcccg ccgcacagcg ttctggtatt cgacgtcgag   600
ctgctcgacg ttctgggtgg gggtgggtcg ggtggtggtg ggtcgcatca tcatcaccac   660
caccga                                                               666
```

<210> SEQ ID NO 207
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207

```
atgtccgaag ttaatctgtc caccgacgaa acccgcgtca gctacggtat cggccgtcag      60
ttgggcgacc aactgcgtga caacccgcca ccgggcgtca gcctggacgc gatcctggcc     120
ggcctgaccg acgcgttcgc aggcaagcca agccgtgttg accaagagca aatggcggcc     180
agcttcaaag tgatccgcga aatcatgcaa gccgaagccg ctgccaaggc tgaagctgca     240
gcaggcgctg gcctggcttt cctggcggaa aacgccaagc gtgatggcat caccaccctg     300
ggtgggggtg ggtcgggtgg tggtgggtcg catcatcatc accaccaccg a              351
```

<210> SEQ ID NO 208
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208

```
atgtccgaag ttaatctgtc caccgacgaa acccgcgtca gctacggtat cggccgtcag      60
ttgggcgacc aactgcgtga caacccgcca ccgggcgtca gcctggacgc gatcctggcc     120
ggcctgaccg acgcgttcgc aggcaagcca ggtgggggtg ggtcgggtgg tggtgggtcg     180
catcatcatc accaccaccg a                                                201
```

<210> SEQ ID NO 209
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
atgagtactc ccctgaaaat cgatttcgtc agcgacgtat cctgcccctg gtgcatcatc      60
ggcctgcgcg gcttgaccga agccctcgac cagctcggca gcgaggtgca ggccgagatt     120
cattttcaac cgttcgaact gaacccgaac atgcccgccg aaggtcagaa catcgtcgag     180
cacattaccg aaaagtacgg ctccacggct gaagagtccc aggctaatcg tgcgcgtatc     240
cgtgacatgg gcgccgcgtt gggctttgct tttcgcaccg atggccagag ccgtatctac     300
aacaccttcg acgcgcaccg tctgttgcac tgggccgggt tggaaggctt gcagtacaac     360
ctcaaggaag cgctgttcaa ggcgtacttc agcgatggcc aggacccttc cgaccacgcg     420
accttggcga tcatcgccga aagcgtcggg ctggaccttg cgcgcgccgc cgagattctt     480
gccagcgatg aatacgccgc cgaggtccgc gagcaggagc agctgtgggt ttcccgtggg     540
gtgagttcgg tgccgaccat tgtcttcaat gaccaatatg cggtgagcgg tgggcaaccg     600
gctgaagcct tcgtgggtgc gattcgccag atcatcaacg aatccaaatc cggtgggggt     660
gggtcgggtg gtggtgggtc gcatcatcat caccaccacc ga                         702
```

<210> SEQ ID NO 210
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
atgagtactc ccctgaaaat cgatttcgtc agcgacgtat cctgcccctg gtgcatcatc      60
```

```
ggcctgcgcg gcttgaccga agccctcgac cagctcggca gcgaggtgca ggccgagatt     120
cattttcaac cgttcgaact gaacccgaac atgcccgccg aaggtcagaa catcgtcgag     180
cacattaccg aaaagtacgg ctccacggct gaagagtccc aggctaatcg tgcgcgtatc     240
cgtgacatgg gcgccgcgtt gggctttgct tttcgcaccg atggccagag ccgtatctac     300 ggtggggtg ggtcgggtgg tggtgggtcg catcatcatc accaccaccg a               351
```

<210> SEQ ID NO 211
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

```
atgagtactc ccctgaaaat cgatttcgtc agcgacgtat cctgcccctg gtgcatcatc     60
ggcctgcgcg gcttgaccga agccctcgac cagctcggca gcgaggtgca ggccgagatt     120
cattttcaac cgttcgaact gaacccgaac ggtggggtg ggtcgggtgg tggtgggtcg     180
catcatcatc accaccaccg a                                              201
```

<210> SEQ ID NO 212
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212

```
atgaaagtcg aaccagggct ctaccagcat tacaagggc cgcagtaccg tgttttcagc     60
gtggcgcgcc actctgaaac cgaagaagaa gtggtgtttt accaagcgct gtatggcgaa     120
tacggctttt gggtgcgccc tttgagcatg ttcctggaga ccgtcgaagt tgacggcgag     180
caggtcccgc gctttgcttt ggtcacggcc gaacccagtc ttttacagg gcaaggtggg     240 ggtgggtcgg gtggtggtgg gtcgcatcat catcaccacc acgatgatga tgataag        297
```

<210> SEQ ID NO 213
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213

```
atgtcgtgca cacgtgcatt caaaccactg ctgctgatcg gcctggccac actgatgtgt     60
tcccatgcat tcgctgcagt ggtgattacc ggtacgcgcc tggtctatcc ggcggaccag     120
aaagaaatca ccgtaaaact gaacaataac ggcacgttgc ccgcactggt ccaatcatgg     180
atcgacaccg gcagcgtcga atcgacaccc accagctcca aggcgccgtt cctattgtcg     240
cccccggtgg cgcgcattga cccgaccaag ggccaaagct tgcgagtgct ctttaccggc     300 gcgccttttgg cgcaggacaa agagtcggtg ttctggctca acgttctcga atcccgccc     360 aaacccgagg cgggtgcaga cctcaacacg ctgcaaatgg ctttccgttc gcgcatcaag     420
ctgttctatc gcccggtcgg cttgcctgga aatcccaatg aggcggttga gcaggtgcag     480
tggcaattgg ttacggcacg cgatggccaa ggcctggcgc tgaaggcgta caacccgtcg     540
```

```
gcgttccacg tctcgctgat cgagttggac ctggtggcgg gtaaccaacg ctatcgcagt    600
gaggacggca tggtcggccc tggggaaacc cggcagttcg cgctgcccac gctcaaggcc    660
aggccgtcga gccaggcaca agtggagttc agcgccatca acgattacgg cgcgttggtc    720
ccgacccgca acacgctgca gcccggtggg ggtgggtcgg gtggtggtgg gtcgcatcat    780
catcaccacc acgatgatga tgataag                                       807

<210> SEQ ID NO 214
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
atgtcgtgca cacgtgcatt caaaccactg ctgctgatcg gcctggccac actgatgtgt     60
tcccatgcat tcgctgcagt ggtgattacc ggtacgcgcc tggtctatcc ggcggaccag    120
aaagaaatca ccgtaaaact gaacaataac ggcacgttgc ccgcactggt ccaatcatgg    180
atcgacaccg gcagcgtcga atcgacaccc accagctcca aggcgccgtt cctattgtcg    240
cccccggtgg cgcgcattga cccgaccaag ggccaaagct tgcgagtgct ctttaccggc    300 ggtggggggtg ggtcgggtgg tggtgggtcg catcatcatc accaccacga tgatgatgat    360
aag                                                                 363

<210> SEQ ID NO 215
<211> LENGTH: 213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
atgtcgtgca cacgtgcatt caaaccactg ctgctgatcg gcctggccac actgatgtgt     60
tcccatgcat tcgctgcagt ggtgattacc ggtacgcgcc tggtctatcc ggcggaccag    120
aaagaaatca ccgtaaaact gaacaataac ggtgggggtg ggtcgggtgg tggtgggtcg    180
catcatcatc accaccacga tgatgatgat aag                                213

<210> SEQ ID NO 216
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216
atgtccgaag ttaatctgtc caccgacgaa acccgcgtca gctacggtat cggccgtcag     60
ttgggcgacc aactgcgtga caacccgcca ccgggcgtca gcctggacgc gatcctggcc    120
ggcctgaccg acgcgttcgc aggcaagcca agccgtgttg accaagagca aatggcggcc    180
agcttcaaag tgatccgcga aatcatgcaa gccgaagccg ctgccaaggc tgaagctgca    240
gcaggcgctg gcctggcttt cctggcgaaa acgccaagc gtgatggcat caccaccctg    300
gcttccggcc tgcaatttga agtgctgacg gctggtaccg cgccaagcc gacccgtgaa    360 gaccaagtgc gtactcacta ccacggcacc ctgatcgacg gcactgtgtt cgacagctcc    420
```

```
tacgagcgcg gccagcctgc agaattcccg gttggcggcg tgatcgccgg ctggaccgaa      480
gccctgcaac tgatgaatgc cggcagcaaa tggcgcgtgt acgtgccgag cgaactggct      540
tacggcgctc aaggcgttgg cagcatcccg ccgcacagcg ttctggtatt cgacgtcgag      600
ctgctcgacg ttctgggtgg gggtgggtcg ggtggtggtg ggtcgcatca tcatcaccac      660
cacgatgatg atgataag                                                    678

<210> SEQ ID NO 217
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217
atgtccgaag ttaatctgtc caccgacgaa acccgcgtca gctacggtat cggccgtcag       60
ttgggcgacc aactgcgtga caacccgcca ccgggcgtca gcctggacgc gatcctggcc      120
ggcctgaccg acgcgttcgc aggcaagcca agccgtgttg accaagagca aatggcggcc      180
agcttcaaag tgatccgcga aatcatgcaa gccgaagccg ctgccaaggc tgaagctgca      240
gcaggcgctg gcctggcttt cctggcggaa aacgccaagc gtgatggcat caccaccctg      300 ggtggggggtg ggtcgggtgg tggtgggtcg catcatcatc accaccacga tgatgatgat      360
aag                                                                    363

<210> SEQ ID NO 218
<211> LENGTH: 213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218
atgtccgaag ttaatctgtc caccgacgaa acccgcgtca gctacggtat cggccgtcag       60
ttgggcgacc aactgcgtga caacccgcca ccgggcgtca gcctggacgc gatcctggcc      120
ggcctgaccg acgcgttcgc aggcaagcca ggtgggggtg ggtcgggtgg tggtgggtcg      180
catcatcatc accaccacga tgatgatgat aag                                   213

<210> SEQ ID NO 219
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 219
atgagtactc ccctgaaaat cgatttcgtc agcgacgtat cctgcccctg gtgcatcatc       60
ggcctgcgcg gcttgaccga agccctcgac cagctcggca gcgaggtgca ggccgagatt      120
cattttcaac cgttcgaact gaaccccgaac atgcccgccg aaggtcagaa catcgtcgag      180
cacattaccg aaaagtacgg ctccacggct gaagagtccc aggctaatcg tgcgcgtatc      240
cgtgacatgg gcgccgcgtt gggctttgct tttcgcaccg atggccagag ccgtatctac      300 aacacccttcg acgcgcaccg tctgttgcac tgggccgggt tggaaggctt gcagtacaac      360
ctcaaggaag cgctgttcaa ggcgtacttc agcgatggcc aggacccttc cgaccacgcg      420
```

```
accttggcga tcatcgccga aagcgtcggg ctggaccttg cgcgcgccgc cgagattctt    480
gccagcgatg aatacgccgc cgaggtccgc gagcaggagc agctgtgggt ttcccgtggg    540
gtgagttcgg tgccgaccat tgtcttcaat gaccaatatg cggtgagcgg tgggcaaccg    600
gctgaagcct tcgtgggtgc gattcgccag atcatcaacg aatccaaatc cggtgggggt    660
gggtcgggtg gtggtgggtc gcatcatcat caccaccacg atgatgatga taag          714

<210> SEQ ID NO 220
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220
atgagtactc ccctgaaaat cgatttcgtc agcgacgtat cctgcccctg gtgcatcatc     60
ggcctgcgcg gcttgaccga agccctcgac cagctcggca gcgaggtgca ggccgagatt    120
cattttcaac cgttcgaact gaacccgaac atgcccgccg aaggtcagaa catcgtcgag    180
cacattaccg aaaagtacgg ctccacggct gaagagtccc aggctaatcg tgcgcgtatc    240
cgtgacatgg gcgccgcgtt gggctttgct tttcgcaccg atggccagag ccgtatctac    300
ggtgggggtg ggtcgggtgg tggtgggtcg catcatcatc accaccacga tgatgatgat    360
aag                                                                  363

<210> SEQ ID NO 221
<211> LENGTH: 213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
atgagtactc ccctgaaaat cgatttcgtc agcgacgtat cctgcccctg gtgcatcatc     60
ggcctgcgcg gcttgaccga agccctcgac cagctcggca gcgaggtgca ggccgagatt    120
cattttcaac cgttcgaact gaacccgaac ggtgggggtg gtcgggtgg tggtgggtcg    180 catcatcatc accaccacga tgatgatgat aag                                 213

<210> SEQ ID NO 222
<211> LENGTH: 30
<212> TYPE: PRT
<213> ORGANISM: Homo sapiens

<400> SEQUENCE: 222

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 223
<211> LENGTH: 21
<212> TYPE: PRT
<213> ORGANISM: Homo sapiens

<400> SEQUENCE: 223

Gly Ile Val Glu Gln Cys Cys Thr Ser Ile Cys Ser Leu Tyr Gln Leu
1               5                   10                  15
```

Glu Asn Tyr Cys Asn
            20

<210> SEQ ID NO 224
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 225
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Gly Gly Gly Ser Gly Gly Gly Ser His His His His His His
1               5                   10                  15

Arg

<210> SEQ ID NO 227
<211> LENGTH: 549
<212> TYPE: PRT
<213> ORGANISM: Pseudomonas fluorescens

<400> SEQUENCE: 227

Met Thr Val Val Lys Val Phe Ser Met Trp Glu Leu Tyr Arg Ala Asp
1               5                   10                  15

Asn Gly Ala Val Gly Ile Gly Asn Ser His Ile Trp Thr Val Asn Phe
            20                  25                  30

Pro Leu Phe Arg Val Ser Lys His Met His Ile Pro Val Arg Gln Ser
            35                  40                  45

Ser Tyr Ser Arg Pro Ser Asp Lys Leu Gln Pro Asp Leu Ser Pro Asp
        50                  55                  60

Glu His Gln Val Val Leu Trp Ala Asn Asn Lys Lys Ser Phe Thr Thr
65                  70                  75                  80

Asp Gln Ala Ala Lys His Ile Thr Arg Gly Gly Phe Lys Phe His Asp
                85                  90                  95

```
Arg Asn Asn Asp Gly Lys Ile Val Val Gly Tyr Asn Phe Ala Gly Gly
                100                 105                 110

Phe Asn Ala Ala Gln Lys Glu Arg Ala Arg Gln Ala Leu Gln Tyr Trp
            115                 120                 125

Ala Asp Val Ala Asn Ile Glu Phe Val Glu Asn Gly Pro Asn Thr Asp
        130                 135                 140

Gly Thr Ile Ser Ile Lys Gly Val Pro Gly Ser Ala Gly Val Ala Gly
145                 150                 155                 160

Leu Pro Asn Lys Tyr Asn Ser Asn Val Gln Ala Asn Ile Gly Thr Gln
                165                 170                 175

Gly Gly Gln Asn Pro Ala Met Gly Ser His Phe Leu Gly Leu Leu Ile
            180                 185                 190

His Glu Leu Gly His Thr Leu Gly Leu Ser His Pro Gly Lys Tyr Asp
        195                 200                 205

Gly Gln Gly Phe Asn Tyr Asp Arg Ala Ala Glu Tyr Ala Gln Asp Thr
    210                 215                 220

Lys Ala Arg Ser Val Met Ser Tyr Trp Thr Glu Thr His Gln Pro Gly
225                 230                 235                 240

His Asn Phe Ala Gly Arg Ser Pro Gly Ala Pro Met Met Asp Asp Ile
                245                 250                 255

Ala Ala Ala Gln Arg Leu Tyr Gly Ala Asn Thr Lys Thr Arg Asn Thr
            260                 265                 270

Asp Thr Thr Tyr Gly Phe Asn Ser Asn Ser Gly Arg Glu Ala Tyr Ser
        275                 280                 285

Leu Lys Gln Gly Ser Asp Lys Pro Ile Phe Thr Val Trp Asp Gly Gly
    290                 295                 300

Gly Asn Asp Thr Leu Asp Phe Ser Gly Phe Thr Gln Asn Gln Thr Ile
305                 310                 315                 320

Asn Leu Lys Ala Glu Ser Phe Ser Asp Val Gly Gly Leu Arg Gly Asn
                325                 330                 335

Val Ser Ile Ala Lys Gly Val Ser Val Glu Asn Ala Ile Gly Gly Thr
            340                 345                 350

Gly Asn Asp Thr Leu Thr Gly Asn Glu Gly Asn Asn Arg Leu Thr Gly
        355                 360                 365

Gly Lys Gly Ala Asp Lys Leu His Gly Gly Ala Gly Ala Asp Thr Phe
    370                 375                 380

Val Tyr Arg Arg Ala Ser Asp Ser Thr Pro Gln Ala Pro Asp Ile Ile
385                 390                 395                 400

Gln Asp Phe Gln Ser Gly Ser Asp Lys Ile Asp Leu Thr Gly Val Val
                405                 410                 415

Gln Glu Ala Gly Leu Lys Ser Leu Ser Phe Val Glu Lys Phe Ser Gly
            420                 425                 430

Lys Ala Gly Glu Ala Val Leu Gly Gln Asp Ala Lys Thr Gly Arg Phe
        435                 440                 445

Thr Leu Ala Val Asp Thr Thr Gly Asn Gly Thr Ala Asp Leu Leu Val
    450                 455                 460

Ala Ser Gln Ser Gln Ile Lys Gln Ala Asp Val Ile Trp Asn Gly Gln
465                 470                 475                 480

Ala Pro Thr Val Thr Pro Thr Pro Glu Pro Thr Val Pro Val Ser
                485                 490                 495

Asp Pro Val Pro Thr Pro Ser Glu Pro Thr Glu Pro Thr
            500                 505                 510

Pro Glu Pro Ala Pro Leu Pro Val Pro Thr Pro Arg Pro Gly Gly Gly
```

```
                515                 520                 525
Phe Ile Gly Lys Ile Phe Ser Ser Phe Lys Gly Phe Ile Lys Lys Val
        530                 535                 540

Trp Ser Ile Phe Arg
545
```

<210> SEQ ID NO 228
<211> LENGTH: 795
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228

```
atgtcgtgca cacgtgcatt caaaccactg ctgctgatcg gcctggccac actgatgtgt    60
tcccatgcat tcgctgcagt ggtgattacc ggtacgcgcc tggtctatcc ggcggaccag   120
aaagaaatca ccgtaaaact gaacaataac ggcacgttgc ccgcactggt ccaatcatgg   180
atcgacaccg gcagcgtcga atcgacaccc accagctcca aggcgccgtt cctattgtcg   240
cccccggtgg cgcgcattga cccgaccaag ggccaaagct tgcgagtgct ctttaccggc   300
gcgcctttgg cgcaggacaa agagtcggtg ttctggctca cgttctcga aatcccgccc   360
aaacccgagg cgggtgcaga cctcaacacg ctgcaaatgg ctttccgttc gcgcatcaag   420
ctgttctatc gcccggtcgg cttgcctgga aatcccaatg aggcggttga gcaggtgcag   480
tggcaattgg ttacggcacg cgatggccaa ggcctggcgc tgaaggcgta caacccgtcg   540
gcgttccacg tctcgctgat cgagttggac ctggtggcgg gtaaccaacg ctatcgcagt   600
gaggacggca tggtcggccc tggggaaacc cggcagttcg cgctgcccac gctcaaggcc   660
aggccgtcga gccaggcaca gtggagttca gcgccatca acgattacgg cgcgttggtc   720
ccgacccgca acacgctgca gcccggtggg ggtgggtcgg tggtggtgg gtcgcatcat   780
catcaccacc accga                                                   795
```

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

```
Asp Tyr Lys Asp Asp Asp Asp Lys
1               5
```

<210> SEQ ID NO 230
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

```
Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

```
<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Tyr Pro Tyr Asp Val Pro Asp Tyr Ala
1               5

<210> SEQ ID NO 232
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Ala Pro Val Pro Tyr Pro Asp Pro Leu Glu Pro Arg
1               5                   10

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Lys Glu Thr Ala Ala Ala Lys Phe Glu Arg Gln His Met Asp Ser
1               5                   10                  15

<210> SEQ ID NO 234
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Thr Gln Asp Pro Ser Arg Val Gly
1               5

<210> SEQ ID NO 236
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 236

Gly Lys Pro Ile Pro Asn Pro Leu Leu Gly Leu Asp Ser Thr
1               5                   10

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Tyr Thr Asp Ile Glu Met Asn Arg Leu Gly Lys
1               5                   10

<210> SEQ ID NO 238
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Gly Gly Gly Ser
1               5

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Gly Gly Gly Ser Gly Gly Gly Gly Ser Gly Gly Gly Gly Ser
1               5                   10                  15

<210> SEQ ID NO 240
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Gly Gly Gly Ser Gly Gly Gly Gly Ser Gly Gly Gly Gly Ser Gly
1               5                   10                  15

Gly Gly Gly Ser
            20

<210> SEQ ID NO 241
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241
```

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 242
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 242

His His His His His His
1               5
```

FUSION PARTNERS FOR PEPTIDE PRODUCTION

CROSS-REFERENCE

This application is a division of U.S. patent application Ser. No. 14/954,766, filed Nov. 30, 2015, which claims the benefit of U.S. Provisional Patent Application No. 62/086,119, filed Dec. 1, 2014, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 19, 2018, is named 38194-745.401_SL.txt and is 392,729 bytes in size.

BACKGROUND OF THE INVENTION

Heterologous recombinant polypeptides often are difficult to express at high yield in bacterial expression systems due to causes that include proteolysis, low expression level, improper protein folding, which can result in poor solubility, and poor secretion from the host cell.

SUMMARY OF THE INVENTION

The present invention provides a recombinant fusion protein comprising a polypeptide of interest. Expression of a polypeptide of interest as part of the recombinant fusion protein as described allows production of high quality polypeptide in large amounts. Polypeptides of interest include small or rapidly-degraded peptides, e.g., parathyroid hormone N-terminal fragment (PTH 1-34), proteins having an N-terminus that is vulnerable to degradation, e.g., GCSF and P. falciparum circumsporozoite protein, and proteins that typically are produced in insoluble form in microbial expression systems, e.g., proinsulin that can be processed to insulin or an insulin analog, GCSF, or IFN-β. The recombinant fusion protein, shown schematically in FIG. 1, comprises an N-terminal bacterial fusion partner, e.g., a bacterial chaperone or folding modulator. The polypeptide of interest and N-terminal bacterial chaperone or folding modulator are connected by a flexible linker sequence that contains a protease cleavage site. When cleaved, the polypeptide of interest is released from the N-terminal fusion partner. The present invention further discloses a vector for expressing the recombinant fusion protein, and a method for producing the recombinant fusion protein in a bacterial host cell at high yield.

The recombinant fusion constructs of the present invention are useful for producing a high yield of a recombinant polypeptide of interest that is difficult to overexpress in a bacterial expression system, due to, e.g., proteolysis, low expression level, poor folding, and/or poor secretion. In embodiments of the invention, a recombinant fusion protein of the invention is produced in a bacterial host cell at a titer of higher than 0.5 g/L. In embodiments, the bacterial host cell in which the recombinant polypeptide of interest is difficult to overexpress is E. coli.

For example, the PTH 1-34 protein, previously reported as expressed as part of a fusion protein in inclusion bodies which require high concentrations of urea (e.g. 7 M) to solubilize, is described herein as produced as part of a soluble PTH 1-34 fusion protein at high titer expression (higher than 0.5 g/L). Furthermore, purification can be carried out under non-denaturing conditions, e.g. 4 M or lower concentrations of urea, or without the use of urea altogether. Also using the methods of the invention, a protein with an easily degraded N terminus, e.g., N-met-GCSF or P. falciparum circumsporozoite protein, can be produced as part of the described fusion protein and separated from the N-terminal fusion partner by cleavage after host cell proteases have been removed from the fusion protein preparation. As also described herein, a proinsulin normally produced in insoluble form can be produced in significant amounts in soluble form in a recombinant fusion protein of the invention, eliminating the need for refolding.

The present invention thus provides a recombinant fusion protein comprising: an N-terminal fusion partner, wherein the N-terminal fusion partner is a bacterial chaperone or folding modulator; a polypeptide of interest; and a linker comprising a cleavage site between the N-terminal fusion partner and the polypeptide of interest. In embodiments, the N-terminal fusion partner is selected from: a DnaJ-like protein; an FklB protein or a truncation thereof; an FrnE protein or a truncation thereof; an FkpB2 protein or a truncation thereof; an EcpD protein or a truncation thereof; and a Skp protein or a truncation thereof. In embodiments, the N-terminal fusion partner is selected from: P. fluorescens DnaJ-like protein; P. fluorescens FklB protein or a C-terminal truncation thereof; P. fluorescens FrnE protein or a truncation thereof; P. fluorescens FkpB2 protein or a C-terminal truncation thereof; and P. fluorescens EcpD protein or a C-terminal truncation thereof. In certain embodiments, the N-terminal fusion partner is P. fluorescens FklB protein, truncated to remove 1 to 200 amino acids from the C-terminus, P. fluorescens EcpD protein, truncated to remove 1 to 200 amino acids from the C-terminus, or P. fluorescens FrnE protein, truncated to remove 1 to 180 amino acids from the C-terminus. In embodiments, the polypeptide of interest is a difficult-to-express protein selected from: a small or rapidly-degraded peptide; a protein with an easily degraded N-terminus; and a protein typically expressed in a bacterial expression system in insoluble form. In embodiments, the polypeptide of interest is a small or rapidly-degraded peptide, wherein the polypeptide of interest is selected from: hPTH1-34 (SEQ ID NO: 1), Glp1 (SEQ ID NO: 36), Glp2 (SEQ ID NO: 38), IGF-1 (SEQ ID NO: 35), Exenatide (SEQ ID NO: 37), Teduglutide (SEQ ID NO: 39), Pramlintide (SEQ ID NO: 40), Ziconotide (SEQ ID NO: 41), Becaplermin (SEQ ID NO: 42), Enfuvirtide (SEQ ID NO: 43), and Nesiritide (SEQ ID NO: 44). In embodiments, the polypeptide of interest is a protein with easily degraded N-terminus, wherein the polypeptide of interest is N-met-GCSF (SEQ ID NO: 69) or P. falciparum circumsporozoite protein. In embodiments, the polypeptide of interest is a protein typically expressed in a bacterial expression system as insoluble protein, wherein the polypeptide of interest is a proinsulin that is processed to insulin or an insulin analog, GCSF, or IFN-β. In any of these embodiments, the proinsulin C-peptide has an amino acid sequence selected from: SEQ ID NO: 97; SEQ ID NO: 98; SEQ ID NO: 99; and SEQ ID NO: 100. In embodiments, the insulin analog is insulin glargine, insulin aspart, lispro, glulisine, detemir, or degludec. In certain embodiments, the N-terminal fusion partner is P. fluorescens DnaJ-like protein having the amino acid sequence set forth in SEQ ID NO: 2. In embodiments, the N-terminal fusion partner is P. fluorescens FklB protein having the amino acid sequence set forth in SEQ ID NO: 4, SEQ ID NO: 28, SEQ ID NO: 61, or SEQ ID NO: 62. In embodiments, the N-terminal fusion partner is P. fluorescens FrnE protein having the amino acid sequence set forth in SEQ ID NO: 3, SEQ ID NO: 63, or SEQ ID NO: 64. In embodiments, the N-terminal fusion partner is *P. fluorescens* EcpD protein having the amino acid sequence set forth in SEQ ID NO: 7, SEQ ID NO: 65, SEQ ID NO: 66, or SEQ ID NO: 67. In embodiments, the cleavage site in the recombinant fusion protein is recognized by a cleavage enzyme in the group consisting of: enterokinase; trypsin, Factor Xa; and furin. The recombinant fusion protein of any of claims 1 to 15, wherein the linker comprises an affinity tag. In certain embodiments, the affinity tag is selected from: polyhistidine; a FLAG tag; a myc tag; a GST tag; a MBP tag; a calmodulin tag; an HA tag; an E-tag; an S-tag; an SBP tag; a Softag 3; a V5 tag; and a VSV tag. In embodiments, the linker has an amino acid sequence selected from: SEQ ID NO: 9; SEQ ID NO: 10; SEQ ID NO: 11; SEQ ID NO: 12; and SEQ ID NO: 226. In embodiments, the polypeptide of interest is hPTH1-34, and the recombinant fusion protein comprises an amino acid sequence selected from: SEQ ID NO: 45; SEQ ID NO: 46; and SEQ ID NO: 47. In embodiments, the isoelectric point of the polypeptide of interest is at least about 1.5 times higher than the isoelectric point of the N-terminal fusion partner. In embodiments, the molecular weight of the polypeptide of interest constitutes about 10% to about 50% of the molecular weight of the recombinant fusion protein.

The invention also provides an expression vector for expression of a recombinant fusion protein. In embodiments, the expression vector is for expression of a recombinant fusion protein in any of the embodiments described above. In embodiments, the expression vector comprises a nucleotide sequence encoding a recombinant fusion protein of any of the above embodiments.

The invention further provides a method for producing a polypeptide of interest, comprising:
(i) culturing a microbial host cell transformed with an expression vector comprising an expression construct, wherein the expression construct comprises a nucleotide sequence encoding a recombinant fusion protein;
(ii) inducing the host cell of step (i) to express the recombinant fusion protein; (iii) purifying the recombinant fusion protein expressed in the induced host cells of step (ii); and (iv) cleaving the purified recombinant fusion protein of step (iii) by incubation with a cleavage enzyme that recognizes the cleavage site in the linker, to release the polypeptide of interest; thereby obtaining the polypeptide of interest. In embodiments, the recombinant fusion protein of step (i) is that described in any of the embodiments described above. In embodiments, the method further comprises measuring the expression level of the fusion protein expressed in step (ii), measuring the amount of the recombinant fusion protein purified in step (iii), or measuring the amount of the polypeptide of interest obtained in step (iv) that has been properly released, or a combination thereof. In embodiments, the expression level of the fusion protein expressed in step (ii) is greater than 0.5 g/L. In embodiments, the expression level of the fusion protein expressed in step (ii) is about 0.5 g/L to about 25 g/L. In embodiments, the fusion protein expressed in step (ii) is directed to the cytoplasm. In embodiments, the fusion protein expressed in step (ii) is directed to the periplasm. In embodiments, the incubation of step (iv) is about one hour to about 16 hours, and the cleavage enzyme is enterokinase.

In embodiments, the incubation of step (iv) is about one hour to about 16 hours, the cleavage enzyme is enterokinase, and wherein the amount of the recombinant fusion protein purified in step (iii) that is properly released in step (iv) is about 90% to about 100%. In embodiments, the amount of the recombinant fusion protein purified in step (iii) that is properly released in step (iv) is about 100%. In embodiments, the amount of the polypeptide of interest obtained in step (iii) or step (iv) is about 0.1 g/L to about 25 g/L. In embodiments, the properly released polypeptide of interest obtained is soluble, intact, or both. In embodiments, step (iii) is carried out under non-denaturing conditions. In embodiments, the recombinant fusion protein is solubilized without the use of urea. In embodiments, the non-denaturing conditions comprise lysing the induced cells of step (ii) with a buffer comprising a non-denaturing concentration of a chaotropic agent. In embodiments, the non-denaturing concentration of a chaotropic agent is less than 4M urea.

In embodiments, the microbial host cell is a Pseudomonad or *E. coli* host cell. In embodiments, the Pseudomonad host cell is a *Pseudomonas* host cell. In embodiments, the *Pseudomonas* host cell is *Pseudomonas fluorescens*.

In specific embodiments, the host cell is deficient in at least one protease selected from the group consisting of: Lon (SEQ ID NO: 14); Lal (SEQ ID NO: 15); AprA (SEQ ID NO: 16); HtpX (SEQ ID NO: 17); DegP1 (SEQ ID NO: 18); DegP2 (SEQ ID NO: 19); Npr (SEQ ID NO: 20); Prc1 (SEQ ID NO: 21); Prc2 (SEQ ID NO: 22); M50 (SEQ ID NO: 24); PrlC (SEQ ID NO: 30); Serralysin (RXF04495) (SEQ ID NO: 227) and PrtB (SEQ ID NO: 23). In related embodiments, the host cell is deficient in proteases Lon (SEQ ID NO: 14), Lal (SEQ ID NO: 15), and AprA (SEQ ID NO: 16). In embodiments, the host cell is deficient in proteases AprA (SEQ ID NO: 16) and HtpX (SEQ ID NO: 17). In other embodiments, the host cell is deficient in proteases Lon (SEQ ID NO: 14), Lal (SEQ ID NO: 15) and DegP2 (SEQ ID NO: 19). In embodiments, the host cell is deficient in proteases Npr (SEQ ID NO: 20), DegP1 (SEQ ID NO: 18) and DegP2 (SEQ ID NO: 19). In related embodiments, the host cell is deficient in proteases Serralysin (SEQ ID NO: 227), and AprA (SEQ ID NO: 16).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A to 2C. Three Recombinant Fusion Protein Amino Acid Sequences. The amino acid sequences of three recombinant fusion proteins comprising hPTH 1-34 as the polypeptide of interest are shown. The hPTH 1-34 sequence is italicized in each, and the linker between the N-terminal fusion partner and PTH 1-34 is underlined. FIG. 2A. Recombinant fusion protein comprising a DnaJ-like protein N-terminal fusion partner. (DnaJ-like protein, aa 1-77; linker, aa 78-98; hPTH 1-34, aa 99-132) (SEQ ID NO: 45) FIG. 2B. Recombinant fusion protein comprising an FklB N-terminal fusion partner. (FklB, aa 1-205; linker, aa 206-226; hPTH 1-34, aa 227-260) (SEQ ID NO: 46) FIG. 2C. Recombinant fusion protein comprising an FrnE N-terminal fusion partner. (FrnE, aa 1-216; linker, aa 217-237; hPTH 1-34, aa 238-271) (SEQ ID NO: 47)

FIG. 7A. FklB-PTH fusion protein purified from STR36034. FIG. 7B. FklB-PTH fusion protein purified from STR36085. FIG. 7C. FklB-PTH fusion protein purified from STR36098.

SEQUENCES

This application includes nucleotide sequences SEQ ID NO: 1-242, and these nucleotide sequences are listed in the Table of Sequences before the claims.

DETAILED DESCRIPTION OF THE INVENTION

Overview

The present invention relates to recombinant fusion proteins for overexpressing recombinant polypeptides of interest in bacterial expression systems, constructs for expressing the recombinant fusion proteins, and methods for producing high yields of the recombinant fusion proteins and the recombinant polypeptide of interest in soluble form. In embodiments, the methods of the invention enable production of greater than 0.5 g/L of recombinant fusion proteins following purification. In embodiments, the methods of the invention produce high yields of recombinant fusion proteins without the use of a denaturing concentration of a chaotropic agent. In embodiments, the methods of the invention produce high yields of recombinant fusion proteins without the use of any chaotropic agent.

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In embodiments of any of the compositions and methods provided herein, "comprising" may be replaced with "consisting essentially of" or "consisting of." The phrase "consisting essentially of" is used herein to require the specified feature(s) as well as those which do not materially affect the character or function of the claimed invention. As used herein, the term "consisting" is used to indicate the presence of the recited feature (e.g. nucleobase sequence) alone (so that in the case of an antisense oligomer consisting of a specified nucleobase sequence, the presence of additional, unrecited nucleobases is excluded).

Recombinant Fusion Protein

Figure 1:
FIG. 1. Schematic Representation of a Recombinant Fusion Protein. Domain 1 corresponds to an N-terminal fusion partner, domain 2 corresponds to a linker, and domain 3 corresponds to a polypeptide of interest. Non-limiting examples of N-terminal fusion partners and polypeptides of interest are listed below each respective domain.

A recombinant fusion protein of the present invention comprises three domains, as generally illustrated in FIG. 1. From left, the fusion protein comprises an N-terminal fusion partner, a linker, and a polypeptide of interest, wherein the linker is between the N-terminal fusion partner and the polypeptide of interest is C-terminal to the linker. In embodiments, the linker sequence comprises a protease cleavage site. In embodiments, the polypeptide of interest can be released from the recombinant fusion protein, by cleavage at the protease cleavage site within the linker.

In embodiments, the molecular weight of the recombinant fusion protein is about 2 kDa to about 1000 kDa. In embodiments, the molecular weight of the recombinant fusion protein is about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 20 kDa, about 25 kDa, about 26 kDa, about 27 kDa, about 28 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 200 kDa, about 300 kDa, about 400 kDa, about 500 kDa, about 550 kDa, about 600 kDa, about 700 kDa, about 800 kDa, about 900 kDa, about 1000 kDa, or greater. In embodiments, the molecular weight of the recombinant fusion protein is about 2 kDa to about 1000 kDa, about 2 kDa to about 500 kDa, about 2 kDa to about 250 kDa, about 2 kDa to about 100 kDa, about 2 kDa to about 50 kDa, about 2 kDa to about 25 kDa, about 2 kDa to about 30 kDa, about 2 kDa to about 1000 kDa, about 2 kDa to about 500 kDa, about 2 kDa to about 250 kDa, about 2 kDa to about 100 kDa, about 2 kDa to about 50 kDa, about 2 kDa to about 25 kDa, about 3 kDa to about 1000 kDa, about 3 kDa to about 500 kDa, about 3 kDa to about 250 kDa, about 3 kDa to about 100 kDa, about 3 kDa to about 50 kDa, about 3 kDa to about 25 kDa, about 3 kDa to about 30 kDa, about 4 kDa to about 1000 kDa, about 4 kDa to about 500 kDa, about 4 kDa to about 250 kDa, about 4 kDa to about 100 kDa, about 4 kDa to about 50 kDa, about 4 kDa to about 25 kDa, about 4 kDa to about 30 kDa, about 5 kDa to about 1000 kDa, about 5 kDa to about 500 kDa, about 5 kDa to about 250 kDa, about 5 kDa to about 100 kDa, about 5 kDa to about 50 kDa, about 5 kDa to about 25 kDa, about 5 kDa to about 30 kDa, about 10 kDa to about 1000 kDa, about 10 kDa to about 500 kDa, about 10 kDa to about 250 kDa, about 10 kDa to about 100 kDa, about 10 kDa to about 50 kDa, about 10 kDa to about 25 kDa, about 10 kDa to about 30 kDa, about 20 kDa to about 1000 kDa, about 20 kDa to about 500 kDa, about 20 kDa to about 250 kDa, about 20 kDa to about 100 kDa, about 20 kDa to about 50 kDa, about 20 kDa to about 25 kDa, about 20 kDa to about 30 kDa, about 25 kDa to about 1000 kDa, about 25 kDa to about 500 kDa, about 25 kDa to about 250 kDa, about 25 kDa to about 100 kDa, about 25 kDa to about 50 kDa, about 25 kDa to about 25 kDa, or about 25 kDa to about 30 kDa.

In embodiments, the recombinant fusion protein is about 50, 100, 150, 200, 250, 300, 350, 400, 450, 470, 500, 530, 560, 590, 610, 640, 670, 700, 750, 800, 850, 900, 950, 1000, 1200, 1400, 1600, 1800, 2000, 2500, or more, amino acids in length. In embodiments, the recombinant fusion protein is about 50 to 2500, 100 to 2000, 150 to 1800, 200 to 1600, 250 to 1400, 300 to 1200, 350 to 1000, 400 to 950, 450 to 900, 470 to 850, 500 to 800, 530 to 750, 560 to 700, 590 to 670, or 610 to 640 amino acids in length.

In embodiments, the recombinant fusion protein comprises an N-terminal fusion partner selected from:

*P. fluorescens* DnaJ-like protein (e.g., SEQ ID NO: 2), FrnE (SEQ ID NO: 3), FrnE2 (SEQ ID NO: 63), FrnE3 (SEQ ID NO: 64), FklB (SEQ ID NO: 4), FklB3* (SEQ ID NO: 28), FklB2 (SEQ ID NO: 61), FklB3 (SEQ ID NO: 62), FkpB2 (SEQ ID NO: 5), SecB (SEQ ID NO: 6), a truncation of SecB, EcpD (SEQ ID NO: 7), EcpD (SEQ ID NO: 65), EcpD2 (SEQ ID NO: 66), and EcpD3 (SEQ ID NO: 67);

a linker selected from: SEQ ID NO: 9, 10, 11, 12, and 226; and a polypeptide of interest selected from: hPTH 1-34 (SEQ ID NO: 1), Met-GCSF (SEQ ID NO: 69), rCSP, a Proinsulin (e.g., any of Human Proinsulin SEQ ID NO: 32, Insulin Glargine Proinsulin SEQ ID NO: 88, 89, 90, or 91, Insulin Lispro SEQ ID NO: 33, Insulin Glulisine SEQ ID NO: 34), Insulin C-peptide (SEQ ID NO: 97); Mecasermin (SEQ ID NO: 35), Glp-1 (SEQ ID NO: 36), Exenatide (SEQ ID NO: 37), Teduglutide (SEQ ID NO: 39), Pramlintide (SEQ ID NO: 40), Ziconotide (SEQ ID NO: 41), Becaplermin (SEQ ID NO: 42), Enfuvirtide (SEQ ID NO: 43), Nesiritide (SEQ ID NO: 44) or Enterokinase (e.g., SEQ ID NO: 31).

In embodiments, the recombinant fusion protein comprises a *P. fluorescens* DnaJ-like protein N-terminal fusion partner and a trypsin cleavage site linker, together having the amino acid sequence of SEQ ID NO: 101. In embodiments, the nucleotide sequence encoding SEQ ID NO: 101 is SEQ ID NO: 202.

In embodiments, the recombinant fusion protein comprises a *P. fluorescens* EcpD1 protein N-terminal fusion partner and a trypsin cleavage site linker, together having the amino acid sequence of SEQ ID NO: 102 or 103. In embodiments, the nucleotide sequence encoding SEQ ID NO: 102 or 103 is SEQ ID NO: 202 or 228, respectively.

In embodiments, the recombinant fusion protein comprises a *P. fluorescens* EcpD2 protein N-terminal fusion partner and a trypsin cleavage site linker, together having the amino acid sequence of SEQ ID NO: 104. In embodiments, the nucleotide sequence encoding SEQ ID NO: 104 is SEQ ID NO: 204.

In embodiments, the recombinant fusion protein comprises a *P. fluorescens* EcpD3 protein N-terminal fusion partner and a trypsin cleavage site linker, together having the amino acid sequence of SEQ ID NO: 105. In embodiments, the nucleotide sequence encoding SEQ ID NO: 105 is SEQ ID NO: 205.

In embodiments, the recombinant fusion protein comprises a *P. fluorescens* FklB1 protein N-terminal fusion partner and a trypsin cleavage site linker, together having the amino acid sequence of SEQ ID NO: 106. In embodiments, the nucleotide sequence encoding SEQ ID NO: 106 is SEQ ID NO: 206.

In embodiments, the recombinant fusion protein comprises a *P. fluorescens* FklB2 protein N-terminal fusion partner and a trypsin cleavage site linker, together having the amino acid sequence of SEQ ID NO: 107. In embodiments, the nucleotide sequence encoding SEQ ID NO: 107 is SEQ ID NO: 207.

In embodiments, the recombinant fusion protein comprises a *P. fluorescens* FklB3 protein N-terminal fusion partner and a trypsin cleavage site linker, together having the amino acid sequence of SEQ ID NO: 108. In embodiments, the nucleotide sequence encoding SEQ ID NO: 108 is SEQ ID NO: 208.

In embodiments, the recombinant fusion protein comprises a *P. fluorescens* FrnE1 protein N-terminal fusion partner and a trypsin cleavage site linker, together having the amino acid sequence of SEQ ID NO: 109. In embodiments, the nucleotide sequence encoding SEQ ID NO: 109 is SEQ ID NO: 209.

In embodiments, the recombinant fusion protein comprises a *P. fluorescens* FrnE2 protein N-terminal fusion partner and a trypsin cleavage site linker, together having the amino acid sequence of SEQ ID NO: 110. In embodiments, the nucleotide sequence encoding SEQ ID NO: 110 is SEQ ID NO: 210.

In embodiments, the recombinant fusion protein comprises a *P. fluorescens* FrnE3 protein N-terminal fusion partner and a trypsin cleavage site linker, together having the amino acid sequence of SEQ ID NO: 111. In embodiments, the nucleotide sequence encoding SEQ ID NO: 111 is SEQ ID NO: 211.

In embodiments, the recombinant fusion protein comprises a *P. fluorescens* DnaJ-like protein N-terminal fusion partner and a enterokinase cleavage site linker, together having the amino acid sequence of SEQ ID NO: 112. In embodiments, the nucleotide sequence encoding SEQ ID NO: 112 is SEQ ID NO: 212.

In embodiments, the recombinant fusion protein comprises a *P. fluorescens* EcpD1 protein N-terminal fusion partner and a enterokinase cleavage site linker, together having the amino acid sequence of SEQ ID NO: 113. In embodiments, the nucleotide sequence encoding SEQ ID NO: 113 is SEQ ID NO: 213, respectively.

In embodiments, the recombinant fusion protein comprises a *P. fluorescens* EcpD2 protein N-terminal fusion partner and a enterokinase cleavage site linker, together having the amino acid sequence of SEQ ID NO: 114. In embodiments, the nucleotide sequence encoding SEQ ID NO: 114 is SEQ ID NO: 214.

In embodiments, the recombinant fusion protein comprises a *P. fluorescens* EcpD3 protein N-terminal fusion partner and a enterokinase cleavage site linker, together having the amino acid sequence of SEQ ID NO: 115. In embodiments, the nucleotide sequence encoding SEQ ID NO: 115 is SEQ ID NO: 215.

In embodiments, the recombinant fusion protein comprises a *P. fluorescens* FklB1 protein N-terminal fusion partner and a enterokinase cleavage site linker, together having the amino acid sequence of SEQ ID NO: 216. In embodiments, the nucleotide sequence encoding SEQ ID NO: 116 is SEQ ID NO: 216.

In embodiments, the recombinant fusion protein comprises a *P. fluorescens* FklB2 protein N-terminal fusion partner and a enterokinase cleavage site linker, together having the amino acid sequence of SEQ ID NO: 217. In embodiments, the nucleotide sequence encoding SEQ ID NO: 117 is SEQ ID NO: 217.

In embodiments, the recombinant fusion protein comprises a *P. fluorescens* FklB3 protein N-terminal fusion partner and a enterokinase cleavage site linker, together having the amino acid sequence of SEQ ID NO: 118. In embodiments, the nucleotide sequence encoding SEQ ID NO: 118 is SEQ ID NO: 218.

In embodiments, the recombinant fusion protein comprises a *P. fluorescens* FrnE1 protein N-terminal fusion partner and a enterokinase cleavage site linker, together having the amino acid sequence of SEQ ID NO: 119. In embodiments, the nucleotide sequence encoding SEQ ID NO: 119 is SEQ ID NO: 219.

In embodiments, the recombinant fusion protein comprises a *P. fluorescens* FrnE2 protein N-terminal fusion partner and a enterokinase cleavage site linker, together having the amino acid sequence of SEQ ID NO: 120. In embodiments, the nucleotide sequence encoding SEQ ID NO: 120 is SEQ ID NO: 220.

In embodiments, the recombinant fusion protein comprises a *P. fluorescens* FmE3 protein N-terminal fusion partner and a enterokinase cleavage site linker, together having the amino acid sequence of SEQ ID NO: 121. In embodiments, the nucleotide sequence encoding SEQ ID NO: 121 is SEQ ID NO: 221.

In embodiments, the N-terminal fusion partner, linker, and polypeptide of interest of the recombinant fusion protein are, respectively: *P. fluorescens* folding modulator DnaJ-like protein (SEQ ID NO: 2), the linker set forth as SEQ ID NO: 9, and human parathyroid hormone amino acids 1-34 (hPTH 1-34) (SEQ ID NO: 1). In embodiments, the N-terminal fusion partner, linker, and polypeptide of interest of the recombinant fusion protein are, respectively: *P. fluorescens* folding modulator FrnE (SEQ ID NO: 3), the linker set forth as SEQ ID NO: 9, and hPTH 1-34 (SEQ ID NO: 1). In embodiments, the N-terminal fusion partner, linker, and polypeptide of interest of the recombinant fusion protein are, respectively: *P. fluorescens* folding modulator FklB (SEQ ID NO: 4), the linker set forth as SEQ ID NO: 9, and hPTH 1-34 (SEQ ID NO: 1). In embodiments, the recombinant hPTH fusion protein has the amino acid sequence as set forth in one of SEQ ID NOS: 45, 46, and 47.

In embodiments, the recombinant fusion protein is an insulin fusion protein having the following elements:

an N-terminal fusion partner selected from *P. fluorescens*: DnaJ-like protein (e.g., SEQ ID NO: 2), FrnE (SEQ ID NO: 3), FrnE2 (SEQ ID NO: 63), FrnE3 (SEQ ID NO: 64), FklB (SEQ ID NO: 4), FklB3* (SEQ ID NO: 28), FklB2 (SEQ ID NO: 61), FklB3 (SEQ ID NO: 62), FkpB2 (SEQ ID NO: 5), EcpD EcpD (SEQ ID NO: 65), EcpD2 (SEQ ID NO: 66), or EcpD3 (SEQ ID NO: 67);

a linker having the sequence set forth as SEQ ID NO: 226; and a polypeptide of interest selected from: Glargine Proinsulin SEQ ID NO: 88, 89, 90, or 91.

In embodiments, the polypeptide of interest is the Glargine Proinsulin set forth as SEQ ID NO: 88, encoded by the nucleotide sequence set forth as SEQ ID NO: 80 or 84. In embodiments, the polypeptide of interest is the Glargine Proinsulin set forth as SEQ ID NO: 89, encoded by the nucleotide sequence set forth as SEQ ID NO: 81 or 85. In embodiments, the polypeptide of interest is the Glargine Proinsulin set forth as SEQ ID NO: 90, encoded by the nucleotide sequence set forth as SEQ ID NO: 82 or 86. In embodiments, the polypeptide of interest is the Insulin Glargine Proinsulin set forth as SEQ ID NO: 91, encoded by the nucleotide sequence set forth as SEQ ID NO: 83 or 87.

In embodiments, the insulin fusion protein comprises a *P. fluorescens* DnaJ-like protein N-terminal fusion partner and a trypsin cleavage site linker, together having the amino acid sequence of SEQ ID NO: 101. In embodiments, the nucleotide sequence encoding SEQ ID NO: 101 is SEQ ID NO: 202.

In embodiments, the insulin fusion protein comprises a *P. fluorescens* EcpD1 protein N-terminal fusion partner and a trypsin cleavage site linker, together having the amino acid sequence of SEQ ID NO: 102 or 103. In embodiments, the nucleotide sequence encoding SEQ ID NO: 102 or 103 is SEQ ID NO: 202 or 228, respectively.

In embodiments, the insulin fusion protein comprises a *P. fluorescens* EcpD2 protein N-terminal fusion partner and a trypsin cleavage site linker, together having the amino acid sequence of SEQ ID NO: 104. In embodiments, the nucleotide sequence encoding SEQ ID NO: 104 is SEQ ID NO: 204.

In embodiments, the insulin fusion protein comprises a *P. fluorescens* EcpD3 protein N-terminal fusion partner and a trypsin cleavage site linker, together having the amino acid sequence of SEQ ID NO: 105. In embodiments, the nucleotide sequence encoding SEQ ID NO: 105 is SEQ ID NO: 205.

In embodiments, the insulin fusion protein comprises a *P. fluorescens* FklB1 protein N-terminal fusion partner and a trypsin cleavage site linker, together having the amino acid sequence of SEQ ID NO: 106. In embodiments, the nucleotide sequence encoding SEQ ID NO: 106 is SEQ ID NO: 206.

In embodiments, the insulin fusion protein comprises a *P. fluorescens* FklB2 protein N-terminal fusion partner and a trypsin cleavage site linker, together having the amino acid sequence of SEQ ID NO: 107. In embodiments, the nucleotide sequence encoding SEQ ID NO: 107 is SEQ ID NO: 207.

In embodiments, the insulin fusion protein comprises a *P. fluorescens* FklB3 protein N-terminal fusion partner and a trypsin cleavage site linker, together having the amino acid sequence of SEQ ID NO: 108. In embodiments, the nucleotide sequence encoding SEQ ID NO: 108 is SEQ ID NO: 208.

In embodiments, the insulin fusion protein comprises a *P. fluorescens* FrnE1 protein N-terminal fusion partner and a trypsin cleavage site linker, together having the amino acid sequence of SEQ ID NO: 109. In embodiments, the nucleotide sequence encoding SEQ ID NO: 109 is SEQ ID NO: 209.

In embodiments, the insulin fusion protein comprises a *P. fluorescens* FrnE2 protein N-terminal fusion partner and a trypsin cleavage site linker, together having the amino acid sequence of SEQ ID NO: 110. In embodiments, the nucleotide sequence encoding SEQ ID NO: 110 is SEQ ID NO: 210.

In embodiments, the insulin fusion protein comprises a *P. fluorescens* FrnE3 protein N-terminal fusion partner and a trypsin cleavage site linker, together having the amino acid sequence of SEQ ID NO: 111. In embodiments, the nucleotide sequence encoding SEQ ID NO: 111 is SEQ ID NO: 211.

In embodiments, the insulin fusion protein comprises a *P. fluorescens* DnaJ-like protein N-terminal fusion partner and a enterokinase cleavage site linker, together having the amino acid sequence of SEQ ID NO: 112. In embodiments, the nucleotide sequence encoding SEQ ID NO: 112 is SEQ ID NO: 212.

In embodiments, the insulin fusion protein comprises a *P. fluorescens* EcpD1 protein N-terminal fusion partner and a enterokinase cleavage site linker, together having the amino acid sequence of SEQ ID NO: 113. In embodiments, the nucleotide sequence encoding SEQ ID NO: 113 is SEQ ID NO: 213, respectively.

In embodiments, the insulin fusion protein comprises a *P. fluorescens* EcpD2 protein N-terminal fusion partner and a enterokinase cleavage site linker, together having the amino acid sequence of SEQ ID NO: 114. In embodiments, the nucleotide sequence encoding SEQ ID NO: 114 is SEQ ID NO: 214.

In embodiments, the insulin fusion protein comprises a *P. fluorescens* EcpD3 protein N-terminal fusion partner and a enterokinase cleavage site linker, together having the amino acid sequence of SEQ ID NO: 115. In embodiments, the nucleotide sequence encoding SEQ ID NO: 115 is SEQ ID NO: 215.

In embodiments, the insulin fusion protein comprises a *P. fluorescens* FklB1 protein N-terminal fusion partner and a enterokinase cleavage site linker, together having the amino acid sequence of SEQ ID NO: 216. In embodiments, the nucleotide sequence encoding SEQ ID NO: 116 is SEQ ID NO: 216.

In embodiments, the insulin fusion protein comprises a *P. fluorescens* FklB2 protein N-terminal fusion partner and a enterokinase cleavage site linker, together having the amino acid sequence of SEQ ID NO: 217. In embodiments, the nucleotide sequence encoding SEQ ID NO: 117 is SEQ ID NO: 217.

In embodiments, the insulin fusion protein comprises a *P. fluorescens* FklB3 protein N-terminal fusion partner and a enterokinase cleavage site linker, together having the amino acid sequence of SEQ ID NO: 118. In embodiments, the nucleotide sequence encoding SEQ ID NO: 118 is SEQ ID NO: 218.

In embodiments, the insulin fusion protein comprises a *P. fluorescens* FrnE1 protein N-terminal fusion partner and a enterokinase cleavage site linker, together having the amino acid sequence of SEQ ID NO: 119. In embodiments, the nucleotide sequence encoding SEQ ID NO: 119 is SEQ ID NO: 219.

In embodiments, the insulin fusion protein comprises a *P. fluorescens* FrnE2 protein N-terminal fusion partner and a enterokinase cleavage site linker, together having the amino acid sequence of SEQ ID NO: 120. In embodiments, the nucleotide sequence encoding SEQ ID NO: 120 is SEQ ID NO: 220.

In embodiments, the insulin fusion protein comprises a *P. fluorescens* FrnE3 protein N-terminal fusion partner and a enterokinase cleavage site linker, together having the amino acid sequence of SEQ ID NO: 121. In embodiments, the nucleotide sequence encoding SEQ ID NO: 121 is SEQ ID NO: 221.

In embodiments, the recombinant insulin fusion protein has the amino acid sequence as set forth in one of SEQ ID NOS: 122 to 201.

In embodiments, the recombinant fusion protein is a GCSF fusion protein having the following elements:

an N-terminal fusion partner selected from: *P. fluorescens* DnaJ-like protein (e.g., SEQ ID NO: 2), FrnE (SEQ ID NO: 3), FrnE2 (SEQ ID NO: 63), FrnE3 (SEQ ID NO: 64), FklB (SEQ ID NO: 4), FklB3* (SEQ ID NO: 28), FklB2 (SEQ ID NO: 61), FklB3 (SEQ ID NO: 62), FkpB2 (SEQ ID NO: 5), EcpD EcpD (SEQ ID NO: 65), EcpD2 (SEQ ID NO: 66), or EcpD3 (SEQ ID NO: 67);

a linker having the sequence set forth as SEQ ID NO: 9; and a polypeptide of interest having the sequence set forth as SEQ ID NO: 68.

Polypeptide of Interest

The protein or polypeptide of interest of the recombinant fusion protein, also referred to as the C-terminal polypeptide of interest, recombinant polypeptide of interest, and C-terminal fusion partner, is a polypeptide desired to be expressed in soluble form and at high yield. In embodiments, the polypeptide of interest is a heterologous polypeptide that has been found not to be expressed at high yield in a bacterial expression system due to, e.g., proteolysis, low expression level, improper protein folding, and/or poor secretion from the host cell. Polypeptides of interest include small or rapidly-degraded peptides, proteins having an N-terminus that is vulnerable to degradation, and proteins that typically are produced in insoluble form in microbial or bacterial expression systems. In embodiments, the N-terminus of the polypeptide of interest is protected from degradation while fused to the N-terminal fusion partner, resulting in a greater yield of N-terminally intact protein. In embodiments, the heterologous polypeptide has been described as not expressed in soluble form at high yield in a microbial or bacterial expression system. For example, in embodiments, the heterologous polypeptide has been described as not expressed in soluble form at high yield in an *E. coli*, *B. subtilis*, or *L. plantarum*, *L. casei*, *L. fermentum* or *Corynebacterium glutamicum* host cell. In embodiments, the polypeptide of interest is a eukaryotic polypeptide or derived from (e.g., is an analog of) a eukaryotic polypeptide. In embodiments, the polypeptide of interest is a mammalian polypeptide or derived from a mammalian polypeptide. In embodiments, the polypeptide of interest is a human polypeptide or derived from a human polypeptide. In embodiments, the polypeptide of interest is a prokaryotic polypeptide or derived from a prokaryotic polypeptide. In embodiments, the polypeptide of interest is a microbial polypeptide or derived from a microbial polypeptide. In embodiments, the polypeptide of interest is a bacterial polypeptide or derived from a bacterial polypeptide. By "heterologous" it is meant that the polypeptide of interest is derived from an organism other than the expression host cell. In embodiments, the fusion protein and/or polypeptide of interest is produced in a Pseudomonad host cell (i.e., a host cell of the order Pseudomonadales) according to the methods of the present invention at higher yield than in another microbial expression system. In embodiments, the fusion protein or polypeptide of interest is produced in a Pseudomonad, *Pseudomonas*, or *Pseudomonas fluorescens* expression system according to the methods of the present invention at higher yield, e.g., about 1.5-fold to about 10-fold, about 1.5-fold, about 2-fold, about 2.5-fold, about 3-fold, about 5-fold, or about 10-fold higher, than in an *E. coli* or other microbial or bacterial expression system, e.g., those listed above, under substantially comparable conditions. In embodiments, the fusion protein or C-terminal polypeptide is produced in an *E. coli* expression system at a yield of less than 0.5, less than 0.4, less than 0.3, less than 0.2, or less than 0.1 grams/liter.

In embodiments, the polypeptide of interest is a small and/or rapidly degraded peptide. In embodiments, the small and/or rapidly degraded peptide is parathyroid hormone (PTH). In embodiments, the polypeptide of interest is human hPTH 1-34 (SEQ ID NO: 1). PTH is an 84 amino acid (aa) peptide derived from a 115 aa pre-pro-peptide, secreted by the parathyroid gland, that acts to increase calcium concentration in the blood and is known to stimulate bone formation. The N-terminal 34 aa peptide is approved to treat osteoporosis (Forteo®, Eli Lilly and Company; see package insert). The active ingredient in Forteo®, PTH 1-34, is produced in *E. coli* as part of a C-terminal fusion protein (NDA 21-319 for Forteo®; see Chemistry Review, Center for Drug Evaluation and Research, 2000-2001; see also Clinical Pharmacology and Biopharmaceutics review, Center for Drug Evaluation and Research, 2000-2001). Purification of Forteo® (Eli Lilly's LY333334) is described by, e.g., Jin, et al. ("Crystal Structure of Human Parathyroid Hormone 1-34 at 0.9 Å Resolution," J. Biol. Chem. 275 (35):27238-44, 2000), incorporated herein by reference. This report describes expression of the protein as inclusion bodies, and subsequent solubilization in 7 M urea.

In embodiments, the polypeptide of interest typically is produced in insoluble form when overexpressed in a bacterial expression system. In embodiments, the polypeptide of interest typically produced in insoluble form when overexpressed in a bacterial expression system is a eukaryotic polypeptide or derivative or analog thereof. In embodiments, the polypeptide of interest typically produced in insoluble form when overexpressed in a bacterial expression system is a proinsulin (a precursor of insulin). Proinsulin is comprised of three designated segments (from N to C terminus: B-C-A). Proinsulin is processed to insulin (or an insulin analog, depending on the proinsulin) when the internal C-peptide is removed by protease cleavage. Disulfide bonding between the A and B-peptides maintains their association following excision of the C-peptide insulin. In reference to insulin and insulin analogs here, "A-peptide" and "A-chain" are used interchangeably, and "B-peptide" and "B-chain" are used interchangeably. Positions within these chains are referred to by the chain and amino acid number from the amino terminus of the chain, for example, "B30" refers to the thirtieth amino acid in the B-peptide, i.e., the B-chain. In embodiments, the polypeptide of interest is a proinsulin that is processed to form a long-acting insulin analog or a rapid-acting insulin analog.

In embodiments, the polypeptide of interest is a proinsulin that is processed to form a long-acting insulin analog. Long-acting insulin analogs include, e.g., insulin glargine, a 43-amino acid (6050.41 Da), long-acting insulin analog marketed as Lantus®, insulin degludec, marketed as Tresiba®, and insulin detemir, marketed as Levemir®. In insulin glargine the asparagine at N21 (Asn21) is substituted with glycine, and two arginines are present at the C-terminus of the B-peptide. In insulin, these two arginines are present in proinsulin but not in the processed mature molecule. In embodiments, the polypeptide of interest is processed to glargine, and the polypeptide of interest is the 87-amino acid proinsulin as set forth in SEQ ID NOS: 88, 89, 90, or 91. In nonlimiting embodiments, the coding sequence for SEQ ID NO: 88 is the nucleotide sequence set forth in SEQ ID NO: 80 or 84. In nonlimiting embodiments, the coding sequence for SEQ ID NO: 89 is the nucleotide sequence set forth in SEQ ID NO: 81 or 85. In nonlimiting embodiments, the coding sequence for SEQ ID NO: 90 is the nucleotide sequence set forth in SEQ ID NO: 82 or 86. In nonlimiting embodiments, the coding sequence for SEQ ID NO: 91 is the nucleotide sequence set forth in SEQ ID NO: 83 or 87. Each of SEQ ID NOS: 80-87 include an initial 15 bp cloning site at the 5' end, therefore in these embodiments the proinsulin coding sequences referred to are the sequences starting at the first Phe codon, TTT (in SEQ ID NO: 80), or TTC (in SEQ ID NOS: 81-87). Insulin degludec has a deletion of Threonine at position B30 and is conjugated to hexadecanedioic acid via gamma-L-glutamyl spacer at the amino acid lysine at position B29. Insulin detemir has a fatty acid (myristic acid) is bound to the lysine amino acid at position B29.

In embodiments, the polypeptide of interest is proinsulin that is processed to form a rapid-acting insulin analog. Rapid-acting (or fast-acting) insulin analogs include, e.g., insulin aspart (NovoLog/NovoRapid®) (SEQ ID NO: 94), where the proline at position B28 is replaced with aspartic acid, and insulin lispro (Humalog®) (lispro proinsulin, SEQ ID NO: 33), where the last lysine and proline residues occurring at the C-terminal end of the B-chain are reversed, and insulin glulisine (Apidra®) (glulisine proinsulin, SEQ ID NO: 34), where the asparagine at position B3 is replaced with lysine and the lysine in position B29 is replaced with glutamic acid). At all other positions, these molecules have an identical amino acid sequence to regular insulin (proinsulin, SEQ ID NO: 32; insulin A-peptide, SEQ ID NO:95; insulin B-peptide, SEQ ID NO:96).

In embodiments, the polypeptide of interest typically produced in insoluble form when overexpressed in a bacterial expression system is GCSF, e.g., Met-GCSF. In embodiments, the polypeptide of interest typically produced in insoluble form when overexpressed in a bacterial expression system is IFN-β, e.g., IFN-β-1b. In embodiments, the bacterial expression system in which the recombinant polypeptide of interest is difficult to overexpress is an *E. coli* expression system.

In embodiments, the polypeptide of interest is a protein that has an easily-degraded N terminus. Because a fusion protein produced according to the methods of the present invention is separated from host proteases before cleavage to release the polypeptide of interest, the N-terminus of the polypeptide of interest is protected throughout the purification process. This allows the production of a preparation of up to 100% N-terminally intact polypeptide of interest.

In embodiments, the polypeptide of interest having an easily-degraded N-terminus is filgrastim, an analog of GCSF (granulocyte colony stimulating factor, or colony-stimulating factor 3 (CSF 3)). GCSF is a 174 amino acid glycoprotein that stimulates the bone marrow to produce granulocytes and stem cells and release them into the bloodstream. Filgrastim, which is nonglycosylated and has an N-terminal methionine, is marketed as Neupogen®. The amino acid sequence of GCSF (filgrastim) is set forth in SEQ ID NO: 69. In embodiments, the methods of the invention are used to produce a high level of GCSF (filgrastim) with an intact N-terminus, including the N-terminal methionine. GCSF production in a protease-deficient host cell is described in U.S. Pat. No. 8,455,218, "Methods for G-CSF production in a *Pseudomonas* host cell," incorporated herein by reference in its entirety. In embodiments of the present invention intact GCSF, including the N-terminal methionine, is produced within a fusion protein at a high level in a bacterial host cell, e.g., a *Pseudomonas* host cell, which is not protease-deficient.

In embodiments, the polypeptide of interest having an easily-degraded N-terminus is recombinant *P. falciparum* circumsporozoite protein (rCSP), described in, e.g., U.S. Pat. No. 9,169,304, "Process for Purifying Recombinant *Plasmodium Falciparum* Circumsporozoite Protein," incorporated herein by reference in its entirety.

In embodiments, the polypeptide of interest is: a reagent protein; a therapeutic protein; an extracellular receptor or ligand; a protease; a kinase; a blood protein; a chemokine; a cytokine; an antibody; an antibody-based drug; an antibody fragment, e.g., a single-chain antibody, an antigen binding (ab) fragment, e.g., F(ab), F (ab)', F(ab)'$_2$, Fv, generated from the variable region of IgG or IgM, an Fc fragment generated from the heavy chain constant region of an antibody, a reduced IgG fragment (e.g., generated by reducing the hinge region disulfide bonds of IgG), an Fc fusion protein, e.g., comprising the Fc domain of IgG fused together with a protein or peptide of interest, or any other antibody fragment described in the art, e.g., in U.S. Pat. No. 5,648,237, "Expression of Functional Antibody Fragments," incorporated by reference herein in its entirety; an anticoagulant; a blood factor; a bone morphogenetic protein; an engineered protein scaffold; an enzyme; a growth factor; an interferon; an interleukin; a thrombolytic agent; or a hormone. In embodiments, the polypeptide of interest is selected from: Human Antihemophilic Factor; Human Antihemophilic Factor-von Willebrand Factor Complex; Recombinant Antihemophilic Factor (Turoctocog Alfa); Ado-trastuzumab emtansine; Albiglutide; Alglucosidase Alpha; Human Alpha-1 Proteinase Inhibitor; Botulinum Toxin Type B (Rimabotulinumtoxin B); Coagulation Factor IX Fc Fusion; Recombinant Coagulation factor IX; Recombinant Coagulation factor VIIa; Recombinant Coagulation factor XIII A-subunit; Human Coagulation Factor VIII-von Willebrand Factor Complex; Collagenase *Clostridium Histolyticum*; Human Platelet-derived Growth Factor (Cecaplermin); Abatacept; Abciximab; Adalimumab; Aflibercept; Agalsidase Beta; Aldesleukin; Alefacept; Alemtuzumab; Alglucosidase Alfa; Alteplase; Anakinra; Octocog Alfa; Recombinant Human Antithrombin; Azficel-T; Basiliximab; Belatacept; Belimumab; Bevacizumab; Botulinum Toxin Type A; Brentuximab Vedotin; Recombinant C1 Esterase Inhibitor; Canakinumab; Certolizumab Pegol; Cetuximab; Nonacog Alfa; Daclizumab; Darbepoetin Alfa; Denosumab; Digoxin Immune Fab; Dornase Alfa; Ecallantide; Eculizumab; Etanercept; Fibrinogen; Filgrastim; Galsulfase; Golimumab; Ibritumomab Tiuxetan; Idursulfase; Infliximab; Interferon Alfa; Interferon Alfa-2b; Interferon Alfacon-1; Interferon Alfa-2a; Interferon Alfa-n3; Interferon Beta-1a; Interferon Beta-1b; Interferon Gamma-1b; Ipilimumab; Laronidase; Epoetin Alfa; Moroctocog Alfa; Muromonab-CD3; Natalizumab; Ocriplasmin; Ofatumumab; Omalizumab; Oprelvekin; Palifermin; Palivizumab; Panitumumab; Pegfilgrastim; Pertuzumab; Human Papilloma Virus (HPV) Types 6; 11; 16; 18-L1 viral protein Virus like Particles (VLP); HPV Type 16 and 18 L1 protein VLPs; Ranibizumab; Rasburicase; Raxibacumab; Recombinant Factor IX; Reteplase; Rilonacept; Rituximab; Romiplostim; Sargramostim; Tenecteplase; Tocilizumab; Trastuzumab; Ustekinumab; Abarelix; Cetrorelix; Desirudin; Enfuvirtide; Exenatide; Follitropin Beta; Ganirelix; Degarelix; Hyaluronidase; Insulin Aspart; Insulin Degludec; Insulin Detemir; Insulin Glargine rDNA Injection (long-acting human insulin analog); Recombinant Insulin Glulisine; Human Insulin; Insulin Lispro (rapid acting insulin analog); Recombinant Insulin Lispro Protamine; Recombinant Insulin Lispro; Lanreotide; Liraglutide; Surfaxin (Lucinactant; Sinapultide); Mecasermin; Insulin like Growth Factor; Nesiritide; Pramlintide; Recombinant Teduglutide; Tesamorelin Acetate; Ziconotide Acetate; 10.8 mg Goserelin Acetate Implant; AbobotulinumtoxinA; Agalsidase Alfa; Alipogene Tiparvovec; Ancestim; Anistreplase; Ardeparin Sodium; Avian TB Vaccine; Batroxobin; Bivalirudin; Buserelin (Gonadotropin-releasing Hormone Agonist); Cabozantinib S-Malate; Carperitide; Catumaxomab; Ceruletide; Coagulation Factor VIII; Coccidiosis Vaccine; Dalteparin Sodium; Deferiprone; Defibrotide; Dibotermin Alfa; Drotrecogin Alfa; Edotreotide; Efalizumab; Enoxaparin Sodium; Epoetin Delta; Eptifibatide; Eptotermin Alfa; Follitropin Alfa for Injection; Fomivirsen; Gemtuzumab ozogamicin; Gonadorelin; Recombinant Chorionic Human Gonadotropin; Histrelin Acetate (gonadotropin releasing hormone agonist); HVT IBD vaccine; Imiglucerase; Insulin Isophane; Lenograstim (Granulocyte-Colony Stimulating Factor); Lepirudin; Leptospira Vaccine for Dogs; Leuprorelin; Linaclotide; Lipegfilgrastim; Lixisenatide; Lutropin Alfa (human leutinizing hormone); Mepolizumab; Mifamurtide; Mipomersen Sodium; Mirimostim (macrophage-colony stimulating factor); Mogamulizumab; Molgramostim (granulocyte macrophage-colony stimulating factor); Monteplase; Nadroparin calcium; Nafarelin; Nebacumab; Octreotide; Pamiteplase; Pancrelipase; Parnaparin sodium; Pasireotide daspartate; Peginesatide acetate; Pegvisomant; Pentetreotide; Poractant alfa; Pralmorelin (growth hormone releasing peptide); Protirelin; PTH 1-84; rhBMP-2; rhBMP-7; Eptortermin Alfa; Romurtide; Sermorelin; Somatostatin; Somatrem; Vassopressin; Desmopressin; Taliglucerase Alfa; Taltirelin (thyrotropin-releasing hormone analog); Tasonermin; Taspoglutide; Thrombomodulin Alfa; Thyrotropin Alfa; Trafermin; Triptorelin Pamoate; Urofollitropin for Injection; Urokinase; Velaglucerase Alfa; Cholera Toxin B; Recombinant Antihemophilic Factor (Efraloctocog Alfa); Human Alpha-1 Proteinase Inhibitor; Asparaginase *Erwinia Chrysanthemi*; Capromab; Denileukin Diftitox; Ovine Digoxin Immune Fab; Elosulfase Alfa; Epoetin Alfa; Factor IX Complex; Factor XIII Concentrate; Technetium (Fanolesomab); Fibrinogen; Thrombin; Influenza Hemagglutinin and Neuraminidase; Glucarpidase; Hemin for Injection; Hep B Surface Antigen; Human Albumin; Incobotulinumtoxin; Nofetumomab; Obinutuzumab; L-asparaginase (from *Escherichia. coli; Erwinia* sp.; *Pseudomonas* sp.; etc.);

Pembrolizumab; Protein C Concentrate; Ramucirumab; Siltuximab; Tbo-Filgrastim; Pertussis Toxin Subunits A-E; Topical Bovine Thrombin; Topical Human Thrombin; Tositumomab; Vedolizumab; Ziv-Aflibercept; Glucagon; Somatropin; *Plasmodium falciparum* or a *Plasmodium vivax* Antigen (e.g., CSP, CelTOS, TRAP, Rh5, AMA-1, LSA-1, LSA-3, Pfs25, MSP-1, MSP-3, STARP, EXP1, pb9, GLURP). The sequences of these polypeptides, including variations, are available in the literature and known to those of skill in the art. Any known sequence of any of the polypeptides listed is contemplated for use in the methods of the present invention.

In embodiments, the polypeptide of interest is enterokinase (e.g., SEQ ID NO: 31 [bovine]), insulin, proinsulin (e.g., SEQ ID NO: 32), a long-acting insulin analog or a proinsulin that is processed to form a long-acting insulin analog (e.g., insulin glargine, SEQ ID NO: 88, insulin detemir, or insulin degludec), a rapid-acting insulin analog or a proinsulin that is processed to form a rapid-acting insulin analog (e.g., insulin lispro, insulin aspart, or insulin glulisine), insulin C-peptide (e.g., SEQ ID NO: 97), IGF-1 (e.g., Mecasermin, SEQ ID NO: 35), Glp-1 (e.g., SEQ ID NO: 36), a Glp-1 analog (e.g., Exenatide, SEQ ID NO: 37), Glp-2 (e.g., SEQ ID NO: 38), a Glp-2 analog (e.g., Teduglutide, SEQ ID NO: 39), Pramlintide (e.g., SEQ ID NO: 40), Ziconotide (e.g., SEQ ID NO: 41), Becaplermin (e.g., SEQ ID NO: 42), Enfuvirtide (e.g., SEQ ID NO: 43), or Nesiritide (e.g., SEQ ID NO: 44).

In embodiments, the molecular weight of the polypeptide of interest is about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 30 kDa, about 40 kDa, about 50 kDa, about 60 kDa, about 70 kDa, about 80 kDa, about 90 kDa, about 100 kDa, about 150 kDa, about 200 kDa, about 250 kDa, about 300 kDa, about 350 kDa, about 400 kDa, about 450 kDa, about 500 kDa, or more. In embodiments, the molecular weight of the recombinant polypeptide is about 1 to about 10 kDa, about 1 to about 20 kDA, about 1 to about 30 kDA, about 1 to about 40 kDA, about 1 to about 50 kDA, about 1 to about 60 kDA, about 1 to about 70 kDA, about 1 to about 80 kDA, about 1 to about 90 kDA, about 1 to about 100 kDA about 1 kDa to about 200 kDa, about 1 kDa to about 300 kDa, about 1 kDa to about 400 kDa, about 1 kDa to about 500 kDa, about 2 to about 10 kDA, about 2 to about 20 kDA, about 2 to about 30 kDA, about 2 to about 40 kDA, about 2 to about 50 kDA, about 2 to about 60 kDA, about 2 to about 70 kDA, about 2 to about 80 kDA, about 2 to about 90 kDA, about 2 to about 100 kDA, about 2 kDa to about 200 kDa, about 2 kDa to about 300 kDa, about 2 kDa to about 400 kDa, about 2 kDa to about 500 kDa, about 3 to about 10 kDA, about 3 to about 20 kDA, about 3 to about 30 kDA, about 3 to about 40 kDA, about 3 to about 50 kDA, about 3 to about 60 kDA, about 3 to about 70 kDA, about 3 to about 80 kDA, about 3 to about 90 kDA, about 3 to about 100 kDA, about 3 kDa to about 200 kDa, about 3 kDa to about 300 kDa, about 3 kDa to about 400 kDa, or about 3 kDa to about 500 kDa. In embodiments the molecular weight of the polypeptide of interest is about 4.1 kDa.

In embodiments, the polypeptide of interest is 25 or more amino acids in length. In embodiments, the polypeptide of interest is about 25 to about 2000 or more amino acids in length. In embodiments, the polypeptide of interest is about or at least about 25, 30, 35, 40, 45, 50, 100, 150, 200, 250, 300, 350, 400, 450, 475, 500, 525, 550, 575, 600, 625, 650, 700, 750, 800, 850, 900, 950, 1000, 1200, 1400, 1600, 1800, or 2000 amino acids in length. In embodiments, the polypeptide of interest is about: 25 to about 2000, 25 to about 1000, 25 to about 500, 25 to about 250, 25 to about 100, or 25 to about 50, amino acids in length. In embodiments, the polypeptide of interest is 32, 36, 39, 71, 109, or 110 amino acids in length. In embodiments, the polypeptide of interest is 34 amino acids in length.

N-Terminal Fusion Partner

The N-terminal fusion partner of the recombinant fusion protein is a bacterial protein that improves the yield of the recombinant fusion protein obtained using a bacterial expression system. In embodiments, the N-terminal fusion partner can be stably overexpressed from a recombinant construct in a bacterial host cell. In embodiments, the yield and/or solubility of the polypeptide of interest are increased or improved by the presence of the N-terminal fusion partner. In embodiments, the N-terminal fusion partner facilitates proper folding of the recombinant fusion protein. In embodiments, the N-terminal fusion partner is a bacterial folding modulator or chaperone protein.

In embodiments, the N-terminal fusion partner is a large-sized affinity tag protein, a folding modulator, a molecular chaperone, a ribosomal protein, a translation-related factor, an OB-fold protein (oligonucleotide binding fold protein), or another protein described in the literature, e.g. by Ahn, et al., 2011, "Expression screening of fusion partners from an *E. coli* genome for soluble expression of recombinant proteins in a cell-free protein synthesis system," PLoS One, 6(11): e26875, incorporated herein by reference. In embodiments, the N-terminal fusion partner is a large-sized affinity tag protein selected from MBP, GST, NusA, Ubiquitin, Domain 1 of IF-2, and the N-terminal domain of L9. In embodiments, the N-terminal fusion partner is a ribosomal protein from the 30S ribosomal subunit, or a ribosomal protein from the 50S ribosomal subunit. In embodiments, the N-terminal fusion partner is an *E. coli* or Pseudomonad chaperone or folding modulator protein. In embodiments, the N-terminal fusion partner is a *P. fluorescens* chaperone or folding modulator protein. In embodiments, the N-terminal fusion partner is a chaperone or folding modulator protein selected from Table 1.

In embodiments, the N-terminal fusion partner is *P. fluorescens* DnaJ-like protein (SEQ ID NO: 2), FrnE (SEQ ID NO: 3), FrnE2 (SEQ ID NO: 63), FrnE3 (SEQ ID NO: 64), FklB (SEQ ID NO: 4), FklB3* (SEQ ID NO: 28), FklB2 (SEQ ID NO: 61), FklB3 (SEQ ID NO: 62), FkpB2 (SEQ ID NO: 5), SecB (SEQ ID NO: 6), EcpD (RXF04553.1, SEQ ID NO: 7), EcpD (RXF04296.1, SEQ ID NO: 65, also referred to herein as EcpD1), EcpD2 (SEQ ID NO: 66), or EcpD3 (SEQ ID NO: 67). In embodiments, the N-terminal fusion partner is *Escherichia coli* protein Skp (SEQ ID NO: 8).

In embodiments, the N-terminal fusion partner is truncated relative to the full-length fusion partner polypeptide. In embodiments, the N-terminal fusion partner is truncated from the C-terminus, to remove at least one C-terminal amino acid. In embodiments, the N-terminal fusion partner is truncated to remove 1 to 300 amino acids from the C-terminus of the full-length polypeptide. In embodiments, the N-terminal fusion partner is truncated to remove 300, 290, 280, 270, 260, 250, 240, 230, 220, 210, 200, 190, 180, 170, 160, 150, 140, 130, 120, 110, 100, 90, 80, 70, 60, 50, 40, 30, 20, 10, 5, 1 to 300, 1 to 295, 1 to 290, 1 to 280, 1 to 270, 1 to 260, 1 to 250, 1 to 240, 1 to 230, 1 to 220, 1 to 210, 1 to 200, 1 to 190, 1 to 180, 1 to 170, 1 to 160, 1 to 150, 1 to 140, 1 to 130, 1 to 120, 1 to 110, 1 to 100, 1 to 90, 1 to 80, 1 to 70, 1 to 60, 1 to 50, 1 to 40, 1 to 30, 1 to 20, 1 to 15, 1 to 10, or 1 to 5 amino acids from the C-terminus of the polypeptide. In embodiments, the N-terminal fusion partner polypeptide is truncated from the C-terminus, to retain the first N-terminal 300, 290, 280, 270, 260, 250, 240, 230, 220, 210, 200, 190, 180, 170, 160, 150, 140, 130, 120, 110, 100, 90, 80, 70, 60, 50, 40, 150 to 40, the first 150 to 50, the first 150 to 75, the first 150-100, the first 100 to 40, the first 100 to 50, the first 100 to 75, the first 75-40, the first 75-50, the first 300, the first 250, the first 200, the first 150, the first 140, the first 130, the first 120, the first 110, the first 100, the first 90, the first 80, the first 75, the first 70, the first 65, the first 60, the first 55, the first 50, or the first 40 amino acids of the full-length polypeptide.

In embodiments, the N-terminal fusion partner that is truncated is FklB, FrnE, or EcpD1. In embodiments, the N-terminal fusion partner that is truncated is FklB, wherein the FklB is truncated from the C-terminus to remove 148, 198, 210, 200, 190, 180, 170, 160, 150, 140, 130, 120, 110, 100, 90, 80, 70, 60, 50, 40, 30, 20, 10, 5, 1, 1 to 210, 1 to 200, 1 to 190, 1 to 180, 1 to 170, 1 to 160, 1 to 150, 1 to 140, 1 to 130, 1 to 120, 1 to 110, 1 to 100, 1 to 90, 1 to 80, 1 to 70, 1 to 60, 1 to 50, 1 to 40, 1 to 30, 1 to 20, 1 to 15, 1 to 10, or 1 to 5 amino acids. In embodiments, the N-terminal fusion partner that is truncated is EcpD, wherein the EcpD is truncated from the C-terminus to remove 148, 198, 210, 200, 190, 180, 170, 160, 150, 140, 130, 120, 110, 100, 90, 80, 70, 60, 50, 40, 30, 20, 10, 5, 1, 1 to 210, 1 to 200, 1 to 190, 1 to 180, 1 to 170, 1 to 160, 1 to 150, 1 to 140, 1 to 130, 1 to 120, 1 to 110, 1 to 100, 1 to 90, 1 to 80, 1 to 70, 1 to 60, 1 to 50, 1 to 40, 1 to 30, 1 to 20, 1 to 15, 1 to 10, or 1 to 5 amino acids. In embodiments, the N-terminal fusion partner that is truncated is FrnE, wherein the FrnE is truncated from the C-terminus to remove 118, 168, 190, 180, 170, 160, 150, 140, 130, 120, 110, 100, 90, 80, 70, 60, 50, 40, 30, 20, 10, 5, 1, 1 to 190, 1 to 180, 1 to 170, 1 to 160, 1 to 150, 1 to 140, 1 to 130, 1 to 120, 1 to 110, 1 to 100, 1 to 90, 1 to 80, 1 to 70, 1 to 60, 1 to 50, 1 to 40, 1 to 30, 1 to 20, 1 to 15, 1 to 10, or 1 to 5 amino acids.

In embodiments, the N-terminal fusion partner is not β-galactosidase. In embodiments, the N-terminal fusion partner is not thioredoxin. In embodiments, the N-terminal fusion partner is neither β-galactosidase nor thioredoxin.

In embodiments, the molecular weight of the N-terminal fusion partner is about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 30 kDa, about 40 kDa, about 50 kDa, about 60 kDa, about 70 kDa, about 80 kDa, about 90 kDa, about 100 kDa, about 150 kDa, about 200 kDa, about 250 kDa, about 300 kDa, about 350 kDa, about 400 kDa, about 450 kDa, about 500 kDa, or more. In embodiments, the molecular weight of the N-terminal fusion partner is about 1 to about 10 kDA, about 1 to about 20 kDA, about 1 to about 30 kDA, about 1 to about 40 kDA, about 1 to about 50 kDA, about 1 to about 60 kDA, about 1 to about 70 kDA, about 1 to about 80 kDA, about 1 to about 90 kDA, about 1 to about 100 kDA about 1 kDa to about 200 kDa, about 1 kDa to about 300 kDa, about 1 kDa to about 400 kDa, about 1 kDa to about 500 kDa, about 2 to about 10 kDA, about 2 to about 20 kDA, about 2 to about 30 kDA, about 2 to about 40 kDA, about 2 to about 50 kDA, about 2 to about 60 kDA, about 2 to about 70 kDA, about 2 to about 80 kDA, about 2 to about 90 kDA, about 2 to about 100 kDA, about 2 kDa to about 200 kDa, about 2 kDa to about 300 kDa, about 2 kDa to about 400 kDa, about 2 kDa to about 500 kDa, about 3 to about 10 kDA, about 3 to about 20 kDA, about 3 to about 30 kDA, about 3 to about 40 kDA, about 3 to about 50 kDA, about 3 to about 60 kDA, about 3 to about 70 kDA, about 3 to about 80 kDA, about 3 to about 90 kDA, about 3 to about 100 kDA, about 3 kDa to about 200 kDa, about 3 kDa to about 300 kDa, about 3 kDa to about 400 kDa, or about 3 kDa to about 500 kDa.

In embodiments, the N-terminal fusion partner or truncated N-terminal fusion partner is 25 or more amino acids in length. In embodiments, the N-terminal fusion partner is about 25 to about 2000 or more amino acids in length. In embodiments, the N-terminal fusion partner is about or at least about 25, 35, 40, 45, 50, 100, 150, 200, 250, 300, 350, 400, 450, 470, 500, 530, 560, 590, 610, 640, 670, 700, 750, 800, 850, 900, 950, 1000, 1200, 1400, 1600, 1800, 2000 amino acids in length. In embodiments, the polypeptide of interest is about: 25 to about 2000, 25 to about 1000, 25 to about 500, 25 to about 250, 25 to about 100, or 25 to about 50, amino acids in length.

Relative Sizes of the Polypeptide of Interest and the Recombinant Fusion Protein The yield of the polypeptide of interest is proportional to the yield of the full recombinant fusion protein. This proportion depends on the relative sizes (e.g., molecular weight and/or length in amino acids) of the polypeptide of interest and the recombinant fusion protein. For example, decreasing the size of the N-terminal fusion partner in the fusion protein would result in a greater proportion of the fusion protein produced being the polypeptide of interest. In embodiments, to maximize yield of the polypeptide of interest, the N-terminal fusion partner is selected based on its size relative to the polypeptide of interest. In embodiments, an N-terminal fusion partner is selected to be a certain minimal size (e.g., MW or length in amino acids) relative to the polypeptide of interest. In embodiments, the recombinant fusion protein is designed so that the molecular weight of the polypeptide of interest constitutes from about 10% to about 50% of the molecular weight of the recombinant fusion protein. In embodiments, the molecular weight of the polypeptide of interest constitutes about or at least about: 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50% of the molecular weight of the recombinant fusion protein. In embodiments, the molecular weight of the polypeptide of interest constitutes about or at least about: 10% to about 50%, 11% to about 50%, 12% to about 50%, 13% to about 50%, 14% to about 50%, 15% to about 50%, 20% to about 50%, 25% to about 50%, 30% to about 50%, 35% to about 50%, 40% to about 50%, 13% to about 40%, 14% to about 40%, 15% to about 40%, 20% to about 40%, 25% to about 40%, 30% to about 40%, 35% to about 40%, 13% to about 30%, 14% to about 30%, 15% to about 30%, 20% to about 30%, 25% to about 30%, 13% to about 25%, 14% to about 25%, 15% to about 25%, or 20% to about 25%, of the molecular weight of the recombinant fusion protein. In embodiments, the polypeptide of interest is hPTH and the molecular weight of the polypeptide of interest constitutes about 14.6% of the molecular weight of the recombinant fusion protein. In embodiments, the polypeptide of interest is hPTH and the molecular weight of the polypeptide of interest constitutes about 13.6% of the molecular weight of the recombinant fusion protein. In embodiments, the polypeptide of interest is hPTH and the molecular weight of the polypeptide of interest constitutes about 27.3% of the molecular weight of the recombinant fusion protein. In embodiments, the polypeptide of interest is met-GCSF and the molecular weight of the polypeptide of interest constitutes about 39% to about 72% of the molecular weight of the recombinant fusion protein. In embodiments, the polypeptide of interest is a proinsulin and the molecular weight of the polypeptide of interest constitutes about 20% to about 57% of the molecular weight of the recombinant fusion protein.

In embodiments, the length of the polypeptide of interest constitutes between about 10% to about 50% of the total length of the recombinant fusion protein. In embodiments, the length of the polypeptide of interest constitutes about or at least about: 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50% of the total length of the recombinant fusion protein. In embodiments, the length of the polypeptide of interest constitutes about or at least about: 10% to about 50%, 11% to about 50%, 12% to about 50%, 13% to about 50%, 14% to about 50%, 15% to about 50%, 20% to about 50%, 25% to about 50%, 30% to about 50%, 35% to about 50%, 40% to about 50%, 13% to about 40%, 14% to about 40%, 15% to about 40%, 20% to about 40%, 25% to about 40%, 30% to about 40%, 35% to about 40%, 13% to about 30%, 14% to about 30%, 15% to about 30%, 20% to about 30%, 25% to about 30%, 13% to about 25%, 14% to about 25%, 15% to about 25%, or 20% to about 25%, of the total length of the recombinant fusion protein. In embodiments, the polypeptide of interest is hPTH and the length of the polypeptide of interest constitutes about 13.1% of the total length of the recombinant fusion protein. In embodiments, the polypeptide of interest is hPTH and the length of the polypeptide of interest constitutes about 12.5% of the total length of the recombinant fusion protein. In embodiments, the polypeptide of interest is hPTH and the length of the polypeptide of interest constitutes about 25.7% of the total length of the recombinant fusion protein. In embodiments, the polypeptide of interest is met-GCSF and the length of the polypeptide of interest constitutes about 40% to about 72% of the total length of the recombinant fusion protein. In embodiments, the polypeptide of interest is a proinsulin and the length of the polypeptide of interest constitutes about 19% to about 56% of the total length of the recombinant fusion protein.

Difference in Polypeptide of Interest and N-terminal Fusion Partner Isoelectric Points The isoelectric point of a protein (pI), is defined as the pH at which the protein carries no net electrical charge. The pI value is known to affect the solubility of a protein at a given pH. At a pH below its pI, a protein carries a net positive charge and at a pH above its pI, it carries a net negative charge. Proteins can be separated according to their isoelectric point (overall charge). In embodiments, the pI of the polypeptide of interest and that of the N-terminal fusion protein are substantially different. This can facilitate purification of the polypeptide of interest away from the N-terminal fusion protein. In embodiments, the pI of the polypeptide of interest is at least two times higher than that of the N-terminal fusion partner. In embodiments, the pI of the polypeptide of interest is 1.5 to 3 times higher than that of the N-terminal fusion partner. In embodiments, the pI of the polypeptide of interest is 1.5, 1.6, 1.7, 1.8, 1.9, 2, 2.1, 2.2, 2.3, 2.4, 2.5, 2.6, 2.7, 2.8, 2.9, or 3 times higher than that of the N-terminal fusion partner. In embodiments, the pI of the N-terminal fusion partner is about 4, about 4.1, about 4.2, about 4.3, about 4.4, about 4.5, about 4.6, about 4.7, about 4.8, about 4.9 or about 5. In embodiments, the pI of the N-terminal fusion partner is about 4 to about 5, about 4.1 to about 4.9, about 4.2 to about 4.8, about 4.3 to about 4.7, about 4.4 to about 4.6.

In embodiments, the N-terminal fusion partner is one listed in Table 8 or 18, having the pI listed therein. In embodiments, the C-terminal polypeptide of interest is hPTH 1-34, having a pI of 8.52 and a molecular weight of 4117.65 daltons. In embodiments, the C-terminal polypeptide of interest is Met-GCSF, having a pI of 5.66 and a molecular weight of 18801.9 daltons. In embodiments, the C-terminal polypeptide of interest is proinsulin as set forth in SEQ ID NO: 88, having a pI of about 5.2 and a molecular weight of about 9.34 KDa. In embodiments, the C-terminal polypeptide of interest is proinsulin as set forth in SEQ ID NO: 89, having a pI of about 6.07 and a molecular weight of about 8.81 KDa. In embodiments, the C-terminal polypeptide of interest is proinsulin as set forth in SEQ ID NO: 90, having a pI of about 5.52 and a molecular weight of about 8.75 KDa. In embodiments, the C-terminal polypeptide of interest is proinsulin as set forth in SEQ ID NO: 91, having a pI of 6.07 and a molecular weight of about 7.3 KDa. The pI of a protein can be determined according to any method as described in the literature and known to those of skill in the art.

Chaperones and Protein Folding Modulators

An obstacle to the production of a heterologous protein at a high yield in a non-native host cell (a cell to which the heterologous protein is not native) is that the cell often is not adequately equipped to produce the heterologous protein in soluble and/or active form. While the primary structure of a protein is defined by its amino acid sequence, the secondary structure is defined by the presence of alpha helices or beta sheets, and the tertiary structure by amino acid sidechain interactions within the protein, e.g., between protein domains. When expressing heterologous proteins, particularly in large-scale production, the secondary and tertiary structure of the protein itself are of critical importance. Any significant change in protein structure can yield a functionally inactive molecule, or a protein with significantly reduced biological activity. In many cases, a host cell expresses chaperones or protein folding modulators (PFMs) that are necessary for proper production of active heterologous protein. However, at the high levels of expression generally required to produce usable, economically satisfactory biotechnology products, a cell often cannot produce enough native protein folding modulator or modulators to process the heterologously-expressed protein.

In certain expression systems, overproduction of heterologous proteins can be accompanied by their misfolding and segregation into insoluble aggregates. In bacterial cells these aggregates are known as inclusion bodies. Proteins processed to inclusion bodies can, in certain cases, be recovered through additional processing of the insoluble fraction. Proteins found in inclusion bodies typically have to be purified through multiple steps, including denaturation and renaturation. Typical renaturation processes for inclusion body proteins involve attempts to dissolve the aggregate in concentrated denaturant with subsequent removal of the denaturant by dilution. Aggregates are frequently formed again in this stage. The additional processing adds cost, there is no guarantee that the in vitro refolding will yield biologically active product, and the recovered proteins can include large amounts of fragment impurities.

In vivo protein folding is assisted by molecular chaperones, which promote the proper isomerization and cellular targeting of other polypeptides by transiently interacting with folding intermediates, and by foldases, which accelerate rate-limiting steps along the folding pathway. In certain cases, the overexpression of chaperones has been found to increase the soluble yields of aggregation-prone proteins (see Baneyx, F., 1999, *Curr. Opin. Biotech.* 10:411-421). The beneficial effect associated with an increase in the intracellular concentration of these chaperones appears highly dependent on the nature of the overproduced protein, and may not require overexpression of the same protein folding modulator(s) for all heterologous proteins. Protein folding modulators, including chaperones, disulfide bond isomerases, and peptidyl-prolyl cis-trans isomerases (PPIases) are a class of proteins present in all cells which aid in the folding, unfolding and degradation of nascent polypeptides.

Chaperones act by binding to nascent polypeptides, stabilizing them and allowing them to fold properly. Proteins possess both hydrophobic and hydrophilic residues, the former are usually exposed on the surface while the latter are buried within the structure where they interact with other hydrophilic residues rather than the water which surrounds the molecule. However in folding polypeptide chains, the hydrophilic residues are often exposed for some period of time as the protein exists in a partially folded or misfolded state. It is during this time when the forming polypeptides can become permanently misfolded or interact with other misfolded proteins and form large aggregates or inclusion bodies within the cell. Chaperones generally act by binding to the hydrophobic regions of the partially folded chains and preventing them from misfolding completely or aggregating with other proteins. Chaperones can even bind to proteins in inclusion bodies and allow them to disaggregate. The GroES/EL, DnaKJ, Clp, Hsp90 and SecB families of folding modulators are all examples of proteins with chaperone-like activity.

The disulfide bond isomerases are another important type of folding modulator. These proteins catalyze a very specific set of reactions to help folding polypeptides form the proper intra-protein disulfide bonds. Any protein that has more than two cysteines is at risk of forming disulfide bonds between the wrong residues. The disulfide bond formation family consists of the Dsb proteins which catalyze the formation of disulfide bonds in the non-reducing environment of the periplasm. When a periplasmic polypeptide misfolds disulfide bond isomerase, DsbC is capable of rearranging the disulfide bonds and allowing the protein to reform with the correct linkages.

The FklB and FrnE proteins belong to the Peptidyl-prolyl cis-trans isomerase family of folding modulators. This is a class of enzymes that catalyzE the cis-trans isomerization of proline imidic peptide bonds in oligopeptides. The proline residue is unique among amino acids in that the peptidyl bond immediately preceding it can adopt either a cis or trans conformation. For all other amino acids this is not favored due to steric hindrance. Peptidyl-prolyl cis-trans isomerases (PPIases) catalyze the conversion of this bond from one form to the other. This isomerization may accelerate and/or aid protein folding, refolding, assembly of subunits and trafficking in the cell.

In addition to the general chaperones which seem to interact with proteins in a non-specific manner, there are also chaperones which aid in the folding of specific targets. These protein-specific chaperones form complexes with their targets, preventing aggregation and degradation and allowing time for them to assemble into multi-subunit structures. The PapD chaperone is an example (described in Lombardo et al., 1997, *Escherichia coli* PapD, in Guidebook to Molecular Chaperones and Protein-Folding Catalysts, Gething M-J Ed. Oxford University Press Inc., New York:463-465), incorporated herein by reference.

Folding modulators include, for example, HSP70 proteins, HSP110/SSE proteins, HSP40 (DnaJ-related) proteins, GRPE-like proteins, HSP90 proteins, CPN60 and CPN10 proteins, cytosolic chaperoning, HSP100 proteins, small HSPs, calnexin and calreticulin, PDI and thioredoxin-related proteins, peptidyl-prolyl isomerases, cyclophilin PPIases, FK-506 binding proteins, parvulin PPIases, individual chaperoning, protein specific chaperones, or intramolecular chaperones. Folding modulators are generally described in "Guidebook to Molecular Chaperones and Protein-Folding Catalysts," 1997, ed. M. Gething, Melbourne University, Australia, incorporated herein by reference.

The best characterized molecular chaperones in the cytoplasm of *E. coli* are the ATP-dependent DnaK-DnaJ-GrpE and GroEL-GroES systems. In *E. coli*, the network of folding modulators/chaperones includes the Hsp70 family. The major Hsp70 chaperone, DnaK, efficiently prevents protein aggregation and supports the refolding of damaged proteins. The incorporation of heat shock proteins into protein aggregates can facilitate disaggregation. Based on in vitro studies and homology considerations, a number of additional cytoplasmic proteins have been proposed to function as molecular chaperones in *E. coli*. These include ClpB, HtpG and IbpA/B, which, like DnaK-DnaJ-GrpE and GroEL-GroES, are heat-shock proteins (Hsps) belong to the stress regulon.

The *P. fluorescens* DnaJ-like protein is a molecular chaperone belonging to the DnaJ/Hsp40 family of proteins, characterized by their highly conserved J-domain. The J-domain, which is a region of 70 amino acids, is located at the C terminus of the DnaJ protein. The N terminus has a transmembrane (TM) domain that promotes insertion into the membrane. The A-domain separates the TM domain from the J-domain. Proteins in the DnaJ family play a critical role in protein folding, by interacting with another chaperone protein, DnaK (as a co-chaperone). The highly conserved J-domain is the site of interaction between DnaJ proteins and DnaK proteins. Type I DnaJ proteins are considered true DnaJ proteins, while types II and III are usually referred to as DnaJ-like proteins. The DnaJ-like protein is also known to participate actively in the response to hyperosmotic and heat shock by preventing the aggregation of stress-denatured proteins and by disaggregating proteins, in both DnaK dependent and DnaK-independent manners.

The trans conformation of X-Pro bonds is energetically favored in nascent protein chains; however, approximately 5% of all prolyl peptide bonds are found in a cis conformation in native proteins. The trans to cis isomerization of X-Pro bonds is rate limiting in the folding of many polypeptides and is catalyzed in vivo by peptidyl prolyl cis/trans isomerases (PPIases). Three cytoplasmic PPIases, SlyD, SlpA and trigger factor (TF), have been identified to date in *E. coli*. TF, a 48 kDa protein associated with 50S ribosomal subunits that has been postulated to cooperate with chaperones in *E. coli* to guarantee proper folding of newly synthesized proteins. At least five proteins (thioredoxins 1 and 2, and glutaredoxins 1, 2 and 3, the products of the trxA, trxc, grxA, grxB and grxC genes, respectively) are involved in the reduction of disulfide bridges that transiently arise in cytoplasmic enzymes. Thus, the N-terminal fusion partner can be a disulfide bond forming protein or a chaperone that allows proper disulfide bond formation.

Examples of folding modulators useful in the methods of the present invention are shown in Table 1. RXF numbers refer to the open reading frame. U.S. Pat. App. Pub. Nos.

2008/0269070 and 2010/0137162, both titled "Method for Rapidly Screening Microbial Hosts to Identify Certain Strains with Improved Yield and/or Quality in the Expression of Heterologous Proteins," incorporated by reference herein in their entirety, disclose the open reading frame sequences for the proteins listed in Table 1. Proteases and folding modulators also are provided in Tables A to F of U.S. Pat. No. 8,603,824, "Process for improved protein expression by strain engineering," incorporated by reference herein in its entirety.

TABLE 1

*P. fluorescens* Folding Modulators

| ORF ID | GENE | FUNCTION | FAMILY | LOCATION |
|---|---|---|---|---|
| GroES/EL | | | | |
| RXF02095.1 | groES | Chaperone | Hsp10 | Cytoplasmic |
| RXF06767.1::Rxf02090 | groEL | Chaperone | Hsp60 | Cytoplasmic |
| RXF01748.1 | ibpA | Small heat-shock protein (sHSP) IbpA PA3126; Acts as a holder for GroESL folding | Hsp20 | Cytoplasmic |
| RXF03385.1 | hscB | Chaperone protein hscB | Hsp20 | Cytoplasmic |
| Hsp70 (DnaK/J) | | | | |
| RXF05399.1 | dnaK | Chaperone | Hsp70 | Periplasmic |
| RXF06954.1 | dnaK | Chaperone | Hsp70 | Cytoplasmic |
| RXF03376.1 | hscA | Chaperone | Hsp70 | Cytoplasmic |
| RXF03987.2 | cbpA | Curved dna-binding protein, dnaJ like activity | Hsp40 | Cytoplasmic |
| RXF05406.2 | dnaJ | Chaperone protein dnaJ | Hsp40 | Cytoplasmic |
| RXF03346.2 | dnaJ | Molecular chaperones (DnaJ family) | Hsp40 | Non-secretory |
| RXF05413.1 | grpE | heat shock protein GrpE PA4762 | GrpE | Cytoplasmic |
| Hsp100 (Clp/Hsl) | | | | |
| RXF04587.1 | clpA | atp-dependent clp protease atp-binding subunit | Hsp100 | Cytoplasmic |
| RXF08347.1 | clpB | ClpB protein | Hsp100 | Cytoplasmic |
| RXF04654.2 | clpX | atp-dependent clp protease atp-binding subunit | Hsp100 | Cytoplasmic |
| RXF04663.1 | clpP | atp-dependent Clp protease proteolytic subunit (ec 3.4.21.92) | MEROPS peptidase family S14 | Cytoplasmic |
| RXF01957.2 | hslU | atp-dependent hsl protease atp-binding subunit | Hsp100 | Cytoplasmic |
| RXF01961.2 | hslV | atp-dependent hsl protease proteolytic subunit | MEROPS peptidase subfamily T1B | Cytoplasmic |
| Hsp33 | | | | |
| RXF04254.2 | yrfI | 33 kDa chaperonin (Heat shock protein 33 homolog) (HSP33). | Hsp33 | Cytoplasmic |
| Hsp90 | | | | |
| RXF05455.2 | htpG | Chaperone protein htpG | Hsp90 | Cytoplasmic |
| SecB | | | | |
| RXF02231.1 | secB | secretion specific chaperone SecB | SecB | Non-secretory |
| Disulfide Bond Isomerases | | | | |
| RXF07017.2 | dsbA | disulfide isomerase | DSBA oxido-reductase | Cytoplasmic |
| RXF08657.2 | frnE | disulfide isomerase | DSBA oxido-reductase | Cytoplasmic |
| RXF01002.1 | dsbA homolog | disulfide isomerase | DSBA oxido-reductase/ Thioredoxin | Periplasmic |
| RXF03307.1 | dsbC | disulfide isomerase | Glutaredoxin/ Thioredoxin | Periplasmic |
| RXF04890.2 | dsbG | disulfide isomerase | Glutaredoxin/ Thioredoxin | Periplasmic |
| RXF03204.1 | dsbB | Disulfide bond formation protein B (Disulfide oxidoreductase). | DSBA oxido-reductase | Periplasmic |
| RXF04886.2 | dsbD | Thiol: disulfide interchange protein dsbD | DSBA oxido-reductase | Periplasmic |
| Peptidyl-prolyl Cis-trans Isomerases | | | | |
| RXF03768.1 | ppiA | Peptidyl-prolyl cis-trans isomerase A (ec 5.2.1.8) | PPIase: cyclophilin type | Periplasmic |
| RXF05345.2 | ppiB | Peptidyl-prolyl cis-trans isomerase B. | PPIase: cyclophilin type | Cytoplasmic |

TABLE 1-continued

*P. fluorescens* Folding Modulators

| ORF ID | GENE | FUNCTION | FAMILY | LOCATION |
|---|---|---|---|---|
| RXF06034.2 | fklB | Peptidyl-prolyl cis-trans isomerase FklB. | PPIase: FKBP type | OuterMembrane |
| RXF06591.1 | fklB/fkbP | fk506 binding protein Peptidyl-prolyl cis-transisomerase (EC 5.2.1.8) | PPIase: FKBP type | Periplasmic |
| RXF05753.2 | fklB/fkbP | Peptidyl-prolyl cis-trans isomerase (ec 5.2.1.8) | PPIase: FKBP type | OuterMembrane |
| RXF01833.2 | slyD | Peptidyl-prolyl cis-trans isomerase SlyD. | PPIase: FKBP type | Non-secretory |
| RXF04655.2 | tig | Trigger factor, ppiase (ec 5.2.1.8) | PPIase: FKBP type | Cytoplasmic |
| RXF05385.1 | yaad | Probable FKBP-type 16 kDa peptidyl-prolyl cis-trans isomerase (EC 5.2.1.8) (PPiase) (Rotamase). | PPIase: FKBP type | Non-secretory |
| RXF00271.1 | | Peptidyl-prolyl cis-trans isomerase (ec 5.2.1.8) | PPIase: FKBP type | Non-secretory |
| Pili Assembly Chaperones (papD-like) | | | | |
| RXF06068.1 | cup | Chaperone protein cup | pili assembly papD | Periplasmic |
| RXF05719.1 | ecpD | Chaperone protein ecpD | pili assembly papD | Signal peptide |
| RXF05319.1 | ecpD | Hnr protein | pili assembly chaperone | Periplasmic |
| RXF03406.2 | ecpD; csuC | Chaperone protein ecpD | pili assembly papD | Signal peptide |
| RXF04296.1 | ecpD; cup | Chaperone protein ecpD | pili assembly papD | Periplasmic |
| RXF04553.1 | ecpD; cup | Chaperone protein ecpD | pili assembly papD | Periplasmic |
| RXF04554.2 | ecpD; cup | Chaperone protein ecpD | pili assembly papD | Periplasmic |
| RXF05310.2 | ecpD; cup | Chaperone protein ecpD | pili assembly papD | Periplasmic |
| RXF05304.1 | ecpD; cup | Chaperone protein ecpD | pili assembly papD | Periplasmic |
| RXF05073.1 | gltF | Gram-negative pili assembly chaperone periplasmic function | pili assembly papD | Signal peptide |
| Type II Secretion Complex | | | | |
| RXF05445.1 | YacJ | Histidinol-phosphate aminotransferase (ec 2.6.1.9) | Class-II pyridoxal-phosphate-dependent aminotransferase family. Histidinol-phosphate amino-transferase subfamily | Membrane |
| RXF05426.1 | SecD | Protein translocase subunit secd | Type II secretion complex | Membrane |
| RXF05432.1 | SecF | protein translocase subunit secf | Type II secretion complex | Membrane |
| Disulfide Bond Reductases | | | | |
| RXF08122.2 | trxC | Thioredoxin 2 | Disulfide Bond Reductase | Cytoplasmic |
| RXF06751.1 | Gor | Glutathione reductase (EC 1.8.1.7) (GR) (GRase) PA2025 | Disulfide Bond Reductase | Cytoplasmic |
| RXF00922.1 | gshA | Glutamate--cysteine ligase (ec 6.3.2.2) PA5203 | Disulfide Bond Reductase | Cytoplasmic |

Linkers

The recombinant fusion proteins of the present invention contain a linker between the N-terminal fusion partner and the C-terminal polypeptide of interest. In embodiments, the linker comprises a cleavage site that is recognized by a cleavage enzyme, i.e., a proteolytic enzyme that cleaves a protein internally. In embodiments, cleavage of the linker at the cleavage site separates the polypeptide of interest from the N-terminal fusion partner. The proteolytic enzyme can be any protease known in the art or described in the literature, e.g., in PCT Pub. No. WO 2003/010204, "Process for Preparing Polypeptides of Interest from Fusion Polypeptides," U.S. Pat. No. 5,750,374, "Process for Producing Hydrophobic Polypeptides and Proteins, and Fusion Proteins for Use in Producing Same," and U.S. Pat. No. 5,935,824, each incorporated by reference herein in its entirety.

In embodiments, the linker comprises a cleavage site cleaved by, e.g., a serine protease, threonine protease, cysteine protease, aspartate protease, glutamic acid protease, metalloprotease, asparagine protease, mixed protease, or a protease of unknown catalytic type. In embodiments, the serine protease is, e.g., trypsin, chymotrypsin, endoproteinase Arg-C, endoproteinase Glu-C, endoproteinase Lys-C, elastase, proteinase K, subtilisin, carboxypeptidase P, carboxypeptidase Y, Acylaminoacid Releasing Enzyme. In embodiments, the metalloprotease is, e.g., endoproteinase Asp-N, thermolysin, carboxypeptidase A, carboxypeptidase B. In embodiments, the cysteine protease is, e.g., papain, clostripain, cathepsin C, or pyroglutamate aminopeptidase. In embodiments, the aspartate protease is, e.g., pepsin, chymosin, cathepsin D. In embodiments, the glutamic protease is, e.g., scytalidoglutamic peptidase. In embodiments, the asparagine protease is, e.g., nodavirus peptide lyase, intein-containing chloroplast ATP-dependent peptide lyase, intein-containing replicative DNA helicase precursor, or reovirus type 1 coat protein. In embodiments, the protease of unknown catalytic type is, e.g., collagenase, protein P5 murein endopeptidase, homomultimeric peptidase, microcin-processing peptidase 1, or Dop isopeptidase.

In embodiments, the linker comprises a cleavage site for Achromopeptidase, Aminopeptidase, Ancrod, Angiotensin Converting Enzyme, Bromelain, Calpain, Calpain I, Calpain II, Carboxypeptidase A, Carboxypeptidase B, Carboxypeptidase G, Carboxypeptidase P, Carboxypeptidase W, Carboxypeptidase Y, Caspases (general), Caspase 1, Caspase 2, Caspase 3, Caspase 4, Caspase 5, Caspase 6, Caspase 7, Caspase 8, Caspase 9, Caspase 10, Caspase 11, Caspase 12, Caspase 13, Cathepsin B, Cathepsin C, Cathepsin D, Cathepsin E, Cathepsin G, Cathepsin H, Cathepsin L, Chymopapain, Chymase, Chymotrypsin, a-Clostripain, Collagenase, Complement C1r, Complement C1s, Complement Factor D, Complement factor I, Cucumisin, Dipeptidyl Peptidase IV, Elastase, leukocyte, Elastase, Endoproteinase Arg-C, Endoproteinase Asp-N, Endoproteinase Glu-C, Endoproteinase Lys-C, Enterokinase, Factor Xa, Ficin, Furin, Granzyme A, Granzyme B, HIV Protease, IGase, Kallikrein tissue, Leucine Aminopeptidase (General), Leucine aminopeptidase, cytosol, Leucine aminopeptidase, microsomal, Matrix metalloprotease, Methionine Aminopeptidase, Neutrase, Papain, Pepsin, Plasmin, Prolidase, Pronase E, Prostate Specific Antigen, Protease, Alkalophilic from *Streptomyces griseus*, Protease from *Aspergillus*, Protease from *Aspergillus saitoi*, Protease from *Aspergillus sojae*, Protease (*B. licheniformis*) (Alkaline), Protease (*B. licheniformis*) (Alcalase), Protease from *Bacillus polymyxa*, Protease from *Bacillus* sp. (Esperase), Protease from *Rhizopus* sp., Protease S, Proteasomes, Proteinase from *Aspergillus oryzae*, Proteinase 3, Proteinase A, Proteinase K, Protein C, Pyroglutamate aminopeptidase, Renin, Rennin, Streptokinase, Subtilisin, Thermolysin, Thrombin, Tissue Plasminogen Activator, Trypsin, Tryptase, or Urokinase. In embodiments, the linker comprises a cleavage site recognized by Enterokinase, Factor Xa, or Furin. In embodiments, the linker comprises a cleavage site recognized by Enterokinase or trypsin. In embodiments, the linker comprises a cleavage site recognized by bovine Enterokinase. These and other proteases useful in the methods of the present invention, and their cleavage recognition sites, are known in the art and described in the literature, e.g., by Harlow and Lane, ANTIBODIES: A LABORATORY MANUAL, Cold Spring Harbor Laboratory Press, Cold Spring Harbor, N.Y. (1988); Walsh, PROTEINS: BIOCHEMISTRY AND BIOTECHNOLOGY, John Wiley & Sons, Ltd., West Sussex, England (2002), incorporated herein by reference.

In embodiments, the linker comprises an affinity tag. An affinity tag is a peptide sequence that can aid in protein purification. Affinity tags are fused to proteins to facilitate purification of the protein from a crude biological source, using an affinity technique. Any suitable affinity tag known in the art can be used as desired. In embodiments, an affinity tag used in the present invention is, e.g., Chitin Binding Protein, Maltose Binding Protein, or Glutathione-S-transferase Protein, Polyhistidine, FLAG tag (SEQ ID NO: 229), Calmodulin tag (SEQ ID NO: 230), Myc tag, BP tag, HA-tag (SEQ ID NO: 231), E-tag (SEQ ID NO: 232), S-tag (SEQ ID NO: 233), SBP tag (SEQ ID NO: 234), Softag 1, Softag 3 (SEQ ID NO: 235), V5 tag (SEQ ID NO: 236), Xpress tag, Green Fluorescent Protein, Nus tag, Strep tag, Thioredoxin tag, MBP tag, VSV tag (SEQ ID NO: 237), or Avi tag.

Affinity tags can be removed by chemical agents or by enzymatic means, such as proteolysis. Methods for using affinity tags in protein purification are described in the literature, e.g., by Lichty, et al., 2005, "Comparison of affinity tags for protein purification," Protein Expression and Purification 41: 98-105. Other affinity tags useful in linkers of the invention are known in the art and described in the literature, e.g., by U.S. Pat. No. 5,750,374, referenced above, and Terpe K., 2003, "Overview of Tag Protein Fusions: from molecular and biochemical fundamentals to commercial systems," Applied Microbiology and Biotechnology (60):523-533, both incorporated by reference herein in their entirety.

In embodiments, the linker is 4, 5, 6, 7, 8, 9, 10, 11, 12, 13, 14, 15, 16, 17, 18, 19, 20, 21, 22, 23, 24, 25, 30, 35, 40, 45, 50, or more, amino acids in length. In embodiments, the linker is 4 to 50, 4 to 45, 4 to 40, 4 to 35, 4 to 30, 4 to 25, 4 to 20, 4 to 15, 4 to 10, 5 to 50, 5 to 45, 5 to 40, 5 to 35, 5 to 30, 5 to 25, 5 to 20, 5 to 15, 5 to 10, 10 to 50, 10 to 45, 10 to 40, 10 to 35, 10 to 30, 10 to 25, 10 to 20, 10 to 15, 15 to 50, 15 to 45, 15 to 40, 15 to 35, 15 to 30, 15 to 25, 15 to 20, 20 to 50, 20 to 45, 20 to 40, 20 to 35, 20 to 30, or 20 to 25 amino acids in length. In embodiments, the linker is 18 amino acids in length. In embodiments, the linker is 19 amino acids in length.

In embodiments the linker includes multiple glycine residues. In embodiments, the linker includes 1, 2, 3, 4, 5, 6, 7, 8, or more glycine residues. In embodiments, the linker includes 1 to 8, 1 to 7, 1 to 6, 1 to 5, or 1 to 4 glycine residues. In embodiments, the glycine residues are consecutive. In embodiments, the linker contains at least one serine residue. In embodiments, the glycine and/or serine residues comprise a spacer. In embodiments, the spacer is a $(G4S)_2$ spacer having 10 amino acids, as set forth in SEQ ID NO: 59. In embodiments, the spacer is a $(G4S)_1$ (SEQ ID NO:238), $(G4S)_2$ (SEQ ID NO:59), $(G4S)_3$ (SEQ ID NO:239), $(G4S)_4$ (SEQ ID NO:240), or a $(G4S)_5$ (SEQ ID NO:241) spacer. In embodiments, the linker contains six histidine residues (SEQ ID NO:242), or a His-tag. In embodiments the linker includes an enterokinase cleavage site, e.g., as set forth by SEQ ID NO: 13 (DDDDK). In embodiments, the recombinant fusion protein comprises a linker as set forth in any of SEQ ID NOS: 9 to 12, or 226, listed in Table 2. The enterokinase cleavage site in SEQ ID NO: 9 is underlined. The polyhistidine affinity tags are italicized in each of SEQ ID NOS: 9 to 12 and 226. In embodiments, the recombinant fusion protein comprises a linker corresponding to SEQ ID NO: 9.

TABLE 2

Linker Sequences

| SEQ ID NO: | Amino Acid Sequence |
|---|---|
| 9 | GGGGSGGGG*HHHHHH*<u>DDDDK</u> |
| 10 | GGGGSGGGG*HHHHHH*RKR |
| 11 | GGGGSGGGG*HHHHHH*RRR |
| 12 | GGGGSGGGG*HHHHHH*LVPR |
| 226 | GGGGSGGGGS*HHHHHH*R |

Expression Vector

In embodiments, gene fragments coding for recombinant fusion proteins are introduced into suitable expression plasmids to generate expression vectors for expressing recombinant fusion proteins. The expression vector can be, for example, a plasmid. In some embodiments, a plasmid encoding a recombinant fusion protein sequence can comprise a selection marker, and host cells maintaining the plasmid can be grown under selective conditions. In some embodiments, the plasmid does not comprise a selection marker. In some embodiments, the expression vector can be integrated into the host cell genome. In some embodiments, the expression vector encodes hPTH 1-34 fused to a linker and a protein that can direct the expressed fusion protein to the cytoplasm. In embodiments, expression vector encodes hPTH 1-34 fused to a linker and a protein that can direct the expressed fusion protein to the periplasm. In some embodiments, the expression vector encodes hPTH 1-34 fused to a linker and *P. fluorescens* DnaJ-like protein. In some embodiments, the expression vector encodes hPTH 1-34 fused to a linker and *P. fluorescens* FklB protein.

Examples of nucleotide sequences encoding PTH 1-34 fusion proteins are provided in the Table of Sequences herein. Examples of nucleotide sequences that encode a fusion protein comprising a DnaJ-like protein N-terminal fusion partner are designated gene ID 126203 (SEQ ID NO: 52), corresponding to a coding sequence optimized for *P. fluorescens*. The sequence designated gene ID 126206 (SEQ ID NO: 53) corresponds to a native *P. fluorescens* DnaJ coding sequence fused to an optimized linker and PTH 1-34 coding sequence. The gene sequences 126203 and 126206 are those present in the expression plasmids p708-001 and p708-004, respectively. Examples of nucleotide sequences that encode a fusion protein comprising an FklB N-terminal fusion partner are designated gene ID 126204 (SEQ ID NO: 54), corresponding to a coding sequence optimized for *P. fluorescens*. The gene ID 126207 (SEQ ID NO: 55) corresponds to a native *P. fluorescens* FklB coding sequence fused to an optimized linker and PTH1-34 coding sequence. The gene sequences 126204 and 126207 are those present in the expression plasmids p708-002 and p708-005, respectively. Examples of nucleotide sequences that encode a fusion protein comprising an FrnE N-terminal fusion partner are designated gene ID 126205 (SEQ ID NO: 56), corresponding to a coding sequence optimized for *P. fluorescens*. The sequence designated gene ID 126208 (SEQ ID NO: 57) corresponds to a native *P. fluorescens* FrnE coding sequence fused to an optimized linker and PTH1-34 coding sequence. The gene sequences 126205 and 126208 are present in the expression plasmids p708-003 and p708-006, respectively.

Codon Optimization

The present invention contemplates the use of any appropriate coding sequence for the fusion protein and/or each of its individual components, including any sequence that has been optimized for expression in the host cell being used. Methods for optimizing codons to improve expression in bacterial hosts are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety. Codon optimization for expression in *E. coli* is described, e.g., by Welch, et al., 2009, PLoS One, "Design Parameters to Control Synthetic Gene Expression in *Escherichia coli*, 4(9): e7002, incorporated by reference herein. Nonlimiting examples of coding sequences for fusion protein components are provided herein, however it is understood that any suitable sequence can be generated as desired according to methods well known by those of skill in the art.

Expression Systems

An appropriate bacterial expression system useful for producing the polypeptide of interest according to the present methods can be identified by one of skill in the art based on the teachings herein. In embodiments, an expression construct comprising a nucleotide sequence encoding a recombinant fusion protein comprising the polypeptide of interest are provided as part of an inducible expression vector. In embodiments, a host cell that has been transformed with the expression vector is cultured, and expression of the fusion protein from the expression vector is induced. The expression vector can be, for example, a plasmid. In embodiments, the expression vector is a plasmid encoding a recombinant fusion protein coding sequence further comprising a selection marker, and the host cells are grown under selective conditions that allow maintenance of the plasmid. In embodiments, the expression construct is integrated into the host cell genome. In embodiments, the expression construct encodes a recombinant fusion protein fused to a secretory signal that can direct the recombinant fusion protein to the periplasm.

Methods for expressing heterologous proteins, including useful regulatory sequences (e.g., promoters, secretion leaders, and ribosome binding sites), in host cells useful in the methods of the present invention, including *Pseudomonas* host cells, are described, e.g., in U.S. Pat. App. Pub. Nos. 2008/0269070 and 2010/0137162, U.S. Pat. App. Pub. No. 2006/0040352, "Expression of Mammalian Proteins in *Pseudomonas fluorescens*," and U.S. Pat. No. 8,603,824, each incorporated herein by reference in its entirety. These publications also describe bacterial host strains useful in practicing the methods of the invention, that have been engineered to overexpress folding modulators or wherein protease mutations have been introduced, e.g., to eliminate, inactivate or decrease activity of the protease, in order to increase heterologous protein expression. Sequence leaders are described in detail in U.S. Pat. No. 7,618,799, "Bacterial leader sequences for increased expression," and U.S. Pat. No. 7,985,564, "Expression systems with Sec-system Secretion," both incorporated herein by reference in their entirety, as well as in U.S. Pat. App. Pub. No. 2010/0137162, previously referenced.

Promoters used in accordance with the present invention may be constitutive promoters or regulated promoters. Examples of inducible promoters include those of the family derived from the lac promoter (i.e. the lacZ promoter), e.g., the tac and trc promoters described in U.S. Pat. No. 4,551, 433, "Microbial Hybrid Promoters," incorporated herein by reference, as well as Ptac16, Ptac17, PtacII, PlacUV5, and the T7lac promoter. In embodiments, the promoter is not derived from the host cell organism. In embodiments, the promoter is derived from an *E. coli* organism. In embodiments, a lac promoter is used to regulate expression of a recombinant fusion protein from a plasmid. In the case of the lac promoter derivatives or family members, e.g., the tac promoter, an inducer is IPTG (isopropyl-β-D-1-thiogalactopyranoside, "isopropylthiogalactoside"). In embodiments, IPTG is added to the host cell culture to induce expression of the recombinant fusion protein from a lac promoter in a *Pseudomonas* host cell according to methods known in the art and described in the literature, e.g., in U.S. Pat. Pub. No. 2006/0040352.

Examples of non-lac promoters useful in expression systems according to the present invention include, $P_R$ (induced by high temperature), $P_L$ (induced by high temperature), $P_m$ (induced by Alkyl- or halo-benzoates), $P_u$ (induced by alkyl- or halo-toluenes), or $P_{sal}$ (induced by salicylates), described in, e.g. J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK). A promoter having the nucleotide sequence of a promoter native to the selected bacterial host cell also may be used to control expression of the expression construct encoding the polypeptide of interest, e.g., a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, derived from the same or different organisms. In embodiments, the promoter is Pmtl, as described in, e.g., U.S. Pat. Nos. 7,476,532, and 8,017,355, both titled "Mannitol induced promoter systems in bacterial host cells," incorporated by reference herein in their entirety.

Regulated (inducible) promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lacI gene can also be present in the system. The lad gene, which is normally a constitutively expressed gene, encodes the Lac repressor protein LacI protein, which binds to the lac operator of lac family promoters. Thus, where a lac family promoter is utilized, the lac gene can also be included and expressed in the expression system.

Other Regulatory Elements

In embodiments, other regulatory elements are present in the expression construct encoding the recombinant fusion protein. In embodiments, the soluble recombinant fusion protein is present in either the cytoplasm or periplasm of the cell during production. Secretion leaders useful for targeting the fusion proteins are described elsewhere herein. In embodiments, an expression construct of the present invention encodes a recombinant fusion protein fused to a secretion leader that can transport the recombinant fusion protein to the cytoplasm of a Pseudomonad cell. In embodiments, an expression construct encodes a recombinant fusion protein fused to a secretion leader that can transport a recombinant fusion protein to the periplasm of a Pseudomonad cell. In embodiments, the secretion leader is cleaved from the recombinant fusion protein.

Other elements include, but are not limited to, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" polypeptide coding sequences, which facilitate identification, separation, purification, and/or isolation of an expressed polypeptide, as previously described. In embodiments, the expression construct includes, in addition to the protein coding sequence, any of the following regulatory elements operably linked thereto: a promoter, a ribosome binding site (RBS), a transcription terminator, and translational start and stop signals. Useful RBSs can be obtained from any of the species useful as host cells in expression systems according to, e.g., U.S. Pat. App. Pub. No. 2008/0269070 and 2010/0137162, previously referenced. Many specific and a variety of consensus RBSs are known, e.g., those described in and referenced by D. Frishman et al., Gene 234(2):257-65 (8 Jul. 1999); and B. E. Suzek et al., Bioinformatics 17(12):1123-30 (December 2001), incorporated herein by reference. In addition, either native or synthetic RBSs may be used, e.g., those described in: EP 0207459 (synthetic RBSs); O. Ikehata et al., Eur. J. Biochem. 181(3):563-70 (1989). In embodiments, a "Hi" ribosome binding site, aggagg, (SEQ ID NO: 60) is used in the construct. Ribosome binding sites, including the optimization of spacing between the RBS and translation initiation codon, are described in the literature, e.g., by Chen, et al., 1994, "Determination of the optimal aligned spacing between the Shine-Dalgarno sequence and the translation initiation codon of *Escherichia coli* mRNAs," Nucleic Acids Research 22(23):4953-4957, and Ma, et al., 2002, "Correlations between Shine-Dalgarno Sequences and Gene Features Such as Predicted Expression Levels and Operon Structures," J. Bact. 184(20): 5733-45, incorporated herein by reference.

Further examples of methods, vectors, and translation and transcription elements, and other elements useful in the present invention are well known in the art and described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox, all incorporated herein by reference, as well as in many of the other publications incorporated herein by reference.

Secretion Leader Sequences

In embodiments, a secretion signal or leader coding sequence is fused to the N-terminus of the sequence encoding the recombinant fusion protein. Use of secretion signal sequences can increase production of recombinant proteins in bacteria. Additionally, many types of proteins require secondary modifications that are inefficiently achieved using known methods. Secretion leader utilization can increase the harvest of properly folded proteins by secreting the protein from the intracellular environment. In Gram-negative bacteria, a protein secreted from the cytoplasm can end up in the periplasmic space, attached to the outer membrane, or in the extracellular broth. These methods also avoid formation of inclusion bodies. Secretion of proteins into the periplasmic space also has the effect of facilitating proper disulfide bond formation (Bardwell et al., 1994, Phosphate Microorg, Chapter 45, 270-5, and Manoil, 2000, Methods in Enzymol. 326:35-47). Other benefits of secretion of recombinant protein include more efficient isolation of the protein, proper folding and disulfide bond formation of the protein leading to an increase in yield represented by, e.g., the percentage of the protein in active form, reduced formation of inclusion bodies and reduced toxicity to the host cell, and an increased percentage of the recombinant protein in soluble form. The potential for excretion of the protein of interest into the culture medium can also potentially promote continuous, rather than batch, culture for protein production.

In embodiments, the recombinant fusion protein or polypeptide of interest is targeted to the periplasm of the host cell or into the extracellular space. In embodiments, the expression vector further comprises a nucleotide sequence encoding a secretion signal polypeptide operably linked to the nucleotide sequence encoding the recombinant fusion protein or polypeptide of interest.

Therefore, in one embodiment, the recombinant fusion protein comprises a secretion signal, an N-terminal fusion partner, a linker, and a polypeptide of interest, wherein the secretion signal is N-terminal to the fusion partner. The secretion signal can be cleaved from the recombinant fusion protein when the protein is targeted to the periplasm. In embodiments, the linkage between the secretion signal and the protein or polypeptide is modified to increase cleavage of the secretion signal from the fusion protein.

Host Cells and Strains

Bacterial host cells, including Pseudomonads (i.e., host cells in the order Pseudomonadales) and closely related bacterial organisms are contemplated for use in practicing the methods of the invention. In certain embodiments, the Pseudomonad host cell is *Pseudomonas fluorescens*. The host cell also can be *E. coli*.

Host cells and constructs useful in practicing the methods of the invention can be identified or made using reagents and methods known in the art and described in the literature, e.g., in U.S. Pat. No. 8,288,127, "Protein Expression Systems," incorporated herein by reference in its entirety. This patent describes production of a recombinant polypeptide by introduction of a nucleic acid construct into an auxotrophic *Pseudomonas fluorescens* host cell comprising a chromosomal lad gene insert. The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841). U.S. Pat. No. 8,288,127, "Protein Expression Systems," and Schneider, et al., 2005, "Auxotrophic markers pyrF and proC can replace antibiotic markers on protein production plasmids in high-cell-density *Pseudomonas fluorescens* fermentation," Biotechnol. Progress 21(2): 343-8, both incorporated herein by reference in their entirety, describe a production host strain auxotrophic for uracil that was constructed by deleting the pyrF gene in strain MB101. The pyrF gene was cloned from strain MB214 (ATCC deposit PTA-7840) to generate a plasmid that can complement the pyrF deletion to restore prototropy. In particular embodiments, a dual pyrF-proC dual auxotrophic selection marker system in a *P. fluorescens* host cell is used. Given the published literature, a PyrF production host strain as described can be produced by one of skill in the art according to standard recombinant methods and used as the background for introducing other desired genomic changes, including those described herein as useful in practicing the methods of the invention.

In embodiments, the host cell is of the order Pseudomonadales (referred to herein as a "Pseudomonad." Where the host cell is of the order Pseudomonadales, it may be a member of the family Pseudomonadaceae, including the genus *Pseudomonas*. Gamma Proteobacterial hosts include members of the species *Escherichia coli* and members of the species *Pseudomonas fluorescens*. Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA), all are incorporated by reference herein in its entirety. (i.e., a host cell of the order Pseudomonadales) Table 3 presents these families and genera of organisms.

TABLE 3

Families and Genera ("Gram-Negative Aerobic Rods and Cocci," Bergey's, 1974)

| | |
|---|---|
| Family I. Pseudomonaceae *Gluconobacter* | *Pseudomonas* |
| | *Xanthomonas* |
| | *Zoogloea* |
| Family II. Azotobacteraceae *Azomonas* | *Azotobacter* |
| | *Beijerinckia* |
| | *Derxia* |
| Family III. Rhizobiaceae *Agrobacterium* | *Rhizobium* |
| Family IV. Methylomonadaceae *Methylococcus* | *Methylomonas* |
| Family V. Halobacteriaceae *Halobacterium* | *Halococcus* |
| Other Genera *Acetobacter* | *Alcaligenes* |
| | *Bordetella* |
| | *Brucella* |
| | *Francisella* |
| | *Thermus* |

*Pseudomonas* and closely related bacteria are generally part of the group defined as "Gram(-) Proteobacteria Subgroup 1" or "Gram-Negative Aerobic Rods and Cocci" (Buchanan and Gibbons (eds.) (1974) Bergey's Manual of Determinative Bacteriology, pp. 217-289). *Pseudomonas* host strains are described in the literature, e.g., in U.S. Pat. App. Pub. No. 2006/0040352, incorporated by reference herein in its entirety.

"Gram-negative Proteobacteria Subgroup 1" also includes Proteobacteria that would be classified in this heading according to the criteria used in the classification. The heading also includes groups that were previously classified in this section but are no longer, such as the genera Acidovorax, *Brevundimonas, Burkholderia*, Hydrogenophaga, Oceanimonas, *Ralstonia*, and *Stenotrophomonas*, the genus *Sphingomonas* (and the genus Blastomonas, derived therefrom), which was created by regrouping organisms belonging to (and previously called species of) the genus *Xanthomonas*, the genus Acidomonas, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis*,

*Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus*; 2) Pseudomonadaceae family bacteria of the genera *Cellvibrio*, *Oligella*, and *Teredinibacter*; 3) Rhizobiaceae family bacteria of the genera *Chelatobacter*, *Ensifer*, *Liberibacter* (also called "*Candidatus Liberibacter*"), and *Sinorhizobium*; and 4) Methylococcaceae family bacteria of the genera *Methylobacter*, *Methylocaldum*, *Methylomicrobium*, *Methylosarcina*, and *Methylosphaera*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila*; *Pseudomonas alginovora*; *Pseudomonas andersonii*; *Pseudomonas asplenii* (ATCC 23835); *Pseudomonas azelaica* (ATCC 27162); *Pseudomonas beyerinckii* (ATCC 19372); *Pseudomonas borealis*; *Pseudomonas boreopolis* (ATCC 33662); *Pseudomonas brassicacearum*; *Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens*; *Pseudomonas diterpeniphila*; *Pseudomonas elongata* (ATCC 10144); *Pseudomonas flectens* (ATCC 12775); *Pseudomonas azotoformans*; *Pseudomonas brenneri*; *Pseudomonas cedrella*; *Pseudomonas corrugata* (ATCC 29736); *Pseudomonas extremorientalis*; *Pseudomonas fluorescens* (ATCC 35858); *Pseudomonas gessardii*; *Pseudomonas libanensis*; *Pseudomonas mandelii* (ATCC 700871); *Pseudomonas marginalis* (ATCC 10844); *Pseudomonas migulae*; *Pseudomonas mucidolens* (ATCC 4685); *Pseudomonas orientalis*; *Pseudomonas rhodesiae*; *Pseudomonas synxantha* (ATCC 9890); *Pseudomonas tolaasii* (ATCC 33618); *Pseudomonas veronii* (ATCC 700474); *Pseudomonas frederiksbergensis*; *Pseudomonas geniculata* (ATCC 19374); *Pseudomonas gingeri*; *Pseudomonas graminis*; *Pseudomonas grimontii*; *Pseudomonas halodenitrificans*; *Pseudomonas halophila*; *Pseudomonas hibiscicola* (ATCC 19867); *Pseudomonas huttiensis* (ATCC 14670); *Pseudomonas hydrogenovora*; *Pseudomonas jessenii* (ATCC 700870); *Pseudomonas kilonensis*; *Pseudomonas lanceolata* (ATCC 14669); *Pseudomonas lini*; *Pseudomonas marginate* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila*; *Pseudomonas filva* (ATCC 31418); *Pseudomonas monteilii* (ATCC 700476); *Pseudomonas mosselii*; *Pseudomonas oryzihabitans* (ATCC 43272); *Pseudomonas plecoglossicida* (ATCC 700383); *Pseudomonas putida* (ATCC 12633); *Pseudomonas reactans*; *Pseudomonas spinosa* (ATCC 14606); *Pseudomonas balearica*; *Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae*; *Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans*; *Pseudomonas thivervalensis*; *Pseudomonas vancouverensis* (ATCC 700688); *Pseudomonas wisconsinensis*; and *Pseudomonas xiamenensis*. In one embodiment, the host cell is *Pseudomonas fluorescens*.

The host cell can also be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans*; *Pseudomonas brenneri*; *Pseudomonas cedrella*; *Pseudomonas corrugata*; *Pseudomonas extremorientalis*; *Pseudomonas fluorescens*; *Pseudomonas gessardii*; *Pseudomonas libanensis*; *Pseudomonas mandelii*; *Pseudomonas marginalis*; *Pseudomonas migulae*; *Pseudomonas mucidolens*; *Pseudomonas orientalis*; *Pseudomonas rhodesiae*; *Pseudomonas synxantha*; *Pseudomonas tolaasii*; and *Pseudomonas veronii*.

In embodiments, a bacterial host cell used in the methods of the invention is defective in the expression of a protease. In embodiments, the bacterial host cell defective in the expression of a protease is a Pseudomonad. In embodiments, the bacterial host cell defective in the expression of a protease is a *Pseudomonas*. In embodiments, the bacterial host cell defective in the expression of a protease is *Pseudomonas fluorescens*.

In embodiments, a bacterial host cell used in the methods of the invention is not defective in the expression of a protease. In embodiments, the bacterial host cell that is not defective in the expression of a protease is a Pseudomonad. In embodiments, the bacterial host cell that is not defective in the expression of a protease is a *Pseudomonas*. In embodiments, the bacterial host cell that is not defective in the expression of a protease is *Pseudomonas fluorescens*.

In embodiments, a *Pseudomonas* host cell used in the methods of the invention is defective in the expression of Lon protease (e.g., SEQ ID NO: 14), Lal protease (e.g., SEQ ID NO: 15), AprA protease (e.g., SEQ ID NO: 16), or a combination thereof. In embodiments, the *Pseudomonas* host cell is defective in the expression of AprA (e.g., SEQ ID NO: 16), HtpX (e.g., SEQ ID NO: 17), or a combination thereof. In embodiments, the *Pseudomonas* host cell is defective in the expression of Lon (e.g., SEQ ID NO: 14), La 1 (e.g., SEQ ID NO: 15), AprA (e.g., SEQ ID NO: 16), HtpX (e.g., SEQ ID NO: 17), or a combination thereof. In embodiments, the *Pseudomonas* host cell is defective in the expression of Npr (e.g., SEQ ID NO: 20), DegP1 (e.g., SEQ ID NO: 18), DegP2 (e.g., SEQ ID NO: 19), or a combination thereof. In embodiments, the *Pseudomonas* host cell is defective in the expression of Lal (e.g., SEQ ID NO: 15), Prc1 (e.g., SEQ ID NO: 21, Prc2 (e.g., SEQ ID NO 22), PrtB (e.g., SEQ ID NO: 23), or a combination thereof. These proteases are known in the art and described in, e.g., U.S. Pat. No. 8,603,824, "Process for Improved Protein Expression by Strain Engineering," U.S. Pat. App. Pub. No. 2008/0269070 and U.S. Pat. App. Pub. No. 2010/0137162, which disclose the open reading frame sequences for the proteases listed above.

Examples of *P. fluorescens* host strains derived from base strain MB101 (ATCC deposit PTA-7841) are useful in the methods of the present invention. In embodiments, the *P. fluorescens* used to express an hPTH fusion protein is, e.g., DC454, DC552, DC572, DC1084, DC1106, DC508, DC992.1, PF1201.9, PF1219.9, PF1326.1, PF1331, PF1345.6, or DC1040.1-1. In embodiments, the *P. fluorescens* host strain is PF1326.1. In embodiments, the *P. fluorescens* host strain is PF1345.6. These and other strains useful in the methods of the invention can be readily constructed by those of skill in the art using information provided herein, recombinant DNA methods known in the art and described in the literature, and materials available, e.g., *P. fluorescens* strain MB101, on deposit with the ATCC as described.

Expression Strains

Expression strains useful for practicing the methods of the invention can be constructed using methods described herein and in the published literature. In embodiments, an expression strain useful in the methods of the invention comprises a plasmid overexpressing one or more *P. fluorescens* chaperone or folding modulator protein. For example, DnaJ-like protein, FrnE, FklB, or EcpD, can be overexpressed in the expression strain. In embodiments, a *P. fluorescens* folding modulator overexpression (FMO) plasmid encodes ClpX, FklB3, FrnE, ClpA, Fkbp, or ppiA. An example of an expression plasmid encoding Fkbp is pDOW1384-1. In embodiments, an expression plasmid not encoding a folding modulator is introduced into an expression strain. In these embodiments, the plasmid is, e.g., pDOW2247. In embodiments, a *P. fluorescens* expression strain useful for expressing an hPTH fusion protein in the methods of the invention is STR35970, STR35984, STR36034, STR36085, STR36150, STR36169, STR35949, STR36098, or STR35783, as described elsewhere herein.

In embodiments, a *P. fluorescens* host strain used in the methods of the invention is DC1106 (mtlDYZ knock-out mutant ΔpyrF ΔproC ΔbenAB lsc::lacI$^{Q1}$), a derivative of deposited strain MB101 in which the genes pyrF, proC, benA, benB, and mtlDYZ from the mannitol (mtl) operon are deleted, and the *E. coli* lad transcriptional repressor is inserted and fused with the levansucrase gene (lsc). Sequences for these genes and methods for their use are known in the art and described in the literature, e.g., in U.S. Pat. Nos. 8,288,127, 8,017,355, "Mannitol induced promoter systems in bacterial host cells," and U.S. Pat. No. 7,794,972, "Benzoate- and anthranilate-inducible promoters," each incorporated by reference herein.

A host cell equivalent to DC1106 or any of the host cells or expression strains described herein can be constructed from MB101 using methods described herein and in the published literature. In embodiments, a host cell equivalent to DC1106 is used. Host cell DC454 is described by Schneider, et al., 2005, where it is referred to as DC206, and in U.S. Pat. No. 8,569,015, "rPA Optimization," incorporated herein by reference in its entirety. DC206 is the same strain as DC454; it was renamed DC454 after passage three times in animal-free media.

One with ordinary skill in the art will appreciate that in embodiments, a genomic deletion or mutation (e.g., an inactivating or debilitating mutation) can be made by, e.g., allele exchange, using a deletion plasmid carrying regions that flank the gene to be deleted, which does not replicate in *P. fluorescens*. The deletion plasmid can be constructed by PCR amplifying the gene to be deleted, including the upstream and downstream regions of the gene to be deleted. The deletion can be verified by sequencing a PCR product amplified from genomic DNA using analytical primers, observed after separation by electrophoresis in an agarose slab gel, followed by DNA sequencing of the fragment. In embodiments, a gene is inactivated by complete deletion, partial deletion, or mutation, e.g., frameshift, point, or insertion mutation.

In embodiments, a strain used has been transformed with an FMO plasmid according to methods known in the art. For example, DC1106 host cells can be transformed with FMO plasmid pDOW1384, which overexpresses FkbP (RXF06591.1), a folding modulator belonging to the peptidyl-prolyl cis-trans isomerase family, to generate the expression strain STR36034. The genotypes for certain examples of hPTH fusion protein expression strains and corresponding host cells useful for expressing hPTH according to the methods of the invention are set forth in Table 4. In embodiments, a host cell equivalent to any host cell described in Table 4 is transformed with an equivalent FMO plasmid as described herein, to obtain an expression strain equivalent to one described herein for expressing hPTH1-34 using the methods of the invention. As discussed, appropriate expression strains can be similarly derived according to methods described herein and in the literature.

TABLE 4

*P. fluorescens* Host Cells and Expression Strains for PTH 1-34 Fusion Protein Production

| Host Strain | Expression Strain | Protease Deletions | FMO plasmid | Fusion Protein |
|---|---|---|---|---|
| DC508-1 | STR35970 | M50 S2P Protease Family Membrane metalloprotease | — | DnaJ-like protein-PTH |
| DC992.1 | STR35984 | PrlC, AprA | pDOW2247 (empty vector; no folding modulator) | DnaJ-like protein-PTH |
| DC1084-1 | STR35949 | Lon, Lal, DegP2 | pDOW2247 | DnaJ-like protein-PTH |
| PF1201.9 | STR35985 | AprA, Lon, Lal, DegP1, DegP2, Prc1 | pDOW2247 | DnaJ-like protein-PTH |
| PF1326.1 | STR36005 | HtpX, AprA | pDOW2247 | DnaJ-like protein-PTH |
| DC1106-1 | STR36034 | AprA, Lon, Lal | pDOW1384-1 FkbP (RXF06591.1) | FklB-PTH |
| PF1326.1 | STR36085 | HtpX, AprA | pDOW2247 | FklB-PTH |
| PF1345.6 | STR36098 | HtpX, AprA, Lon, Lal | pDOW2247 | FklB-PTH |

TABLE 4-continued

P. fluorescens Host Cells and Expression Strains
for PTH 1-34 Fusion Protein Production

| Host Strain | Expression Strain | Protease Deletions | FMO plasmid | Fusion Protein |
|---|---|---|---|---|
| DC1040.1-1 | STR35783 | rxf04495 (Serralysin) AprA | pDOW2247 | FklB-PTH |
| PF1219.9 | STR36150 | Npr, DegP1, DegP2 | — | FrnE-PTH |
| PF1331 | STR36169 | La1, Prc1, Prc2, PrtB | — | FrnE-PTH |

In embodiments, a host cell or strain listed in Table 4, or equivalent to any host cell or strain described in Table 4, is used to express a fusion protein comprising a polypeptide of interest as described herein, using the methods of the invention. In embodiments, a host cell or strain listed in Table 4, or equivalent to any host cell or strain described in Table 4, is used to express a fusion protein comprising hPTH, GCSF, or an insulin polypeptide, e.g., a proinsulin as described herein, using the methods of the invention. In embodiments, a wild-type host cell, e.g., DC454 or an equivalent, is used to express a fusion protein comprising a polypeptide of interest as described herein, using the methods of the invention.

The sequences of these and other proteases and folding modulators useful for generating host strains of the present invention are known in the art and published in the literature, for example, as provided in Tables A to F of U.S. Pat. No. 8,603,824, described above and incorporated by reference herein in its entirety. For example, the M50 S2P Protease Family Membrane metalloprotease open reading frame sequence is provided therein as RXF04692.

High Throughput Screens

In some embodiments, a high throughput screen can be conducted to determine optimal conditions for expressing a soluble recombinant fusion protein. The conditions that can be varied in the screen include, for example, the host cell, genetic background of the host cell (e.g., deletions of different proteases), type of promoter in an expression construct, type of secretion leader fused to the sequence encoding the recombinant protein, growth temperature, OD at induction when an inducible promoter is used, concentration of IPTG used for induction when a lacZ promoter is used, duration of protein induction, growth temperature following addition of an inducing agent to a culture, rate of agitation of culture, method of selection for plasmid maintenance, volume of culture in a vessel, and method of cell lysing.

In some embodiments, a library (or "array") of host strains is provided, wherein each strain (or "population of host cells") in the library has been genetically modified to modulate the expression of one or more target genes in the host cell. An "optimal host strain" or "optimal expression system" can be identified or selected based on the quantity, quality, and/or location of the expressed recombinant fusion protein compared to other populations of phenotypically distinct host cells in the array. Thus, an optimal host strain is the strain that produces the recombinant fusion protein according to a desired specification. While the desired specification will vary depending on the protein being produced, the specification includes the quality and/or quantity of protein, e.g., whether the protein is sequestered or secreted, and in what quantities, whether the protein is properly or desirably processed and/or folded, and the like. In embodiments, improved or desirable quality can be production of the recombinant fusion protein with high titer expression and low levels of degradation. In embodiments, the optimal host strain or optimal expression system produces a yield, characterized by the amount or quantity of soluble recombinant fusion protein, the amount or quantity of recoverable recombinant fusion protein, the amount or quantity of properly processed recombinant fusion protein, the amount or quantity of properly folded recombinant fusion protein, the amount or quantity of active recombinant fusion protein, and/or the total amount or quantity of recombinant fusion protein, of a certain absolute level or a certain level relative to that produced by an indicator strain, i.e., a strain used for comparison.

Methods of screening microbial hosts to identify strains with improved yield and/or quality in the expression of recombinant fusion proteins are described, e.g., in U.S. Patent Application Publication No. 2008/0269070.

Fermentation Format

An expression strain of the present invention can be cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, Davis, B. D., and Mingioli, E. S., 1950, J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media can also contain mineral salts and a carbon source, but can be supplemented with, e.g., low levels of amino acids, vitamins, peptones, or other ingredients, though these are added at very minimal levels. Suitable media for use in the methods of the present invention can be prepared using methods described in the literature, e.g., in U.S. Pat. App. Pub. No. 2006/0040352, referenced and incorporated by reference above. Details of cultivation procedures and mineral salts media useful in the methods of the present invention are described by Riesenberg, D et al., 1991, "High cell density cultivation of *Escherichia coli* at controlled specific growth rate," J. Biotechnol. 20 (1):17-27, incorporated by reference herein.

In embodiments, production can be achieved in bioreactor cultures. Cultures can be grown in, e.g., up to 2 liter bioreactors containing a mineral salts medium, and maintained at 32° C. and pH 6.5 through the addition of ammonia. Dissolved oxygen can be maintained in excess through increases in agitation and flow of sparged air and oxygen into the fermentor. Glycerol can be delivered to the culture throughout the fermentation to maintain excess levels. In embodiments, these conditions are maintained until a target culture cell density, e.g., an optical density of 575 nm (A575), for induction is reached and IPTG is added to initiate the target protein production. It is understood that the cell density at induction, the concentration of IPTG, pH, temperature, $CaCl_2$ concentration, dissolved oxygen flow rate, each can be varied to determine optimal conditions for expression. In embodiments, cell density at induction can be varied from A575 of 40 to 200 absorbance units (AU). IPTG concentrations can be varied in the range from 0.02 to 1.0 mM, pH from 6 to 7.5, temperature from 20 to 35° C., $CaCl_2$) concentration from 0 to 0.5 g/L, and the dissolved oxygen flow rate from 1 LPM (liters per minute) to 10 LPM. After 6-48 hours, the culture from each bioreactor can be harvested by centrifugation and the cell pellet frozen at −80° C. Samples can then be analyzed, e.g., by SDS-CGE, for product formation.

Fermentation may be performed at any scale. The expression systems according to the present invention are useful for recombinant protein expression at any scale. Thus, e.g., microliter-scale, milliliter scale, centiliter scale, and deciliter scale fermentation volumes may be used, and 1 Liter scale and larger fermentation volumes can be used.

In embodiments, the fermentation volume is at or above about 1 Liter. In embodiments, the fermentation volume is about 1 Liter to about 100 Liters. In embodiments, the fermentation volume is about 1 Liter, about 2 Liters, about 3 Liters about 4 Liters, about 5 Liters, about 6 Liters, about 7 Liters, about 8 Liters, about 9 Liters, or about 10 Liters. In embodiments, the fermentation volume is about 1 Liter to about 5 Liters, about 1 Liter to about 10 Liters, about 1 Liter to about 25 Liters, about 1 Liter to about 50 Liters, about 1 Liter to about 75 Liters, about 10 Liters to about 25 Liters, about 25 Liters to about 50 Liters, or about 50 Liters to about 100 Liters. In other embodiments, the fermentation volume is at or above 5 Liters, 10 Liters, 15 Liters, 20 Liters, 25 Liters, 50 Liters, 75 Liters, 100 Liters, 200 Liters, 250 Liters, 300 Liters, 500 Liters, 1,000 Liters, 2,000 Liters, 5,000 Liters, 10,000 Liters, or 50,000 Liters.

In general, the amount of a recombinant protein yielded by a larger culture volume, e.g., a 50 mL shake-flask culture, a 1 Liter culture, or greater, is increased relative to that observed in a smaller culture volume, e.g, a 0.5 mL high-throughput screening culture. This can be due to not only the increase in culture size but, e.g., the ability to grow cells to a higher density in large-scale fermentation (e.g., as reflected by culture absorbance). For example, the volumetric yield from the same strain can increase up to ten-fold from HTP scale to large-scale fermentation. In embodiments, the volumetric yield observed for the same expression strain is 2-fold to 10-fold greater following large-scale fermentation than HTP scale growth. In embodiments, the yield observed for the same expression strain is 2-fold, 3-fold, 4-fold, 5-fold, 6-fold, 7-fold, 8-fold, 9-fold, 2-fold to 10-fold, 2-fold to 9-fold, 2-fold to 8-fold, 2-fold to 7-fold, 2-fold to 6-fold, 2-fold to 5-fold, 2-fold to 4-fold, 2-fold to 3-fold, 3-fold to 10-fold, 3-fold to 9-fold, 3-fold to 8-fold, 3-fold to 7-fold, 3-fold to 6-fold, 3-fold to 5-fold, 3-fold to 4-fold, 4-fold to 10-fold, 4-fold to 9-fold, 4-fold to 8-fold, 4-fold to 7-fold, 4-fold to 6-fold, 4-fold to 5-fold, 5-fold to 10-fold, 5-fold to 9-fold, 5-fold to 8-fold, 5-fold to 7-fold, 5-fold to 6-fold, 6-fold to 10-fold, 6-fold to 9-fold, 6-fold to 8-fold, 6-fold to 7-fold, 7-fold to 10-fold, 7-fold to 9-fold, 7-fold to 8-fold, 8-fold to 10-fold, 8-fold to 9-fold, 9-fold to 10-fold, greater following large-scale fermentation than following HTP-scale growth. See, e.g., Retallack, et al., 2012, "Reliable protein production in a *Pseudomonas fluorescens* expression system," Prot. Exp. and Purif. 81:157-165, incorporated herein by reference in its entirety.

Bacterial Growth Conditions

Growth conditions useful in the methods of the provided invention can comprise a temperature of about 4° C. to about 42° C. and a pH of about 5.7 to about 8.8. When an expression construct with a lacZ promoter is used, expression can be induced by adding IPTG to a culture at a final concentration of about 0.01 mM to about 1.0 mM.

The pH of the culture can be maintained using pH buffers and methods known to those of skill in the art. Control of pH during culturing also can be achieved using aqueous ammonia. In embodiments, the pH of the culture is about 5.7 to about 8.8. In embodiments, the pH is about 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8. In embodiments, the pH is about 5.7 to about 8.8, about 5.7 to about 8.5, about 5.7 to about 8.3, about 5.7 to about 8, about 5.7 to about 7.8, about 5.7 to about 7.6, about 5.7 to about 7.4, about 5.7 to about 7.2, about 5.7 to about 7, about 5.7 to about 6.8, about 5.7 to about 6.6, about 5.7 to about 6.4, about 5.7 to about 6.2, about 5.7 to about 6, about 5.9 to about 8.8, about 5.9 to about 8.5, about 5.9 to about 8.3, about 5.9 to about 8, about 5.9 to about 7.8, about 5.9 to about 7.6, about 5.9 to about 7.4, about 5.9 to about 7.2, about 5.9 to about 7, about 5.9 to about 6.8, about 5.9 to about 6.6, about 5.9 to about 6.4, about 5.9 to about 6.2, about 6 to about 8.8, about 6 to about 8.5, about 6 to about 8.3, about 6 to about 8, about 6 to about 7.8, about 6 to about 7.6, about 6 to about 7.4, about 6 to about 7.2, about 6 to about 7, about 6 to about 6.8, about 6 to about 6.6, about 6 to about 6.4, about 6 to about 6.2, about 6.1 to about 8.8, about 6.1 to about 8.5, about 6.1 to about 8.3, about 6.1 to about 8, about 6.1 to about 7.8, about 6.1 to about 7.6, about 6.1 to about 7.4, about 6.1 to about 7.2, about 6.1 to about 7, about 6.1 to about 6.8, about 6.1 to about 6.6, about 6.1 to about 6.4, about 6.2 to about 8.8, about 6.2 to about 8.5, about 6.2 to about 8.3, about 6.2 to about 8, about 6.2 to about 7.8, about 6.2 to about 7.6, about 6.2 to about 7.4, about 6.2 to about 7.2, about 6.2 to about 7, about 6.2 to about 6.8, about 6.2 to about 6.6, about 6.2 to about 6.4, about 6.4 to about 8.8, about 6.4 to about 8.5, about 6.4 to about 8.3, about 6.4 to about 8, about 6.4 to about 7.8, about 6.4 to about 7.6, about 6.4 to about 7.4, about 6.4 to about 7.2, about 6.4 to about 7, about 6.4 to about 6.8, about 6.4 to about 6.6, about 6.6 to about 8.8, about 6.6 to about 8.5, about 6.6 to about 8.3, about 6.6 to about 8, about 6.6 to about 7.8, about 6.6 to about 7.6, about 6.6 to about 7.4, about 6.6 to about 7.2, about 6.6 to about 7, about 6.6 to about 6.8, about 6.8 to about 8.8, about 6.8 to about 8.5, about 6.8 to about 8.3, about 6.8 to about 8, about 6.8 to about 7.8, about 6.8 to about 7.6, about 6.8 to about 7.4, about 6.8 to about 7.2, about 6.8 to about 7, about 7 to about 8.8, about 7 to about 8.5, about 7 to about 8.3, about 7 to about 8, about 7 to about 7.8, about 7 to about 7.6, about 7 to about 7.4, about 7 to about 7.2, about 7.2 to about 8.8, about 7.2 to about 8.5, about 7.2 to about 8.3, about 7.2 to about 8, about 7.2 to about 7.8, about 7.2 to about 7.6, about 7.2 to about 7.4, about 7.4 to about 8.8, about 7.4 to about 8.5, about 7.4 to about 8.3, about 7.4 to about 8, about 7.4 to about 7.8, about 7.4 to about 7.6, about 7.6 to about 8.8, about 7.6 to about 8.5, about 7.6 to about 8.3, about 7.6 to about 8, about 7.6 to about 7.8, about 7.8 to about 8.8, about 7.8 to about 8.5, about 7.8 to about 8.3, about 7.8 to about 8, about 8 to about 8.8, about 8 to about 8.5, or about 8 to about 8.3. In embodiments, the pH is about 6.5 to about 7.2.

In embodiments, the growth temperature is maintained at about 4° C. to about 42° C. In embodiments, the growth temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. In embodiments, the growth temperature is about 25° C. to about 32° C. In embodiments, the growth temperature is maintained at about 22° C. to about 27° C., about 22° C. to about 28° C., about 22° C. to about 29° C., about 22° C. to about 30° C., 23° C. to about 27° C., about 23° C. to about 28° C., about 23° C. to about 29° C., about 23° C. to about 30° C., about 24° C. to about 27° C., about 24° C. to about 28° C., about 24° C. to about 29° C., about 24° C. to about 30° C., about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 26° C. to about 33° C., about 27° C. to about 29° C., about 27° C. to about 30° C., about 27° C. to about 31° C., about 27° C. to about 32° C., about 27° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 33° C., about 31° C. to about 32° C., about 21° C. to about 42° C., about 22° C. to about 42° C., about 23° C. to about 42° C., about 24° C. to about 42° C., about 25° C. to about 42° C. In embodiments, the growth temperature is about 25° C. to about 28.5° C. In embodiments, the growth temperature is above about 20° C., above about 21° C., above about 22° C., above about 23° C., above about 24° C., above about 25° C., above about 26° C., above about 27° C., above about 28° C., above about 29° C., or above about 30° C.

In embodiments, the temperature is changed during culturing. In embodiments, the temperature is maintained at about 30° C. to about 32° C. before an agent, e.g., IPTG, is added to the culture to induce expression from the construct, and after adding the induction agent, the temperature is reduced to about 25° C. to about 28° C. In embodiments, the temperature is maintained at about 30° C. before an agent, e.g., IPTG, is added to the culture to induce expression from the construct, and after adding the induction agent, the temperature is reduced to about 25° C.

As described elsewhere herein, inducible promoters can be used in the expression construct to control expression of the recombinant fusion protein, e.g., a lac promoter. In the case of the lac promoter derivatives or family members, e.g., the tac promoter, the effector compound is an inducer, such as a gratuitous inducer like IPTG. In embodiments, a lac promoter derivative is used, and recombinant protein expression is induced by the addition of IPTG to a final concentration of about 0.01 mM to about 1.0 mM, when the cell density has reached a level identified by an $OD_{575}$ of about 40 to about 180. In embodiments, the $OD_{575}$ at the time of culture induction for the recombinant protein can be about 40, about 50, about 60, about 70, about 80, about 90, about 110, about 120, about 130, about 140, about 150, about 160, about 170 about 180. In other embodiments, the $OD_{575}$ is about 40 to about 50, about 50 to about 60, about 60 to about 70, about 70 to about 80, about 80 to about 90, or about 90 to about 100. In other embodiments, the $OD_{575}$ is about 40 to about 100, about 100 to about 120, about 120 to about 130, about 130 to about 140, about 140 to about 150, about 150 to about 160, about 160 to about 170, or about 170 to about 180. In other embodiments, the $OD_{575}$ is about 40 to about 140, or about 80 to 180. The cell density can be measured by other methods and expressed in other units, e.g., in cells per unit volume. For example, an $OD_{575}$ of about 40 to about 160 of a *P. fluorescens* culture is equivalent to approximately $4 \times 10^{10}$ to about $1.6 \times 10^{11}$ colony forming units per mL or 17.5 to 70 g/L dry cell weight. In embodiments, the cell density at the time of culture induction is equivalent to the cell density as specified herein by the absorbance at $OD_{575}$, regardless of the method used for determining cell density or the units of measurement. One of skill in the art will know how to make the appropriate conversion for any cell culture.

In embodiments, the final IPTG concentration of the culture is about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.2 mM, about 0.3 mM, about 0.4 mM, about 0.5 mM, about 0.6 mM, about 0.7 mM, about 0.8 mM, about 0.9 mM, or about 1 mM. In embodiments, the final IPTG concentration of the culture is about 0.08 mM to about 0.1 mM, about 0.1 mM to about 0.2 mM, about 0.2 mM to about 0.3 mM, about 0.3 mM to about 0.4 mM, about 0.2 mM to about 0.4 mM, about 0.08 to about 0.2 mM, or about 0.1 to 1 mM.

In embodiments wherein a non-lac type promoter is used, as described herein and in the literature, other inducers or effectors can be used. In one embodiment, the promoter is a constitutive promoter.

After adding and inducing agent, cultures can be grown for a period of time, for example about 24 hours, during which time the recombinant protein is expressed. After adding an inducing agent, a culture can be grown for about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 36 hr, or about 48 hr. After an inducing agent is added to a culture, the culture can be grown for about 1 to 48 hr, about 1 to 24 hr, about 1 to 8 hr, about 10 to 24 hr, about 15 to 24 hr, or about 20 to 24 hr. Cell cultures can be concentrated by centrifugation, and the culture pellet resuspended in a buffer or solution appropriate for the subsequent lysis procedure.

In embodiments, cells are disrupted using equipment for high pressure mechanical cell disruption (which are available commercially, e.g., Microfluidics Micro fluidizer, Constant Cell Disruptor, Niro-Soavi homogenizer or APV-Gaulin homogenizer). Cells expressing the recombinant protein can be disrupted, for example, using sonication. Any appropriate method known in the art for lysing cells can be used to release the soluble fraction. For example, in embodiments, chemical and/or enzymatic cell lysis reagents, such as cell-wall lytic enzyme and EDTA, can be used. Use of frozen or previously stored cultures is also contemplated in the methods of the invention. Cultures can be OD-normalized prior to lysis. For example, cells can be normalized to an OD600 of about 10, about 11, about 12, about 13, about 14, about 15, about 16, about 17, about 18, about 19, or about 20.

Centrifugation can be performed using any appropriate equipment and method. Centrifugation of cell culture or lysate for the purposes of separating a soluble fraction from an insoluble fraction is well-known in the art. For example, lysed cells can be centrifuged at 20,800×g for 20 minutes (at 4° C.), and the supernatants removed using manual or automated liquid handling. The cell pellet obtained by centrifugation of cell culture, or the insoluble fraction obtained by centrifugation of cell lysate, can be resuspended in a buffered solution. Resuspension of the cell pellet or insoluble fraction can be carried out using, e.g., equipment such as impellers connected to an overhead mixer, magnetic stir-bars, rocking shakers, etc.

Non-Denaturing Conditions

Lysis of the induced host cells is carried out under non-denaturing conditions. In embodiments, the non-denaturing conditions comprise use of a non-denaturing treatment buffer, e.g., to resuspend the cell pellet or paste. In embodiments, the non-denaturing treatment buffer comprises sodium phosphate or Tris buffer, glycerol, and sodium chloride. In embodiments wherein affinity chromatography is carried out by immobilized metal affinity chromatography (IMAC), the non-denaturing treatment buffer comprises imidazole. In embodiments, the non-denaturing treatment buffer comprises 0 to 50 mM imidazole. In embodiments, the non-denaturing treatment buffer comprises no imidazole. In embodiments, the non-denaturing treatment buffer comprises 25 mM imidazole. In embodiments, the non-denaturing treatment buffer comprises 10-30 mM sodium phosphate or Tris, pH 7 to 9. In embodiments, the non-denaturing treatment buffer has a pH of 7.3, 7.4, or 7.5. In embodiments, the non-denaturing treatment buffer comprises 2-10% glycerol. In embodiments, the non-denaturing treatment buffer comprises 50 mM to 750 mM NaCl. In embodiments, the cell paste is resuspended to 10-50% solids. In embodiments, the non-denaturing treatment buffer comprises 20 mM sodium phosphate, 5% glycerol, 500 mM sodium chloride, 20 mM imidazole, at pH 7.4, and is resuspended to 20% solids. In embodiments, the non-denaturing treatment buffer comprises 20 mM Tris, 50 mM NaCl, at pH 7.5, and is resuspended to 20% solids.

In embodiments, the non-denaturing treatment buffer does not comprise a chaotropic agent. Chaotropic agents disrupt the 3-dimensional structure of a protein or nucleic acid, causing denaturation. In embodiments, the non-denaturing treatment buffer comprises a non-denaturing concentration of a chaotropic agent. In embodiments, the chaotropic agent is, e.g., urea or guanidinium hydrochloride. In embodiments, the non-denaturing treatment buffer comprises 0 to 4M urea or guanidinium hydrochloride. In embodiments, the non-denaturing treatment buffer comprises urea or guanidinium hydrochloride at a concentration of less than 4M, less than 3.5M, less than 3M, less than 2.5M, less than 2M, less than 1.5M, less than 1M, less than 0.5M, about 0.1M, about 0.2M, about 0.3M, about 0.4M, about 0.5M, about 0.6M, about 0.7M, about 0.8M, about 0.9M, about 1.0M, about 1.1M, about 1.2M, about 1.3M, about 1.4M, about 1.5M, about 1.6M, about 1.7M, about 1.8M, about 1.9M, or about 2.0M, about 2.1M, about 2.2M, about 2.3M, about 2.4M, about 2.5M, about 2.6M, about 2.7M, about 2.8M, about 2.9M, about 3M, about 3.1M, about 3.2M, about 3.3M, about 3.4M, about 3.5M, about 3.6M, about 3.7M, about 3.8M, about 3.9M, about 4M, about 0.5 to about 3.5M, about 0.5 to about 3M, about 0.5 to about 2.5M, about 0.5 to about 2M, about 0.5 to about 1.5M, about 0.5 to about 1M, about 1 to about 4M, about 1 to about 3.5M, about 1 to about 3M, about 1 to about 2.5M, about 1 to about 2M, about 1 to about 1.5M, about 1.5 to about 4M, about 1.5 to about 3.5M, about 1.5 to about 3M, about 1.5 to about 2.5M, about 1.5 to about 2M, about 2 to about 4M, about 2 to about 3.5M, about 2 to about 3M, about 2 to about 2.5M, about 2.5 to about 4M, about 2.5 to about 3.5M, about 2.5 to about 3M, about 3 to about 4M, about 3 to about 3.5M, or 0.5 to about 1M.

In embodiments wherein a non-denaturing treatment buffer is used, the cell paste is slurried at 20% solids in 20 mM Tris, 50 mM NaCl, 4 M urea, pH 7.5, for about 1-2.5 hours at 2-8° C. In embodiments the cell paste is subjected to lysis with a Niro homogenizer, e.g., at 15,000 psi, and batch-centrifuged 35 minutes at 14,000×g or continuous centrifuge at 15,000×g and 340 mL/min feed, the supe/centrate filtered with a depth filter and a membrane filter, diluted 2× in resuspension buffer, e.g., 1×PBS pH 7.4, and loaded to a capture column. In embodiments the non-denaturing treatment buffer comprises additional components, e.g., imidazole for IMAC as described elsewhere herein.

It is understood by those of skill in the art that a denaturing concentration of a chaotropic agent may be influenced by the pH, and that the denaturing levels depend on the characteristics of the protein. For example, the pH can be increased to cause protein denaturation despite a lower concentration of a chaotropic agent.

Product Evaluation

The quality of the produced recombinant fusion protein or polypeptide of interest can be evaluated by any method known in the art or described in the literature. In embodiments, denaturation of a protein is evaluated based on its solubility, or by lack or loss of biological activity. For many proteins biological activity assays are commercially available. A biological activity assay can include, e.g., an antibody binding assay. In embodiments, physical characterization of the recombinant fusion protein or polypeptide of interest is carried out using methods available in the art, e.g., chromatography and spectrophotometric methods. Evaluation of the polypeptide of interest can include a determination that it has been properly released, e.g., its N-terminus is intact.

The activity of hPTH, e.g., hPTH 1-34 or 1-84, can be evaluated using any method known in the art or described herein or in the literature, e.g., using antibodies that recognize the N-terminus of the protein. Methods include, e.g., intact mass analysis. PTH bioactivity can be measured, by, e.g., cAMP ELISA, homogenous time-resolved fluorescence (HTRF) assay (Charles River Laboratories), or as described by Nissenson, et al., 1985, "Activation of the Parathyroid Hormone Receptor-Adenylate Cyclase System in Osteosarcoma Cells by a Human Renal Carcinoma Factor," Cancer Res. 45:5358-5363, and U.S. Pat. No. 7,150,974, "Parathyroid Hormone Receptor Binding Method," each incorporated by reference herein. Methods of evaluating PTH also are described by Shimizu, et al., 2001, "Parathyroid hormone (1-14) and (1-11) analogs conformationally constrained by α-aminoisobutyric acid mediate full agonist responses via the Juxtamembrane region of the PTH-1 receptor," J. Biol. Chem. 276: 49003-49012, incorporated by reference herein.

Purification of the Recombinant Fusion Protein and Polypeptide of Interest

The solubilized recombinant fusion protein or polypeptide of interest can be isolated or purified from other protein and cellular debris by any method known by those of skill in the art or described in the literature, for example, centrifugation methods and/or chromatography methods such as size exclusion, anion or cation exchange, hydrophobic interaction, or affinity chromatography. In embodiments, the solubilized protein can be purified using Fast Performance Liquid Chromatography (FPLC). FPLC is a form of liquid chromatography used to separate proteins based on affinity towards various resins. In embodiments, the affinity tag expressed with the fusion proteins causes the fusion protein, dissolved in a solubilization buffer, to bind to a resin, while the impurities are carried out in the solubilization buffer. Subsequently, an elution buffer is used, in gradually increasing gradient or added in a step-wise manner, to dissociate the fusion protein from the ion exchange resin and isolate the pure fusion protein, in the elution buffer.

In embodiments, after the completion of induction, the fermentation broth is harvested by centrifugation, e.g., at 15,900×g for 60 to 90 minutes. The cell paste and supernatant are separated and the paste is frozen at −80° C. The frozen cell paste is thawed in a buffer as described elsewhere herein, e.g., a non-denaturing buffer or buffer with no urea. In embodiments, the frozen cell paste is thawed in and resuspended in 20 mM sodium phosphate, 5% glycerol, 500 mM sodium chloride, pH 7.4. In embodiments, the buffer comprises imidazole. In embodiments, the final volume of the suspension is adjusted to the desired percent solids, e.g., 20% solids. The cells can be lysed chemically or mechanically, e.g., the material can then be homogenized by through a microfluidizer at 15,000 psi. Lysates are centrifuged, e.g., at 12,000×g for 30 minutes, and filtered, e.g., through a Sartorius Sartobran 150 (0.45/0.2 μm) filter capsule.

In embodiments, fast protein liquid chromatography (FPLC) can be used for purification, e.g., using ÄKTA explorer 100 chromatography systems (GE Healthcare) equipped with Frac-950 fraction collectors. In embodiments wherein a His-tag is used, samples can be loaded onto HisTrap FF, 10 mL columns (two 5 mL HisTrap FF cartridges [GE Healthcare, part number 17-5255-01] connected in series), washed, and eluted, e.g., using a 10 column volume linear gradient of an elution buffer, by varying the imidazole concentration from 0 mM to 200 mM, and fractions collected.

In embodiments, chromatography can be carried out as appropriate for the polypeptide of interest. For example, immobilized metal ion affinity chromatography purification can be carried out (e.g., using using Nickel IMAC) as described herein in the Examples.

Cleavage of Recombinant Fusion Protein

In embodiments, the purified recombinant fusion protein fractions are incubated with a cleavage enzyme, to cleave the polypeptide of interest from the linker and N-terminal fusion partner. In embodiments, the cleavage enzyme is a protease, for example, a serine protease, e.g., bovine enterokinase, porcine enterokinase, trypsin or any other appropriate protease as described elsewhere herein. Any appropriate protease cleavage method known in the art and described in the literature, including in the manufacturer's instructions, can be used. Proteases are available commercially, e.g., from Sigma-Aldrich (St. Louis, Mo.), ThermoFisher Scientific (Waltham, Mass.), and Promega (Madison, Wis.). For example, in embodiments, bovine enterokinase (e.g., Novagen cat #69066-3, batch D00155747) cleavage fusion protein purification fractions can be concentrated and resuspended in a buffer containing 20 mM Tris pH 7.4, 50 mM NaCl, and 2 mM $CaCl_2$. Two units of bovine enterokinase are be added to 100 μg protein in a 100 μL reaction. The mixture of fusion protein purification fraction and enterokinase are incubated for an appropriate length of time. In embodiments, control reactions with no enterokinase also are incubated, for comparison. The enzyme reactions can be stopped by the addition of complete protease inhibitor cocktail containing 4-benzenesulfonyl fluoride hydrochloride (AEBSF, Sigma cat #P8465).

In embodiments, the cleavage enzyme incubation is carried out for about 1 hour to about 24 hours. In embodiments, the incubation is carried out for about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 1 hr to about 24 hr, about 1 hr to about 23 hr, about 1 hr to about 22 hr, about 1 hr to about 21 hr, about 1 hr to about 20 hr, about 1 hr to about 19 hr, about 1 hr to about 18 hr, about 1 hr to about 17 hr, about 1 hr to about 16 hr, about 1 hr to about 15 hr, about 1 hr to about 14 hr, about 1 hr to about 13 hr, about 1 hr to about 12 hr, about 1 hr to about 11 hr, about 1 hr to about 10 hr, about 1 hr to about 9 hr, about 1 hr to about 8 hr, about 1 hr to about 7 hr, about 1 hr to about 6 hr, about 1 hr to about 5 hr, about 1 hr to about 4 hr, about 1 hr to about 3 hr, about 1 hr to about 2 hr, about 2 hr to about 24 hr, about 2 hr to about 23 hr, about 2 hr to about 22 hr, about 2 hr to about 21 hr, about 2 hr to about 20 hr, about 2 hr to about 19 hr, about 2 hr to about 18 hr, about 2 hr to about 17 hr, about 2 hr to about 16 hr, about 2 hr to about 15 hr, about 2 hr to about 14 hr, about 2 hr to about 13 hr, about 2 hr to about 12 hr, about 2 hr to about 11 hr, about 2 hr to about 10 hr, about 2 hr to about 9 hr, about 2 hr to about 8 hr, about 2 hr to about 7 hr, about 2 hr to about 6 hr, about 2 hr to about 5 hr, about 2 hr to about 4 hr, about 2 hr to about 3 hr, about 3 hr to about 24 hr, about 3 hr to about 23 hr, about 3 hr to about 22 hr, about 3 hr to about 21 hr, about 3 hr to about 20 hr, about 3 hr to about 19 hr, about 3 hr to about 18 hr, about 3 hr to about 17 hr, about 3 hr to about 16 hr, about 3 hr to about 15 hr, about 3 hr to about 14 hr, about 3 hr to about 13 hr, about 3 hr to about 12 hr, about 3 hr to about 11 hr, about 3 hr to about 10 hr, about 3 hr to about 9 hr, about 3 hr to about 8 hr, about 3 hr to about 7 hr, about 3 hr to about 6 hr, about 3 hr to about 5 hr, about 3 hr to about 4 hr, about 4 hr to about 24 hr, about 4 hr to about 23 hr, about 4 hr to about 22 hr, about 4 hr to about 21 hr, about 4 hr to about 20 hr, about 4 hr to about 19 hr, about 4 hr to about 18 hr, about 4 hr to about 17 hr, about 4 hr to about 16 hr, about 4 hr to about 15 hr, about 4 hr to about 14 hr, about 4 hr to about 13 hr, about 4 hr to about 12 hr, about 4 hr to about 11 hr, about 4 hr to about 10 hr, about 4 hr to about 9 hr, about 4 hr to about 8 hr, about 4 hr to about 7 hr, about 4 hr to about 6 hr, about 4 hr to about 5 hr, about 5 hr to about 24 hr, about 5 hr to about 23 hr, about 5 hr to about 22 hr, about 5 hr to about 21 hr, about 5 hr to about 20 hr, about 5 hr to about 19 hr, about 5 hr to about 18 hr, about 5 hr to about 17 hr, about 5 hr to about 16 hr, about 5 hr to about 15 hr, about 5 hr to about 14 hr, about 5 hr to about 13 hr, about 5 hr to about 12 hr, about 5 hr to about 11 hr, about 5 hr to about 10 hr, about 5 hr to about 9 hr, about 5 hr to about 8 hr, about 5 hr to about 7 hr, about 5 hr to about 6 hr, about 6 hr to about 24 hr, about 6 hr to about 23 hr, about 6 hr to about 22 hr, about 6 hr to about 21 hr, about 6 hr to about 20 hr, about 6 hr to about 19 hr, about 6 hr to about 18 hr, about 6 hr to about 17 hr, about 6 hr to about 16 hr, about 6 hr to about 15 hr, about 6 hr to about 14 hr, about 6 hr to about 13 hr, about 6 hr to about 12 hr, about 6 hr to about 11 hr, about 6 hr to about 10 hr, about 6 hr to about 9 hr, about 6 hr to about 8 hr, about 6 hr to about 7 hr, about 7 hr to about 24 hr, about 7 hr to about 23 hr, about 7 hr to about 22 hr, about 7 hr to about 21 hr, about 7 hr to about 20 hr, about 7 hr to about 19 hr, about 7 hr to about 18 hr, about 7 hr to about 17 hr, about 7 hr to about 16 hr, about 7 hr to about 15 hr, about 7 hr to about 14 hr, about 7 hr to about 13 hr, about 7 hr to about 12 hr, about 7 hr to about 11 hr, about 7 hr to about 10 hr, about 7 hr to about 9 hr, about 7 hr to about 8 hr, about 8 hr to about 24 hr, about 8 hr to about 23 hr, about 8 hr to about 22 hr, about 8 hr to about 21 hr, about 8 hr to about 20 hr, about 8 hr to about 19 hr, about 8 hr to about 18 hr, about 8 hr to about 17 hr, about 8 hr to about 16 hr, about 8 hr to about 15 hr, about 8 hr to about 14 hr, about 8 hr to about 13 hr, about 8 hr to about 12 hr, about 8 hr to about 11 hr, about 8 hr to about 10 hr, about 8 hr to about 9 hr, about 9 hr to about 24 hr, about 9 hr to about 23 hr, about 9 hr to about 22 hr, about 9 hr to about 21 hr, about 9 hr to about 20 hr, about 9 hr to about 19 hr, about 9 hr to about 18 hr, about 9 hr to about 17 hr, about 9 hr to about 16 hr, about 9 hr to about 15 hr, about 9 hr to about 14 hr, about 9 hr to about 13 hr, about 9 hr to about 12 hr, about 9 hr to about 11 hr, about 9 hr to about 10 hr, about 10 hr to about 24 hr, about 10 hr to about 23 hr, about 10 hr to about 22 hr, about 10 hr to about 21 hr, about 10 hr to about 20 hr, about 10 hr to about 19 hr, about 10 hr to about 18 hr, about 10 hr to about 17 hr, about 10 hr to about 16 hr, about 10 hr to about 15 hr, about 10 hr to about 14 hr, about 10 hr to about 13 hr, about 10 hr to about 12 hr, about 10 hr to about 11 hr, about 11 hr to about 24 hr, about 11 hr to about 23 hr, about 11 hr to about 22 hr, about 11 hr to about 21 hr, about 11 hr to about 20 hr, about 11 hr to about 19 hr, about 11 hr to about 18 hr, about 11 hr to about 17 hr, about 11 hr to about 16 hr, about 11 hr to about 15 hr, about 11 hr to about 14 hr, about 11 hr to about 13 hr, about 11 hr to about 12 hr, about 12 hr to about 24 hr, about 12 hr to about 23 hr, about 12 hr to about 22 hr, about 12 hr to about 21 hr, about 12 hr to about 20 hr, about 12 hr to about 112 hr, about 12 hr to about 18 hr, about 12 hr to about 17 hr, about 12 hr to about 16 hr, about 12 hr to about 15 hr, about 12 hr to about 14 hr, about 12 hr to about 13 hr, about 13 hr to about 24 hr, about 13 hr to about 23 hr, about 13 hr to about 22 hr, about 13 hr to about 21 hr, about 13 hr to about 20 hr, about 13 hr to about 19 hr, about 13 hr to about 18 hr, about 13 hr to about 17 hr, about 13 hr to about 16 hr, about 13 hr to about 15 hr, about 13 hr to about 14 hr, about 14 hr to about 24 hr, about 14 hr to about 23 hr, about 14 hr to about 22 hr, about 14 hr to about 21 hr, about 14 hr to about 20 hr, about 14 hr to about 19 hr, about 14 hr to about 18 hr, about 14 hr to about 17 hr, about 14 hr to about 16 hr, about 14 hr to about 15 hr, about 15 hr to about 24 hr, about 15 hr to about 23 hr, about 15 hr to about 22 hr, about 15 hr to about 21 hr, about 15 hr to about 20 hr, about 15 hr to about 19 hr, about 15 hr to about 18 hr, about 15 hr to about 17 hr, about 16 hr to about 24 hr, about 16 hr to about 23 hr, about 16 hr to about 22 hr, about 16 hr to about 21 hr, about 16 hr to about 20 hr, about 16 hr to about 19 hr, about 16 hr to about 18 hr, or about 16 hr to about 17 hr, about 17 hr to about 24 hr, about 17 hr to about 23 hr, about 17 hr to about 22 hr, about 17 hr to about 21 hr, about 17 hr to about 20 hr, about 17 hr to about 19 hr, about 17 hr to about 18 hr, about 18 hr to about 24 hr, about 18 hr to about 23 hr, about 18 hr to about 22 hr, about 18 hr to about 21 hr, about 18 hr to about 20 hr, about 18 hr to about 19 hr, about 19 hr to about 24 hr, about 19 hr to about 23 hr, about 19 hr to about 22 hr, about 19 hr to about 21 hr, about 19 hr to about 20 hr, about 20 hr to about 24 hr, about 20 hr to about 23 hr, about 20 hr to about 22 hr, about 20 hr to about 21 hr, about 21 hr to about 24 hr, about 21 hr to about 23 hr, about 21 hr to about 22 hr, about 22 hr to about 24 hr, or about 22 hr to about 23 hr.

In embodiments, the extent of cleavage of the recombinant fusion protein after incubation with the protease is about 90% to about 100%. In embodiments, the extent of cleavage after incubation with the protease is about 90%, about 91%, about 92%, about 93%, about 94%, about 95%, about 96%, about 97%, about 98%, about 99%, about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, about 90% to about 99%, about 91% to about 99%, about 92% to about 99%, about 93% to about 99%, about 94% to about 99%, about 95% to about 99%, about 96% to about 99%, about 97% to about 99%, about 98% to about 99%, about 90% to about 98%, about 91% to about 98%, about 92% to about 98%, about 93% to about 98%, about 94% to about 98%, about 95% to about 98%, about 96% to about 98%, about 97% to about 98%, about 90% to about 97%, about 91% to about 97%, about 92% to about 97%, about 93% to about 97%, about 94% to about 97%, about 95% to about 97%, about 96% to about 97%, about 90% to about 96%, about 91% to about 96%, about 92% to about 96%, about 93% to about 96%, about 94% to about 96%, about 95% to about 96%, about 90% to about 95%, about 91% to about 95%, about 92% to about 95%, about 93% to about 95%, about 94% to about 95%, about 90% to about 94%, about 91% to about 94%, about 92% to about 94%, about 93% to about 94%, about 90% to about 93%, about 91% to about 93%, about 92% to about 93%, about 90% to about 92%, about 91% to about 92%, or about 90% to about 91%.

In embodiments, the protease cleavage results in release of the polypeptide of interest from the recombinant fusion protein. In embodiments, the recombinant fusion protein is properly cleaved, to properly release the polypeptide of interest. In embodiments, proper cleavage of the recombinant fusion protein results in a properly released polypeptide of interest having an intact (undegraded) N-terminus. In embodiments, proper cleavage of the recombinant fusion protein results in a properly released polypeptide of interest that contains the first (N-terminal) amino acid. In embodiments, the amount of properly released polypeptide following protease cleavage is about 90% to about 100%. In embodiments, the amount of properly released polypeptide following protease cleavage is about 90%, about 91%, about 92%, about 93%, about 94%, about 95%, about 96%, about 97%, about 98%, about 99%, about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, about 90% to about 99%, about 91% to about 99%, about 92% to about 99%, about 93% to about 99%, about 94% to about 99%, about 95% to about 99%, about 96% to about 99%, about 97% to about 99%, about 98% to about 99%, about 90% to about 98%, about 91% to about 98%, about 92% to about 98%, about 93% to about 98%, about 94% to about 98%, about 95% to about 98%, about 96% to about 98%, about 97% to about 98%, about 90% to about 97%, about 91% to about 97%, about 92% to about 97%, about 93% to about 97%, about 94% to about 97%, about 95% to about 97%, about 96% to about 97%, about 90% to about 96%, about 91% to about 96%, about 92% to about 96%, about 93% to about 96%, about 94% to about 96%, about 95% to about 96%, about 90% to about 95%, about 91% to about 95%, about 92% to about 95%, about 93% to about 95%, about 94% to about 95%, about 90% to about 94%, about 91% to about 94%, about 92% to about 94%, about 93% to about 94%, about 90% to about 93%, about 91% to about 93%, about 92% to about 93%, about 90% to about 92%, about 91% to about 92%, or about 90% to about 91%.

Recombinant Fusion Protein Evaluation and Yield

The produced fusion protein and/or polypeptide of interest can be characterized in any appropriate fraction, using any appropriate assay method known in the art or described in the literature for characterizing a protein, e.g., for evaluating the yield or quality of the protein.

In embodiments, LC-MS or any other appropriate method as known in the art is used to monitor proteolytic clipping, deamidation, oxidation, and fragmentation, and to verify that the N-terminus of the polypeptide of interest is intact following linker cleavage. The yield of recombinant fusion protein or polypeptide of interest can be determined by methods known to those of skill in the art, for example, by SDS-PAGE, capillary gel electrophoresis (CGE), or Western blot analysis. In embodiments, ELISA methods are used to measure host cell protein. For example, the host cell protein (HCP) ELISA can be performed using the "Immunoenzymetric Assay for the Measurement of *Pseudomonas fluorescens* Host Cell Proteins" kit from Cygnus Technologies, Inc., catalog number F450, according to the manufacturer's protocol. The plate can be read on a SPECTRAmax Plus (Molecular Devices), using Softmax Pro v3.1.2 software.

SDS-CGE can be carried out using a LabChip GXII instrument (Caliper LifeSciences, Hopkinton, Mass.) with a HT Protein Express v2 chip and corresponding reagents (part numbers 760499 and 760328, respectively, Caliper LifeSciences). Samples can be prepared following the manufacturer's protocol (Protein User Guide Document No. 450589, Rev. 3) and electrophoresed on polyacrylamide gels. After separation the gel can be stained, destained, and digitally imaged.

The concentration of a protein, e.g., a purified recombinant fusion protein or polypeptide of interest as described herein, can be determined by absorbance spectroscopy by methods known to those of skill in the art and described in the literature. In embodiments, the absorbance of a protein sample at 280 nm is measured (e.g., using an Eppendorf BioPhotometer, Eppendorf, Hamburg, Germany) and the concentration of protein calculated using the Beer-Lambert Law. An accurate molar absorption coefficient for the protein can be calculated by known methods, e.g., as described by Grimsley, G. R., and Pace, C. N., "Spectrophotometric Determination of Protein Concentration," in Current Protocols in Protein Science 3.1.1-3.1.9, Copyright © 2003 by John Wiley & Sons, Inc., incorporated by reference herein.

Table 5 lists the concentration of proteins described herein at an A280 of 1, determined using molar extinction coefficients calculated by VectorNTI, Invitrogen.

TABLE 5

Protein Concentrations for an $A_{280}$ of 1

| Amino Acid SEQ ID NO | Protein | Concentration of Protein (mg/mL) for An $A_{280}$ of 1 | Molar Extinction Coefficient |
|---|---|---|---|
| 1 | PTH1-34 | 0.72 | |
| 45 | DnaJ-like protein-PTH 1-34 fusion | 0.8 | |
| 46 | FklB-PTH 1-34 fusion | 1.18 | |
| 47 | FrnE-PTH 1-34 fusion | 0.98 | |
| 70 | DnaJ-like protein-EK-GCSF fusion | 1.02 | 29190 |
| 71 | EcpD1-EK-GCSF fusion (Full length EcpD1) | 1.21 | 39530 |
| 72 | EcpD2-EK-GCSF fusion | 1.37 | 23030 |
| 73 | EcpD3-EK-GCSF fusion (50 aa truncated EcpD1) | 1.51 | 17430 |
| 74 | FklB-EK-GCSF fusion (Full length FklB) | 1.26 | 33600 |
| 75 | FklB2-EK-GCSF fusion (100 aa truncated FklB) | 1.83 | 17100 |
| 76 | FklB3-EK-GCSF fusion (500 aa truncated FklB) | 1.52 | 17100 |
| 77 | FrnE-EK-GCSF fusion (Full length FrnE) | 1.09 | 40810 |
| 78 | FrnE2-EK-GCSF fusion (aa) (100 aa truncated FrnE) | 1.31 | 24310 |
| 79 | FrnE3-EK-GCSF fusion (50 aa truncated FrnE) | 1.21 | 21750 |
| 122 | DnaJ-like protein-EK-Proinsulin-CP-A | 1.06 | 19210 |
| 123 | DnaJ-like protein-EK-Proinsulin-CP-B | 1.04 | 19210 |
| 124 | DnaJ-like protein-EK-Proinsulin-CP-C | 1.03 | 19210 |
| 125 | DnaJ-like protein-Trypsin-Proinsulin-CP-A | 1.04 | 19210 |
| 126 | DnaJ-like protein-Trypsin-Proinsulin-CP-B | 1.01 | 19210 |
| 127 | DnaJ-like protein-Trypsin-Proinsulin-CP-C | 1.01 | 19210 |
| 128 | DnaJ-like protein-EK-Proinsulin-CP-D | 1.05 | 19210 |
| 129 | DnaJ-like protein-Trypsin-Proinsulin-CP-D | 1.07 | 19210 |
| 130 | FklB-EK-Proinsulin-CP-A | 1.40 | 23620 |
| 131 | FklB-EK-Proinsulin-CP-B | 1.38 | 23620 |
| 132 | FlkB-EK-Proinsulin-CP-C | 1.37 | 23620 |
| 133 | FklB-Trypsin-Proinsulin-CP-A | 1.38 | 23620 |
| 134 | FlkB-Trypsin-Proinsulin-CP-B | 1.36 | 23620 |
| 135 | FlkB-Trypsin-Proinsulin-CP-C | 1.35 | 23620 |
| 136 | FlkB-EK-Proinsulin-CP-D | 1.31 | 23620 |
| 137 | FlkB-Trypsin-Proinsulin-CP-D | 1.29 | 23620 |
| 138 | FklB2-EK-Proinsulin-CP-A | 3.06 | 7120 |
| 139 | FklB2-EK-Proinsulin-CP-B | 2.99 | 7120 |
| 140 | FklB2-EK-Proinsulin-CP-C | 2.98 | 7120 |
| 141 | FklB2-Trypsin-Proinsulin-CP-A | 3.0 | 7120 |
| 142 | FlkB2-Trypsin-Proinsulin-CP-B | 2.93 | 7120 |
| 143 | FlkB2-Trypsin-Proinsulin-CP-C | 2.92 | 7120 |
| 144 | FlkB2-EK-Proinsulin-CP-D | 2.78 | 7120 |

TABLE 5-continued

Protein Concentrations for an $A_{280}$ of 1

| Amino Acid SEQ ID NO | Protein | Concentration of Protein (mg/mL) for An $A_{280}$ of 1 | Molar Extinction Coefficient |
|---|---|---|---|
| 145 | FlkB2-Trypsin-Proinsulin-CP-D | 2.72 | 7120 |
| 146 | FlkB3.1-EK-Proinsulin-CP-A | 2.33 | 7120 |
| 147 | FklB3-EK-Proinsulin-CP-B | 2.26 | 7120 |
| 148 | FlkB3.1-EK-Proinsulin-CP-C | 2.25 | 7120 |
| 149 | FklB3-Trypsin-Proinsulin-CP-A | 2.27 | 7120 |
| 150 | FlkB3.1-Trypsin-Proinsulin-CP-B | 2.20 | 7120 |
| 151 | FlkB3.1-Trypsin-Proinsulin-CP-C | 2.19 | 7120 |
| 152 | FklB-EK-Proinsulin-CP-D | 2.04 | 7120 |
| 153 | FlkB3.1-Trypsin-Proinsulin-CP-D | 1.98 | 7120 |
| 154 | FmE-EK-Proinsulin-CP-A | 1.14 | 30830 |
| 155 | FrnE-EK-Proinsulin-CP-B | 1.12 | 30830 |
| 156 | FrnE-EK-Proinsulin-CP-C | 1.12 | 30830 |
| 157 | FrnE-Trypsin-Proinsulin-CP-A | 1.13 | 30830 |
| 158 | FrnE-Trypsin-Proinsulin-CP-B | 1.11 | 30830 |
| 159 | FrnE-Trypsin-Proinsulin-CP-C | 1.11 | 30830 |
| 160 | FrnE-EK-Proinsulin-CP-D | 1.08 | 30830 |
| 161 | FrnE-Trypsin-Proinsulin-CP-D | 1.06 | 30830 |
| 162 | FrnE2-EK-Proinsulin-CP-A | 1.57 | 14330 |
| 163 | FrnE2-EK-Proinsulin-CP-B | 1.53 | 14330 |
| 164 | FrnE2-EK-Proinsulin-CP-C | 1.53 | 14330 |
| 165 | FrnE2-Trypsin-Proinsulin-CP-A | 1.53 | 14330 |
| 166 | FrnE2-Trypsin-Proinsulin-CP-B | 1.50 | 14330 |
| 167 | FrnE2-Trypsin-Proinsulin-CP-C | 1.50 | 14330 |
| 168 | FrnE2-EK-Proinsulin-CP-D | 1.42 | 14330 |
| 169 | FrnE2-Trypsin-Proinsulin-CP-D | 1.39 | 14330 |
| 170 | FrnE3-EK-Proinsulin-CP-A | 1.44 | 11770 |
| 171 | FrnE3-EK-Proinsulin-CP-B | 1.39 | 11770 |
| 172 | FrnE3-EK-Proinsulin-CP-C | 1.39 | 11770 |
| 173 | FrnE3-Trypsin-Proinsulin-CP-A | 1.40 | 11770 |
| 174 | FrnE3-Trypsin-Proinsulin-CP-B | 1.36 | 11770 |
| 175 | FrnE3-Trypsin-Proinsulin-CP-C | 1.35 | 11770 |
| 176 | FrnE3-EK-Proinsulin-CP-D | 1.26 | 11770 |
| 177 | FrnE3-Trypsin-Proinsulin-CP-D | 1.23 | 11770 |
| 178 | EcpD1-EK-Proinsulin-CP-A | 1.30 | 29550 |
| 179 | EcpD1-EK-Proinsulin-CP-B | 1.28 | 29550 |
| 180 | EcpD1-EK-Proinsulin-CP-C | 1.28 | 29550 |
| 181 | EcpD1-EK-Proinsulin-CP-D | 1.23 | 29550 |
| 182 | EcpD1-Trypsin-Proinsulin-CP-A (EcpD1-Trypsin as encoded by pFNX4402 does not contain the underlined N residue) | 1.28 | 29550 |
| 183 | EcpD1-Trypsin-Proinsulin-CP-B (EcpD1-Trypsin as encoded by pFNX4402 does not contain the underlined N residue) | 1.26 | 29550 |
| 184 | EcpD1-Trypsin-Proinsulin-CP-C (EcpD1-Trypsin as encoded by pFNX4402 does not contain the underlined N residue) | 1.26 | 29550 |
| 185 | EcpD1-Trypsin-Proinsulin-CP-D (EcpD1-Trypsin as encoded by pFNX4402 does not contain the underlined N residue) | 1.21 | 29550 |
| 186 | EcpD2-EK-Proinsulin-CP-A | 1.69 | 13050 |
| 187 | EcpD2-EK-Proinsulin-CP-B | 1.65 | 13050 |
| 188 | EcpD2-EK-Proinsulin-CP-C | 1.64 | 13050 |
| 189 | EcpD2-Trypsin-Proinsulin-CP-A | 1.65 | 13050 |
| 190 | EcpD2-Trypsin-Proinsulin-CP-B | 1.61 | 13050 |
| 191 | EcpD2-Trypsin-Proinsulin-CP-C | 1.61 | 13050 |
| 192 | EcpD2-EK-Proinsulin-CP-D | 1.53 | 13050 |
| 193 | EcpD2-Trypsin-Proinsulin-CP-D | 1.50 | 13050 |
| 194 | EcpD3-EK-Proinsulin-CP-A | 2.28 | 7360 |
| 195 | EcpD3-EK-Proinsulin-CP-B | 2.21 | 7360 |
| 196 | EcpD3-EK-Proinsulin-CP-C | 2.20 | 7360 |
| 197 | EcpD3-Trypsin-Proinsulin-CP-A | 2.22 | 7360 |
| 198 | EcpD3-Trypsin-Proinsulin-CP-B | 2.15 | 7360 |
| 199 | EcpD3-Trypsin-Proinsulin-CP-C | 2.14 | 7360 |
| 200 | EcpD3-EK-Proinsulin-CP-D | 2.00 | 7360 |
| 201 | EcpD3-Trypsin-Proinsulin-CP-D | 1.95 | 7360 |

Western blot analysis to determine yield or purity of the polypeptide of interest can be carried out according to any appropriate method known in the art by transferring protein separated on SDS-PAGE gels to a nitrocellulose membrane and incubating the membrane with a monoclonal antibody specific for the polypeptide of interest. Antibodies useful for any analytical methods described herein can be generated by suitable procedures known to those of skill in the art.

Activity assays, as described herein and known in the art, also can provide information regarding protein yield. In embodiments, these or any other methods known in the art are used to evaluate proper processing of a protein, e.g., proper secretion leader cleavage.

Useful measures of recombinant fusion protein yield include, e.g., the amount of soluble recombinant fusion protein per culture volume (e.g., grams or milligrams of protein/liter of culture), percent or fraction of soluble recombinant fusion protein obtained (e.g., amount of soluble recombinant fusion protein/amount of total recombinant fusion protein), percent or fraction of total cell protein (tcp), and percent or proportion of dry biomass. In embodiments, the measure of recombinant fusion protein yield as described herein is based on the amount of soluble recombinant fusion protein obtained. In embodiments, the measurement of soluble recombinant fusion protein is made in a soluble fraction obtained after cell lysis, e.g., a soluble fraction obtained after one or more centrifugation steps, or after purification of the recombinant fusion protein.

Useful measures of polypeptide of interest yield include, e.g., the amount of soluble polypeptide of interest obtained per culture volume (e.g., grams or milligrams of protein/liter of culture), percent or fraction of soluble polypeptide of interest obtained (e.g., amount of soluble polypeptide of interest/amount of total polypeptide of interest), percent or fraction of active polypeptide of interest obtained (e.g., amount of active polypeptide of interest/total amount polypeptide of interest in the activity assay), percent or fraction of total cell protein (tcp), and percent or proportion of dry biomass.

In embodiments wherein yield is expressed in terms of culture volume the culture cell density may be taken into account, particularly when yields between different cultures are being compared. In embodiments, the methods of the present invention can be used to obtain a soluble and/or active and/or properly processed (e.g., having the secretion leader cleaved properly) recombinant fusion protein yield of about 0.5 grams per liter to about 25 grams per liter. In embodiments, the recombinant fusion protein comprises an N-terminal fusion partner which is a cytoplasmic chaperone or folding modulator from the heat shock protein family, and the fusion protein is directed to the cytoplasm after expression. In embodiments, the recombinant fusion protein comprises an N-terminal fusion partner which is a periplasmic chaperone or folding modulator from the periplasmic peptidylprolyl isomerase family, and the fusion protein is directed to the periplasm after expression. In embodiments, the yield of the fusion protein, the cytoplasmically expressed fusion protein, or the periplasmically expressed fusion protein, is about 0.5 g/L, about 1 g/L, about 1.5 g/L, about 2 g/L, about 2.5 g/L, about 3 g/L, about 3.5 g/L, about 4 g/L, about 4.5 g/L, about 5 g/L, about 6 g/L, about 7 g/L, about 8 g/L, about 9 g/L, about 10 g/L, about 11 g/L, about 12 g/L, about 13 g/L, about 14 g/L, about 15 g/L, about 16 g/L, about 17 g/L, about 18 g/L, about 19 g/L, about 20 g/L, about 21 g/L, about 22 g/L, about 23 g/L, about 24 g/L, about 25 g/L, about 0.5 g/L to about 25 g/L, about 0.5 g/L to about 23 g/L, about 1 g/L to about 23 g/L, about 1.5 g/L to about 23 g/L, about 2 g/L to about 23 g/L, about 2.5 g/L to about 23 g/L, about 3 g/L to about 23 g/L, about 3.5 g/L to about 23 g/L, about 4 g/L to about 23 g/L, about 4.5 g/L to about 23 g/L, about 5 g/L to about 23 g/L, about 6 g/L to about 23 g/L, about 7 g/L to about 23 g/L, about 8 g/L to about 23 g/L, about 9 g/L to about 23 g/L, about 10 g/L to about 23 g/L, about 15 g/L to about 23 g/L, about 20 g/L to about 23 g/L, about 0.5 g/L to about 20 g/L, about 1 g/L to about 20 g/L, about 1.5 g/L to about 20 g/L, about 2 g/L to about 20 g/L, about 2.5 g/L to about 20 g/L, about 3 g/L to about 20 g/L, about 3.5 g/L to about 20 g/L, about 4 g/L to about 20 g/L, about 4.5 g/L to about 20 g/L, about 5 g/L to about 20 g/L, about 6 g/L to about 20 g/L, about 7 g/L to about 20 g/L, about 8 g/L to about 20 g/L, about 9 g/L to about 20 g/L, about 10 g/L to about 20 g/L, about 15 g/L to about 20 g/L, about 0.5 g/L to about 15 g/L, about 1 g/L to about 15 g/L, about 1.5 g/L to about 15 g/L, about 2 g/L to about 15 g/L, about 2.5 g/L to about 15 g/L, about 3 g/L to about 15 g/L, about 3.5 g/L to about 15 g/L, about 4 g/L to about 15 g/L, about 4.5 g/L to about 15 g/L, about 5 g/L to about 15 g/L, about 6 g/L to about 15 g/L, about 7 g/L to about 15 g/L, about 8 g/L to about 15 g/L, about 9 g/L to about 15 g/L, about 10 g/L to about 15 g/L, about 0.5 g/L to about 12 g/L, about 1 g/L to about 12 g/L, about 1.5 g/L to about 12 g/L, about 2 g/L to about 12 g/L, about 2.5 g/L to about 12 g/L, about 3 g/L to about 12 g/L, about 3.5 g/L to about 12 g/L, about 4 g/L to about 12 g/L, about 4.5 g/L to about 12 g/L, about 5 g/L to about 12 g/L, about 6 g/L to about 12 g/L, about 7 g/L to about 12 g/L, about 8 g/L to about 12 g/L, about 9 g/L to about 12 g/L, about 10 g/L to about 12 g/L, about 0.5 g/L to about 10 g/L, about 1 g/L to about 10 g/L, about 1.5 g/L to about 10 g/L, about 2 g/L to about 10 g/L, about 2.5 g/L to about 10 g/L, about 3 g/L to about 10 g/L, about 3.5 g/L to about 10 g/L, about 4 g/L to about 10 g/L, about 4.5 g/L to about 10 g/L, about 5 g/L to about 10 g/L, about 6 g/L to about 10 g/L, about 7 g/L to about 10 g/L, about 8 g/L to about 10 g/L, about 9 g/L to about 10 g/L, about 0.5 g/L to about 9 g/L, about 1 g/L to about 9 g/L, about 1.5 g/L to about 9 g/L, about 2 g/L to about 9 g/L, about 2.5 g/L to about 9 g/L, about 3 g/L to about 9 g/L, about 3.5 g/L to about 9 g/L, about 4 g/L to about 9 g/L, about 4.5 g/L to about 9 g/L, about 5 g/L to about 9 g/L, about 6 g/L to about 9 g/L, about 7 g/L to about 9 g/L, about 8 g/L to about 9 g/L, about 0.5 g/L to about 8 g/L, about 1 g/L to about 8 g/L, about 1.5 g/L to about 8 g/L, about 2 g/L to about 8 g/L, about 2.5 g/L to about 8 g/L, about 3 g/L to about 8 g/L, about 3.5 g/L to about 8 g/L, about 4 g/L to about 8 g/L, about 4.5 g/L to about 8 g/L, about 5 g/L to about 8 g/L, about 6 g/L to about 8 g/L, about 7 g/L to about 8 g/L, about 0.5 g/L to about 7 g/L, about 1 g/L to about 7 g/L, about 1.5 g/L to about 7 g/L, about 2 g/L to about 7 g/L, about 2.5 g/L to about 7 g/L, about 3 g/L to about 7 g/L, about 3.5 g/L to about 7 g/L, about 4 g/L to about 7 g/L, about 4.5 g/L to about 7 g/L, about 5 g/L to about 7 g/L, about 6 g/L to about 7 g/L, about 0.5 g/L to about 6 g/L, about 1 g/L to about 6 g/L, about 1.5 g/L to about 6 g/L, about 2 g/L to about 6 g/L, about 2.5 g/L to about 6 g/L, about 3 g/L to about 6 g/L, about 3.5 g/L to about 6 g/L, about 4 g/L to about 6 g/L, about 4.5 g/L to about 6 g/L, about 5 g/L to about 6 g/L, about 0.5 g/L to about 5 g/L, about 1 g/L to about 5 g/L, about 1.5 g/L to about 5 g/L, about 2 g/L to about 5 g/L, about 2.5 g/L to about 5 g/L, about 3 g/L to about 5 g/L, about 3.5 g/L to about 5 g/L, about 4 g/L to about 5 g/L, about 4.5 g/L to about 5 g/L, about 0.5 g/L to about 4 g/L, about 1 g/L to about 4 g/L, about 1.5 g/L to about 4 g/L, about 2 g/L to about 4 g/L, about 2.5 g/L to about 4 g/L, about 3 g/L to about 4 g/L, about 0.5 g/L to about 3 g/L, about 1 g/L to about 3 g/L, about 1.5 g/L to about 3 g/L, about 2 g/L to about 3 g/L, about 0.5 g/L to about 2 g/L, about 1 g/L to about 2 g/L, or about 0.5 g/L to about 1 g/L.

In embodiments, the polypeptide of interest is hPTH and the yield of the recombinant fusion protein directed to the cytoplasm is about 0.5 g/L to about 2.4 grams per liter.

In embodiments, the polypeptide of interest is hPTH and the yield of the recombinant fusion protein directed to the periplasm is about 0.5 grams per liter to about 6.7 grams per liter.

Yield of Polypeptide of Interest

In embodiments, the polypeptide of interest is released from the full recombinant fusion protein, by protease cleavage within the linker. In embodiments, the polypeptide of interest obtained after cleavage with protease is the properly released polypeptide of interest. In embodiments, the yield of the polypeptide of interest—either based on measurement of properly released protein, or calculated based on the known proportion of polypeptide of interest to total fusion protein—is about 0.7 grams per liter to about 25.0 grams per liter. In embodiments, the yield of the polypeptide of interest is about 0.5 g/L (500 mg/L), about 1 g/L, about 1.5 g/L, about 2 g/L, about 2.5 g/L, about 3 g/L, about 3.5 g/L, about 4 g/L, about 4.5 g/L, about 5 g/L, about 6 g/L, about 7 g/L, about 8 g/L, about 9 g/L, about 10 g/L, about 11 g/L, about 12 g/L, about 13 g/L, about 14 g/L, about 15 g/L, about 16 g/L, about 17 g/L, about 18 g/L, about 19 g/L, about 20 g/L, about 21 g/L, about 22 g/L, about 23 g/L, about 24 g/L, about 25 g/L, about 0.5 g/L to about 23 g/L, about 1 g/L to about 23 g/L, about 1.5 g/L to about 23 g/L, about 2 g/L to about 23 g/L, about 2.5 g/L to about 23 g/L, about 3 g/L to about 23 g/L, about 3.5 g/L to about 23 g/L, about 4 g/L to about 23 g/L, about 4.5 g/L to about 23 g/L, about 5 g/L to about 23 g/L, about 6 g/L to about 23 g/L, about 7 g/L to about 23 g/L, about 8 g/L to about 23 g/L, about 9 g/L to about 23 g/L, about 10 g/L to about 23 g/L, about 15 g/L to about 23 g/L, about 20 g/L to about 23 g/L, about 0.5 g/L to about 20 g/L, about 1 g/L to about 20 g/L, about 1.5 g/L to about 20 g/L, about 2 g/L to about 20 g/L, about 2.5 g/L to about 20 g/L, about 3 g/L to about 20 g/L, about 3.5 g/L to about 20 g/L, about 4 g/L to about 20 g/L, about 4.5 g/L to about 20 g/L, about 5 g/L to about 20 g/L, about 6 g/L to about 20 g/L, about 7 g/L to about 20 g/L, about 8 g/L to about 20 g/L, about 9 g/L to about 20 g/L, about 10 g/L to about 20 g/L, about 15 g/L to about 20 g/L, about 0.5 g/L to about 15 g/L, about 1 g/L to about 15 g/L, about 1.5 g/L to about 15 g/L, about 2 g/L to about 15 g/L, about 2.5 g/L to about 15 g/L, about 3 g/L to about 15 g/L, about 3.5 g/L to about 15 g/L, about 4 g/L to about 15 g/L, about 4.5 g/L to about 15 g/L, about 5 g/L to about 15 g/L, about 6 g/L to about 15 g/L, about 7 g/L to about 15 g/L, about 8 g/L to about 15 g/L, about 9 g/L to about 15 g/L, about 10 g/L to about 15 g/L, about 0.5 g/L to about 12 g/L, about 1 g/L to about 12 g/L, about 1.5 g/L to about 12 g/L, about 2 g/L to about 12 g/L, about 2.5 g/L to about 12 g/L, about 3 g/L to about 12 g/L, about 3.5 g/L to about 12 g/L, about 4 g/L to about 12 g/L, about 4.5 g/L to about 12 g/L, about 5 g/L to about 12 g/L, about 6 g/L to about 12 g/L, about 7 g/L to about 12 g/L, about 8 g/L to about 12 g/L, about 9 g/L to about 12 g/L, about 10 g/L to about 12 g/L, about 0.5 g/L to about 10 g/L, about 1 g/L to about 10 g/L, about 1.5 g/L to about 10 g/L, about 2 g/L to about 10 g/L, about 2.5 g/L to about 10 g/L, about 3 g/L to about 10 g/L, about 3.5 g/L to about 10 g/L, about 4 g/L to about 10 g/L, about 4.5 g/L to about 10 g/L, about 5 g/L to about 10 g/L, about 6 g/L to about 10 g/L, about 7 g/L to about 10 g/L, about 8 g/L to about 10 g/L, about 9 g/L to about 10 g/L, about 0.5 g/L to about 9 g/L, about 1 g/L to about 9 g/L, about 1.5 g/L to about 9 g/L, about 2 g/L to about 9 g/L, about 2.5 g/L to about 9 g/L, about 3 g/L to about 9 g/L, about 3.5 g/L to about 9 g/L, about 4 g/L to about 9 g/L, about 4.5 g/L to about 9 g/L, about 5 g/L to about 9 g/L, about 6 g/L to about 9 g/L, about 7 g/L to about 9 g/L, about 8 g/L to about 9 g/L, about 0.5 g/L to about 8 g/L, about 1 g/L to about 8 g/L, about 1.5 g/L to about 8 g/L, about 2 g/L to about 8 g/L, about 2.5 g/L to about 8 g/L, about 3 g/L to about 8 g/L, about 3.5 g/L to about 8 g/L, about 4 g/L to about 8 g/L, about 4.5 g/L to about 8 g/L, about 5 g/L to about 8 g/L, about 6 g/L to about 8 g/L, about 7 g/L to about 8 g/L, about 0.5 g/L to about 7 g/L, about 1 g/L to about 7 g/L, about 1.5 g/L to about 7 g/L, about 2 g/L to about 7 g/L, about 2.5 g/L to about 7 g/L, about 3 g/L to about 7 g/L, about 3.5 g/L to about 7 g/L, about 4 g/L to about 7 g/L, about 4.5 g/L to about 7 g/L, about 5 g/L to about 7 g/L, about 6 g/L to about 7 g/L, about 0.5 g/L to about 6 g/L, about 1 g/L to about 6 g/L, about 1.5 g/L to about 6 g/L, about 2 g/L to about 6 g/L, about 2.5 g/L to about 6 g/L, about 3 g/L to about 6 g/L, about 3.5 g/L to about 6 g/L, about 4 g/L to about 6 g/L, about 4.5 g/L to about 6 g/L, about 5 g/L to about 6 g/L, about 0.5 g/L to about 5 g/L, about 1 g/L to about 5 g/L, about 1.5 g/L to about 5 g/L, about 2 g/L to about 5 g/L, about 2.5 g/L to about 5 g/L, about 3 g/L to about 5 g/L, about 3.5 g/L to about 5 g/L, about 4 g/L to about 5 g/L, about 4.5 g/L to about 5 g/L, about 0.5 g/L to about 4 g/L, about 1 g/L to about 4 g/L, about 1.5 g/L to about 4 g/L, about 2 g/L to about 4 g/L, about 2.5 g/L to about 4 g/L, about 3 g/L to about 4 g/L, about 0.5 g/L to about 3 g/L, about 1 g/L to about 3 g/L, about 1.5 g/L to about 3 g/L, about 2 g/L to about 3 g/L, about 0.5 g/L to about 2 g/L, about 1 g/L to about 2 g/L, or about 0.5 g/L to about 1 g/L, at 0.5 mL to 100 L, 0.5 mL, 50 mL, 100 mL, 1 L, 2 L, or larger scale.

In embodiments, hPTH is produced as a fusion protein having an N-terminal fusion partner and hPTH construct as described in Table 8. In embodiments, expression of the hPTH fusion protein produces at least 100, at least 125, at least 150, at least 175, at least 200, at least 250, at least 300, at least 350, at least 400, at least 450, at least 500, at least 550, at least 600, at least 650, or at least 1000 mg/L total hPTH fusion protein, at 0.5 mL to 100 L, 0.5 mL, 50 mL, 100 mL, 1 L, 2 L, or larger scale.

In embodiments, a proinsulin, e.g., proinsulin for an insulin analog, for example, glargine, is produced as a proinsulin fusion protein having an N-terminal fusion partner and proinsulin construct comprising a C-peptide sequence as described in Table 19. In embodiments, expression of a proinsulin fusion protein according to the methods of the invention produces at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 200, or at least about 250 mg/L soluble proinsulin, at 0.5 mL to 100 L, 50 mL, 100 mL, 1 L, 2 L, or larger scale, either as measured when properly released or calculated based on its known proportion of the fusion protein.

In embodiments, expression of a proinsulin fusion protein according to the methods of the invention produces about 10 to about 500, about 15 to about 500, about 20 to about 500, about 30 to about 500, about 40 to about 500, about 50 to about 500, about 60 to about 500, about 70 to about 500, about 80 to about 500, about 90 to about 500, about 100 to about 500, about 200 to about 500, about 10 to about 400, about 15 to about 400, about 20 to about 400, about 30 to about 400, about 40 to about 400, about 50 to about 400, about 60 to about 400, about 70 to about 400, about 80 to about 400, about 90 to about 400, about 100 to about 400, about 200 to about 400, about 10 to about 300, about 15 to about 300, about 20 to about 300, about 30 to about 300, about 40 to about 300, about 50 to about 300, about 60 to about 300, about 70 to about 300, about 80 to about 300, about 90 to about 300, about 100 to about 300, about 200 to about 300, about 10 to about 250, about 15 to about 250, about 20 to about 250, about 30 to about 250, about 40 to about 250, about 50 to about 250, about 60 to about 250, about 70 to about 250, about 80 to about 250, about 90 to about 250, about 100 to about 250, about 10 to about 200, about 15 to about 200, about 20 to about 200, about 30 to about 200, about 40 to about 200, about 50 to about 200, about 60 to about 200, about 70 to about 200, about 80 to about 200, about 90 to about 200, or about 100 to about 200 mg/L soluble proinsulin, at 0.5 mL to 100 L, 0.5 mL, 50 mL, 100 mL, 1 L, 2 L, or larger scale, either as measured when properly released or calculated based on its known proportion of the fusion protein.

In embodiments, expression of a proinsulin fusion protein produces at least about 100, at least about 125, at least about 150, at least about 175, at least about 200, at least about 250, at least about 300, at least about 350, at least about 400, at least about 450, at least about 500, at least about 550, at least about 600, at least about 650, or at least about 1000 mg/L of total soluble and insoluble proinsulin. In embodiments, expression of the proinsulin fusion protein produces about 100 to about 2000 mg/L, about 100 to about 1500 mg/L, about 100 to about 1000 mg/L, about 100 to about 900 mg/L, about 100 to about 800 mg/L, about 100 to about 700 mg/L, about 100 to about 600 mg/L, about 100 to about 500 mg/L, about 100 to about 400 mg/L, about 200 to about 2000 mg/L, about 200 to about 1500 mg/L, about 200 to about 1000 mg/L, about 200 to about 900 mg/L, about 200 to about 800 mg/L, about 200 to about 7000 mg/L, about 200 to about 600 mg/L, about 200 to about 500 mg/L, about 300 to about 2000 mg/L, about 300 to about 1500 mg/L, about 300 to about 1000 mg/L, about 300 to about 900 mg/L, about 300 to about 800 mg/L, about 300 to about 7000 mg/L, or about 300 to about 600 mg/L of total soluble and insoluble proinsulin, at 0.5 mL to 100 L, 0.5 mL, 50 mL, 100 mL, 1 L, 2 L, or larger scale. In embodiments, the proinsulin is cleaved to release the C-peptide and produce mature insulin. In embodiments, expression of the proinsulin fusion protein produces at least about 100, at least about 200, at least about 250, at least about 300, at least about 400, at least about 500, about 100 to about 2000 mg/L, about 200 to about 2000 mg/L, about 300 to about 2000 mg/L, about 400 to about 2000 mg/L, about 500 to about 2000 mg/L, about 100 to about 1000 mg/L, about 200 to about 1000 mg/L, about 300 to about 1000 mg/L, about 400 to about 1000 mg/L, about 500 to about 1000 mg/L, mature insulin, at 0.5 mL to 100 L, 0.5 mL, 50 mL, 100 mL, 1 L, 2 L, or larger scale, either as measured when properly released or calculated based on its known proportion of the fusion protein.

In embodiments, GCSF is produced as a GCSF fusion protein having an N-terminal fusion partner as described in Table 21. In embodiments, expression of a GCSF fusion according to the methods of the invention produces soluble fusion protein comprising at least 100, at least 200, at least 250, at least 300, at least 400, at least 500, or at least 1000, about 100 to about 1000, about 200 to about 1000, about 300 to about 1000, about 400 to about 1000, or about 500 to about 1000 mg/L soluble GCSF, at 0.5 mL to 100 L, 0.5 mL, 50 mL, 100 mL, 1 L, 2 L, or larger scale, either as measured when properly released or calculated based on its known proportion of the fusion protein. In embodiments, expression of a GCSF fusion according to the methods of the invention produces at least 100, at least 200, at least 250, at least 300, at least 400, at least 500, or at least 1000 mg/L soluble GCSF. In embodiments, expression of the GCSF fusion produces at least 300, at least 350, at least 400, at least 450, at least 500, at least 550, at least 600, at least 650, at least 700, at least 850, at least, at least 550, at least 600, at least 650, about 100 to about 1000, about 200 to about 1000, about 300 to about 1000, about 400 to about 1000, or about 500 to about 1000 mg/L of total soluble and insoluble GCSF, at 0.5 mL to 100 L, 0.5 mL, 50 mL, 100 mL, 1 L, 2 L, or larger scale.

In embodiments, the amount of recombinant fusion protein produced is about 1% to about 75% of the total cell protein. In certain embodiments, the amount of recombinant fusion protein produced is about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 1% to about 5%, about 1% to about 10%, about 1% to about 20%, about 1% to about 30%, about 1% to about 40%, about 1% to about 50%, about 1% to about 60%, about 1% to about 75%, about 2% to about 5%, about 2% to about 10%, about 2% to about 20%, about 2% to about 30%, about 2% to about 40%, about 2% to about 50%, about 2% to about 60%, about 2% to about 75%, about 3% to about 5%, about 3% to about 10%, about 3% to about 20%, about 3% to about 30%, about 3% to about 40%, about 3% to about 50%, about 3% to about 60%, about 3% to about 75%, about 4% to about 10%, about 4% to about 20%, about 4% to about 30%, about 4% to about 40%, about 4% to about 50%, about 4% to about 60%, about 4% to about 75%, about 5% to about 10%, about 5% to about 20%, about 5% to about 30%, about 5% to about 40%, about 5% to about 50%, about 5% to about 60%, about 5% to about 75%, about 10% to about 20%, about 10% to about 30%, about 10% to about 40%, about 10% to about 50%, about 10% to about 60%, about 10% to about 75%, about 20% to about 30%, about 20% to about 40%, about 20% to about 50%, about 20% to about 60%, about 20% to about 75%, about 30% to about 40%, about 30% to about 50%, about 30% to about 60%, about 30% to about 75%, about 40% to about 50%, about 40% to about 60%, about 40% to about 75%, about 50% to about 60%, about 50% to about 75%, about 60% to about 75%, or about 70% to about 75%, of the total cell protein.

Solubility and Activity

The "solubility" and "activity" of a protein, though related qualities, are generally determined by different means. Solubility of a protein, particularly a hydrophobic protein, indicates that hydrophobic amino acid residues are improperly located on the outside of the folded protein. Protein activity, which can be evaluated using methods as determined to be appropriate for the polypeptide of interest by one of skill in the art, is another indicator of proper protein conformation. "Soluble, active, or both" as used herein, refers to protein that is determined to be soluble, active, or both soluble and active, by methods known to those of skill in the art.

In general, with respect to an amino acid sequence, the term "modification" includes substitutions, insertions, elongations, deletions, and derivatizations alone or in combination. In embodiments, the recombinant fusion proteins may include one or more modifications of a "non-essential" amino acid residue. In this context, a "non-essential" amino acid residue is a residue that can be altered, e.g., deleted or substituted, in the novel amino acid sequence without abolishing or substantially reducing the activity (e.g., the agonist activity) of the recombinant fusion protein. By way of example, the recombinant fusion protein may include 1, 2, 3, 4, 5, 6, 7, 8, 9, 10, or more substitutions, both in a consecutive manner or spaced throughout the recombinant fusion protein molecule. Alone or in combination with the substitutions, the recombinant fusion protein may include 1, 2, 3, 4, 5, 6, 7, 8, 9, 10, or more insertions, again either in consecutive manner or spaced throughout the recombinant fusion protein molecule. The recombinant fusion protein, alone or in combination with the substitutions and/or insertions, may also include 1, 2, 3, 4, 5, 6, 7, 8, 9, 10, or more deletions, again either in consecutive manner or spaced throughout the recombinant fusion protein molecule. The recombinant fusion protein, alone or in combination with the substitutions, insertions and/or deletions, may also include 1, 2, 3, 4, 5, 6, 7, 8, 9, 10, or more amino acid additions.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or normatural (unnatural). Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example I: High-Throughput Screening of Strains Expressing hPTH 1-34 Fusions

This study was conducted to test levels recombinant protein produced by *P. fluorescens* strains expressing hPTH 1-34 fusion proteins comprising DNAJ-like protein, FklB, or FrnE as the N-terminal fusion partner.

Materials and Methods

Construction of PTH 1-34 Fusion Protein Expression Plasmids: Gene fragments encoding PTH 1-34 fusion proteins were synthesized using DNA 2.0, a gene design and synthesis service (Menlo Park, Calif.). Each gene fragment included a coding sequence for a *P. fluorescens* folding modulator (DnaJ-like protein, FklB, or FrnE), fused with a coding sequence for PTH 1-34, and a linker. Each gene fragment also included recognition sequences for the restriction enzymes SpeI and XhoI, a "Hi" ribosome binding site, and an 18 basepair spacer that includes a ribosome binding site and a restriction site (SEQ ID NO: 58) added upstream to the coding sequences and three stop codons. Nucleotide sequences encoding these PTH 1-34 fusion proteins are provided as SEQ ID NOS: 52-57.

To generate expression plasmids p'708-004, -005 and -006 (listed in Table 6), the PTH 1-34 fusion protein gene fragments were digested using SpeI and XhoI restriction enzymes, and subcloned into expression vector pDOW1169, containing the pTac promoter and rrnT1T2 transcriptional terminator. pDOW1169 is described in literature, for e.g., in U.S. Pat. No. 7,833,752, "Bacterial Leader Sequences for Increased Expression," and Schneider et al., 2005, "Auxotrophic markers pyrF and proC can replace antibiotic markers on protein production plasmids in high-cell-density *Pseudomonas fluorescens* fermentation," Biotechnol. Progress 21(2): 343-8, both incorporated by reference herein. The plasmids were electroporated into competent *P. fluorescens* DC454 host cells (pyrF 1sc::lacI$^{Q1}$).

TABLE 6

| PTH 1-34 Fusion Protein Plasmids | | |
|---|---|---|
| Plasmid Number | N-terminal Fusion Partner | Fusion Protein |
| p708-004 | DnaJ-like protein | DnaJ-like protein-PTH |
| p708-005 | FklB | FklB-PTH |
| p708-006 | FrnE | FrnE-PTH |

DNA Sequencing: The presence of the cloned fragments in the fusion protein expression plasmids were confirmed by DNA sequencing using a BigDye® Terminator v3.1 Cycle Sequencing Kit (Applied Biosystems, 4337455). The DNA sequencing reactions, containing 50 fmol of plasmid DNA to be analyzed, were prepared by mixing 1 μL of sequencing premix, 0.5 μL of 100 μM primer stock solutions, 3.5 μL of sequencing buffer, and water added to a final volume of 20 μL. The results were assembled and analyzed using the Sequencher™ software (Gene Codes).

Growth and Expression in 96-Well Format (HTP): The fusion protein expression plasmids were transformed into *P. fluorescens* host strains in an array format. The transformation reaction was initiated by mixing 35 μL of *P. fluorescens* competent cells and a 10 μL, volume of plasmid DNA (2.5 ng). A 25 μL, aliquot of the mixture was transferred to a 96-multi-well Nucleovette® plate (Lonza). Electroporation was carried out using the Nucleofector™ 96-well Shuttle™ system (Lonza AG), and the electroporated cells were subsequently transferred to a fresh 96-well deep well plate, containing 500 μL M9 salts supplemented with 1% glucose medium, and trace elements. The plates were incubated at at 30° C. with shaking for 48 hours, to generate seed cultures.

Ten μL aliquots of the seed cultures were transferred in duplicate into 96-well deep well plates. Each well contained 500ᵋ of HTP-YE medium (Teknova), supplemented with trace elements and 5% glycerol. The seed cultures, plated in the glycerol supplemented HTP media, were incubated for 24 hours, in a shaker, at 30° C. Isopropyl-β-D-1-thiogalactopyranoside (IPTG) was added to each well at a final concentration of 0.3 mM to induce expression of the PTH 1-34 fusion proteins. For strains containing folding modulator over-expressing plasmids (see Table 4), IPTG was supplemented with mannitol (Sigma, M1902) at a final concentration of 1% to induce the expression of the folding modulators. In addition, 0.01 μL of a 250 unit/4 stock Benzonase (Novagen, 70746-3) was added per well at the time of induction to reduce the potential for culture viscosity. After 24 hours of induction, cell density was calculated by measuring the optical density at 600 nm ($OD_{600}$). The cells were subsequently harvested, diluted 1:3 with 1× Phosphate Buffered Saline (PBS) to a final volume of 400 μL and frozen for later processing.

Soluble Lysate Sample Preparation for Analytical Characterization: The harvested cell samples were diluted and lysed by sonication with a Cell Lysis Automated Sonication System (CLASS, Scinomix) using a 24 probe tip horn. The lysates were centrifuged at 5,500×g for 15 minutes at 8° C. The supernatant was collected and labeled as the soluble fraction. The pellets were collected, resuspended in 400 µL of 1×PBS pH 7.4 by another round of sonication, and labeled as the insoluble fraction.

SDS-CGE Analysis: The soluble and insoluble fractions were analyzed by HTP microchip SDS capillary gel electrophoresis using a LabChip GXII instrument (Caliper LifeSciences) with a HT Protein Express v2 chip and corresponding reagents (part numbers 760499 and 760328, respectively, Caliper LifeSciences). Samples were prepared following the manufacturer's protocol (Protein User Guide Document No. 450589, Rev. 3). Briefly, 4 µL aliquots of either the soluble or the insoluble fraction samples was mixed with 14 µL of buffer, with or without dithiothreitol (DTT) reducing agent in 96-well polypropylene conical well PCR plates heated at 95° C. for 5 minutes, and diluted with 70 µL deionized water. Lysates from null host strains, which were not transformed with fusion protein expression plasmid, were run as control in parallel with test samples, and quantified using the system internal standard.

Shake Flask Expression: Seed cultures for each of the fusion protein expression strains being evaluated were grown in M9 Glucose (Teknova) to generate intermediate cultures, and a 5 mL volume of each intermediate culture was used to inoculate each of four 1 Liter baffled bottom flasks containing 250 mL HTP medium (Teknova 3H1129). Following 24 hours of growth at 30° C., the cultures were induced with 0.3 mM IPTG and 1% mannitol, and incubated for an additional 24 hours at 30° C. The shake flask broths were then centrifuged to harvest cells and the harvested cell paste was frozen for future use.

Mechanical Release and Purification: Frozen cell pastes, at quantities of 5 grams or 10 grams, were thawed and resuspended in 3×PBS, 5% glycerol, 50 mM imidazole pH 7.4, to prepare final volumes of 50 mL or 100 mL, respectively. The suspensions were subsequently homogenized in two passes through a microfluidizer (Microfluidics, Inc., model M 110Y) at 15,000 psi. Lysates were centrifuged at 12,000×g for 30 minutes and filtered through a Sartorius Sartobran 150 (0.45/0.2 µm) filter capsule.

Chromatography: Fast protein liquid chromatography (FPLC) operations were performed using ÄKTA explorer 100 chromatography systems (GE Healthcare) equipped with Frac-950 fraction collectors. The soluble fraction samples, prepared from HTP expression broths, were loaded onto 5 mL HisTrap FF columns (GE Healthcare, part number 17-5248-02) pre-equilibrated with 3×PBS, 5% glycerol, 50 mM imidazole pH 7.4. The columns were washed with 4 column volumes of equilibration buffer, and the fusion proteins were eluted, from the HisTrap columns, using 10 column volumes of elution buffer, applying a linear gradient of imidazole from 50 mM to 200 mM. The entire process was run at 100 cm/h, which was equivalent to a 1.5 minute residence time. The purification fractions were analyzed by SDS-CGE, using the SDS-CGE analysis methods described above.

Enterokinase Cleavage: A first set of samples was prepared by dialyzing the purification fractions containing the fusion protein overnight at 4° C., against 1×PBS pH 7.4 supplemented with 2 mM CaCl$_2$ using 7000 molecular weight cutoff (MWCO) Slide-A-Lyzer cassettes (Pierce). The dialyzed samples were maintained at about 1 mg/mL concentration. A second set of samples was prepared by 2× dilution of the purification fractions containing the fusion proteins, with water, and stored in a buffer comprising 1.5×PBS, 2.5% glycerol, and ~30-70 mM imidazole at a concentration of 0.5 mg/mL. A stock solution of porcine enterokinase (Sigma E0632-1.5KU) was added to the samples either at 5× or 20× dilution (corresponding to enterokinase concentrations of 40 µg/mL and 10 µg/mL, respectively). CaCl$_2$ was also added to a 2 mM final concentration, and the reaction mixture was incubated overnight at room temperature.

Liquid Chromatography-Mass Spectrometry: A Q-ToF$_{micro}$ mass spectrometer (Waters) with an electro spray interface (ESI) coupled to an Agilent 1100 HPLC equipped with an auto sampler, column heater, and UV detector, was used for Liquid Chromatography-Mass Spectrometry (LC-MS) analysis. A CN-reversed phase column, which had an internal diameter of 2.1 mm ID, length of 150 mm, particle size of 5 µm, and pore size of 300 Å (Agilent, catalog number 883750-905) was used with a guard column (Agilent, catalog number 820950-923). The HPLC run was carried out at a temperature of 50° C. and the flowrate was maintained at 2° C. The HPLC buffers were 0.1% formic acid (mobile phase A) and 90% acetonitrile with 0.1% formic acid (mobile phase B). Approximately 4 µg of fusion protein sample was loaded onto the HPLC column. The HPLC running conditions were set at 95% mobile phase A while loading the sample. The fusion protein was eluted using a reversed-phase gradient exemplified in Table 7.

TABLE 7

Reverse Phase Gradient for Mass Spectrometric Analysis of Purified Protein Sample

| Time | % Mobile Phase A | % Mobile Phase B | Flow (ml/min) | Curve |
|---|---|---|---|---|
| 0.0 | 95.0 | 5 | 0.2 | — |
| 10.0 | 90 | 10 | 0.2 | Linear |
| 50.0 | 35 | 65 | 0.2 | Linear |
| 52.0 | 0 | 100.0 | 0.2 | Linear |
| 57.0 | 0 | 100.0 | 0.2 | Hold |
| 57.1 | 95.0 | 5.0 | 0.2 | Step |
| 65.0 | 95.0 | 5.0 | 0.2 | Hold |

UV absorbance spectra were collected from 180 nm to 500 nm, prior to MS. The ESI-MS source was used in positive mode at 2.5 kV. MS scans were carried out using a range of 600-2600 m/z at 2 scans per second. MS and UV data were analyzed using MassLynx software (Waters). UV chromatograms and MS total ion current (TIC) chromatograms were generated. The MS spectra of the target peaks were summed. These spectra were deconvoluted using MaxEnt 1 (Waters) scanning for a molecular weight range of 2,800-6,000 (for PTH 1-34, which has a theoretical molecular weight of 4118 kDa, and higher window for fusion proteins or N-terminal fusion partners), resolution of 1 Da per channel, and Gaussian width of 0.25 Da.

Results

Design of PTH 1-34 gene fusion fragments: To facilitate high level expression of PTH 1-34 fusion proteins, three folding modulators, DnaJ-like protein (SEQ ID NO: 2, cytoplasmic chaperone), FrnE (SEQ ID NO: 3, cytoplasmic PPIase) and FklB (SEQ ID NO: 4, periplasmic PPIase), from P. fluorescens, were selected based on high soluble expression, molecular weight less than 25 kDa and an isoelectric point (pI) significantly different than that of PTH 1-34 (which has a pI of 8.52). Characteristics of the folding modulators are shown in Table 8. As shown in Table 8, the pIs of DnaJ-like protein, FklB and FrnE, between 4.6 and 4.8, were well separated from that of PTH 1-34. This allowed for ready separation by ion exchange. To further aid the purification of the fusion proteins, a hexa-histidine tag (SEQ ID NO: 242) was included in the linker. The linker also contained an enterokinase cleavage site (DDDDK (SEQ ID NO: 13)) to facilitate separation of the N-terminal fusion partner from the desired PTH 1-34 polypeptide of interest. The amino acid sequences for the PTH 1-34 fusion proteins are shown in FIG. 2A (DnaJ-like protein-PTH, SEQ ID NO: 45), 2B (FklB-PTH, SEQ ID NO: 46), and 2C (FrnE-PTH, SEQ ID NO: 47). The amino acids corresponding to the linker are underlined and those corresponding to PTH 1-34 are italicized in FIGS. 2A, B, and C.

Figure 3:
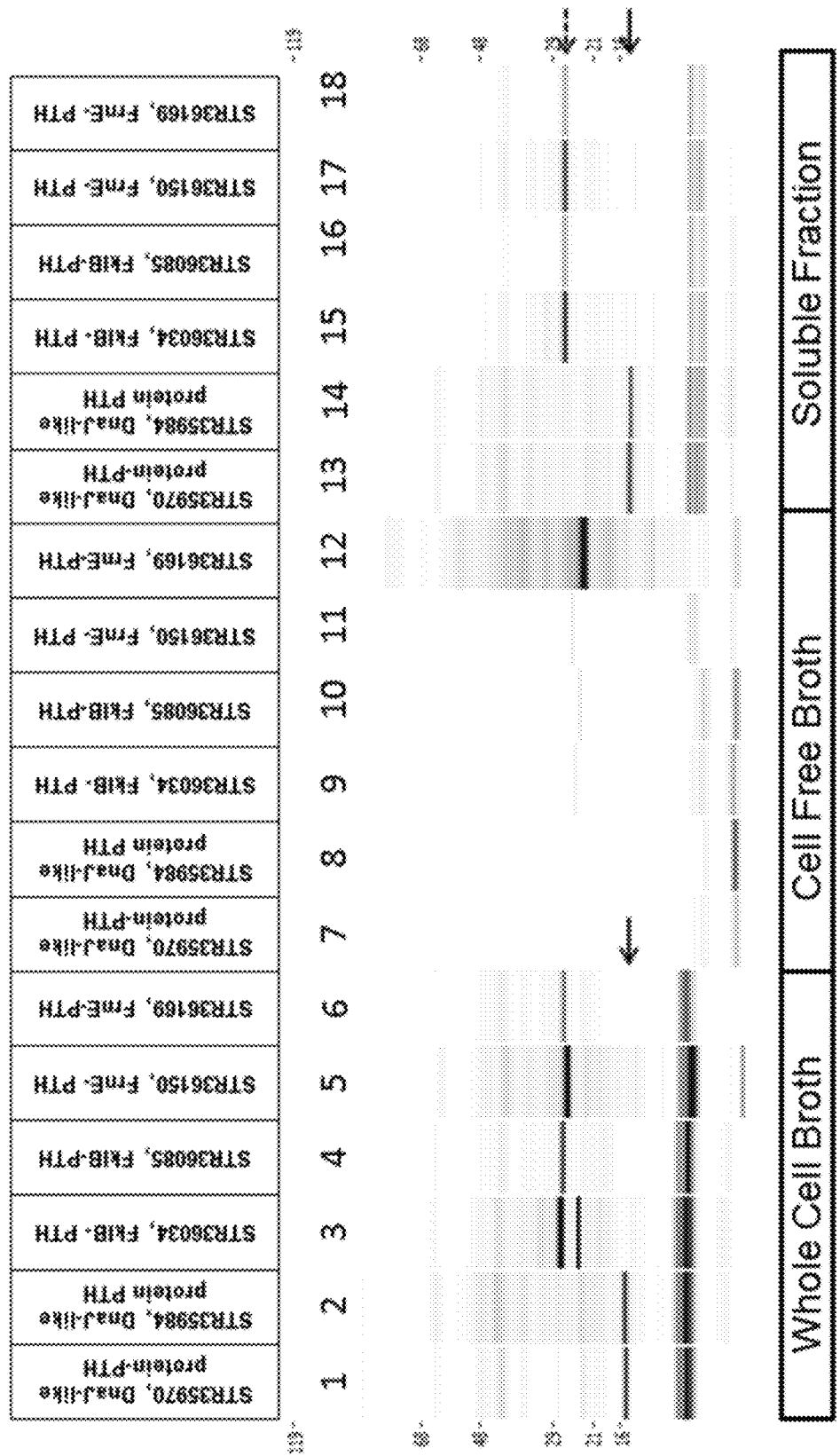
FIG. 3. SDS-CGE Analysis of Shake Flask Expression Samples. Samples are shown in three sets: whole cell broth (lanes 1-6); cell free broth (lanes 7-12); and soluble fraction (lanes 13-18), as indicated at the bottom of the figure. Molecular weight markers are shown on each side of the image (68, 48, 29, 21, 16 kD, from top to bottom). The lanes in each of the three sets represent, from left to right: DNAJ-like protein-PTH 1-34 fusion (STR35970); DNAJ-like protein-PTH 1-34 fusion (STR35984); FklB-PTH 1-34 fusion (STR36034); FklB-PTH 1-34 fusion (STR36085); FrnE-PTH 1-34 fusion (STR36150); and FrnE-PTH 1-34 fusion (STR36169), as indicated above the lanes. The DnaJ-like-PTH fusion protein bands are marked by a solid arrow and FklB-PTH and FrnE-PTH fusion protein bands are marked by a dashed arrow.

Shake Flask Expression: Each of the six strains were grown and induced at 250 mL culture scale (4×250 mL cultures each) as described in the Materials and Methods (Shake Flask Expression) section. Following induction, samples from each culture (whole cell broth, WCB) were retained; a subset of the samples were diluted 3× with PBS, sonicated and centrifuged to produce soluble and insoluble fractions. The remainder of each culture was centrifuged to generate cell paste and a supernatant cell free broth (CFB). The cell paste was retained for purification. The WCB, CFB, and soluble fractions were evaluated by reduced SDS-CGE (FIG. 3).

TABLE 8

Physicochemical Properties of Selected N-terminal Fusion Partners

| Fusion Partner | Molecular Weight (Da) | Molar equivalent of 1 Pg (pMoles) | Molar Extinction Coefficient | A[280 nm] for 1 mg/mL (AU—absorbance unit) | Isoelectric Point (pI) | Charge at pH 7 |
|---|---|---|---|---|---|---|
| DnaJ-like protein (79 aa) | 9176.27 Da | 108.977 | 13370 | 1.46 | 4.83 | −5.04 |
| FklB (206 aa) | 21770.89 | 45.933 | 17780 | 1.22 | 4.71 | −9.94 |
| FmE (218 aa) | 23945 | 41.762 | 24990 | 1.04 | 4.62 | −14.77 |

Construction of PTH Fusion Expression Vectors and HTP Expression: Synthetic gene fragments encoding each of the three PTH fusion proteins listed in Table 6 were synthesized by DNA 2.0. The synthetic gene fragments were digested with SpeI and XhoI and ligated to pDOW1169 (digested with the same enzymes), generating the expression plasmids p708-004, p708-005 and p708-006. Following confirmation of the inserts, the plasmids were used to electroporate an array of *P. fluorescens* host strains and generate the expression strains listed in Table 4. The resulting transformed strains were grown and induced with IPTG and mannitol following the procedures described in the Materials and Methods. After induction the cells were harvested, sonicated, and centrifuged to separate soluble and insoluble fractions. Soluble and insoluble fractions were collected. Both the soluble and insoluble fractions were analyzed using reduced SDS-CGE to measure PTH 1-34 fusion protein expression levels. A total of six strains, including two high HTP expressing strains for each of the three PTH 1-34 fusion proteins, were selected for shake flask expression. The strains screened using the shake flask expression method are listed in Table 9.

Fusion proteins (bands corresponding to a molecular weight of about 14 kDa for the DnaJ-like protein-PTH fusion, and about 26 kDa for the FrnE-PTH and FklB-PTH fusions) were observed in the WCB and in the soluble fractions; no fusion protein was observed in the CFB. The shake flask expression titers for STR35984, STR36085, and STR36169 were 50% of the HTP expression titer, whereas the shake flask expression titers for the strains STR35970, STR36034, and STR36150 were 70-100% of that observed at HTP scale. The HTP and shake flask expression titers are listed in Table 9.

TABLE 9

HTP and Shake Flask Expression Titer of Selected PTH 1-34 Fusion Protein Expression Strains

| Strain Barcode | Plasmid | Host Cell | Fusion Partner | Size (kDa) | HTP Expression Titer (g/L) | Shake Flask Expression Titer (g/L) |
|---|---|---|---|---|---|---|
| STR35970 | p708-004 | DC508-1 | DnaJ-like protein | 14 | 0.552 | 0.382 |
| STR35984 | p708-004 | DC992.1-1 | DnaJ-like protein | 14 | 0.490 | 0.266 |
| STR36034 | p708-005 | DC1106-1 | FklB | 26 | 0.672 | 0.573 |
| STR36085 | p708-005 | PF1326.1-1 | FklB | 26 | 0.670 | 0.233 |
| STR36150 | p708-006 | PF1219.9-1 | FmE | 26 | 0.577 | 0.651 |
| STR36169 | p708-006 | PF1331-1 | FmE | 26 | 0.551 | 0.284 |

IMAC Purification of PTH Fusion Protein Expression Strains Grown in HTP and Shake Flask Scales, to Isolate PTH Fusion Proteins: The cell pastes of the six strains were subjected to mechanical lysis and IMAC purification. Each purification run resulted in highly enriched fractions. Peak fractions derived from the DnaJ-like protein-PTH expression strain STR35970 were 60-80% pure, those from the FklB-PTH expression strain STR36034 were 60-90% pure and those from the FrnE-PTH expression strain STR36150 were 90-95% pure.

Figure 4:
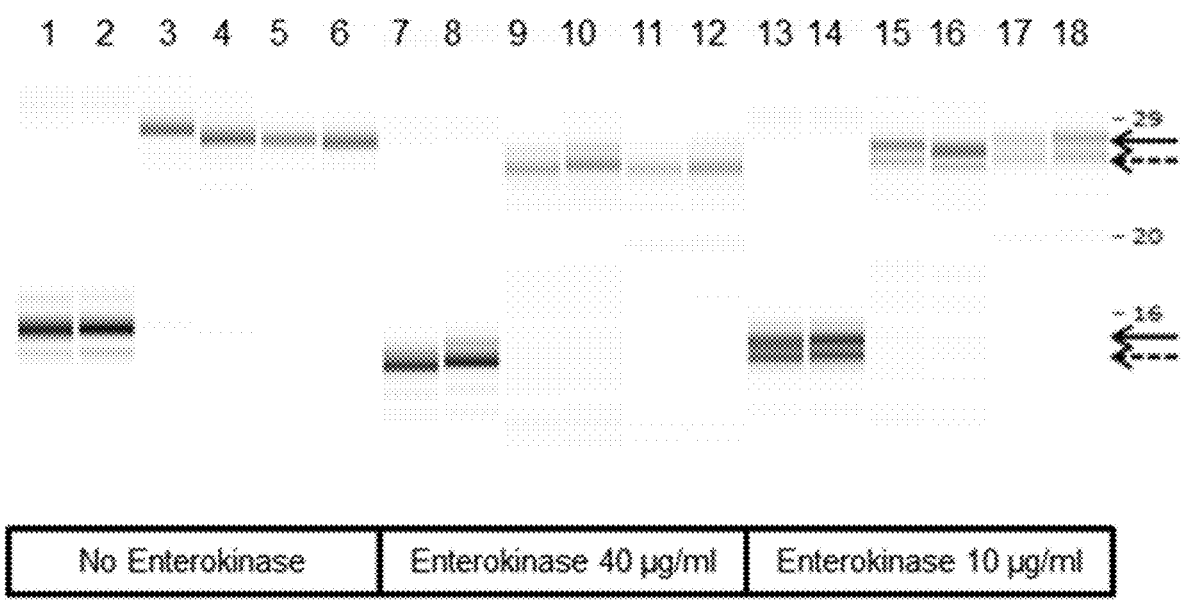
FIG. 4. Enterokinase Cleavage of Purified Recombinant Fusion Proteins. Samples are shown in three sets: no enterokinase treatment (lanes 1-6); enterokinase treatment 40 µg/ml (lanes 7-12); and enterokinase treatment 10 µg/ml (lanes 13-18). The lanes in each of the three sets represent, from left to right: DNAJ-like protein-PTH 1-34 fusion (STR35970); DNAJ-like protein-PTH 1-34 fusion (STR35984); FklB-PTH 1-34 fusion (STR36034); FklB-PTH 1-34 fusion (STR36085); FrnE-PTH 1-34 fusion (STR36150); and FrnE-PTH 1-34 fusion (STR36169). The migration of DnaJ-like fusion protein is indicated by the solid arrow in the lower pair of arrows. The migration of cleaved DnaJ-like-protein N-terminal fusion partners are indicated by the dashed arrow in the lower pair of arrows. The migration of FklB and FrnE fusion proteins are indicated by the solid arrow in the upper pair of arrows. The migration of FklB and FrnE N-terminal fusion partners are indicated by the dashed arrow in the upper pair of arrows. Molecular weight markers are shown on the right side of the image (29, 20, and 16 kD, from top to bottom).

Enterokinase Cleavage of the PTH Fusion Proteins: The highly pure, concentrated fractions from IMAC purification runs, containing the fusion proteins, were selected for enterokinase cleavage reaction to confirm that the N-terminal fusion partner could be cleaved from the PTH 1-34. Porcine-derived enterokinase was used for the study. Since the 4 kDa PTH 1-34 polypeptide of interest was not readily detectable by SDS-CGE, a molecular weight shift of the total fusion protein, from 14 kDa to 10 kDa for DnaJ-like protein-PTH fusion protein, and 26 kDa to 22 kDa for the FklB-PTH and FrnE-PTH fusion proteins, were accepted as evidence of enterokinase cleavage. The samples were treated with either 40 μg/mL or 10 μg/mL enterokinase overnight. Following enterokinase treatment, the samples were analyzed by SDS-CGE. As shown in FIG. 4 by the shift in MW compared with uncleaved samples (lanes 1-6), complete cleavage of the fusion partner from PTH 1-34 was observed when 40 μg/mL enterokinase was used (lanes 7-12) and partial cleavage was observed when 10 μg/mL enterokinase was used (lanes 13-18).

Figure 5:
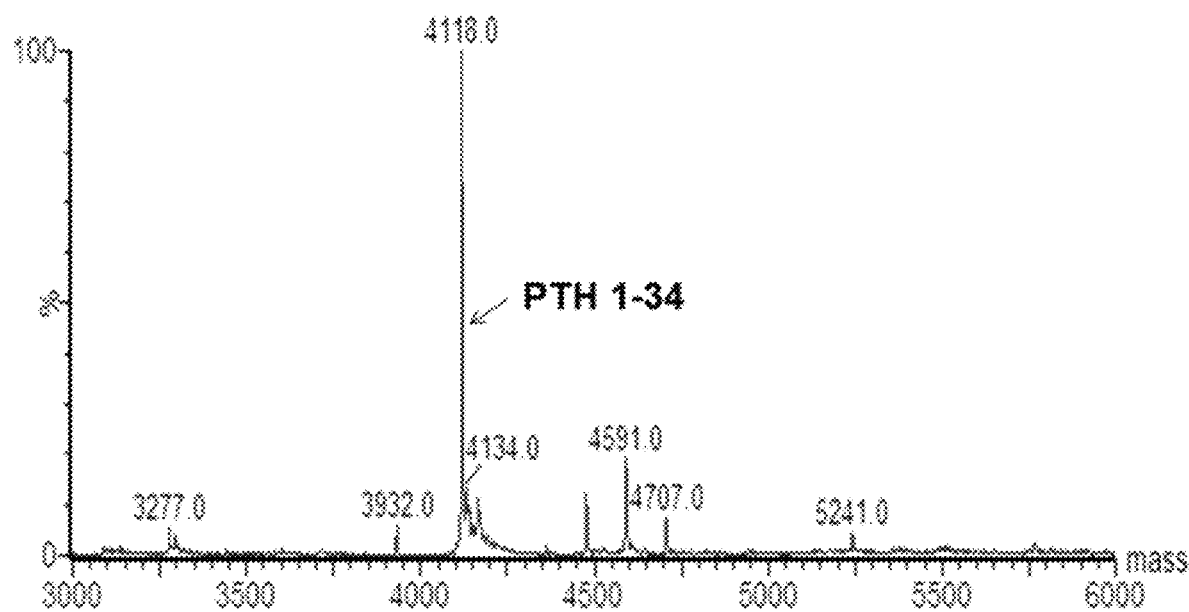
FIG. 5. Intact Mass Analysis of Enterokinase Cleavage Products. Shown is the deconvoluted mass spectra for DnaJ-like protein-PTH 1-34 fusion protein, purified from expression strain STR35970, digested with enterokinase for 1 hour. The peak corresponding to PTH 1-34 is indicated by a solid arrow.

Intact Mass Analysis of PTH Fusion Proteins after Enterokinase Cleavage: The DnaJ-like protein-PTH fusion protein, purified from strain STR35970, was used for additional enterokinase cleavage experiments and intact mass analysis. A purification fraction, containing the DnaJ-like protein-PTH fusion protein, derived from STR35970, was incubated with porcine enterokinase for 1 to 3 hours at room temperature followed by immediate intact mass analysis. As shown in FIG. 5, the C-terminal PTH 1-34 polypeptide was detected. Details of the intact mass analysis are summarized in Table 10. In addition to full length PTH 1-34, fragments corresponding to N-terminal deletions of 5 or 8 amino acids also were detected. The proteolysis observed was likely due to host cell protein contaminants or contaminants in the porcine enterokinase preparation. Recombinant enterokinase also can be used to evaluate cleavage, via similar steps. Observed and theoretical molecular weights (MW) are indicated in Table 10 for the major species detected by intact mass analysis. The retention time for the uncleaved fusion protein was about 33 minutes, compared to an average retention time of 27 minutes for the fusion proteins subjected to enterokinase cleavage for 1 to 3 hours.

Example II. Large-Scale Fermentation and Expression of PTH 1-34 Fusion Proteins

The PTH 1-34 fusion proteins described in Example I also were evaluated for large-scale expression in *P. fluorescens*, to identify a highly productive expression strain for the large-scale manufacture of PTH 1-34. The *P. fluorescens* strains screened in this study were the DnaJ-like protein-PTH fusion expression strains STR35970, STR35984, STR35949, STR36005, STR35985, FklB-PTH fusion protein expression strains, STR36034, STR36085, STR36098, and FrnE-PTH fusion protein expression strains, STR36150, STR36169, listed in Tables 11 and 12.

TABLE 11

DnaJ-like Protein-PTH Fusion Expression Strains for Large-scale Fermentation

| Strain | Plasmid | Host |
|---|---|---|
| STR35949 | p708-004 | DC1084 |
| STR35970 | p708-004 | DC508 |
| STR35984 | p708-004 | DC992.1 |
| STR35985 | p708-004 | PF1201.9 |
| STR36005 | p708-004 | PF1326.1 |

TABLE 12

FrnE-PTH and FklB-PTH Fusion Expression Strains for Large-scale Fermentation

| Strain | Plasmid | Host |
|---|---|---|
| STR36034 | p708-005 | DC1106 |
| STR36085 | p708-005 | PF1326.1 |
| STR36098 | p708-005 | PF1345.6 |
| STR36150 | p708-006 | PF1219.9 |
| STR36169 | p708-006 | PF1331 |

Materials and Methods

MBR Fermentation: Shake flasks containing medium supplemented with yeast extract were inoculated with a frozen culture stock of the selected strain. For the mini bioreactors (MBR), 250 mL shake flasks containing 50 mL

TABLE 10

| Intact Mass Results | | | |
|---|---|---|---|
| | | DnaJ-like protein-PTH | PTH 1-34 |
| Theoretical MW: | | 15207.95 | 4117.8 |
| Sample Name | Major Species, Observed MW | Observed minus Theoretical MW | Observed minus Theoretical MW |
| DnaJ-like protein-PTH fraction (about 3 hrs cleavage reaction) | 4118 | | 0.2 |
| DnaJ-like protein -PTH fraction (about 1 hr cleavage) | 4118 | | 0.2 |
| DnaJ-like protein -PTH fraction (about 2 hrs cleavage) | 4119 | | 1.2 |
| DnaJ-like protein -PTH fraction (no cleavage reaction) | 15207 | −1.0 | |
| 140116 PTH (Reagent Proteins Cat # RAB-391) | 4117 | | −0.8 | of chemically defined medium supplemented with yeast extract were used. Shake flask cultures were incubated for 16 to 24 hours with shaking at 30° C. Aliquots from the shake flask cultures were used to seed the MBR (Pall Micro-24). The MBR cultures were operated at a volume of 4 mL in each 10 mL well of the disposable minibioreactor cassette under controlled conditions for pH, temperature, and dissolved oxygen. Cultures were induced with IPTG when the initial amount of glycerol contained in the medium was depleted. The fermentation was continued for 16 hours, and samples were collected and frozen for analysis.

CBR Fermentation: The inocula for the 1 Liter CBR (conventional bioreactor) fermentor cultures were generated by inoculating a shake flask, containing 600 mL of chemically defined medium supplemented with yeast extract and glycerol, with a frozen culture stock of the selected strain. After 16 to 24 hours incubation, with shaking, at 32° C., equal aliquots from each shake flask culture were then aseptically transferred to each of an 8 unit multiplex fermentation system comprising 2 liter bioreactors (1 liter working volume). The fed-batch high cell density fermentation process consisted of a growth phase followed by an induction phase, initiated by the addition of IPTG once the culture reached the target optical density.

The induction phase of the fermentation was allowed to proceed for 8 hours, and analytical samples were withdrawn from the fermentor to determine cell density at 575 nm ($OD_{575}$). The analytical samples were frozen for subsequent analyses to determine the level of fusion protein expression. After the completion of 8 hours of induction, the entire fermentation broth (approximately 0.8 L broth per 2 L bioreactor) of each vessel was harvested by centrifugation at 15,900×g for 60 to 90 minutes. The cell paste and supernatant were separated and the paste was frozen at −80° C.

Mechanical Homogenization and Purification: Frozen cell paste (20 g), obtained from the CBR fermentation process, as described above, was thawed and resuspended in 20 mM sodium phosphate, 5% glycerol, 500 mM sodium chloride, 20 mM imidazole pH 7.4. The final volume of the suspension was adjusted to ensure that the concentration of solids was 20%. The material was then homogenized in two passes through a microfluidizer (Microfluidics, Inc., model M 110Y) at 15,000 psi. Lysates were centrifuged at 12,000×g for 30 minutes and filtered through a Sartorius Sartobran 150 (0.45/0.2 μm) filter capsule.

Chromatography: Fast protein liquid chromatography (FPLC) operations were performed using ÄKTA explorer 100 chromatography systems (GE Healthcare) equipped with Frac-950 fraction collectors. Samples were loaded onto HisTrap FF, 10 mL columns (two 5 mL HisTrap FF cartridges [GE Healthcare, part number 17-5255-01] connected in series), washed, and eluted using a 10 column volume linear gradient of an elution buffer, by varying the imidazole concentration from 0 mM to 200 mM. Two milliliter volume fractions were collected.

Immobilized metal ion affinity chromatography (IMAC) purification was performed using Nickel IMAC (GE Healthcare, part number 17-5318-01). The analytical samples collected after CBR fermentation were separated into soluble and insoluble fractions. A 600 μL aliquot of the soluble fraction was incubated with 100 μL IMAC resin for one hour on a rocker at room temperature, and centrifuged for one minute at 12,000×g to pellet the resin. The supernatant was removed and labeled as flow-through. The resin was then washed thrice with 1 mL of wash buffer containing 20 mM Na phosphate pH 7.3, 500 mM NaCl, 5% glycerol, and 20 mM imidazole. After the third wash, the resin was resuspended in 200 μL of the wash buffer containing 400 mM imidazole and centrifuged. The supernatant was collected and labeled as elution.

Enterokinase Cleavage: PTH 1-34 fusion protein purification fractions were concentrated and resuspended in a buffer containing 20 mM Tris pH 7.4, 50 mM NaCl, and 2 mM $CaCl_2$. Two units of enterokinase (Novagen cat #69066-3, batch D00155747) were added to 100 μg protein in a 100 μL reaction. The mixture of fusion protein purification fraction and enterokinase were incubated for either one hour, or overnight at room temperature. Control reactions with no enterokinase also were incubated for one hour or overnight, at room temperature. The enzyme reactions were stopped by the addition of complete protease inhibitor cocktail containing 4-benzenesulfonyl fluoride hydrochloride (AEBSF, Sigma cat #P8465).

Results

Fermentation Assessment of DnaJ-like Protein-PTH, FklB-PTH and FrnE-PTH Fusion Expression Strains: The five top expressing DnaJ-like protein-PTH fusion strains, three FklB-PTH expression strains, and two FrnE-PTH expression strains, listed Tables 9 and 10, each were evaluated for fermentation, first in minibioreactors (MBR), and then in conventional bioreactors (CBR).

The soluble fraction from each MBR fermentation of the DnaJ-like protein-PTH fusion expression strains were analyzed by SDS-CGE, following the protocol described in the Materials and Methods section of Example I. The MBR fermentation yields for the DnaJ-like protein-PTH fusion expression strains are listed in Table 13. Overall, the strain with the highest MBR expression level of the soluble fusion protein was STR35949, at 2.1 g/L.

TABLE 13

Soluble Fusion Protein Yield for the DnaJ-like-hPTH Fusion Strains Tested in MBR Fermentors

| Strain | Soluble Fusion Protein Yields |
|---|---|
| STR35949 | 0.6-2.1 g/L |
| STR36005 | 1.5 g/L |
| STR35970 | 1.1 g/L |
| STR35985 | 0.9 g/L |

The DnaJ-like protein PTH fusion strains were assessed for fermentation at the 1 L scale, in conventional bioreactors (CBR). CBR Expression levels of the DnaJ-like protein-PTH fusion protein strains were comparable to the MBR levels, as shown in Table 14. The expression levels were higher at the 8-hour post-induction time points than at the 24-hour post-induction time points.

TABLE 14

Soluble Fusion Protein Yield for the DnaJ-like-hPTH 1-34 Fusion Strains, Evaluated in CBR Fermentors, at 8 (I8) and 24 (I24) Hours Post-induction

| Strain | Soluble Fusion Protein Yields- (I8) | Soluble Fusion Protein Yields- (I24) |
|---|---|---|
| STR35949 | 1.5-2.4 g/L | 1.1-1.9 g/L |
| STR35970 | 2.0 g/L | 0.9 g/L |
| STR35985 | 1.7-2.4 g/L | 0.3-0.6 g/L |
| STR36005 | 2.1 g/L | 1.4 g/L |

The soluble fractions from the MBR fermentations for the FklB-PTH and FrnE-PTH fusion expression strains were analyzed by SDS-CGE under reducing conditions (results shown in Table 15).

TABLE 15

Soluble Fusion Protein Yields for the FklB-hPTH 1-34 and FrnE-hPTH 1-34 Fusion Strains Evaluated in MBR Fermentors

| Strain | Soluble Fusion Protein Yields |
|---|---|
| STR36085 | 6.4 g/L |
| STR36034 | 3.4-5.8 g/L |
| STR36098 | 3.4-4.7 g/L |
| STR36150 | 0.8-2.2 g/L |

Overall, the strain with the highest expression level for the soluble fusion protein was STR36034 at 6.4 g/L. The same strains also were assessed for large scale fermentation in conventional bioreactors (CBR) (results shown in Table 16). The strain with the maximum yield, in CBR fermentation, was STR36034, expressing the FklB-PTH fusion protein at 6.7 g/L, after an induction period of 24 hours.

TABLE 16

Soluble Fusion Protein Yield for the FlkB-hPTH 1-34 and FrnE-hPTH 1-34 Fusion Strains Evaluated in CBR Fermentors, at 24 (I24) Hours Post-induction

| Strain | Soluble Fusion Protein Yields (I24) |
|---|---|
| STR36034 | 4.9-6.7 g/L |
| STR36085 | 4.6-4.9 g/L |
| STR36098 | 2.9-5.2 g/L |
| STR36150 | 2.6-3.8 g/L |

Evaluation of Purification and Enterokinase cleavage of DnaJ-like Protein-PTH and FklB-PTH fusion proteins: The cell paste obtained after induction of expression and growth in DnaJ-like protein-PTH fusion expression strain STR36005 was subjected to mechanical lysis and IMAC purification as described in the Materials and Methods. Each purification run resulted in highly enriched fractions. The purity of the peak fractions was 90% or higher.

Figure 6:
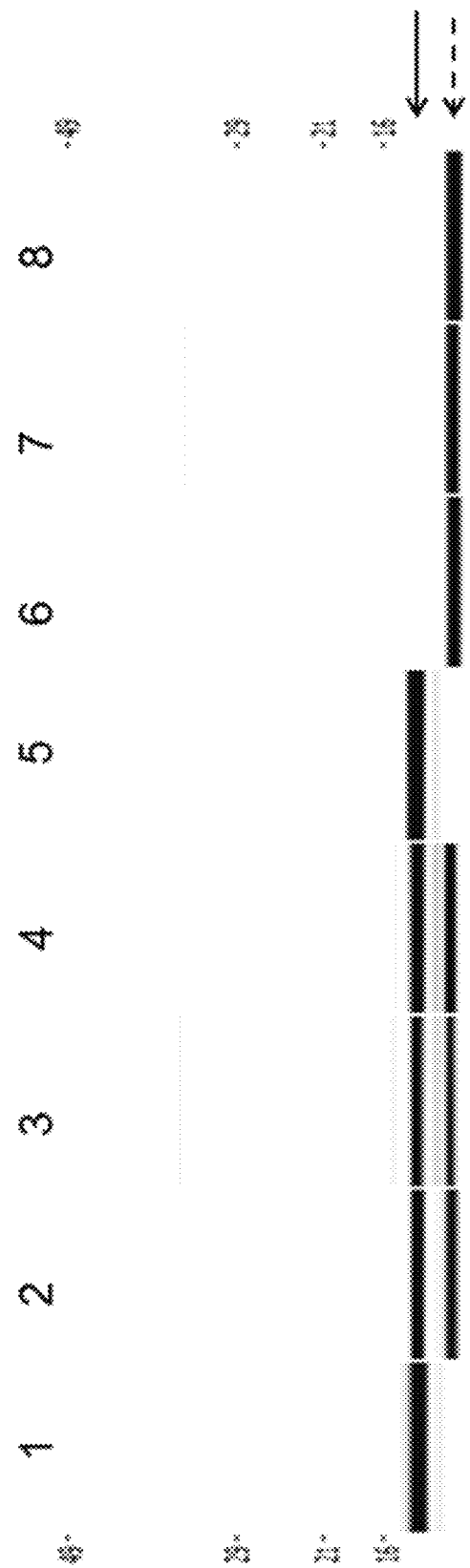
FIG. 6. Enterokinase Cleavage of DnaJ-like protein-PTH 1-34 Fusion Protein Purification Fractions. The DnaJ-like protein-PTH fusion protein was purified from expression strain STR36005 following growth in a conventional bioreactor. Purification fractions were incubated with enterokinase for 1 hour (lanes 2-4), 16 hours (lanes 6-8), without enterokinase (control) for 1 hour (lane 1), or without enterokinase (control) for 16 hours (lane 5). The fractions analyzed were as follows: fraction 1 (lanes 1, 2, 5, and 6); fraction 2 (lanes 3 and 7); and fraction 3 (lanes 4 and 8). The full-length DnaJ-like protein-PTH 1-34 recombinant fusion protein bands are indicated by the solid black arrow. The cleaved DnaJ-like protein-PTH 1-34 fusion partner bands are indicated by a dashed arrow. Molecular weight markers are shown on each side of the image (49, 29, 21, and 16 kD, from top to bottom).

Highly pure concentrated fractions of the DnaJ-like protein-PTH fusion protein purified from strain 36005 were used for enterokinase cleavage testing to confirm that the N-terminal fusion partner could be cleaved from the PTH 1-34 polypeptide of interest. Recombinant bovine enterokinase was used for cleavage reactions. Soluble fractions from the analytical scale samples were used for a small scale batch enrichment of the fusion protein using IMAC resin (FIG. 6). After one hour of incubation with enterokinase, partial cleavage of the DnaJ-like protein fusion partner was observed (lanes 2-4). Cleavage was complete after overnight incubation (lanes 6-8).

Figure 7A:
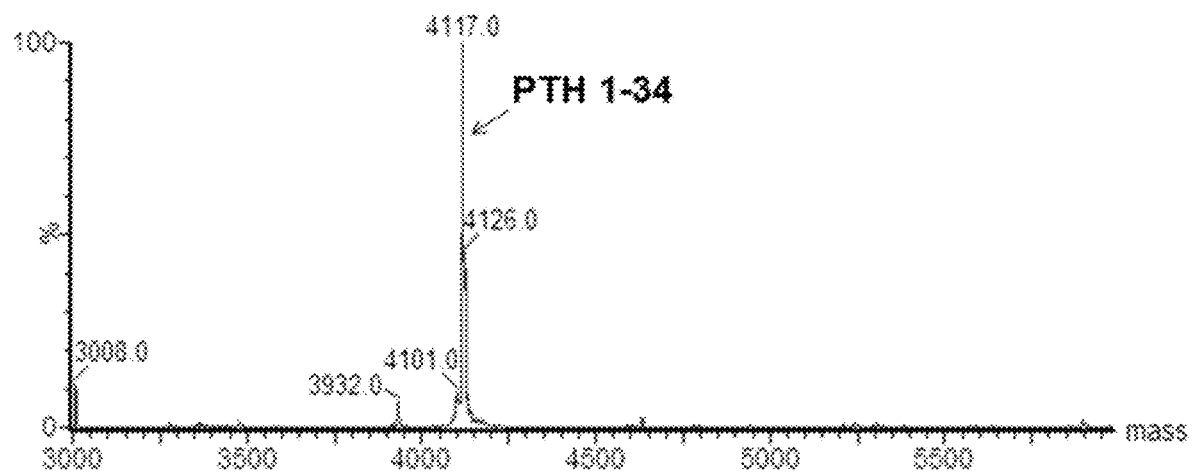
FIGS. 7A to 7C. Intact Mass Analysis of PTH 1-34 enterokinase cleavage products derived from FklB-PTH 1-34 Fusion Proteins. The figures show the deconvoluted mass spectra for FklB-PTH 1-34 fusion protein purification fractions digested with enterokinase. The peaks corresponding to PTH 1-34 are indicated by a solid arrow.
Figure 7B:
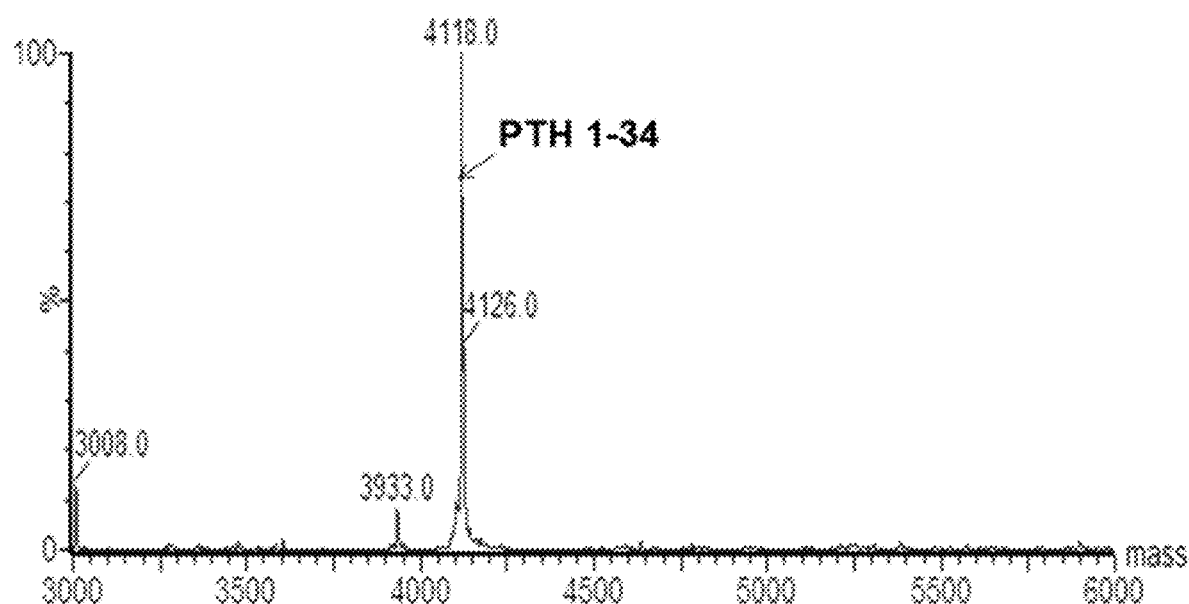
Figure 7C:
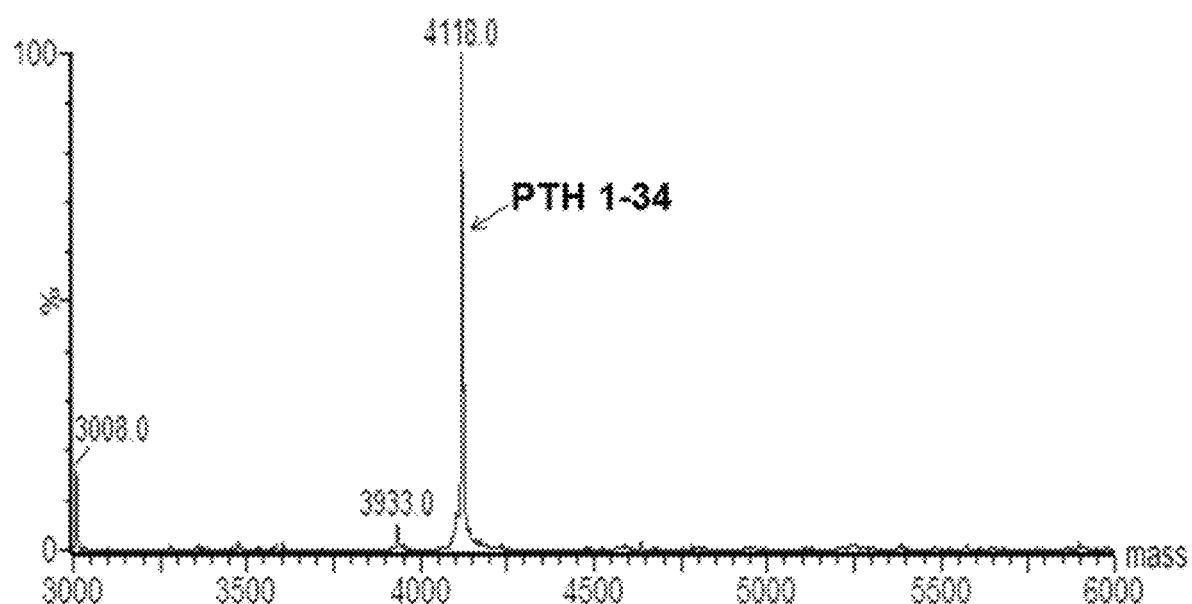

The FklB-PTH fusion strains appeared to be robust at the 1 liter scale. Purification samples were further analyzed to confirm that the fusion protein could be enriched and cleaved with enterokinase. Soluble fractions from the analytical scale samples were used for a small scale batch enrichment of the fusion protein using IMAC resin. One enriched sample for each of the three expression strains, STR36034, STR36085, and STR36098 was treated with enterokinase and subjected to intact mass analysis using methods described in Example I. The PTH 1-34 polypeptide of interest was identified and observed to be of the correct mass, ~4118 Da, for each sample, as shown in FIG. 7.

Example III. Construction of Enterokinase Fusions

DnaJ-like protein, FklB, and FrnE N-terminal fusion partner-Enterokinase fusion proteins were designed and expression constructs generated, for use in expressing recombinant Enterokinase (SEQ ID NO: 31).

Construction of Enterokinase Fusion Expression Plasmids: Enterokinase (EK) fusion coding regions evaluated are listed in Table 17. The gene fragments encoding the fusion proteins were synthesized by DNA2.0. The fragments included SpeI and XhoI restriction enzyme sites, a "Hi" ribosome binding site, an 18 basepair spacer (5'-actagtag-gaggtctaga-3'(SEQ ID NO:58)) added upstream of the coding sequences, and three stop codons.

Standard cloning methods were used to construct expression plasmids. Plasmid DNA containing each enterokinase fusion coding sequence was digested using SpeI and XhoI restriction enzymes, then subcloned into SpeI XhoI digested pDOW1169 expression vector containing the pTac promoter and rrnT1T2 transcriptional terminator. Inserts and vectors were ligated overnight with T4 DNA ligase (Fermentas EL0011), resulting in enterokinase fusion protein expression plasmids. The plasmids were electroporated into competent *P. fluorescens* DC454 host cells. Positive clones were screened for presence of enterokinase fusion protein sequence insert by PCR, using Ptac and Term sequence primers (AccuStart II, PCR SuperMix from Quanta, 95137-500).

TABLE 17

Enterokinase Fusion Proteins

| Gene ID | Fusion Partner | Fusion Protein |
|---|---|---|
| EK1 | DnaJ-like protein (SEQ ID NO: 2) | DnaJ-like protein Enterokinase (SEQ ID NO: 48) |
| EK2 | FklB (SEQ ID NO: 4) | FklB-Enterokinase (SEQ ID NO: 49) |
| EK4 | EcpD (SEQ ID NO: 65) | EcpD-Enterokinase (SEQ ID NO: 50) |
| EK5 | None | Enterokinase SEQ ID NO: 51 |

Example IV. Large-Scale Fermentation of Enterokinase Fusion Proteins (DNAJ-Like, FklB, FrnE N-Term Partners)

The expression strains described in Example III are tested for expression of recombinant protein by HTP analysis, following methods similar to those described in Example I.

Expression strains are selected for fermentation studies based on soluble fusion protein expression levels. The selected strains are grown and induced, and the induced cells are centrifuged, lysed, and centrifuged again as described above for the PTH 1-34 fusion proteins. The resulting insoluble fraction and soluble fractions are extracted using extraction conditions described above, and the EK fusion protein extract supernatants are quantitated using SDS-CGE.

Example V. High Throughput Screening of Strains Expressing Insulin Fusion Proteins This study was conducted to test levels recombinant protein produced by *P. fluorescens* strains expressing proinsulin fusion proteins comprising DNAJ-like protein, EcpD, FklB, FrnE, or a truncation of EcpD, FklB, FrnE as the N-terminal fusion partner.

Materials and Methods

Construction of Proinsulin Expression Vectors: Optimized gene fragments encoding proinsulin (insulin glargine), were synthesized by DNA 2.0 (Menlo Park, Calif.). Gene fragments and proinsulin amino acid sequences encoded by the proinsulin coding sequences contained within the gene fragments are listed in Table 18. Each gene fragment contained peptide A and B coding sequences, and one of four different glargine C peptide sequences: CP-A (MW=9336.94 Da; pI=5.2; 65% of A+B Glargine), CP-B (MW=8806.42 Da; 69% of A+B Glargine), CP-C (MW=8749.32 Da; 69% of A+B Glargine), and CP-D (MW=7292.67 Da; 83% of A+B Glargine). The gene fragments were designed with SapI restriction enzyme sites added upstream and downstream of the proinsulin coding sequences to enable the rapid cloning of the gene fragments into various expression vectors. The gene fragments also included, within the 5' flanking region, either a lysine amino acid codon (AAG) or an arginine amino acid codon (CGA), to facilitate ligation into expression vectors containing an enterokinase cleavage site or a trypsin cleavage site, respectively. In addition, three stop codons (TGA, TAA, TAG) were included within the 3' flanking region of all the gene fragments.

TABLE 18

Proinsulin Gene Fragments and C-peptide Amino Acid Sequences

| Gene Fragment | Nucleotide Sequence | Glargine B - peptide | Glargine C-Peptide | Glargine A-Peptide | Proinsulin Amino Acid Sequence | pI | MW KDa |
|---|---|---|---|---|---|---|---|
| G737-001 | SEQ ID NO: 80 | SEQ ID NO: 93 | CP-A SEQ ID NO: 97 | SEQ ID NO: 92 | SEQ ID NO: 88 | 5.2 | 9.34 |
| G737-002 | SEQ ID NO: 81 | SEQ ID NO: 93 | CP-B SEQ ID NO: 98 | SEQ ID NO: 92 | SEQ ID NO: 89 | 6.07 | 8.81 |
| G737-003 | SEQ ID NO: 82 | SEQ ID NO: 93 | CP-C SEQ ID NO: 99 | SEQ ID NO: 92 | SEQ ID NO: 90 | 5.52 | 8.75 |
| G737-007 | SEQ ID NO: 83 | SEQ ID NO: 93 | CP-D SEQ ID NO: 100 | SEQ ID NO: 92 | SEQ ID NO: 91 | 6.07 | 7.29 |
| G737-009 | SEQ ID NO: 84 | SEQ ID NO: 93 | CP-A SEQ ID NO: 97 | SEQ ID NO: 92 | SEQ ID NO: 88 | 5.2 | 9.34 |
| G737-017 | SEQ ID NO: 85 | SEQ ID NO: 93 | CP-B SEQ ID NO: 98 | SEQ ID NO: 92 | SEQ ID NO: 89 | 6.07 | 8.81 |
| G737-018 | SEQ ID NO: 86 | SEQ ID NO: 93 | CP-C SEQ ID NO: 99 | SEQ ID NO: 92 | SEQ ID NO: 90 | 5.52 | 8.75 |
| G737-031 | SEQ ID NO: 87 | SEQ ID NO: 93 | CP-D SEQ ID NO: 100 | SEQ ID NO: 92 | SEQ ID NO: 91 | 6.07 | 7.29 |

The proinsulin coding sequences were then subcloned into expression vectors containing different fusion partners (Table 19), by ligating of the coding sequences into expression vectors using T4 DNA ligase (New England Biolabs, M0202S). The ligated vectors were electroporated in 96-well format into competent DC454 *P. fluorescens* cells.

TABLE 19

Vectors for Glargine Proinsulin Fusion Protein Expression

| Expression Vector | N-terminal Fusion Partner-Cleavage Site | Amino Acid Sequence (SEQ ID NO) | Nucleic Acid Sequence (SEQ ID NO) | Protein Size (KDa) | pI |
|---|---|---|---|---|---|
| pFNX4401 | DnaJ-like protein-Trypsin | SEQ ID NO: 101 | SEQ ID NO: 202 | 10.67 | 6.03 |
| pFNX4402 | EcpD1-Trypsin | SEQ ID NO: 102 | SEQ ID NO: 203 | 28.52 | 9.15 |
| pFNX4403 | EcpD2-Trypsin | SEQ ID NO: 104 | SEQ ID NO: 204 | 12.25 | 9.78 |
| pFNX4404 | EcpD3-Trypsin | SEQ ID NO: 105 | SEQ ID NO: 205 | 7.04 | 9.70 |
| pFNX4405 | FklB-Trypsin | SEQ ID NO: 106 | SEQ ID NO: 206 | 23.27 | 5.41 |
| pFNX4406 | FklB2-Trypsin | SEQ ID NO: 107 | SEQ ID NO: 207 | 12.07 | 6.04 |
| pFNX4407 | FklB3-Trypsin | SEQ ID NO: 108 | SEQ ID NO: 208 | 6.85 | 6.28 |
| pFNX4408 | FrnE-Trypsin | SEQ ID NO: 109 | SEQ ID NO: 209 | 25.44 | 5.12 |
| pFNX4409 | FrnE2-Trypsin | SEQ ID NO: 110 | SEQ ID NO: 210 | 12.7 | 5.85 |
| pFNX4410 | FrnE3-Trypsin | SEQ ID NO: 111 | SEQ ID NO: 211 | 7.17 | 5.90 |
| pFNX4411 | DnaJ-like protein-EK | SEQ ID NO: 112 | SEQ ID NO: 212 | 11.11 | 5.32 |
| pFNX4412 | EcpD1-EK | SEQ ID NO: 113 | SEQ ID NO: 213 | 28.95 | 7.26 |

TABLE 19-continued

Vectors for Glargine Proinsulin Fusion Protein Expression

| Expression Vector | N-terminal Fusion Partner-Cleavage Site | Amino Acid Sequence (SEQ ID NO) | Nucleic Acid Sequence (SEQ ID NO) | Protein Size (KDa) | pI |
|---|---|---|---|---|---|
| pFNX4413 | EcpD2-EK | SEQ ID NO: 114 | SEQ ID NO: 214 | 12.68 | 8.05 |
| pFNX4414 | EcpD3-EK | SEQ ID NO: 115 | SEQ ID NO: 215 | 7.48 | 7.22 |
| pFNX4415 | FklB-EK | SEQ ID NO: 116 | SEQ ID NO: 216 | 23.70 | 4.99 |
| pFNX4416 | FklB2-EK | SEQ ID NO: 117 | SEQ ID NO: 217 | 12.49 | 5.19 |
| pFNX4417 | FklB3-EK | SEQ ID NO: 118 | SEQ ID NO: 218 | 7.28 | 5.22 |
| pFNX4418 | FrnE-EK | SEQ ID NO: 119 | SEQ ID NO: 219 | 25.88 | 4.84 |
| pFNX4419 | FrnE2-EK | SEQ ID NO: 120 | SEQ ID NO: 220 | 13.13 | 5.17 |
| pFNX4420 | FrnE3-EK | SEQ ID NO: 121 | SEQ ID NO: 221 | 7.60 | 4.99 |

Growth and Expression in 96 Well Format (HTP): The plasmids containing proinsulin coding sequences and the fusion partners were transformed into a *P. fluorescens* DC454 host strain. Twenty-five microliters of competent cells were thawed, transferred into a 96-multi-well Nucleovette® plate (Lonza VHNP-1001) and mixed with the ligation mixture prepared in the previous step. The electroporation was carried out using the Nucleofector™ 96-well Shuttle™ system (Lonza AG) and the transformed cells were then transferred to 96-well deep well plates (seed plates) with 400 µL M9 salts 1% glucose medium and trace elements. The seed plates were incubated at 30° C. with shaking for 48 hours to generate seed cultures.

Ten microliters of seed culture were transferred in duplicate into fresh 96-well deep well plates, each well containing 500 µL of HTP medium (Teknova 3H1129), supplemented with trace elements and 5% glycerol, and incubated at 30° C. with shaking for 24 hours. Isopropyl-β-D-1-thiogalactopyranoside (IPTG) was added to each well at a final concentration of 0.3 mM to induce expression of the proinsulin fusion proteins. In addition, 0.01 µL of 250 units/µl stock Benzonase (Novagen, 70746-3) was added per well at time of induction to reduce the potential for culture viscosity. Cell density was quantified by measuring optical density at 600 nm ($OD_{600}$), 24 hours after induction. Twenty four hours after induction, cells were harvested, diluted 1:3 with 1×PBS to a final volume of 400 µL, and then frozen for later processing.

Soluble Lysate Sample Preparation for Analytical Characterization: The culture broth samples, prepared and stored frozen as described above, were thawed, diluted, and sonicated. The lysates obtained by sonication were centrifuged at 5,500×g for 15 minutes, at a temperature of 8° C., to separate the soluble (supernatant) and insoluble (pellet) fractions. The insoluble fractions were resuspended in PBS using sonication.

SDS-CGE Analysis: The test protein samples prepared as discussed above were analyzed by HTP microchip SDS capillary gel electrophoresis using a LabChip GXII instrument (PerkinElmer) with a HT Protein Express v2 chip and corresponding reagents (Part Numbers 760499 and 760328, respectively, PerkinElmer). Samples were prepared following manufacturer's protocol (Protein User Guide Document No. 450589, Rev. 3). In a 96-well conical well PCR plate, 4 µL sample were mixed with 14 µL of sample buffer, with or without a Dithiotreitol (DTT) reducing agent. The mixture was heated at 95° C. for 5 min and diluted by adding 70 µL of deionized water.

The proinsulin titer at the 96-well scale was determined based on the fusion protein titer multiplied by the percentage of the fusion protein comprised of proinsulin. Total titer represents the sum of soluble and insoluble target expression (mg/L).

Results

As shown in Table 20, the glargine proinsulin fusion proteins having DnaJ-like protein as the N-terminal fusion partner showed the highest levels of proinsulin expression. Surprisingly, proinsulin fusion proteins containing the smallest version of EcpD fusion partner, the 50 amino acid fusion partner EcpD3, showed higher levels of expression compared to full length fusion partner EcpD1 and the 100 amino acid truncated version EcpD2. For proinsulin fusion proteins containing an FklB or FrnE N-terminal fusion partner, the expression of proinsulin fused to the smallest fusion partner fragment, FklB3 and FrnE3 respectively, was equal to or slightly lower than expression of the constructs having the longer N-terminal fusion partners. Table 20 summarizes proinsulin protein titers, both soluble and total, observed during the high throughput expression study.

Therefore, mature glargine was determined to be successfully released from the purified fusion protein (and the C-peptide) following trypsin cleavage. IMAC enrichment followed by trypsin cleavage performed on selected fusion proteins (DnaJ construct G737-031 and FklB construct G737-009, purified in the presence of non-denaturing concentration of urea, and FrnE1 construct G737-018, purified without urea) demonstrated that the fusion protein was cleaved to produce mature insulin as evaluated by SDS-PAGE or SDS-CGE, compared to a glargine standard. Receptor binding assays further indicated activity.

TABLE 20

HTP Expression Titer of Exemplary Proinsulin Fusion Proteins

| Proinsulin Gene Fragment (SEQ ID NOS in Table 18) | N-terminal Fusion Partner-Cleavage Site (SEQ ID NOS in Table 19) | C-peptide Sequence (SEQ ID NOS in Table 18) | Soluble Proinsulin titer (mg/L) | Total Proinsulin titer (mg/L) (Soluble + Insoluble Fractions) |
|---|---|---|---|---|
| G737-001 | DnaJ-like protein-EK | CP-A | 66 | 235 |
| G737-002 | DnaJ-like protein-EK | CP-B | 81 | 241 |
| G737-003 | DnaJ-like protein-EK | CP-C | 88 | 267 |

TABLE 20-continued

HTP Expression Titer of Exemplary Proinsulin Fusion Proteins

| Proinsulin Gene Fragment (SEQ ID NOS in Table 18) | N-terminal Fusion Partner-Cleavage Site (SEQ ID NOS in Table 19) | C-peptide Sequence (SEQ ID NOS in Table 18) | Soluble Proinsulin titer (mg/L) | Total Proinsulin titer (mg/L) (Soluble + Insoluble Fractions) |
|---|---|---|---|---|
| G737-007 | DnaJ-like protein-EK | CP-D | 50 | 499 |
| G737-009 | DnaJ-like protein-Trypsin | CP-A | 9 | 136 |
| G737-017 | DnaJ-like protein-Trypsin | CP-B | 7 | 81 |
| G737-018 | DnaJ-like protein-Trypsin | CP-C | 21 | 331 |
| G737-031 | DnaJ-like protein-Trypsin | CP-D | 10 | 487 |
| G737-001 | FklB-EK | CP-A | 50 | 445 |
| G737-002 | FklB-EK | CP-B | 38 | 321 |
| G737-003 | FklB-EK | CP-C | 33 | 210 |
| G737-007 | FklB-EK | CP-D | 10 | 343 |
| G773-009 | FklB-Trypsin | CP-A | 8 | 578 |
| G737-017 | FklB-Trypsin | CP-B | 23 | 375 |
| G737-018 | FklB-Trypsin | CP-C | 18 | 59 |
| G737-031 | FklB-Trypsin | CP-D | 10 | 321 |
| G737-001 | FklB2-EK | CP-A | 7 | 528 |
| G737-002 | FklB2-EK | CP-B | 46 | 60 |
| G737-003 | FklB2-EK | CP-C | 36 | 69 |
| G737-007 | FklB2-EK | CP-D | 22 | 339 |
| G773-009 | FklB2-Trypsin | CP-A | 10 | 658 |
| G737-017 | FklB2-Trypsin | CP-B | 6 | 92 |
| G737-018 | FklB2-Trypsin | CP-C | 16 | 20 |
| G737-031 | FklB2-Trypsin | CP-D | 11 | 193 |
| G737-001 | FklB3-EK | CP-A | 13 | 565 |
| G737-002 | FklB3-EK | CP-B | 10 | 109 |
| G737-003 | FklB3-EK | CP-C | 11 | 26 |
| G737-007 | FklB3-EK | CP-D | 10 | 12 |
| G737-009 | FklB3-Trypsin | CP-A | 12 | 222 |
| G737-017 | FklB3-Trypsin | CP-B | 9 | 108 |
| G737-018 | FklB3-Trypsin | CP-C | 17 | 70 |
| G737-031 | FklB3-Trypsin | CP-D | 15 | 457 |
| G737-001 | FrnE-EK | CP-A | 132 | 258 |
| G737-007 | FrnE-EK | CP-D | 16 | 52 |
| G737-009 | FrnE-Trypsin | CP-A | 30 | 65 |
| G737-017 | FrnE-Trypsin | CP-B | 41 | 63 |
| G737-018 | FrnE-Trypsin | CP-C | 43 | 56 |
| G737-031 | FrnE-Trypsin | CP-D | 13 | 218 |
| G737-009 | FrnE2-Trypsin | CP-A | 20 | 96 |
| G737-017 | FrnE2-Trypsin | CP-B | 6 | 39 |
| G737-018 | FrnE2-Trypsin | CP-C | 13 | 53 |
| G737-007 | FrnE2-EK | CP-D | 10 | 219 |
| G737-031 | FrnE2-Trypsin | CP-D | 5 | 201 |
| G737-001 | FrnE3-EK | CP-A | 18 | 266 |
| G737-002 | FrnE3-EK | CP-B | 10 | 248 |
| G737-003 | FrnE3-EK | CP-C | 9 | 171 |
| G737-007 | FrnE3-EK | CP-D | 13 | 161 |
| G773-009 | FrnE3-Trypsin | CP-A | 8 | 144 |
| G737-017 | FrnE3-Trypsin | CP-B | 8 | 49 |
| G737-018 | FrnE3-Trypsin | CP-C | 17 | 22 |
| G737-031 | FrnE3-Trypsin | CP-D | 7 | 307 |
| G737-001 | EcpD1-EK | CP-A | 9 | 194 |
| G737-002 | EcpD1-EK | CP-B | 5 | 131 |
| G737-003 | EcpD1-EK | CP-B | 5 | 132 |
| G737-007 | EcpD1-EK | CP-D | 5 | 22 |
| G773-009 | EcpD1-Trypsin | CP-A | 21 | 86 |
| G737-017 | EcpD1-Trypsin | CP-B | 16 | 39 |
| G737-018 | EcpD1-Trypsin | CP-C | 27 | 74 |
| G737-031 | EcpD1-Trypsin | CP-D | 4 | 206 |
| G737-001 | EcpD2-EK | CP-A | 16 | 21 |
| G737-002 | EcpD2-EK | CP-B | 9 | 24 |
| G737-003 | EcpD2-EK | CP-C | 9 | 29 |
| G737-007 | EcpD2-EK | CP-D | 9 | 60 |
| G773-009 | EcpD2-Trypsin | CP-A | 18 | 125 |
| G737-017 | EcpD2-Trypsin | CP-B | 6 | 9 |
| G737-018 | EcpD2-Trypsin | CP-C | 7 | 34 |
| G737-031 | EcpD2-Trypsin | CP-D | 5 | 33 |
| G737-001 | EcpD3-EK | CP-A | 8 | 81 |
| G737-002 | EcpD3-EK | CP-B | 15 | 18 |
| G737-003 | EcpD3-EK | CP-C | 17 | 64 |
| G737-007 | EcpD3-EK | CP-D | 10 | 169 |
| G773-009 | EcpD3-Trypsin | CP-A | 8 | 40 |
| G737-017 | EcpD3-Trypsin | CP-B | 9 | 9 |

TABLE 20-continued

HTP Expression Titer of Exemplary Proinsulin Fusion Proteins

| Proinsulin Gene Fragment (SEQ ID NOS in Table 18) | N-terminal Fusion Partner-Cleavage Site (SEQ ID NOS in Table 19) | C-peptide Sequence (SEQ ID NOS in Table 18) | Soluble Proinsulin titer (mg/L) | Total Proinsulin titer (mg/L) (Soluble + Insoluble Fractions) |
|---|---|---|---|---|
| G737-018 | EcpD3-Trypsin | CP-C | 10 | 12 |
| G737-031 | EcpD3-Trypsin | CP-D | 7 | 57 |

Example VI. High Throughput Screening of GCSF Fusion Proteins

This study was conducted to test levels of recombinant GCSF protein produced by *P. fluorescens* strains expressing GCSF fusion proteins containing DnaJ-like protein, varying lengths of FklB (FklB, FklB2, or FklB3), FrnE (FrnE, FrnE2, or FrnE3), or EcpD (EcpD1, EcpD2, or EcpD3) as the N-terminal fusion partner.

Materials and Methods

Construction of GCSF Expression Vectors: A GCSF gene fragment (SEQ ID NO. 68), containing an optimized gcsf coding sequence, recognition sequences for restriction enzyme SapI both downstream and upstream to the coding sequence, and three stop codons downstream to the coding sequence, was synthesized by DNA2.0 (Menlo Park, Calif.). The GCSF gene fragment of plasmid pJ201:207232, was digested with restriction enzyme SapI to generate fragments containing the optimized gcsf coding sequence. The gcsf coding sequence was then subcloned into expression vectors containing different fusion partners, by ligation of the GCSF gene fragment and the expression vectors using T4 DNA ligase (Fermentas EL0011) and electroporated in 96-well format into competent *P. fluorescens* DC454 host cells. A hexahistidine tag (SEQ ID NO:242) was included in a linker between the GCSF and each N-terminal fusion partner along with an enterokinase cleavage site (DDDDK (SEQ ID NO:13)) for releasing the N-terminal fusion partner from the GCSF. The resulting plasmids containing the fusion protein constructs are listed in the third column of Table 21.

TABLE 21

Plasmids for GCSF Fusion Protein Expression

| Expression Vector | Fusion Partner- Cleavage Site | GCSF Expression Plasmid | Size (kDa) | GCSF Size | % GCSF of Fusion | Fusion Protein Size |
|---|---|---|---|---|---|---|
| pFNX4411 | DnaJ-like protein - EK | p529-301 | 11 | 19 | 0.63 | 30 |
| pFNX4412 | EcpD1-EK | p529-302 | 29 | 19 | 0.40 | 48 |
| pFNX4413 | EcpD2-EK | p529-303 | 13 | 19 | 0.60 | 32 |
| pFNX4414 | EcpD3-EK | p529-304 | 7 | 19 | 0.72 | 27 |
| pFNX4415 | FklB-EK | p529-305 | 24 | 19 | 0.45 | 43 |
| pFNX4416 | FklB2-EK | p529-306 | 12 | 19 | 0.61 | 32 |
| pFNX4417 | FklB3-EK | p529-307 | 7 | 19 | 0.73 | 27 |
| pFNX4418 | FrnE-EK | p529-308 | 26 | 19 | 0.43 | 45 |
| pFNX4419 | FrnE2-EK | p529-309 | 13 | 19 | 0.59 | 32 |
| pFNX4420 | FrnE3-EK | p529-310 | 8 | 19 | 0.72 | 27 |

Growth and Expression in 96 Well Format (HTP): The plasmids containing coding sequences for the gcsf gene and the N-terminal fusion partners were transformed into an array of *P. fluorescens* host strains. Thirty-five microliters of *P. fluorescens* competent cells were thawed and mixed with 10 µL of 10× diluted plasmid DNA (2.5 ng). Twenty-five microlitres of the mixture was transferred into a 96-multi-well Nucleovette® plate (Lonza VHNP-1001), for transformation via electroporation, using the Nucleofector™ 96-well Shuttle™ system (Lonza AG) and the transformed cells were then transferred to 96-well deep well plates (seed plates) containing 500 µL M9 salts 1% glucose medium and trace elements. The seed plates were incubated at 30° C. with shaking for 48 hours to generate seed cultures.

Ten microliters of seed culture were transferred in duplicate into fresh 96-well deep well plates, each well containing 500 µL of HTP medium (Teknova 3H1129), supplemented with trace elements and 5% glycerol, and incubated at 30° C. with shaking for 24 hours. Isopropyl-β-D-1-thiogalactopyranoside (IPTG) was added to each well at a final concentration of 0.3 mM to induce expression of the GCSF fusion proteins. In *Pseudomonas* strains over-expressing folding modulators (FMO strains), Mannitol (Sigma, M1902) at a final concentration of 1% was added along with the IPTG, to induce expression of the folding modulators. In addition, 0.014 of 250 units/µl stock Benzonase (Novagen, 70746-3) was added per well at the time of induction to reduce the potential for culture viscosity. Cell density was quantified by measuring optical density at 600 nm ($OD_{600}$) 24 hours after induction. Twenty four hours after induction, cells were harvested, diluted 1:3 with 1×PBS to a final volume of 400 µL, and then frozen for later processing. Soluble Lysate Sample Preparation for Analytical Characterization: The culture broth samples, prepared and frozen as described above, were thawed, diluted and sonicated using a Cell Lysis Automated Sonication System (CLASS, Scino- mix) with a 24 probe tip horn. The lysates obtained by sonication were centrifuged at 5,500×g for 15 minutes, at a temperature of 8° C., to separate the soluble (supernatant) and insoluble (pellet) fractions. The insoluble fractions were resuspended in 400 µL, of PBS, at pH 7.4, also by sonication.

SDS-CGE Analysis: The test protein samples prepared as discussed above were analyzed by HTP microchip SDS capillary gel electrophoresis using a LabChip GXII instrument (Caliper LifeSciences) with a HT Protein Express v2 chip and corresponding reagents (Part Numbers 760499 and 760328, respectively, Caliper LifeSciences). Samples were prepared following the manufacturer's protocol (Protein User Guide Document No. 450589, Rev. 3). In a 96-well conical well PCR plate, 4 μL sample were mixed with 14 μL of sample buffer, with or without a Dithiotreitol (DTT) reducing agent. The mixture was heated at 95° C. for 5 min and diluted by adding 70 μL of deionized water. In parallel with the test protein samples, lysates from strains containing no fusion protein (null strains) were also analyzed. The null strain lysates were quantified using the system internal standard without background subtraction. One sample per strain was quantitated during the HTP screen; typically the standard deviation of the SDS-CGE method is ~10%.
Results High level expression of GCSF was achieved at the 96-well scale using the fusion partner approach, which presents an alternative to screening protease deficient hosts in order to identify strains that enable high level expression of N-terminal Met-GCSF. Fusion protein and GCSF titers (calculated based on the percent GCSF of total fusion protein, by MW) are shown in Table 22. Wild-type strain DC454 produced 484 mg/L fusion protein, and 305 mg/L GCSF with the dnaJ fusion partner. All fusion partner constructs yielded fusion protein titers of over 100 mg/L, as shown in Table 22. These high levels observed at the HTP scale show great promise for expression at shake flask or fermentation scale. Furthermore, it is common to observe a significant increase in volumetric titer between HTP and larger scale cultures. In a previous study, the prtB protease deficient strain was shown to enable expression of ~247 mg/L Met-GCSF at the 0.5 mL scale (H. Jin et al., 2011, Protein Expression and Purification 78:69-77, and U.S. Pat. No. 8,455,218). In the present study, as described, expression of a high level of Met-GCSF as part of a fusion protein was observed even in a host cell having no protease deficiency. It is noted that a preparation of Met-GCSF, obtained by expressing as part of any of the described fusion proteins and releasing by protease cleavage, contains virtually 100% Met-GCSF (and no des-Met-GCSF), as cleavage is carried out following the removal of any proteases.

TABLE 22

HTP Expression Titer of GCSF Fusion Proteins

| Fusion Partner-Cleavage Site | Fusion Titer (mg/L) | % Target in Fusion | GCSF Titer (mg/L) |
|---|---|---|---|
| DnaJ-like protein EK | 155-758 | 63 | 98-478 |
| EcpD1-EK (FL EcpD) | 247-542 | 40 | 96-211 |
| EcpD2-EK | 101-112 | 60 | 61-67 |
| EcpD3-EK | 137-249 | 72 | 99-179 |
| FklB1-EK (FL FklB) | 226-565 | 44 | 99-249 |
| FklB2-EK | 171-362 | 60 | 103-217 |
| FklB3-EK | 79-145 | 72 | 57-104 |
| FrnE1-EK (FL FmE) | 241-763 | 42 | 101-320 |
| FrnE2-EK | — | 59 | — |
| FrnE3-EK | 141-260 | 71 | 100-185 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A recombinant fusion protein comprising:
   (i) an N-terminal fusion partner, wherein the N-terminal fusion partner is selected from: *P. fluorescens* DnaJ-like protein having the amino acid sequence set forth in SEQ ID NO: 2; *P. fluorescens* FklB protein having the amino acid sequence set forth in SEQ ID NO: 4, SEQ ID NO: 28, SEQ ID NO: 61, or SEQ ID NO: 62; *P. fluorescens* FrnE protein having the amino acid sequence set forth in SEQ ID NO: 3, SEQ ID NO: 63, or SEQ ID NO: 64; *P. fluorescens* FklB/FkbP protein having the amino acid sequence set forth in SEQ ID NO: 5; *P. fluorescens* EcpD protein having the amino acid sequence set forth in SEQ ID NO: 7, SEQ ID NO: 65, SEQ ID NO: 66, or SEQ ID NO: 67; and *P. fluorescens* FkbP protein having the amino acid sequence set forth in SEQ ID NO: 25;
   (ii) a polypeptide of interest; and
   (iii) a linker of 10 to 50 amino acids in length comprising a cleavage site between the N-terminal fusion partner and the polypeptide of interest; wherein the polypeptide of interest is a therapeutic polypeptide or protein from about 1 kDa to about 30 kDa.

2. The recombinant fusion protein of claim 1, wherein the therapeutic polypeptide or protein is selected from: hPTH1-34; a proinsulin that is processed to insulin or an insulin analog; Glp1; Glp2; IGF-1; Exenatide (SEQ ID NO: 37); Teduglutide (SEQ ID NO: 39); Pramlintide (SEQ ID NO: 40); Ziconotide (SEQ ID NO: 41); Becaplermin (SEQ ID NO: 42); Enfuvirtide (SEQ ID NO: 43); and Nesiritide (SEQ ID NO: 44).

3. The recombinant fusion protein of claim 1, wherein the therapeutic polypeptide or protein is N-met-GCSF.

4. The recombinant fusion protein of claim 1, wherein the therapeutic polypeptide or protein is from about 1 kDa to about 20 kDa.

5. The recombinant fusion protein of claim 1, wherein the therapeutic polypeptide or protein is a proinsulin, wherein the proinsulin is processed to insulin or an insulin analog, and wherein the proinsulin comprises a C-peptide that has an amino acid sequence selected from: SEQ ID NO: 97; SEQ ID NO: 98; SEQ ID NO: 99; and SEQ ID NO: 100.

6. The recombinant fusion protein of claim 5, wherein the insulin analog is insulin glargine, insulin aspart, lispro, glulisine, detemir, or degludec.

7. The recombinant fusion protein of claim 1, wherein the cleavage site is recognized by a cleavage enzyme in the group consisting of: enterokinase; trypsin; Factor Xa; and furin.

8. The recombinant fusion protein of claim 1, wherein the linker comprises an affinity tag.

9. The recombinant fusion protein of claim 1, wherein the linker has an amino acid sequence selected from: from the N to C terminus, a $(G4S)_2$ spacer sequence (SEQ ID NO: 59), a hexahistidine affinity tag (SEQ ID NO: 242), and a protease cleavage site DDDDK (SEQ ID NO: 13); from the N to C terminus, a $(G4S)_2$ spacer sequence (SEQ ID NO: 59), a hexahistidine affinity tag (SEQ ID NO: 242), and a protease cleavage site RKR; from the N to C terminus, a $(G4S)_2$ spacer sequence (SEQ ID NO: 59), a hexahistidine affinity tag (SEQ ID NO: 242), and a protease cleavage site RRR; from the N to C terminus, a $(G4S)_2$ spacer sequence (SEQ ID NO: 59), a hexahistidine affinity tag (SEQ ID NO: 242), and a protease cleavage site LVPR (amino acids 16-19 of SEQ ID NO: 12); and SEQ ID NO: 226.

10. The recombinant fusion protein of claim 1, wherein the N-terminal fusion partner is *P. fluorescens* FklB/FkbP protein having the amino acid sequence set forth in SEQ ID NO: 5, and the polypeptide of interest is hPTH1-34.

11. The recombinant fusion protein of claim 10, wherein the linker further comprises an affinity tag.

12. The recombinant fusion protein of claim 11, wherein the linker further comprises a spacer and an affinity tag.

13. The recombinant fusion protein of claim 12, wherein:
   a. the spacer is selected from: (G4S)1, (G4S)2, (G4S)3, (G4S)4, and (G4S)5;
   b. the affinity tag is selected from: a Maltose Binding Protein tag, a Polyhistidine tag, a FLAG tag, a Myc tag, an HA-tag, and a Nus tag; and
   c. the cleavage site is selected from: an enterokinase cleavage site, a trypsin cleavage site, a chymotrypsin cleavage site, a Factor Xa cleavage site, and a Furin cleavage site.

14. The recombinant fusion protein of claim 1, wherein the therapeutic polypeptide or protein is a human polypeptide or protein.

15. The recombinant fusion protein of claim 4, wherein the linker further comprises an affinity tag.

16. The recombinant fusion protein of claim 15, wherein the linker further comprises a spacer and an affinity tag.

17. The recombinant fusion protein of claim 16, wherein:
a. the spacer is selected from: (G4S)1, (G4S)2, (G4S)3, (G4S)4, and (G4S)5;
b. the affinity tag is selected from: a Maltose Binding Protein tag, a Polyhistidine tag, a FLAG tag, a Myc tag, an HA-tag, and a Nus tag; and
c. the cleavage site is selected from: an enterokinase cleavage site, a trypsin cleavage site, a chymotrypsin cleavage site, a Factor Xa cleavage site, and a Furin cleavage site.

18. The recombinant fusion protein of claim 1, wherein the therapeutic polypeptide or protein is a heterologous polypeptide or protein.

19. The recombinant fusion protein of claim 4, wherein the polypeptide of interest is from about 1 kDa to about 10 kDa.

20. The recombinant fusion protein of claim 8, wherein the linker further comprises a spacer.

21. The recombinant fusion protein of claim 20, wherein:
a. the spacer is selected from: (G4S)1, (G4S)2, (G4S)3, (G4S)4, and (G4S)5;
b. the affinity tag is selected from: a Maltose Binding Protein tag, a Polyhistidine tag, a FLAG tag, a Myc tag, an HA-tag, and a Nus tag; and
c. the cleavage site is selected from: an enterokinase cleavage site, a trypsin cleavage site, a chymotrypsin cleavage site, a Factor Xa cleavage site, and a Furin cleavage site.

22. The recombinant fusion protein of claim 1 wherein the molecular weight of the polypeptide of interest is 13% to 50% of the molecular weight of the recombinant fusion protein.

23. The recombinant fusion protein of claim 1 wherein the isoelectric point (pI) of the polypeptide of interest is 1.5 times to 3 times the pI of the N-terminal fusion partner.

24. An expression vector for expression of the recombinant fusion protein of claim 1, wherein the expression vector comprises a nucleotide sequence encoding the recombinant fusion protein.

25. A method for obtaining a polypeptide of interest, comprising:
(i) expressing a recombinant fusion protein of claim 1 in a *P. fluorescens* host cell;
(ii) purifying the recombinant fusion protein expressed in the *P. fluorescens* host cell of step (i); and
(iii) cleaving the purified recombinant fusion protein of step (ii) by incubation with a cleavage enzyme that recognizes the cleavage site in the linker, to release the polypeptide of interest;
thereby obtaining the polypeptide of interest.

26. The method of claim 25, further comprising: measuring the expression level of the recombinant fusion protein expressed in step (i), measuring the amount of the recombinant fusion protein purified in step (ii), measuring the amount of the polypeptide of interest obtained in step (iii) that has been properly released, or a combination thereof.

27. The method of claim 26, wherein the measured amount of the polypeptide of interest purified in step (ii) or obtained as properly released in step (iii) is about 0.1 g/L to about 25 g/L.

28. The method of claim 26, wherein the properly released polypeptide of interest obtained is soluble.

29. The method of claim 26, wherein the properly released polypeptide of interest obtained is intact.

30. The method of claim 26, wherein the properly released polypeptide of interest obtained is soluble and intact.

* * * * *